(12) United States Patent
Kim et al.

(10) Patent No.: US 10,053,492 B2
(45) Date of Patent: Aug. 21, 2018

(54) RED GENETICALLY ENCODED CALCIUM INDICATORS AND METHODS OF USE

(71) Applicant: Howard Hughes Medical Institute, Chevy Chase, MD (US)

(72) Inventors: Douglas S. Kim, Reston, VA (US); Loren L. Looger, Sterling, VA (US); Eric R. Schreiter, Leesburg, VA (US); Karel Svoboda, Leesburg, VA (US)

(73) Assignee: HOWARD HUGHES MEDICAL INSTITUTE, Chevy Chase, MD (US)

( * ) Notice: Subject to any disclaimer, the term of this patent is extended or adjusted under 35 U.S.C. 154(b) by 0 days.

(21) Appl. No.: 15/461,603

(22) Filed: Mar. 17, 2017

(65) Prior Publication Data
US 2017/0198015 A1    Jul. 13, 2017

Related U.S. Application Data

(60) Division of application No. 14/974,483, filed on Dec. 18, 2015, now Pat. No. 9,644,007, which is a continuation of application No. 14/941,406, filed on Nov. 13, 2015.

(60) Provisional application No. 62/096,214, filed on Dec. 23, 2014.

(51) Int. Cl.

| | | |
|---|---|---|
| *C07H 21/04* | (2006.01) | |
| *C07H 19/00* | (2006.01) | |
| *C07H 21/00* | (2006.01) | |
| *C12N 15/00* | (2006.01) | |
| *C12N 15/09* | (2006.01) | |
| *C12N 15/10* | (2006.01) | |
| *C12N 15/11* | (2006.01) | |
| *C12N 15/13* | (2006.01) | |
| *A61K 48/00* | (2006.01) | |
| *C12Q 1/68* | (2018.01) | |
| *C07K 14/00* | (2006.01) | |
| *A01K 67/027* | (2006.01) | |
| *G01N 33/58* | (2006.01) | |
| *A61K 49/00* | (2006.01) | |

(52) U.S. Cl.
CPC .......... *C07K 14/00* (2013.01); *A01K 67/0275* (2013.01); *A61K 49/0045* (2013.01); *G01N 33/582* (2013.01); *A01K 2217/206* (2013.01); *A01K 2227/105* (2013.01); *A01K 2227/40* (2013.01); *A01K 2227/703* (2013.01); *A01K 2227/706* (2013.01); *A01K 2267/0393* (2013.01); *C12N 2750/14143* (2013.01)

(58) Field of Classification Search
CPC ............ C07K 2319/60; C07K 14/4728; C07K 14/00; C07K 14/705; C07K 11/06; G01N 33/6872; G01N 33/5058; G01N 2500/10; G01N 33/5035; G01N 33/5041; G01N 33/582; G01N 2333/4727; G01N 2333/705; G01N 33/48728; G01N 33/502; G01N 33/5008; G01N 21/6428; G01N 2333/726; C12N 2510/00; C12N 5/0619; C12N 15/00; C12N 15/85; C12N 15/86; A61B 17/1128; A61B 5/4064; A61B 2503/40; A61B 2576/026; A61B 5/0042; A61B 5/0071; A61L 27/383; G02B 21/008; G02B 2207/114
USPC ....................................................... 536/23.5
See application file for complete search history.

(56) References Cited

U.S. PATENT DOCUMENTS 9,488,642 B2 * 11/2016 Looger .............. G01N 33/5041
9,518,980 B2 * 12/2016 Looger .............. G01N 33/5041

FOREIGN PATENT DOCUMENTS

JP        2014001161      *  6/2012

OTHER PUBLICATIONS

Ohkura et al. PLos One, Jul. 10, 2012; 7: e39933: 1-7.*
Akerboom et al. Front. Mol. Neurosci., Mar. 4, 2013; 6: 1-29.*

* cited by examiner

*Primary Examiner* — Chang-Yu Wang
(74) *Attorney, Agent, or Firm* — Stites & Harbison, PLLC; Mandy Wilson Decker

(57) ABSTRACT

Protein indicators useful for calcium imaging, in particular, red genetically-encoded calcium indicators (GECIs) disclosed herein rival best-of-class green GECIs in terms of sensitivity for detecting neural activity, and can be monitored in vivo. The presently-disclosed subject matter further includes a method of monitoring cell activity comprising stimulating a cell comprising a red GECI polypeptide; and detecting fluorescence emitted by the cell.

18 Claims, 30 Drawing Sheets

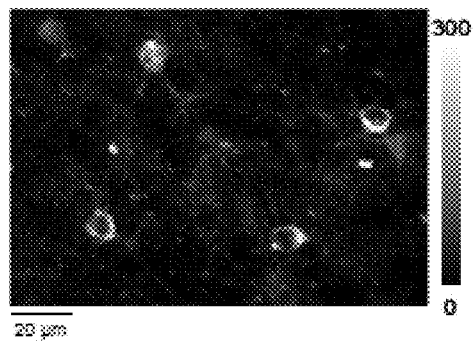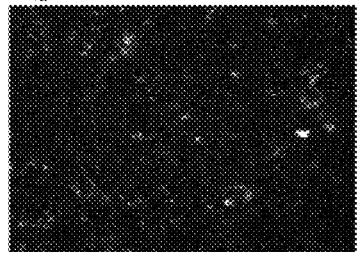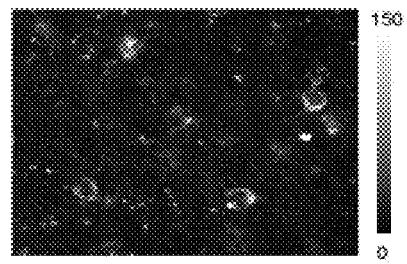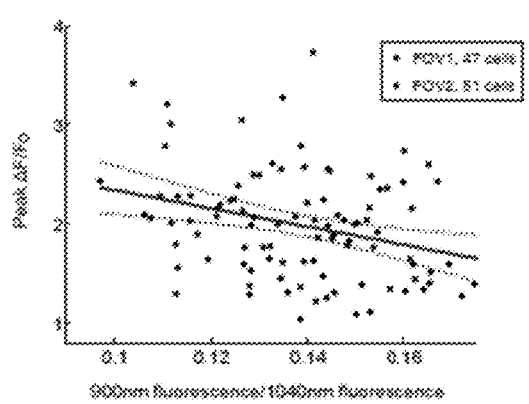
FIGS. 16A-16C

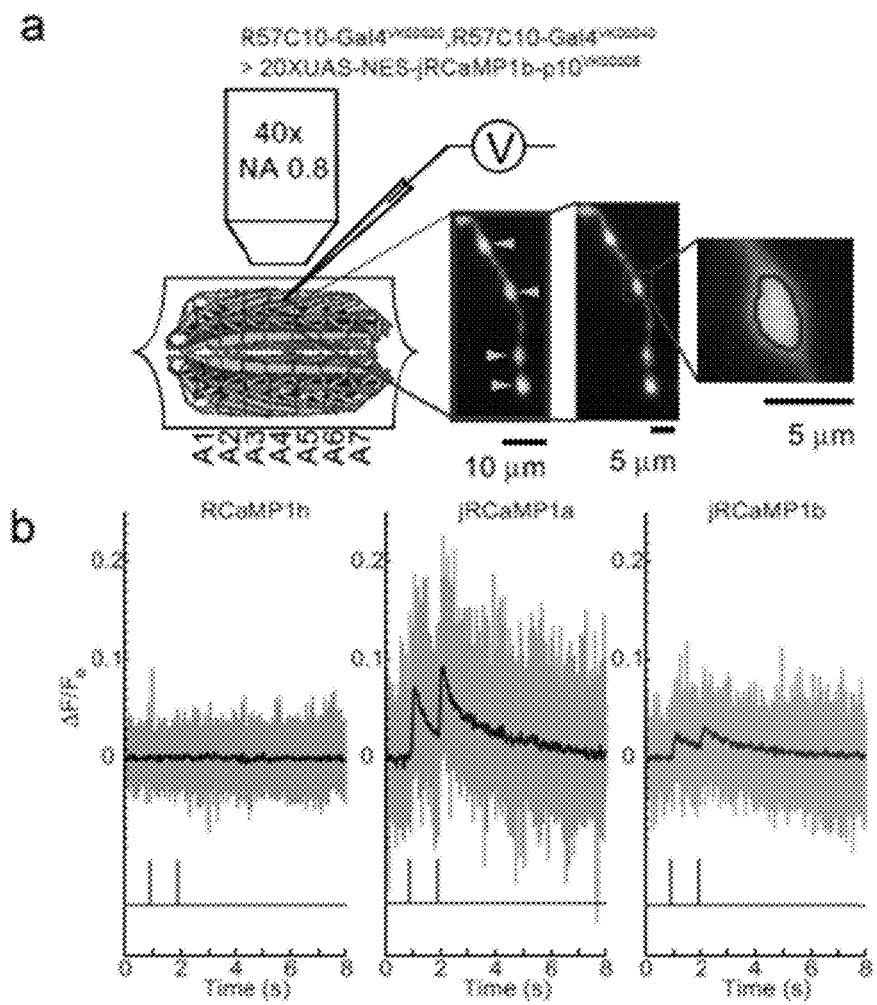
FIGS. 18A-B

US 10,053,492 B2

SEQUENCE LISTING

<160> NUMBER OF SEQ ID NOS: 9

<210> SEQ ID NO 1
<211> LENGTH: 1386
<212> TYPE: DNA
<213> ORGANISM: Artificial Sequence
<220> FEATURE:
<223> OTHER INFORMATION: Synthetic Sequence

<400> SEQUENCE: 1

```
atgctgcaga acgagcttgc tcttaagttg gctggacttg atattaacaa gactggagga       60
ggttctcatc atcatcatca tcatggtatg gctagcatga ctggtggaca gcaaatgggt      120
cgggatctgt acgacgatga cgataaggat ctcgcaacaa tggtcgactc atcacgtcgt      180
aagtggaata agacaggtca cgcagtcaga gctataggtc ggctgagctc agcgatcaac      240
tgcgaaatga tgtacccagc ggatggtggt ctgcgtggtt acactcacat ggcgctgaaa      300
gttgatggcg gcggtcacct gtcctgttct ttcgtgacca cctaccgctc caaaaagact      360
gtcggcaaca ttaagatgcc tgccattcat agcgtcagcc accgtctgga gcgcctggag      420
gagagcgata acgaaatgtt tgtcgtacag cgtgaacacg cagttgccaa gtttgtgggc      480
ctgggtggtg gcggcggtac cggagggagc atgaactccc tgatcaagga gaacatgcgt      540
atgaaagtgg ttctggaagg ctccgtaaac ggccaccagt tcaaatgcac tggtgaaggc      600
```

```
gaaggcaacc cgtatatggg cacccagact atgcgtatca aagtgatcga gggtggtccg    660
ctgccgtttg cgttcgacat cctggcgacg tcctttatgt atggctcccg taccttcatc    720
aaatatccga aaggcatccc ggatttcttt aagcagtcct tcccggaagg ttttacctgg    780
gaacgtgtga cccgttacga agacggcggc gtaattaccg ttatgcaaga cacgtctctg    840
gaggatggct gcctggtgta tcacgtgcag gttcgcggtg tgaacttccc gagcaatggt    900
gctgtaatgc aaaagaaaac caaaggttgg gagcctacgg actcccaaac cactgaagag    960
cagatcgcag aatttaaaga ggctttctcc ctatttgaca aggacgggga tgggacaata   1020
acaaccaagg agctggggac ggtgatgcgg tctctggggc agaaccccac agaagcagag   1080
ctgcaggaca tgatcaatga agtagatgcc gacggtgacg gcacaatcga cttccctgag   1140
ttcctgatta tgatggcaag aaaaatgaaa tacacagaca gtgaagaaga aattagagaa   1200
gcgttcggcg tgtttgataa ggatggcaat ggctacatca gtgcagcaga gcttcgccac   1260
gtgatgacaa accttggaga gaagttaaca gatgaagagg ttgatgaaat gatcagggaa   1320
gcagacagcg atggggatgg tcaggtaaac tacgaagagt ttgtacaaat gatgacagcg   1380
aagtag                                                              1386

<210> SEQ ID NO 2
<211> LENGTH: 461
<212> TYPE: PRT
<213> ORGANISM: Artificial Sequence
<220> FEATURE:
<223> OTHER INFORMATION: Synthetic Sequence

<400> SEQUENCE: 2

Met Leu Gln Asn Glu Leu Ala Leu Lys Leu Ala Gly Leu Asp Ile Asn
1               5                   10                  15

Lys Thr Gly Gly Gly Ser His His His His His Gly Met Ala Ser
            20                  25                  30

Met Thr Gly Gly Gln Gln Met Gly Arg Asp Leu Tyr Asp Asp Asp
        35                  40                  45

Lys Asp Leu Ala Thr Met Val Asp Ser Ser Arg Arg Lys Trp Asn Lys
 50                  55                  60

Thr Gly His Ala Val Arg Ala Ile Gly Arg Leu Ser Ser Ala Ile Asn
65                  70                  75                  80

Cys Glu Met Met Tyr Pro Ala Asp Gly Gly Leu Arg Gly Tyr Thr His
                85                  90                  95

Met Ala Leu Lys Val Asp Gly Gly Gly His Leu Ser Cys Ser Phe Val
            100                 105                 110

Thr Thr Tyr Arg Ser Lys Lys Thr Val Gly Asn Ile Lys Met Pro Ala
        115                 120                 125

Ile His Ser Val Ser His Arg Leu Glu Arg Leu Glu Glu Ser Asp Asn
130                 135                 140

Glu Met Phe Val Val Gln Arg Glu His Ala Val Ala Lys Phe Val Gly
145                 150                 155                 160

Leu Gly Gly Gly Gly Gly Thr Gly Gly Ser Met Asn Ser Leu Ile Lys
                165                 170                 175

Glu Asn Met Arg Met Lys Val Val Leu Glu Gly Ser Val Asn Gly His
            180                 185                 190

Gln Phe Lys Cys Thr Gly Glu Gly Glu Gly Asn Pro Tyr Met Gly Thr
        195                 200                 205

Gln Thr Met Arg Ile Lys Val Ile Glu Gly Gly Pro Leu Pro Phe Ala
```

```
                    210                 215                 220
Phe Asp Ile Leu Ala Thr Ser Phe Met Tyr Gly Ser Arg Thr Phe Ile
225                 230                 235                 240

Lys Tyr Pro Lys Gly Ile Pro Asp Phe Phe Lys Gln Ser Phe Pro Glu
                245                 250                 255

Gly Phe Thr Trp Glu Arg Val Thr Arg Tyr Glu Asp Gly Val Ile
                260                 265                 270

Thr Val Met Gln Asp Thr Ser Leu Glu Asp Gly Cys Leu Val Tyr His
                275                 280                 285

Val Gln Val Arg Gly Val Asn Phe Pro Ser Asn Gly Ala Val Met Gln
                290                 295                 300

Lys Lys Thr Lys Gly Trp Glu Pro Thr Asp Ser Gln Thr Thr Glu Glu
305                 310                 315                 320

Gln Ile Ala Glu Phe Lys Glu Ala Phe Ser Leu Phe Asp Lys Asp Gly
                325                 330                 335

Asp Gly Thr Ile Thr Thr Lys Glu Leu Gly Thr Val Met Arg Ser Leu
                340                 345                 350

Gly Gln Asn Pro Thr Glu Ala Glu Leu Gln Asp Met Ile Asn Glu Val
                355                 360                 365

Asp Ala Asp Gly Asp Gly Thr Ile Asp Phe Pro Glu Phe Leu Ile Met
                370                 375                 380

Met Ala Arg Lys Met Lys Tyr Thr Asp Ser Glu Glu Ile Arg Glu
385                 390                 395                 400

Ala Phe Gly Val Phe Asp Lys Asp Gly Asn Gly Tyr Ile Ser Ala Ala
                405                 410                 415

Glu Leu Arg His Val Met Thr Asn Leu Gly Glu Lys Leu Thr Asp Glu
                420                 425                 430

Glu Val Asp Glu Met Ile Arg Glu Ala Asp Ser Asp Gly Asp Gly Gln
                435                 440                 445

Val Asn Tyr Glu Glu Phe Val Gln Met Met Thr Ala Lys
450                 455                 460

<210> SEQ ID NO 3
<211> LENGTH: 1413
<212> TYPE: DNA
<213> ORGANISM: Artificial Sequence
<220> FEATURE:
<223> OTHER INFORMATION: Synthetic Sequence

<400> SEQUENCE: 3
atgctgcaga acgagcttgc tcttaagttg gctggacttg atattaacaa gactggagga       60
ggttctcatc atcatcatca tcatggtatg gctagcatga ctggtggaca gcaaatgggt      120
cgggatctgt acgacgatga cgataaggat ctcgcaacaa tggtcgactc atcacgtcgt      180
aagtggaata aggcaggtca cgcagtcaga gctataggtc ggctgagctc acccgtggtt      240
tccgagcgga tgtaccccga ggacggcgcc ctgaagagcg agatcaagaa ggggctgagg      300
ctgaaggacg gcggccacta cgccgccgag gtcaagacca cctacaaggc caagaagccc      360
gtgcagctgc ccggcgccta catcgtggac atcaagttgg acatcgtgtc ccacaacgag      420
gactacacca tcgtggaaca gtgcgaacgc gccgagggcc gccactccac cggcggcatg      480
gacgagctgt acaagggagg tacaggcggg agtctggtga gcaagggcga ggaggataac      540
atggccatca tcaaggagtt catgcgcttc aaggtgcaca tggagggctc cgtgaacggc      600
cacgagttcg agatcgaggg cgagggcgag ggccgcccct acgaggcctt tcagaccgct      660
```

```
aagctgaagg tgaccaaggg tggcccccctg cccttcgcct gggacatcct gtcccctcag    720
ttcatgtacg gctccaaggc ctacattaag cacccagccg acatccccga ctacttcaag    780
ctgtccttcc ccgagggctt caggtgggag cgcgtgatga acttcgagga cggcggcatt    840
attcacgtga accaggactc ctccctgcag gacggcgtat tcatctacaa ggtgaagctg    900
cgcggcacca acttccccccc cgacggcccc gtaatgcaga agaagaccat gggctgggag    960
gctacgcgtg acgacctgac tgaagagcag atcgcagaat ttaaagaggc tttctcccta   1020
tttgacaagg acggggatgg gacgataaca accaaggagc ttgggacggt gttccgatcg   1080
ctggggcaga accccacaga agcagagctg caggacatga tcaatgaagt agatgccgac   1140
ggtgacggca cattcgactt ccctgagttc ctgacgatga tggcaagaaa aatgaatgac   1200
acagacagtg aagaggaaat cgcgaagcg ttccgcgtgt ttgataagga cggcaatggc   1260
tacatcggcg cagcagagct tcgccacgtg atgacagacc ttggagagaa gttaacagat   1320
gaggaggttg atgaaatgat cagggtagca gacatcgatg gggatggtca ggtaaactac   1380
gaagagtttg tacaaatgat gacagcgaag taa                                1413
```

<210> SEQ ID NO 4
<211> LENGTH: 470
<212> TYPE: PRT
<213> ORGANISM: Artificial Sequence
<220> FEATURE:
<223> OTHER INFORMATION: Synthetic Sequence

<400> SEQUENCE: 4

```
Met Leu Gln Asn Glu Leu Ala Leu Lys Leu Ala Gly Leu Asp Ile Asn
1               5                   10                  15

Lys Thr Gly Gly Gly Ser His His His His His Gly Met Ala Ser
            20                  25                  30

Met Thr Gly Gly Gln Gln Met Gly Arg Asp Leu Tyr Asp Asp Asp
            35                  40                  45

Lys Asp Leu Ala Thr Met Val Asp Ser Ser Arg Arg Lys Trp Asn Lys
50                  55                  60

Ala Gly His Ala Val Arg Ala Ile Gly Arg Leu Ser Ser Pro Val Val
65                  70                  75                  80

Ser Glu Arg Met Tyr Pro Glu Asp Gly Ala Leu Lys Ser Glu Ile Lys
                85                  90                  95

Lys Gly Leu Arg Leu Lys Asp Gly Gly His Tyr Ala Ala Glu Val Lys
            100                 105                 110

Thr Thr Tyr Lys Ala Lys Lys Pro Val Gln Leu Pro Gly Ala Tyr Ile
            115                 120                 125

Val Asp Ile Lys Leu Asp Ile Val Ser His Asn Glu Asp Tyr Thr Ile
130                 135                 140

Val Glu Gln Cys Glu Arg Ala Glu Gly Arg His Ser Thr Gly Gly Met
145                 150                 155                 160

Asp Glu Leu Tyr Lys Gly Gly Thr Gly Gly Ser Leu Val Ser Lys Gly
                165                 170                 175

Glu Glu Asp Asn Met Ala Ile Ile Lys Glu Phe Met Arg Phe Lys Val
            180                 185                 190

His Met Glu Gly Ser Val Asn Gly His Glu Phe Glu Ile Glu Gly Glu
            195                 200                 205

Gly Glu Gly Arg Pro Tyr Glu Ala Phe Gln Thr Ala Lys Leu Lys Val
            210                 215                 220

Thr Lys Gly Gly Pro Leu Pro Phe Ala Trp Asp Ile Leu Ser Pro Gln
```

```
            225                 230                 235                 240
        Phe Met Tyr Gly Ser Lys Ala Tyr Ile Lys His Pro Ala Asp Ile Pro
                            245                 250                 255

Asp Tyr Phe Lys Leu Ser Phe Pro Glu Gly Phe Arg Trp Glu Arg Val
                            260                 265                 270

Met Asn Phe Glu Asp Gly Gly Ile Ile His Val Asn Gln Asp Ser Ser
                            275                 280                 285

Leu Gln Asp Gly Val Phe Ile Tyr Lys Val Lys Leu Arg Gly Thr Asn
                        290                 295                 300

Phe Pro Pro Asp Gly Pro Val Met Gln Lys Lys Thr Met Gly Trp Glu
        305                 310                 315                 320

Ala Thr Arg Asp Asp Leu Thr Glu Glu Gln Ile Ala Glu Phe Lys Glu
                            325                 330                 335

Ala Phe Ser Leu Phe Asp Lys Asp Gly Asp Gly Thr Ile Thr Thr Lys
                            340                 345                 350

Glu Leu Gly Thr Val Phe Arg Ser Leu Gly Gln Asn Pro Thr Glu Ala
                            355                 360                 365

Glu Leu Gln Asp Met Ile Asn Glu Val Asp Ala Asp Gly Asp Gly Thr
                        370                 375                 380

Phe Asp Phe Pro Glu Phe Leu Thr Met Met Ala Arg Lys Met Asn Asp
        385                 390                 395                 400

Thr Asp Ser Glu Glu Glu Ile Arg Glu Ala Phe Arg Val Phe Asp Lys
                            405                 410                 415

Asp Gly Asn Gly Tyr Ile Gly Ala Ala Glu Leu Arg His Val Met Thr
                            420                 425                 430

Asp Leu Gly Glu Lys Leu Thr Asp Glu Glu Val Asp Glu Met Ile Arg
                            435                 440                 445

Val Ala Asp Ile Asp Gly Asp Gly Gln Val Asn Tyr Glu Glu Phe Val
                        450                 455                 460

Gln Met Met Thr Ala Lys
        465                 470

<210> SEQ ID NO 5
<211> LENGTH: 1386
<212> TYPE: DNA
<213> ORGANISM: Artificial Sequence
<220> FEATURE:
<223> OTHER INFORMATION: Synthetic Sequence

<400> SEQUENCE: 5
atgctgcaga acgagcttgc tcttaagttg gctggacttg atattaacaa gactggagga      60
ggttctcatc atcatcatca tcatggtatg gctagcatga ctggtggaca gcaaatgggt     120
cgggatctgt acgacgatga cgataaggat ctcgcaacaa tggtcgactc atcgcgacgt     180
aagtggaata gtggggtca cgcagtcaga gctataggtc ggctgagctc agcgaacaac      240
accgaaatga tgtacccagc ggatggtggt ctgcgtggtt acactcacat ggcgctgaaa     300
gttgatggcg gcggtcacct gtcctgttct tcgtgaccca cctaccgctc caaaaagact     360
gtcggcaaca ttaagatgcc tgccattcat tacgtcagcc accgtctgga gcgcctggag     420
gagagcgata cgaaatgtt tgtcgtacag cgtgaacacg cagttgccaa gtttgtgggc      480
ctgggtggtg gcggcggtac cggagggagc atgaactccc tgatcaagga gaacatgcgt     540
atgaaagtgg ttctggaagg ctccgtaaac ggccaccagt tcaaatgcac tggtgaaggc     600
gaaggcaacc cgtatatggg cacccagact atgcgtatca aagtgatcga gggtggtccg     660
```

```
ctgccgtttg cgttcgacat cctggcgacg tcctttatgt atggctcccg taccttcatc      720
aaatatccga aaggcatccc ggatttcttt aagcagtcct tcccggaagg ttttacctgg      780
gaacgtgtga cccgttacga agacggcggc gtaattaccg ttatgcaaga cacgtctctg      840
gaggatggct gcctggtgta tcacgtgcag gttcgcggtg tgaacttccc gagcaatggt      900
gctgtaatgc aaaagaaaac caaaggttgg gagcctacgg actcccaact gactgaagag      960
cagatcgcag aatttaaaga ggctttctcc ctatttgaca aggacgggga tgggacaata     1020
acaaccaagg agatggggac ggtgatgcgg tctctggggc agaaccccac agaagcagag     1080
ctgcaggaca tgatcaatga agtagatgcc gacggtgacg gcacaatcga cttccctgag     1140
ttcctgatta tgatggcagg caaaatgaaa tacacagaca gtgaagaaga aattagagaa     1200
gcgttcggcg tgtttgataa ggatggcaat ggctacatca gtgcagcaga gcttcgccac     1260
gtgatgacaa accttggaga gaagttaaca gatgaagagt tgatgaaat gatcagggaa      1320 gcagacagcg atggggatgg tcaggtaaac tacgaagagt ttgtacaaat gatgacagcg     1380
aagtag                                                               1386
```

<210> SEQ ID NO 6
<211> LENGTH: 461
<212> TYPE: PRT
<213> ORGANISM: Artificial Sequence
<220> FEATURE:
<223> OTHER INFORMATION: Synthetic Sequence

<400> SEQUENCE: 6

```
Met Leu Gln Asn Glu Leu Ala Leu Lys Leu Ala Gly Leu Asp Ile Asn
1               5                   10                  15

Lys Thr Gly Gly Gly Ser His His His His His Gly Met Ala Ser
            20                  25                  30

Met Thr Gly Gly Gln Gln Met Gly Arg Asp Leu Tyr Asp Asp Asp
        35                  40                  45

Lys Asp Leu Ala Thr Met Val Asp Ser Ser Arg Lys Trp Asn Lys
50                  55                  60

Trp Gly His Ala Val Arg Ala Ile Gly Arg Leu Ser Ser Ala Asn Asn
65                  70                  75                  80

Thr Glu Met Met Tyr Pro Ala Asp Gly Gly Leu Arg Gly Tyr Thr His
                85                  90                  95

Met Ala Leu Lys Val Asp Gly Gly His Leu Ser Cys Ser Phe Val
            100                 105                 110

Thr Thr Tyr Arg Ser Lys Lys Thr Val Gly Asn Ile Lys Met Pro Ala
        115                 120                 125

Ile His Tyr Val Ser His Arg Leu Glu Arg Leu Glu Glu Ser Asp Asn
    130                 135                 140

Glu Met Phe Val Val Gln Arg Glu His Ala Val Ala Lys Phe Val Gly
145                 150                 155                 160

Leu Gly Gly Gly Gly Thr Gly Gly Ser Met Asn Ser Leu Ile Lys
                165                 170                 175

Glu Asn Met Arg Met Lys Val Val Leu Glu Gly Ser Val Asn Gly His
            180                 185                 190

Gln Phe Lys Cys Thr Gly Glu Gly Glu Gly Asn Pro Tyr Met Gly Thr
        195                 200                 205

Gln Thr Met Arg Ile Lys Val Ile Glu Gly Gly Pro Leu Pro Phe Ala
    210                 215                 220

Phe Asp Ile Leu Ala Thr Ser Phe Met Tyr Gly Ser Arg Thr Phe Ile
```

```
                225                 230                 235                 240
        Lys Tyr Pro Lys Gly Ile Pro Asp Phe Phe Lys Gln Ser Phe Pro Glu
                        245                 250                 255

Gly Phe Thr Trp Glu Arg Val Thr Arg Tyr Glu Asp Gly Gly Val Ile
                        260                 265                 270

Thr Val Met Gln Asp Thr Ser Leu Glu Asp Gly Cys Leu Val Tyr His
                        275                 280                 285

Val Gln Val Arg Gly Val Asn Phe Pro Ser Asn Gly Ala Val Met Gln
                        290                 295                 300

Lys Lys Thr Lys Gly Trp Glu Pro Thr Asp Ser Gln Leu Thr Glu Glu
        305                 310                 315                 320

Gln Ile Ala Glu Phe Lys Glu Ala Phe Ser Leu Phe Asp Lys Asp Gly
                        325                 330                 335

Asp Gly Thr Ile Thr Thr Lys Glu Met Gly Thr Val Met Arg Ser Leu
                        340                 345                 350

Gly Gln Asn Pro Thr Glu Ala Glu Leu Gln Asp Met Ile Asn Glu Val
                        355                 360                 365

Asp Ala Asp Gly Asp Gly Thr Ile Asp Phe Pro Glu Phe Leu Ile Met
                        370                 375                 380

Met Ala Gly Lys Met Lys Tyr Thr Asp Ser Glu Glu Ile Arg Glu
        385                 390                 395                 400

Ala Phe Gly Val Phe Asp Lys Asp Gly Asn Gly Tyr Ile Ser Ala Ala
                        405                 410                 415

Glu Leu Arg His Val Met Thr Asn Leu Gly Glu Lys Leu Thr Asp Glu
                        420                 425                 430

Glu Val Asp Glu Met Ile Arg Glu Ala Asp Ser Asp Gly Asp Gly Gln
                        435                 440                 445

Val Asn Tyr Glu Glu Phe Val Gln Met Met Thr Ala Lys
                450                 455                 460

<210> SEQ ID NO 7
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 7

Asn Glu Leu Ala Leu Lys Leu Ala Gly Leu Asp Ile Asn Lys Thr
1               5                   10                  15

<210> SEQ ID NO 8
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 8

Met Leu Gln Asn Glu Leu Ala Leu Lys Leu Ala Gly Leu Asp Ile Asn
1               5                   10                  15

Lys Thr Gly

<210> SEQ ID NO 9
<211> LENGTH: 14
<212> TYPE: DNA
<213> ORGANISM: Artificial Sequence
<220> FEATURE:
<223> OTHER INFORMATION: Synthetic Sequence
```

-continued

```
<400> SEQUENCE: 9
ggshhhhhhg masm                                           14
```

RED GENETICALLY ENCODED CALCIUM INDICATORS AND METHODS OF USE

RELATED APPLICATIONS

This application is a division of U.S. patent application Ser. No. 14/974,483 filed on Dec. 18, 2015, which claims priority from U.S. patent application Ser. Nos. 14/941,406 filed Nov. 13, 2015 and 62/096,214 filed Dec. 23, 2014, the entire disclosures of which are incorporated herein by this reference.

TECHNICAL FIELD

The presently-disclosed subject matter relates to protein indicators useful for calcium imaging. In particular, the presently-disclosed subject matter relates to red genetically-encoded calcium indicators (GECIs) and their methods of use.

INTRODUCTION

Calcium is a universal second messenger regulating essential cellular signaling events in a broad range of cells, tissues and organisms. In neurons, action potentials (APs) trigger large and rapid changes in cytoplasmic free calcium. Similarly, activation of synaptic glutamate receptors during excitatory synaptic transmission produces $Ca^{2+}$ accumulations in dendritic spines. Imaging neural activity is a widely-used method for in vivo neurophysiology, and calcium imaging using synthetic calcium indicators has been used to measure neuronal spiking and synaptic input across populations of neurons in vitro and in vivo. However, synthetic indicators are difficult to target to specific cell types or sub-cellular locations, and the loading procedures are invasive and damaging to neural tissue, precluding repeated, chronic in vivo measurements.

Genetically-encoded calcium indicators (GECIs) enable non-invasive measurement of neuronal activity in vivo. Activity can be tracked across multiple spatial scales, from synapses to populations of thousands of neurons. Neuronal dynamics can be probed over times of milliseconds to months. Green fluorescent protein (GFP)-based GECIs, such as GCaMP6, are widely used for imaging neural activity. GCaMP6 indicators exhibit excellent signal-to-noise ratio, allowing detection of single action potentials (APs) in favorable situations.

However, applications of GCaMPs and other widely used GECIs are limited by their excitation and emission spectra. GCaMPs are difficult to use in transgenic animals that already express GFP. The blue excitation light used in standard wide-field microscopy can cause photodamage and is highly scattered in tissue. The green GCaMP emission is strongly absorbed by blood, which reduces the penetration depth of imaging in vertebrates in vivo. In addition, the GCaMP excitation spectra overlap with those of light-sensitive ion channels, including channelrhodopsin-2 (ChR2), which complicates the simultaneous use of green GECIs and optogenetics.

Compared to GFP-based GECIs, GECIs with red-shifted excitation and emission spectra are expected to have advantages for in vivo imaging because of reduced absorption and scattering in tissue. Red-shifted GECIs thus promise three main advantages over GFP-based sensors: increasing the maximal imaging depth, parallel use of a red GECI with light-sensitive ion channels for all-optical electrophysiology experiments, and reduced photodamage. In addition, together with existing green GECIs, red GECIs allow simultaneous imaging of multiple components of neuronal circuitry. However, current red GECIs are inferior to the state-of-the-art GFP-based GCaMP6 indicators for detecting and quantifying neural activity.

Current red GECIs share overall architecture with the GCaMP proteins sensors. They are based on circularly permuted red fluorescent proteins (RFPs), a calcium-binding protein (calmodulin or troponin C) and a binding peptide (M13 or ckkap), fused to one or more (e.g., one, two, three, four, or more) fluorescent proteins (FPs). In single-FP GECIs, the fluorescence intensity of a circularly permuted FP (cpFP) is modulated by calcium binding-dependent changes in the chromophore environment. In two-FP GECIs and multiple-FP GECIs, calcium binding modulates fluorescence resonance energy transfer (FRET) between FPs. RCaMP1 contains mRuby, whereas R-GECO and R-CaMP2 contain mApple. R-GECO is more sensitive than RCaMP1. However, mApple-based GECIs, such as R-GECO and R-CaMP2, exhibit photoswitching when illuminated with blue light, leading to a transient increase of emitted red fluorescence, complicating their use in optogenetic experiments.

While there have been some recent developments with GECIs, the properties of all available GECIs have need for improvement in terms of sensitivity, stability, signal-to-noise ratio (SNR), response linearity, photostability, and properly tuned calcium affinity. Moreover, there is a need in the art for the improved the performance of red GECIs to provide sensitivity comparable to GFP-based GCaMP6 indicators for detecting and quantifying neural activity.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

Reported herein are improved GECIs ("jRCaMP1" and "jRGECO1"). As disclosed herein, jRCaMP1 and jRGECO1 variants have improved sensitivity and/or kinetics as compared to previous variants. Further, certain variants disclosed herein show significantly faster rise and decay kinetics to AP-evoked calcium transients. Thus, the variants disclosed herein are better able to resolve and quantitate trains of APs and to precisely measure the times of APs.

Hence, the presently disclosed subject matter includes nucleic acid molecules comprising a sequence that encodes a genetically encoded calcium indicator (GECI) polypeptide. In some instances, the sequence has at least 95%, or at least 99% sequence identity to SEQ ID NO: 2, SEQ ID NO: 4, or SEQ ID NO: 6. In some embodiments, the nucleic acid molecule, comprising a sequence that encodes a GECI polypeptide consisting of the amino acid sequence of SEQ ID NO: 2, SEQ ID NO: 4 or SEQ ID NO: 6. In some embodiments, a vector or cell includes the nucleic acid molecule, and in some embodiments, a cell comprising a vector that includes the nucleic acid molecule are provided.

In some embodiments, the nucleic acid molecule that encodes a GECI polypeptide comprises the sequence of SEQ ID NO: 1, SEQ ID NO: 3 or SEQ ID NO: 5. In some embodiments, a vector comprising the nucleic acid molecule is provided.

Also provided herein are polypeptides comprising a GECI polypeptide sequence. In some instances, the sequence has at least 95%, or at least 99% sequence identity to SEQ ID NO: 2, SEQ ID NO: 4 or SEQ ID NO: 6. In some embodiments, the polypeptide comprises the sequence of SEQ ID NO:2, SEQ ID NO:4, or SEQ ID NO:6. In some embodiments, a cell comprises the GECI polypeptide sequence.

The presently-disclosed subject matter also includes methods of monitoring the activity of a cell, which includes stimulating a cell with a GECI polypeptide sequence and detecting fluorescence emitted by the cell. The monitoring of the cell can be from a biological sample from a subject. In some embodiments, the monitoring is performed in vivo. In some instances, the subject is a mouse, a fish, a worm or a fly. In some instances, the subject is a mouse and the cell activity being monitored is in the primary visual cortex.

In some embodiments, the cell is a neuronal cell, a muscle cell or a cardiomyocyte. In some embodiments, the cell is a motor neuron that extends its terminal to form part of the neuro-muscular junction (NMJ), a trigeminal neuron, or an ASH neuron.

Detecting the fluorescence emitted by the cell can be performed by imaging. In some instances, the imaging is deep-tissue imaging. The imaging can, for example, also be dual-color imaging, or calcium imaging coupled with optogenetic stimulation of neuronal activity.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

FIGS. 16A-C include imaging data showing the complex spectral and functional characteristics of jRGECO1a after long-term expression in vivo. (a) L4 neurons excited by 1040 nm light and detected by the red channel (600/60 nm filter); (b) Same field of view as in (a) excited by 900 nm light. Note the punctate fluorescence image in the red detection channel (right), and the existence of fluorescence signal in the green detection channel (left, 525/50 nm filter); and (c) Scatter plot of the ratio between somatic signal detected at 900 nm excitation (red and green channel summed) and baseline fluorescence detected at 1040 nm excitation, and the peak somatic $\Delta F/F0$ for drifting grating stimuli. Red solid line shows the linear regression model, red dashed lines are 95% confidence interval; $R2=0.094$, F test, $p=0.002$).

FIGS. 18A-K includes data showing the imaging of activity in Drosophila larval NMJ boutons with jRCaMP1 constructs (a) Schematic of experimental setup. Epifluorescence and high magnification $\Delta F/F_0$ images of Type 1b boutons (green arrowheads) from muscle 13 (segments A3-A5), with image segmentation ROIs superimposed (Methods); (b) Single trial and averaged fluorescence transients after 1 Hz stimulus for 2 s for R-GECO1, jRCaMP1a and jRCaMP1b (RCaMP1h: 10 FOVs in 7 flies, 40 boutons; jRCaMP1a: 11 FOVs in 7 flies, 44 boutons; jRCaMP1b: 13 FOVs in 7 flies, 52 boutons. Same data set used for all other analyses); (c-d), $\Delta F/F_0$ (c) and SNR (d) traces (mean±s.e.m.) recorded with 1, 5, 10, 20, 40, 80 and 160 Hz stimulation for 2s (shown by red curves at the bottom, amplitude not to scale); (e-f), $\Delta F/F_0$ (e) and SNR (f) traces (mean±s.e.m.) recorded with 1 and 5 Hz stimulation for 2s (shown by red curves at the bottom, amplitude not to scale); (g-h), Comparison of $\Delta F/F_0$ traces (mean±s.e.m.) of R-GECO1 and jRCaMP1 variants with 1, 5, 10 Hz (g) and 20, 40, 80 Hz (h) stimulation for 2s (shown by red curves at the bottom, amplitude not to scale); (i-j), Comparison of frequency tuned averaged peak $\Delta F/F_0$ (i) and peak SNR (j) (mean±s.e.m.) of RCaMP1h and jRCaMP1 variants, with 1, 5, 10, 20, 40, 80 and 160 Hz stimulation. Note that vertical axes are log scale; and (k) Comparison of kinetics of RCaMP1h and jRCaMP1 variants with 40 Hz stimulation. Horizontal axes are half rise time and vertical axes are half decay time.

BRIEF DESCRIPTION OF THE SEQUENCE LISTING

Figure 1A:
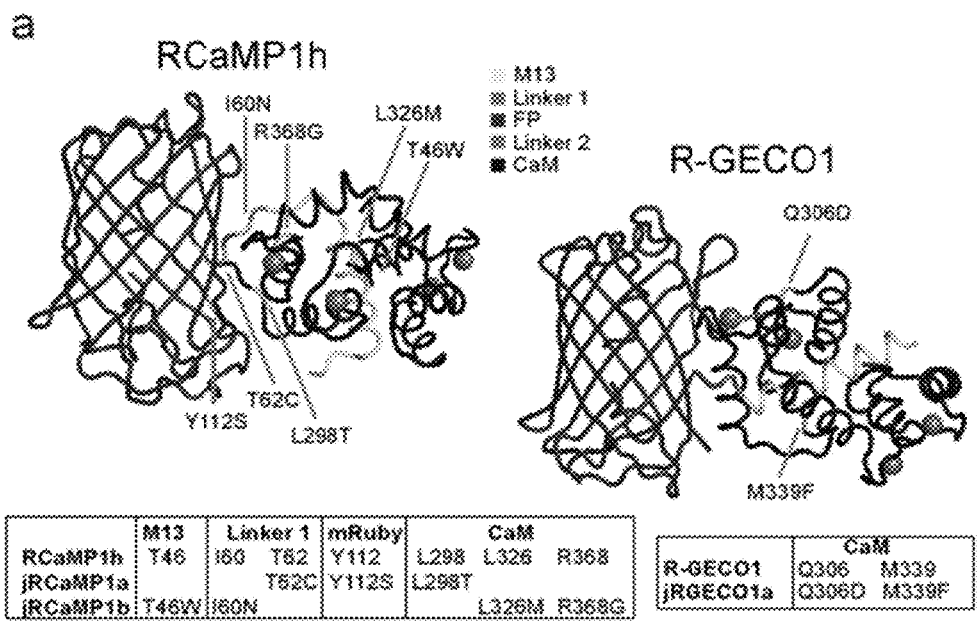
FIGS. 1A-D include data from the mutagenesis of RCaMP1h and R-GECO1 and screening to produce jRCaMP1 and jRGECO1 in dissociated neurons. (a), RCaMP1h and R-GECO1 structure and mutations introduced in jRCaMP1a, jRCaMP1b, and jRGECO1a. M13 peptide (yellow), linker 1 (gray), cpmRuby or cpmApple (red), linker 2 (gray), CaM (blue). Mutations positions for jRCaMP1a (green), jRCaMP1b (cyan), jRGECO1a (green). (b) Schematic of the cultured neuron assay. Field electrodes (gray, upper panel) stimulate cultured neurons expressing a cytosolic red GECI variant and nuclear GFP. Changes in fluorescence are recorded using a microscope and camera (lower panel) and analyzed. An example response trace of a jRGECO1a-expressing neuron after 3 action potential (AP) stimulus is shown. (c) Screening results for 855 R-GECO1 variants. Top, fluorescence changes in response to 1 action potential (vertical bars, $\Delta F/F_0$ amplitudes; black bars, single R-GECO1 mutations and combinatorial mutations; red bars, R-CaMP2 left, jRGECO1a right). Middle, significance value for different AP stimuli (color plot). Bottom, half decay times after 10 APs. Black line indicates R-GECO1 performance levels. (d) Screening results for 1070 RCaMP1h variants. Top, fluorescence changes in response to 1 AP (same order as in b; red bars, R-CaMP2 left, jRCaMP1a and jRCaMP1b right). Middle, significance value for different AP stimuli (color plot). Bottom, half decay times after 10 APs. Black line indicates RCaMP1h performance levels.

SEQ ID NO: 1 is a nucleotide sequence encoding the NES-jRCaMP1a polypeptide of SEQ ID NO: 2.

SEQ ID NO: 2 is an amino acid sequence encoding NES-jRCaMP1a polypeptide.

SEQ ID NO: 3 is a nucleotide sequence encoding the NES-jRGECO1a polypeptide of SEQ ID NO: 4.

SEQ ID NO: 4 is an amino acid sequence encoding the NES-jRGECO1a polypeptide.

SEQ ID NO: 5 is a nucleotide sequence encoding the NES-jRCaMP1b polypeptide of SEQ ID NO: 6.

SEQ ID NO: 6 is an amino acid sequence encoding NES-jRCaMP1b polypeptide.

SEQ ID NO: 7 is an amino acid sequence from Binary expression vector NES-YC3.6 encoding a nuclear export sequence contained in SEQ ID NO: 2, SEQ ID NO: 4, and SEQ ID NO: 6.

SEQ ID NO: 8 is an amino acid export sequence derived from the cAMP-dependent protein kinase inhibitor alpha subunit.

SEQ ID NO: 9 is the first 14 amino acid sequence positions in the numbering of jRGECO1 and jRCaMP1 variants.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter is illustrated by specific but non-limiting examples throughout this description. The examples may include compilations of data that are representative of data gathered at various times during the course of development and experimentation related to the present invention(s). Each example is provided by way of explanation of the present disclosure and is not a limitation thereon. In fact, it will be apparent to those skilled in the art that various modifications and variations can be made to the teachings of the present disclosure without departing from the scope of the disclosure. For instance, features illustrated or described as part of one embodiment can be used with another embodiment to yield a still further embodiment.

All references to singular characteristics or limitations of the present disclosure shall include the corresponding plural characteristic(s) or limitation(s) and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The presently-disclosed subject matter includes genetically-encoded calcium indicators (GECIs) (also called fluorescent calcium indicator proteins; FCIPs) that provide an alternative to synthetic indicators. The GECIs reported herein can be easily targeted to specific cell types or sub-cellular compartments, and are compatible with long-term, repeated in vivo measurements.

Provided herein are nucleic acid sequences encoding genetically encoded calcium indicators (GECIs) such as those within the families designated jRCaMP1 and jRGECO1, which include the NES-jRCaMP1a, NES-jRCaMP1b and NES-jRGECO1a, which include protein-protein fusions of nuclear export signals with each sensor. NES-jRCaMP1a, NES-jRCaMP1b and NES-jRGECO1a are also referred to herein as jRCaMP1a, jRCaMP1b and jRGECO1a and are members of the jRCaMP1 and jRGECO1 families.

In some embodiments, the encoded jRCaMP1 or jRGECO1 polypeptide comprises the amino acid sequence shown in SEQ ID NO: 2, SEQ ID NO: 4 or SEQ ID NO: 6, optionally with one or more conservative amino acid substitutions (e.g., with one, two, three, four, five, six, seven, eight, nine, ten, fifteen, twenty, or a range between any two of the aforementioned numbers, or more than twenty conservative amino acid substitutions, so long as the desired function of the peptide is maintained (e.g., substantially maintained). In some embodiments, the number of amino acid substitutions in SEQ ID NO: 2, SEQ ID NO: 4 or SEQ ID NO: 6 is expressed as a percentage of the total number of amino acids present. For example, about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 2.0%, 2.5%, 3.0%, 3.5% 4.0%, 4.5%, 5.0%, 5.5%, 6.0%, 6.5%, 7%, 7.5%, 8.0%, 8.5%, 9.0%, 9.5%, 10.0%, 15%, 20%, 25%, 30%, 40%, 50%, or a range between any two of the aforementioned numbers, of the amino acids present in SEQ ID NO: 2, SEQ ID NO: 4 or SEQ ID NO: 6 can be substituted with a conservative amino acid(s), so long as the desired function of the peptide is maintained (e.g., substantially maintained). For example, in some instances, the nucleic acid sequence can comprise SEQ ID NO: 1, SEQ ID NO: 3 or SEQ ID NO: 5. In some embodiments, the nucleic acid sequence can consist or consist essentially of SEQ ID NO: 1, SEQ ID NO: 3 or SEQ ID NO: 5.

Also provided are jRCaMP1 or jRGECO1 polypeptides. For example, a jRCaMP1 or jRGECO1 polypeptide can have a sequence that comprises SEQ ID NO: 2, SEQ ID NO: 4 or SEQ ID NO: 6, optionally with one or more conservative amino acid substitutions (e.g., with one, two, three, four, five, six, seven, eight, nine, ten, fifteen, twenty, or a range between any two of the aforementioned numbers, or more than twenty conservative amino acid substitutions, so long as the desired function of the peptide is maintained (e.g., substantially maintained). In some embodiments, the number of amino acid substitutions in SEQ ID NO: 2, SEQ ID NO: 4 or SEQ ID NO: 6 is expressed as a percentage of the total number of amino acids present. For example, about 0.5%, 1.0%, 1.5%, 2.0%, 2.5%, 3.0%, 3.5%, 4.0%, 4.5%, 5.0%, 5.5%, 6.0%, 6.5%, 7%, 7.5%, 8.0%, 8.5%, 9.0%, 9.5%, 10.0%, 15%, 20%, 25%, or 30% (or a range between any of the aforementioned numbers) of the amino acids present in SEQ ID NO: 2, SEQ ID NO: 4 or SEQ ID NO: 6 can be substituted with a conservative amino acid(s), so long as the desired function of the peptide is maintained (e.g., substantially maintained)). In addition to a substitution, an insertion or a deletion can be introduced into a jRCaMP1 or jRGECO1 polypeptide. Insertions include the introduction of single or multiple amino acid residues, while deletions are characterized by the removal of one or more amino acid residues. Methods for predicting tolerance to protein modification are known in the art (see, e.g., Guo et al., 2004, PNAS USA, 101(25):9205-9210).

Nucleic acids that encode the polypeptide sequences, variants, and fragments thereof are disclosed. These sequences include all degenerate sequences related to the specific polypeptide sequence, i.e., all nucleic acids having a sequence that encodes one particular polypeptide sequence as well as all nucleic acids, including degenerate nucleic acids, encoding the disclosed variants and derivatives of the polypeptide sequences. Thus, while each particular nucleic acid sequence may not be written out herein, it is understood that each and every nucleic acid sequence is in fact disclosed and described herein through the disclosed polypeptide sequences.

A GECI polypeptide provided herein, or a nucleic acid encoding such a GECI polypeptide, also provided herein, can have at least 70% sequence identity (e.g., at least 71%, 72%, 73%, or 74% sequence identity), at least 75% sequence identity (e.g., at least 76%, 77%, 78%, or 79% sequence identity), at least 80% sequence identity (e.g., at least 81%, 82%, 83%, or 84% sequence identity), at least 85% sequence identity (e.g., at least 86%, 87%, 88%, or 89% sequence identity), at least 90% sequence identity (e.g., at least 91%, 92%, 93%, or 94% sequence identity), at least 95% sequence identity (e.g., at least 96%, 97%, 98%, or 99% sequence identity) to a GECI polypeptide disclosed herein (e.g., SEQ ID NO: 2 or SEQ ID NO: 4) or a nucleic acid disclosed herein that encodes for a GECI polypeptide (e.g., SEQ ID NO: 1 or SEQ ID NO: 3).

A nucleic acid or polypeptide sequence can be compared to another sequence and described in terms of its percent sequence identity. In calculating percent sequence identity, two sequences are aligned and the number of identical matches of nucleotides or amino acid residues between the two sequences is determined The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It will be appreciated that a single sequence can align differently with other sequences and hence, can have different percent sequence identity values over each aligned region. It is noted that the percent identity value is usually rounded to the nearest integer.

The alignment of two or more sequences to determine percent sequence identity is performed using the algorithm described by Altschul et al. (1997, Nucleic Acids Res., 25:3389-3402) as incorporated into BLAST (basic local alignment search tool) programs, available at ncbi.nlm.nih.gov on the World Wide Web. BLAST searches can be performed to determine percent sequence identity between a first nucleic acid and any other sequence or portion thereof aligned using the Altschul et al. algorithm. BLASTN is the program used to align and compare the identity between nucleic acid sequences, while BLASTP is the program used to align and compare the identity between amino acid sequences. When utilizing BLAST programs to calculate the percent identity between a sequence disclosed herein (e.g., SEQ ID NOs: 1-4) and another sequence, the default parameters of the respective programs are used.

Table 1: Conservative Add Substitutions

TABLE 1

Conservative Acid Substitutions

| Amino Acid | Representative Conservative Amino Acids |
|---|---|
| Ala | Ser, Gly, Cys |
| Arg | Lys, Gln, His |
| Asn | Gln, His, Glu, Asp |
| Asp | Glu, Asn, Gln |
| Cys | Ser, Met, Thr |
| Gln | Asn, Lys, Glu, Asp, Arg |
| Glu | Asp, Asn, Gln |
| Gly | Pro, Ala, Ser |
| His | Asn, Gln, Lys |
| Ile | Leu, Val, Met, Ala |
| Leu | Ile, Val, Met, Ala |
| Lys | Arg, Gln, His |
| Met | Leu, Ile, Val, Ala, Phe |
| Phe | Met, Leu, Tyr, Trp, His |
| Ser | Thr, Cys, Ala |
| Thr | Ser, Val, Ala |
| Trp | Tyr, Phe |
| Tyr | Trp, Phe, His |
| Val | Ile, Leu, Met, Ala, Thr |

Modifications, including substitutions, insertions or deletions are made by known methods. By way of example, modifications are made by site-specific mutagenesis of nucleotides in the DNA encoding the protein, thereby producing DNA encoding the modification, and thereafter expressing the DNA in recombinant cell culture. Techniques for making substitution mutations at predetermined sites in DNA having a known sequence are well known, for example M13 primer mutagenesis and PCR mutagenesis.

Also provided are vectors that include the GECI-encoding nucleic acid sequences disclosed herein. Typically, the GECI-encoding nucleic acid sequences comprise SEQ ID NO: 1 SEQ ID NO: 3 or SEQ ID NO: 5, and sequences with identity thereto, as noted above. Similarly, the GECI polypeptide typically comprises SEQ ID NO: 2, SEQ ID NO: 4 or SEQ ID NO: 6 and sequences with identity thereto, as noted above. Examples of suitable vectors include, but are not limited to, plasmids, artificial chromosomes such as BACs, YACs, or PACs, and any of a number of viral vectors (e.g., retroviral vectors, replication-defective adenoviruses).

Vectors typically contain an origin of replication and one or more regulatory regions. Regulatory regions include, without limitation, promoters, enhancers, inducible elements, protein binding sequences, 5' or 3' untranslated regions (UTRs), transcriptional start sites, termination sequences, and poly-adenylation sequences.

Promoters may be obtained from various sources including, for example, viruses such as polyoma, Simian Virus 40 (SV40), adenovirus, retroviruses, hepatitis B virus, and cytomegalovirus (CMV), or promoters from mammalian cells, e.g. beta-actin promoter or EF1-alpha promoter. In addition, promoters native to the host cell also are useful herein.

Enhancers refer generally to nucleic acid sequences that affect transcription of a sequence. Enhances typically are able to act at a distance from the transcribed sequence, be 5' or 3' to, or within an intron of, the transcribed sequence, and/or can be in cis orientation to the transcribed sequence. Many enhancer sequences are known from mammalian genes (globin, elastase, albumin, fetoprotein, and insulin), as well as from viruses (e.g., the SV40 enhancer on the late side of the replication origin, the cytomegalovirus early promoter enhancer, the polyoma enhancer on the late side of the replication origin, and adenovirus enhancers).

A promoter and/or an enhancer can be inducible (e.g. chemically or physically regulated). A chemically-induced promoter and/or enhancer can be regulated by the presence of, for example, alcohol, tetracycline, a steroid, or a metal. A physically-induced promoter and/or enhancer can be regulated by, for example, environmental factors such as temperature or light. On the other hand, a promoter and/or enhancer can be constitutive. In addition, certain promoters and/or enhancers can be active in a cell type-specific manner.

Vectors also can include a selectable marker. A selectable marker typically confers a phenotype on a cell and allows the cell to survive when placed under selective pressure. The product of the selectable marker can be used to confirm that the vector has been delivered to the cell and is being expressed. Examples of selectable markers include, without limitation, dihydrofolate reductase (DHFR), thymidine kinase, neomycin, neomycin analog G418, hygromycin, puromycin, blasticidin, beta-galactosidase, beta-glucuronidase, green fluorescent protein (GFP), and luciferase.

In addition, a vector can include a sequence encoding a tag, which is designed to facilitate manipulation or detection (e.g., purification or localization) of the expressed polypeptide. Sequences encoding tags such as GFP, glutathione S-transferase (GST), polyhistidine, c-myc, hemagglutinin, or FLAG™ tag (Kodak; New Haven, Conn.) typically are expressed as a fusion with the encoded polypeptide (e.g., at either the carboxyl or amino terminus or within the polypeptide).

Cells containing the GECIs, the GECI-encoding nucleic acid sequences or vectors containing the GECI-encoding nucleic acid sequence are provided. The cell can be, for example, a eukaryotic or prokaryotic cell. Suitable cells include, but are not limited to cells of *E. coli, Pseudomonas, Bacillus, Streptomyces*; fungi cells such as yeasts (*Saccharomyces*, and methylotrophic yeast such as *Pichia, Candida, Hansenula*, and *Torulopsis*); and animal cells, such as CHO, R1.1, B-W and LM cells, African Green Monkey kidney cells (for example, COS 1, COS 7, BSC1, BSC40, and BMT10), and insect cells (for example, Sf9). Suitable cells also include, but are not limited to, human cells and plant cells. Representative human cells include, for example, HeLa cells or human embryonic kidney (HEK) cells. Cells that can be used herein are commercially available from, for example, the American Type Culture Collection (ATCC; PO Box 1549, Manassas, Va. 20108). See also Ausubel et al., 1998, Current Protocols in Molecular Biology, John Wiley & Sons, New York, N.Y. In some instances, the GECI-encoding nucleic acid sequence can be located in the genome of the cell. Cells can also include primary neurons isolated from mouse or rat tissue. Cells can also include neurons in mouse, rats, the nematode worm *Caenorhabditis elegans*, or the zebrafish *Danio rerio*.

Methods of introducing nucleic acids into cells are known and the method of transformation and choice of expression vector will depend on the host system selected. Transformation and transfection methods are described, e.g., in Ausubel et al. (1998, Current Protocols in Molecular Biology, John Wiley & Sons, New York, N.Y., (1998)), and, as described above, expression vectors may be chosen from examples known in the art. There are a number of compositions and methods which can be used to deliver the nucleic acid molecules and subsequently encoded polypeptides to cells, either in vitro or in vivo. These methods and compositions can largely be broken down into two classes: viral-based delivery systems and non-viral-based delivery systems. Such delivery systems are well known in the art and are readily adaptable for use with the compositions and methods described herein.

Simply by way of example, polypeptides and/or nucleic acid molecules can be delivered via virus-like particles. Virus-like particles (VLPs) consist of viral protein(s) derived from the structural proteins of a virus. Methods for making and using virus-like particles are described in, for example, Garcea and Gissmann (2004, Current Opinion in Biotechnology, 15:513-7). Polypeptides also can be delivered by subviral dense bodies (DBs). DBs transport proteins into target cells by membrane fusion. Methods for making and using DBs are described in, for example, Pepperl-Klindworth et al. (2003, Gene Therapy, 10:278-84). In addition, polypeptides can be delivered by tegument aggregates. Methods for making and using tegument aggregates are described in WO 2006/110728.

Also provided are transgenic animals that include a GECI-encoding nucleic acid sequences described herein. "Animal" refers to non-human animals, including, mammals, amphibians and birds. Specifically, examples include sheep, feline, bovines, ovines, pigs, horses, rabbits, guinea pigs, mice, hamsters, rats, non-human primates, and the like. As used herein, transgenic animal refers to any animal in which one or more of the cells of the animal contain a heterologous nucleic acid. Methods for making transgenic animals have been described, for example, in Wagner et al. (1981, PNAS USA, 78:5016-5020); Stewart et al. (1982, Science, 217:1046-1048); Constantini et al. (1981, Nature, 294:92-94); Lacy et al. (1983, Cell, 34:343-358); McKnight et al. (1983, Cell, 34:335-341); Brinstar et al. (1983, Nature, 306:332-336); Palmiter et al. (1982, Nature, 300:611-615); Palmiter et al. (1982, Cell, 29:701-710); and Palmiter et al. (1983, Science, 222:809-814). Methods for making transgenic animals also are described in U.S. Pat. Nos. 6,175,057; 6,180,849; and 6,133,502.

One or more of the nucleic acid sequences, polypeptides, vectors or cells described herein, or combinations thereof, can be packaged into an article of manufacture (i.e., a kit) using containers, vials, or the like. For example, an article of manufacture can include (i) a nucleic acid sequence encoding a GECI, wherein the GECI has a sequence shown in SEQ ID NO: 2 or SEQ ID NO: 4, or a variant of those sequences as discussed above; (ii) a GECI polypeptide having a sequence shown in SEQ ID NO: 2 or SEQ ID NO: 4, or a variant of those sequences as discussed above; (iii) a vector comprising (i); (iv) a cell comprising (i); (v) a cell comprising (iii); or (vi) a cell comprising (ii). An article of manufacture as described herein can include any combination of (i)-(vi).

In addition, an article of manufacture as described herein can include one or more reagents, buffers, culture medium, or neuronal or other type of cell. An article of manufacture also can include instructions for use.

The nucleic acid and polypeptide compositions described above, including, for example, vectors and cells containing such vectors, can be used in methods of deep tissue imaging, dual-color imaging, and parallel use with light-sensitive ion channels (e.g. channelrhodopsin-2, ChR2). The indicators disclosed herein can be used for in vivo imaging of neuronal activity. Other uses include those described in U.S. Patent Application Publication No. 2014/0101785, which is incorporated herein in its entirety by this reference.

Neuronal activity can be imaged by measuring fluorescence. Fluorescence is routinely determined in laboratories, and the level of fluorescence can be determined using any type of fluorometer. Fluorescence can be measured in many ways, including but not limited to, intensity, lifetime, polarization, fluorescence ratio, FRET, anisotropy, or second-harmonic generation. Fluorescence can be excited by 1-photon or multi-photon (e.g. 2- or 3-photon) processes.

Those skilled in the art understand that a determination of an increase or a decrease in fluorescence in the presence of an agent requires the use of an appropriate control. By way of example, one appropriate control can be measuring the level of fluorescence in a cell before and/or after a treatment (i.e., contact with an agent); another appropriate control can be measuring the level of fluorescence in the absence of a treatment (i.e., contact with an agent).

As used herein, an agent that can be screened in the methods described herein includes, for example, a polypeptide, an antibody (e.g., polyclonal or monoclonal; human or humanized) a small molecule, a nucleic acid molecule, a peptidomimetic, or any combination thereof. Nucleic acid molecules used in a method of screening as described herein can be, for example, an inhibitory nucleic acid molecule. Inhibitory nucleic acid molecules include, for example, a triplex forming oligonucleotide, an aptamer, a ribozyme, a short interfering RNA (siRNA), a micro-RNA (miRNA), or antisense nucleic acid. These types of inhibitory nucleic acid molecules are well known in the art and methods of designing them and making them also are well known in the art.

The nucleic acid and polypeptide compositions described above, including, for example, expression vectors and cells containing such expression vectors, can be used in methods of determining the calcium ion status of a cell. In addition, the nucleic acid and polypeptide compositions described above can be used in methods of monitoring neuronal activity. As discussed in more detail below, neuronal activity can be monitored in neuronal cells that are expressing a nucleic acid encoding a GECI polypeptide as described herein (e.g., a nucleic acid encoding a polypeptide having the sequence shown in SEQ ID NO: 2, SEQ ID NO: 4 or SEQ ID NO: 6), and detecting the fluorescence emitted by the cells. Neuronal activity can be natural (e.g. neurons in the brain of an animal that is behaving, or a brain slice exhibiting spontaneous activity), or can be elicited by a chemical stimulus, an electrical stimulus, or another type of stimulus. A chemical stimulus can include a drug or combination of drugs, a toxin, a neurotransmitter, or any other compound. An electrical stimulus can be delivered, for example, from an extracellular electrode, or from an intracellular electrode, a magnetic resonance imaging (MRI) device, or any other type of electrical stimulus.

The neuronal cells can be contacted with the stimulus in vitro (e.g., in cell culture) or in vivo (e.g., in an animal such as, without limitation, a mouse, a worm, a rat, or a fly). Neuronal activity is used herein as an example, but those skilled in the art would understand that the activity of other cells types can be examined. For example, the activity of muscle cells, cardiomyocytes, or astrocytes and other glial cells can be evaluated using the compositions and methods described herein. Other cell types that can be evaluated using the compositions and methods described herein include bacteria, single-cell pathogens, or cells in nematodes, insects, arachnids, and other animals.

In accordance with the present invention, there may be employed conventional molecular biology, microbiology, biochemical, and recombinant DNA techniques within the skill of the art. Such techniques are explained fully in the literature.

Unless defined otherwise, all technical and scientific terms used herein have the same meaning as is commonly understood by one of skill in the art to which the invention(s) belong. All patents, patent applications, published applications and publications, GenBank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

EXAMPLES

Presented herein are improved red GECIs based on mRuby (jRCaMP1a, b) and mApple (jRGECO1a), with sensitivity comparable to GCaMP6. Large-scale structure-guided mutagenesis and neuron-based screening was performed to develop improved red GECIs, starting with RCaMP1h and R-GECO1. mRuby-based jRCaMP1a and jRCaMP1b, and mApple-based jRGECO1a, all showed several-fold improved sensitivity for detecting neural activity compared to their parent scaffolds. The performance of the new red GECIs was characterized in cultured neurons and in mouse, *Drosophila*, zebrafish and *C. elegans* in vivo. As provided herein, red GECIs facilitate deep-tissue imaging, dual-color imaging when used together with GFP-based reagents, and optogenetics together with calcium imaging.

Protein Engineering

R-GECO1 and RCaMP1 are based on circularly permuted mApple and mRuby, respectively, in addition to calmodulin (CaM) and the CaM-interacting M13 peptide. In the presence of calcium, CaM and M13 form a complex proximal to the chromophore inside the RFP β-barrel. This conformational change modifies the chromophore environment, modulating solvent access, chromophore $pK_a$, and quantum yield and causing increased RFP brightness. Structure-guided mutagenesis and screening in a neuron-based assay have been successful in improving GCaMP sensitivity and kinetics. Here a similar approach was applied to red GECIs. Mutagenesis was focused on the interfaces between the RFP and CaM, between CaM and M13, and within CaM itself (78/442 and 87/451 amino acid positions were mutated in RCaMP1h and R-GECO1, respectively, see Tables 6-7) (FIG. 1a).

TABLE 2

Biophysical properties of purified jRGECO1 and jRCaMP1 sensors

| Sensor | Dynamic range ($F_{max}/F_{min}$) | $K_d$ (nM) | Hill coefficient | $pK_{a,\,apo}$ | $pK_{a,\,sat}$ | $\varepsilon_{apo}$ (×1000) ($M^{-1}cm^{-1}$) | $\varepsilon_{sat}$ (×1000) | $\Phi_{apo}$ | $\Phi_{sat}$ |
|---|---|---|---|---|---|---|---|---|---|
| R-GECO1  | 12.0 ± 0.4 | 337 ± 8    | 2.00 ± 0.04 | 8.7 | 6.4 | 5.34 | 54.9 | 0.13 | 0.21 |
| jRGECO1a | 11.6 ± 0.4 | 148 ± 2    | 1.90 ± 0.02 | 8.6 | 6.3 | 6.18 | 53.3 | 0.12 | 0.21 |
| RCaMP1h  | 12.6 ± 0.6 | 1127 ± 35  | 2.20 ± 0.06 | 7.1 | 5.7 | 20.8 | 63.6 | 0.13 | 0.54 |
| jRCaMP1a | 3.2 ± 0.1  | 214 ± 10   | 0.86 ± 0.01 | 5.6 | 6.4 | 33.8 | 54.1 | 0.31 | 0.59 |
| jRCaMP1b | 7.2 ± 0.1  | 712 ± 9    | 1.60 ± 0.01 | 6.4 | 5.5 | 25.3 | 53.4 | 0.15 | 0.54 |

TABLE 3 jRGECO1 performance in Drosophila larval NMJ

| mean dF/F0 | Stim. frequency | R-GECO1 | jRGECO1a | jRGECO1b | SEM | R-GECO1 | jRGECO1a | jRGECO1b |
|---|---|---|---|---|---|---|---|---|
| | 1   | 0.020 | 0.116 | 0.059 | 1   | 0.004 | 0.009 | 0.002 |
| | 5   | 0.044 | 0.462 | 0.228 | 5   | 0.004 | 0.053 | 0.015 |
| | 10  | 0.057 | 1.015 | 0.604 | 10  | 0.010 | 0.119 | 0.041 |
| | 20  | 0.103 | 1.802 | 1.625 | 20  | 0.018 | 0.145 | 0.146 |
| | 40  | 0.505 | 2.475 | 2.486 | 40  | 0.065 | 0.174 | 0.122 |
| | 80  | 1.164 | 2.549 | 2.516 | 80  | 0.068 | 0.176 | 0.098 |
| | 160 | 1.552 | 2.348 | 2.244 | 160 | 0.069 | 0.171 | 0.082 |
| Half rise time (s) | mean | R-GECO1 | jRGECO1a | jRGECO1b | SEM | R-GECO1 | jRGECO1a | jRGECO1b |
| | 1   | 0.128 | 0.133 | 0.128 | 1   | 0.016 | 0.001 | 0.004 |
| | 5   | 0.497 | 0.684 | 0.630 | 5   | 0.065 | 0.026 | 0.033 |
| | 10  | 0.393 | 0.819 | 0.878 | 10  | 0.041 | 0.015 | 0.041 |
| | 20  | 0.490 | 0.669 | 0.820 | 20  | 0.059 | 0.022 | 0.027 |
| | 40  | 0.637 | 0.479 | 0.621 | 40  | 0.030 | 0.017 | 0.019 |
| | 80  | 0.401 | 0.316 | 0.406 | 80  | 0.018 | 0.009 | 0.009 |
| | 160 | 0.254 | 0.220 | 0.282 | 160 | 0.009 | 0.007 | 0.006 |
| Half decay time (s) | mean | R-GECO1 | jRGECO1a | jRGECO1b | SEM | R-GECO1 | jRGECO1a | jRGECO1b |
| | 1   | 0.224 | 0.232 | 0.224 | 1   | 0.069 | 0.033 | 0.030 |
| | 5   | 0.331 | 0.518 | 0.418 | 5   | 0.062 | 0.028 | 0.018 |
| | 10  | 0.210 | 0.533 | 0.439 | 10  | 0.037 | 0.025 | 0.013 |
| | 20  | 0.153 | 0.560 | 0.497 | 20  | 0.016 | 0.019 | 0.014 |
| | 40  | 0.180 | 0.542 | 0.543 | 40  | 0.005 | 0.012 | 0.017 |
| | 80  | 0.177 | 0.446 | 0.543 | 80  | 0.005 | 0.012 | 0.012 |
| | 160 | 0.199 | 0.419 | 0.518 | 160 | 0.000 | 0.015 | 0.013 |

Figure 1B:
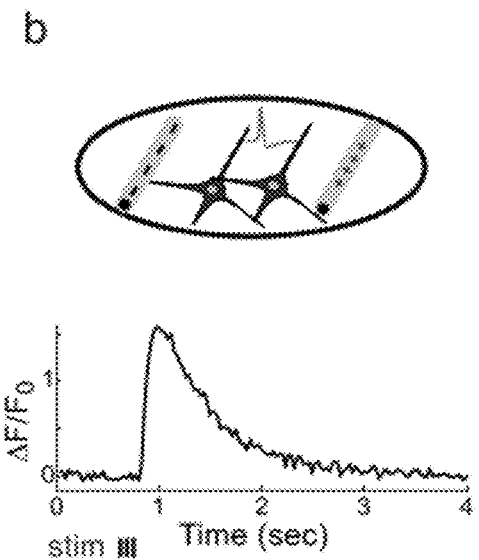
Figure 1C:
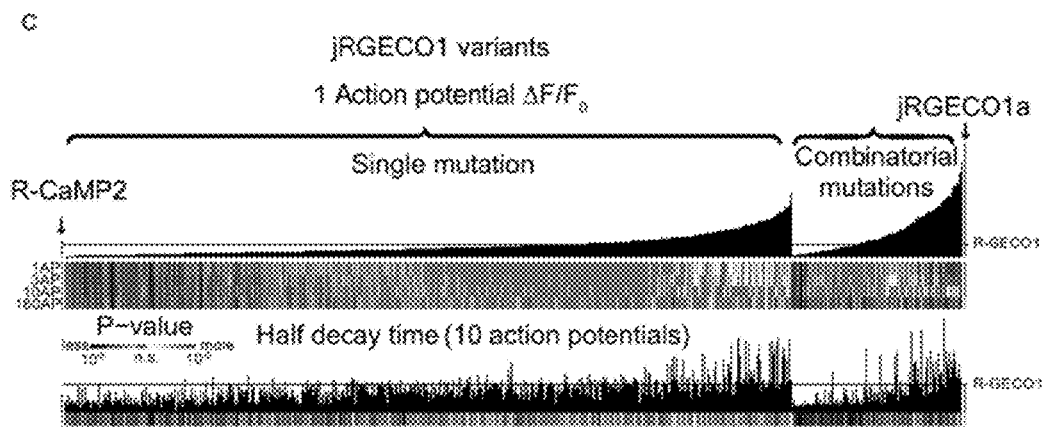
Figure 1D:
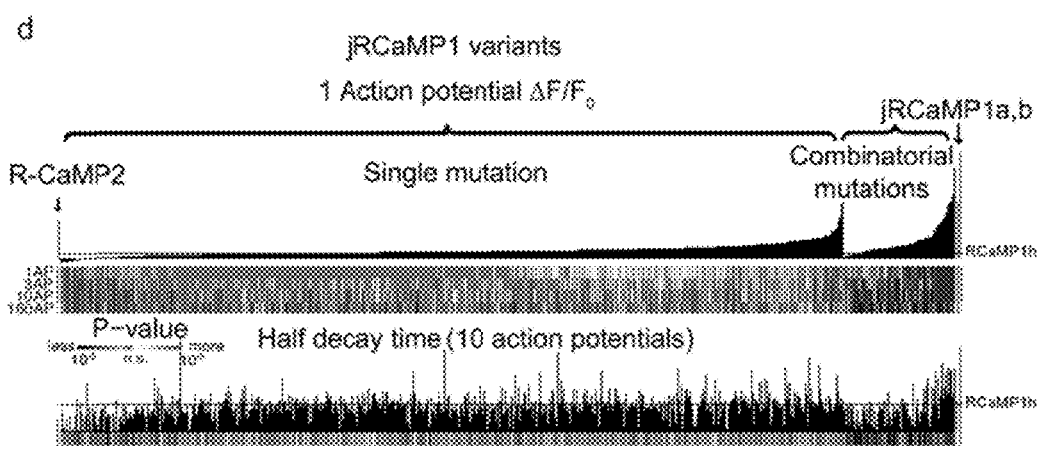

Single-mutation variants (934 RCaMP1h; 689 R-GECO1, Tables 6-7) were produced and tested in an automated neuronal assay (Wardill, Chen et al. 2013) (FIG. 1b-d). Dissociated rat hippocampal neurons in 96-well plates were transfected with plasmids expressing red GECI variants (RCaMP1h-variant or R-GECO1-variant). To normalize for expression level, the plasmid also expressed GFP that was localized to the nucleus. A field electrode triggered trains of action potentials (APs) in all neurons within each well (Methods, (Wardill, Chen et al. 2013)). Time-lapse images (800 μm×800 μm fields of view; 35 Hz) were acquired before, during and after stimulation. Fluorescence changes were extracted from single neurons to compute the sensitivity, dynamic range, and kinetics of the responses to various trains of APs. Individual red GECI variants were compared to the parent constructs and published GECIs, including R-CaMP2 (Inoue, Takeuchi et al. 2015), GCaMP6s, and GCaMP6f (Chen, Wardill et al. 2013).

Numerous single mutations (353/934 RCaMP1h; 187/689 R-GECO1, Tables 6-7) improved sensitivity compared to the parent proteins (higher $\Delta F/F_0$ amplitude in response to one AP; $P<0.01$, Wilcoxon rank sum test) (FIG. 1c, d). For example, T46W, I60N, and I60T exhibited enhanced sensitivity and accelerated kinetics compared to RCaMP1h. I109K had similar effects on R-GECO1. M339F accelerated kinetics but did not affect response amplitude of R-GECO1. Beneficial mutations were sorted based on improved response amplitudes (in response to trains of 1, 3, and 10 APs) and/or faster kinetics, without a significant reduction in the maximal fluorescence change elicited by 160 APs.

Mutations were combined in a second round of mutagenesis (136 RCaMP1h and 163 R-GECO1 variants) (FIG. 1c, d). Based on similar criteria outlined above, two new mRuby-based sensors, jRCaMP1a and jRCaMP1b, and one mApple-based sensor, jRGECO1a, were selected for in-depth analysis (red bars in the histograms of FIG. 1c, d). These sensors have similar absorption and emission spectra to each other and their parent constructs (FIG. 9) but they differ in sensitivity for detecting neural activity, kinetics, and other biophysical properties (FIGS. 2-3, FIGS. 5-6).

TABLE 4 jRCaMP1 performance in *Drosophila* larval NMJ

Figures 2A, 2B, 2C, 2D, 2E, 2F:
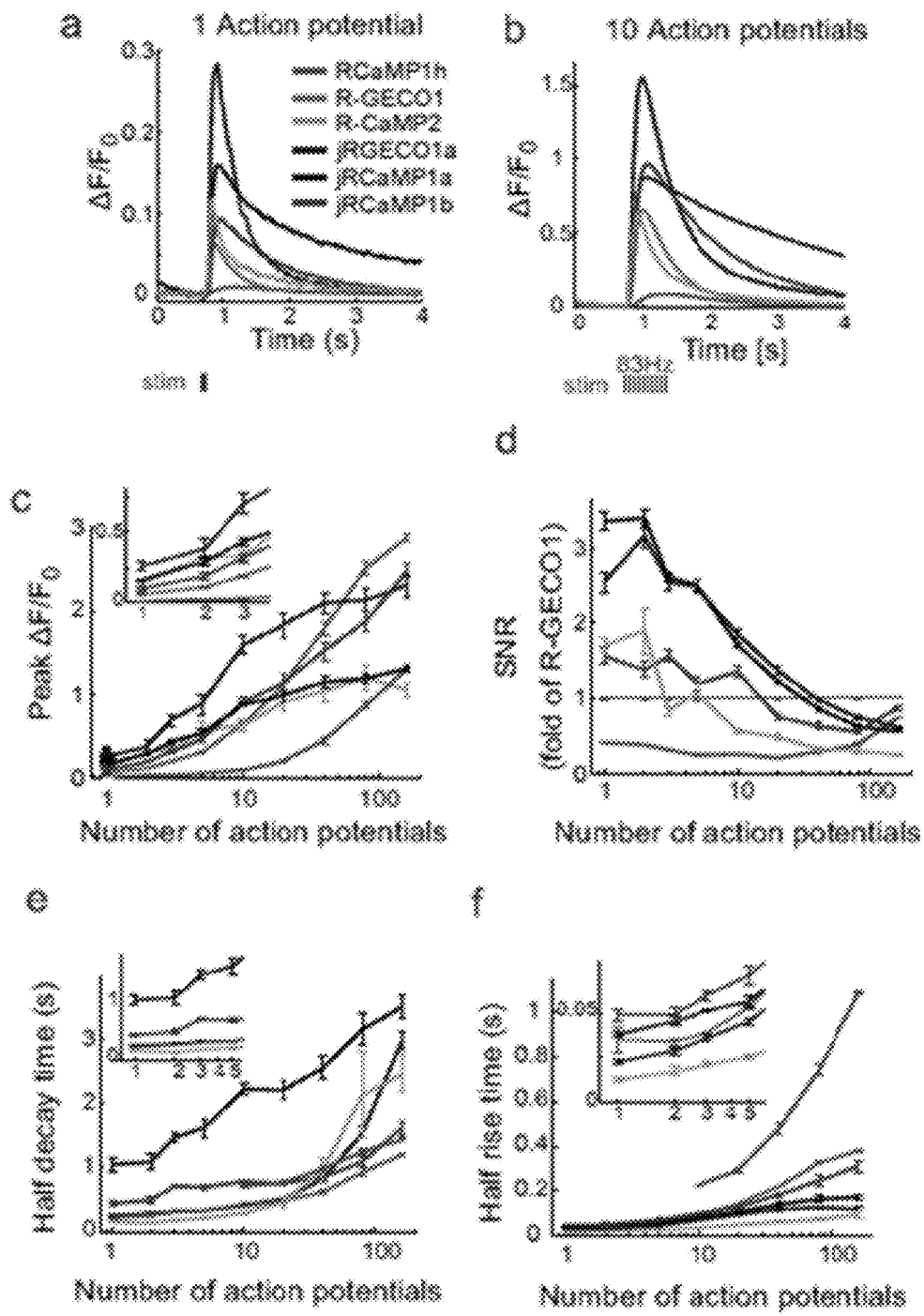
FIGS. 2A-F include data showing jRGECO1 and jRCaMP1 performance in the dissociated neurons. (a) Average responses in response to one action potential (AP) for RCaMP1h (9479 neurons, 605 wells), R-GECO1 (8988 neurons, 539 wells), R-CaMP2 (265 neurons, 22 wells), jRGECO1a (383 neurons, 26 wells), jRCaMP1a (599 neurons, 38 wells), and jRCaMP1b (641 neurons, 31 wells). (b) Same for 10 APs response. (c-f), Comparison of jRGECO1 and jRCaMP1 sensors and other red GECIs, as a function of number of APs (color code as in a). (c) Response amplitude, $\Delta F/F_0$. (d) Signal-to-noise ratio, SNR, defined as the fluorescence signal peak above baseline, divided by the signal standard deviation before the stimulation is given. (e) Half decay time; and (f) Half rise time. Error bars correspond to s.e.m (n=651 wells for RCaMP1h; 633, R-GECO1; 15, R-CaMP2; 41, jRCaMP1a; 36, jRCaMP1b; 37, jRGECO1a).
Figures 10A, 10B, 10C, 10D, 10E, 10F:
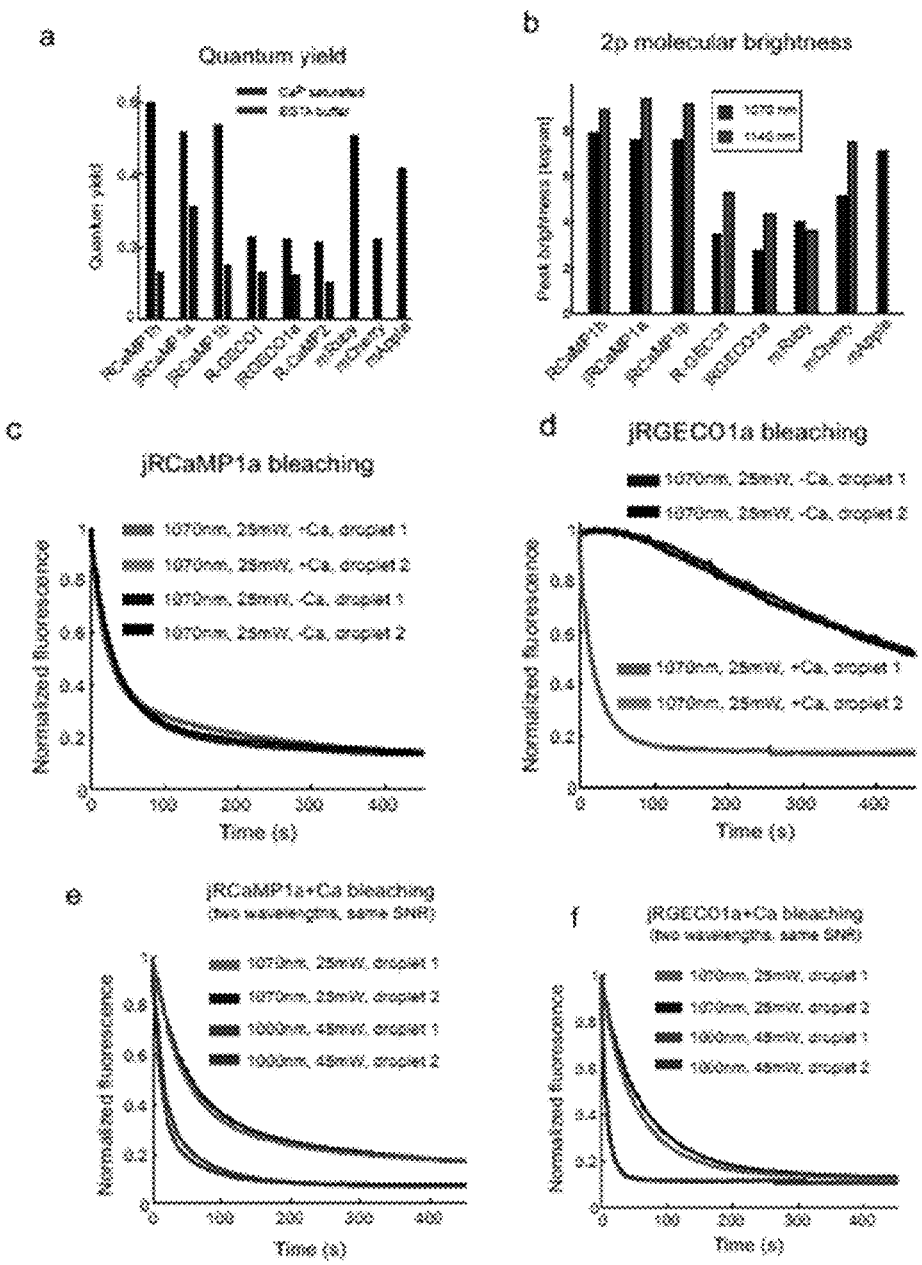
FIGS. 10A-F include data of biophysical properties of fluorescent proteins (FP) and red GECIs (a) Fluorescence quantum yield of red GECIs and red FPs; (b) Peak molecular brightness (calcium-bound state for GECIs) of red GECIs and red FPs; (c-d), Bleaching curves of jRCaMP1a (c) and jRGECO1a (d) in calcium-free and calcium-saturated states; (e-f), Bleaching profile of calcium-saturated jRCaMP1a (e); and jRGECO1a (f) when excited with 2 different wavelengths while maintaining an identical SNR. mApple data in a and b are taken from Akerboom et al., 2013. Measurements were done in a purified protein assay (Methods).
Figure 11:
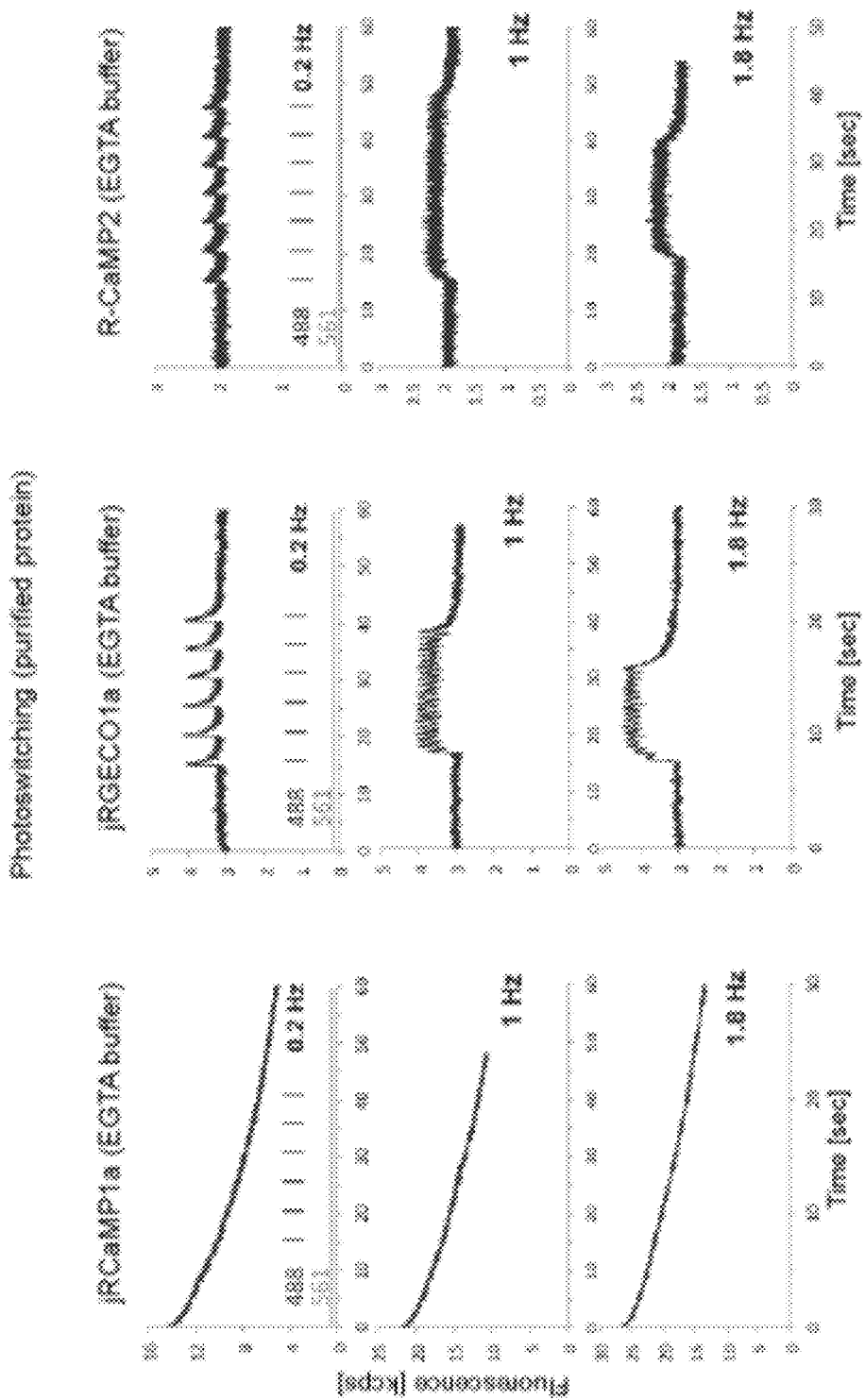
FIG. 11 includes data of photoswitching of GECIs in purified protein assay. Fluorescence traces of purified protein droplets (red traces) of jRCaMP1a (left panel), jRGECO1a (middle), and R-CaMP2 (right) constantly illuminated with 561 nm excitation light (40 mW/mm2), and with blue light pulses (3.2 mW/mm2 peak power, 50 ms duration, 0.2 Hz, 1 Hz, and 1.8 Hz in upper, middle, and lower rows respectively). mApple based GECIs, jRGECO1a and R-CaMP2, exhibit an AP like photoswitching artifact induced by the blue illumination, while jRCaMP1a does not switch, but photobleaches.
Figures 12A, 12B, 12C, 12D:
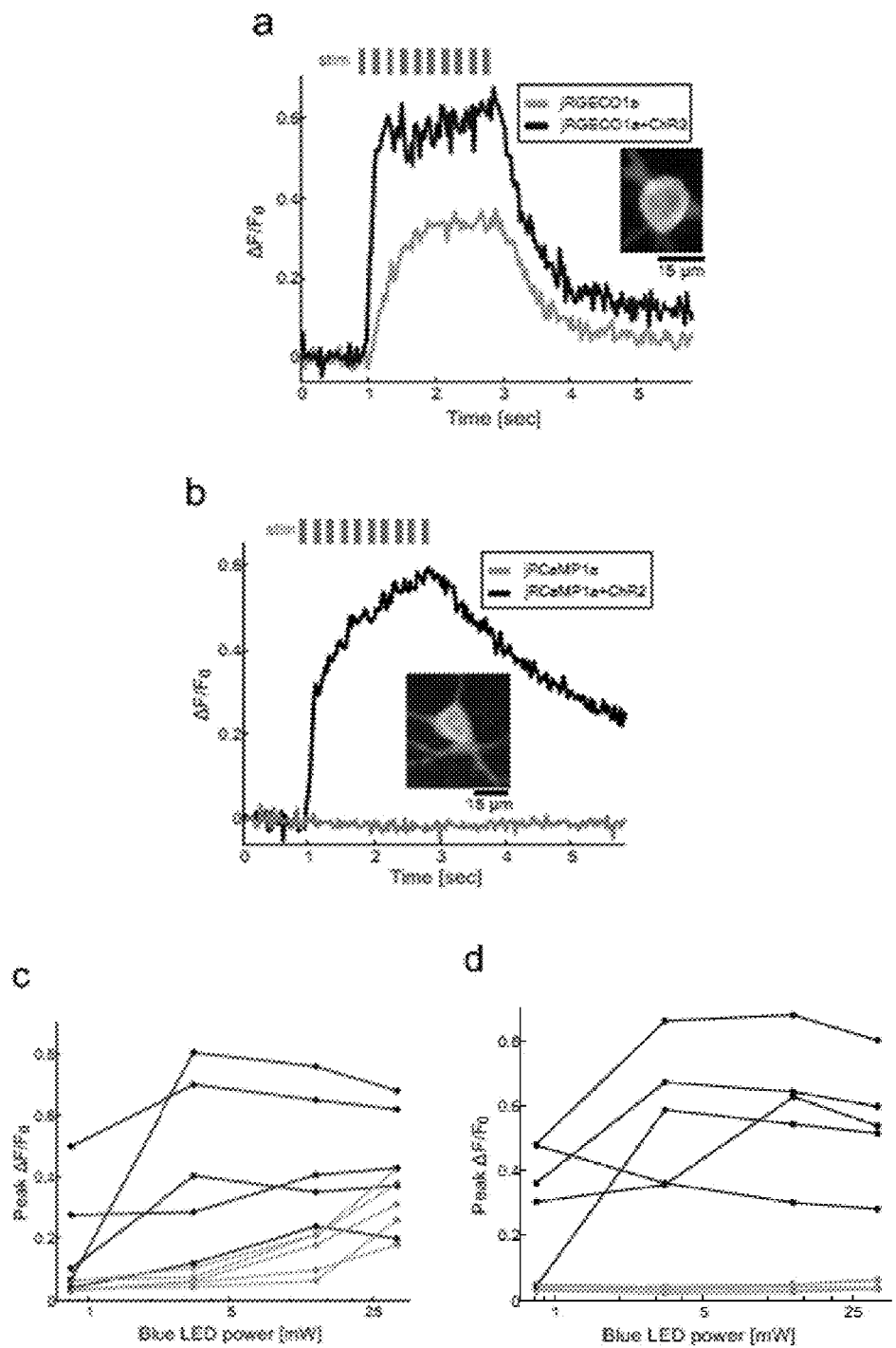
FIGS. 12A-D include data showing blue light induces transient jRGECO1a red fluorescence in cultured neurons (a) Red fluorescence of cultured rat hippocampal neurons transfected with either jRGECO1a alone (gray) or jRGECO1a+ChR2-Venus (blue) following stimulation with blue light (35 mW, 10 ms pulses, 83 Hz, 800 pm×800 pm FOV; Methods) stimulus pulses (light blue bars). Inset, merged image of neuron expressing both jRGECO1a (red) and ChR2-Venus (green); (b) Same experiment as in a with cultured neurons expressing jRCaMP1a alone (gray) or jRCaMP1a+ChR2-Venus (black); (c) Peak $\Delta F/F0$ values for 5 neurons expressing jRGECO1a+ChR2-Venus (blue) and 5 neurons expressing jRGECO1a alone (gray) as a function of blue stimulus light power; and (d) Peak $\Delta F/F0$ for 5 neurons expressing jRCaMP1a+ChR2-Venus (black) and 5 neurons expressing jRCaMP1a alone (gray) as function of blue stimulus light power.

| mean dF/F0 | Stim. Frequency | RCaMP1h | jRCaMP1a | jRCaMP1b | SEM | RCaMP1h | jRCaMP1a | jRCaMP1b |
|---|---|---|---|---|---|---|---|---|
| | 1 | 0.013 | 0.086 | 0.035 | 1 | 0.001 | 0.005 | 0.003 |
| | 5 | 0.020 | 0.296 | 0.125 | 5 | 0.002 | 0.016 | 0.007 |
| | 10 | 0.041 | 0.526 | 0.275 | 10 | 0.004 | 0.029 | 0.013 |
| | 20 | 0.130 | 0.845 | 0.587 | 20 | 0.013 | 0.045 | 0.025 |
| | 40 | 0.367 | 0.992 | 1.011 | 40 | 0.033 | 0.051 | 0.033 |
| | 80 | 0.679 | 0.928 | 1.255 | 80 | 0.052 | 0.047 | 0.034 |
| | 160 | 0.851 | 0.780 | 1.252 | 160 | 0.057 | 0.037 | 0.042 |
| Half rise time | mean | RCaMP1h | jRCaMP1a | jRCaMP1b | SEM | RCaMP1h | jRCaMP1a | jRCaMP1b |
| | 1 | 0.169 | 0.146 | 0.168 | 1 | 0.061 | 0.007 | 0.010 |
| | 5 | 0.534 | 0.636 | 0.746 | 5 | 0.148 | 0.024 | 0.027 |
| | 10 | 1.108 | 0.769 | 0.867 | 10 | 0.075 | 0.014 | 0.017 |
| | 20 | 1.259 | 0.669 | 0.875 | 20 | 0.058 | 0.016 | 0.012 |
| | 40 | 1.222 | 0.444 | 0.693 | 40 | 0.026 | 0.016 | 0.016 |
| | 80 | 1.064 | 0.298 | 0.464 | 80 | 0.015 | 0.009 | 0.010 |
| | 160 | 0.913 | 0.225 | 0.318 | 160 | 0.014 | 0.006 | 0.006 |
| Half decay time | mean | RCaMP1h | jRCaMP1a | jRCaMP1b | SEM | R-GECO1 | jRCaMP1a | jRCaMP1b |
| | 1 | 0.398 | 0.573 | 0.381 | 1 | 0.108 | 0.053 | 0.072 |
| | 5 | 1.731 | 2.081 | 1.292 | 5 | 0.157 | 0.055 | 0.058 |
| | 10 | 1.443 | 2.075 | 1.320 | 10 | 0.091 | 0.033 | 0.047 |
| | 20 | 1.248 | 2.121 | 1.276 | 20 | 0.031 | 0.000 | 0.030 |
| | 40 | 1.245 | 2.088 | 1.002 | 40 | 0.026 | 0.000 | 0.020 |
| | 80 | 1.241 | 2.055 | 0.754 | 80 | 0.026 | 0.000 | 0.020 |
| | 160 | 1.259 | 2.038 | 0.729 | 160 | 0.030 | 0.008 | 0.020 | jRGECO1a jRGECO1a is the most sensitive indicator, with 8.5-fold larger $\Delta F/F_0$ amplitude for 1AP stimuli and faster rise time than R-GECO1 (FIG. 2). Decay time and maximal $\Delta F/F_0$ amplitude were similar to R-GECO1. The improved amplitude and faster rise kinetics were associated with a tighter apparent calcium affinity (Table 2). jRGECO1a response amplitudes and kinetics are comparable to GCaMP6f for brief trains of 1-10 APs (Chen, Wardill et al. 2013). Similar to other mApple-based indicators, jRGECO1a exhibits photoswitching in response to blue light (FIG. 11).

jRCaMP1a and jRCaMP1b jRCaMP1a and jRCaMP1b were also much improved compared to their parent sensors (24-fold and 13-fold improved sensitivity for detecting 1 AP stimuli) (FIG. 2). jRCaMP1a has higher sensitivity and slower decay kinetics than jRCaMP1b. jRCaMP1b has a larger dynamic range, without saturation in the range of 1-160 APs (FIG. 2c). Both jRCaMP1a and jRCaMP1b have higher calcium affinities than RCaMP1h (Table 2). However, jRCaMP1a has very limited dynamic range in cultured neurons and solution. jRCaMP1a and jRCaMP1b are two-fold brighter than jRGECO1a in the calcium-bound state (FIG. 10). Similar to RCaMP1h, jRCaMP1a and jRCaMP1b did not exhibit photoswitching (FIG. 11). This allows independent photostimulation and imaging in neurons that co-express ChR2 and jRCaMP1a/b (FIG. 12).

Figures 3A, 3B, 3C:
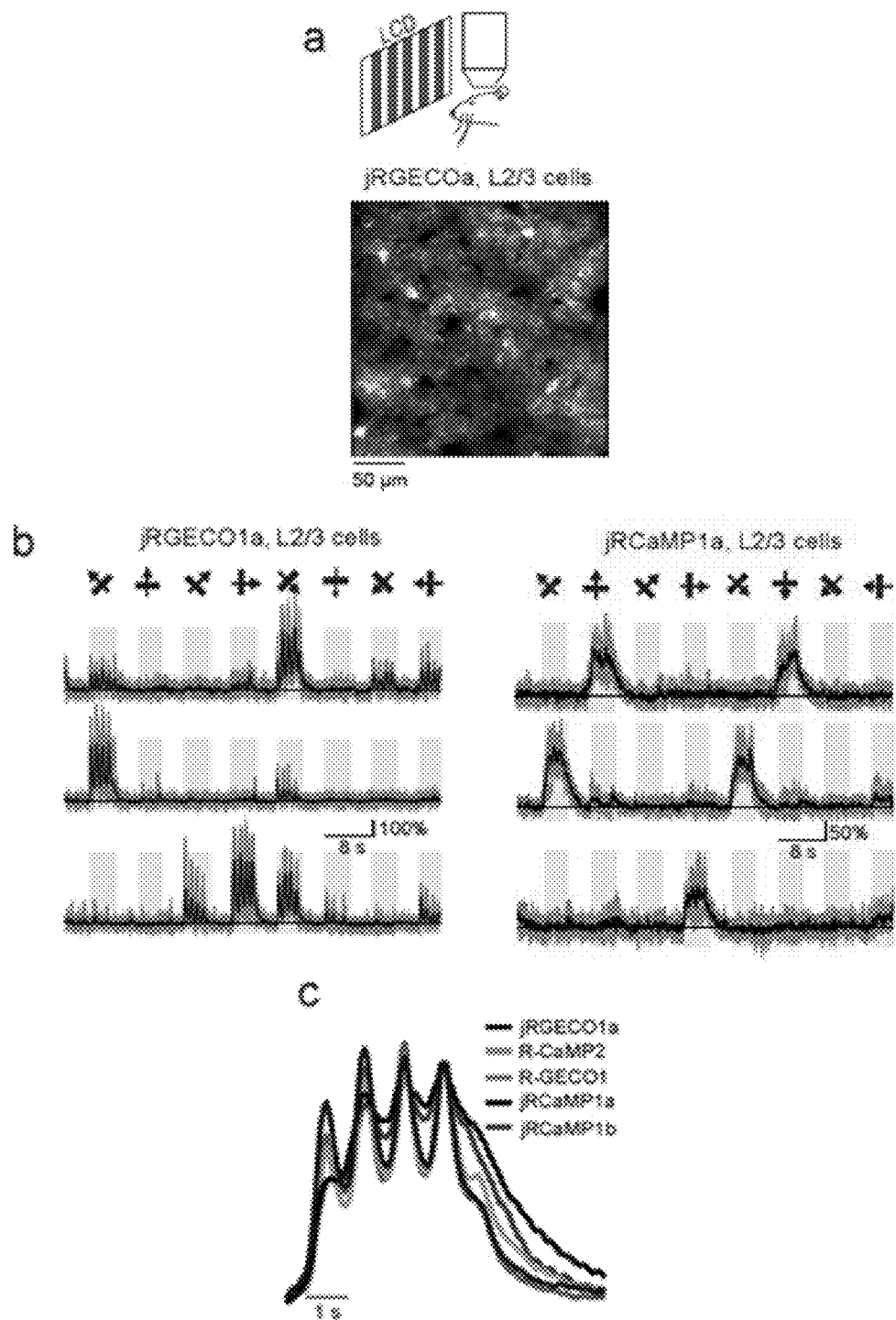
FIGS. 3A-3F include data of jRGECO1a and jRCaMP1a and jRCaMP1b performance in the mouse primary visual cortex. (a) Schematic of the experiment (top) and image of V1 layer 2/3 (L2/3) cells expressing jRCaMP1a (bottom). (b) Example traces from three L2/3 neurons expressing jRGECO1a (left) and jRCaMP1a (right). Single trials (gray) and averages of 5 trials (blue and black for jRGECO1a and jRCaMP1a, respectively) are overlaid. Eight grating motion directions are indicated by arrows and shown above traces. The preferred stimulus is the direction evoking the largest response. (c) Average response of neurons to their preferred stimulus (175 cells, R-GECO1; 310, R-CaMP2; 253, jRGECO1a; 199, jRCaMP1a; 95, jRCaMP1b). (d) Fourier spectra normalized to the amplitude at 0 Hz for neurons driven with 1 Hz drifting gratings, transduced with RCaMP1h, R-GECO1, R-CaMP2, jRGECaMP1a, jRCaMP1b, and jRGECO1a. Inset, zoomed-in view of 1 Hz response amplitudes. (e) Fraction of cells detected as responding to visual stimulus (ANOVA test, p<0.01) when expressing different calcium indicators. Error bars correspond to s.e.m (26 fields-of-view, RCaMP1h; 35, jRCaMP1a; 31, jRCaMP1b; 30, R-GECO1; 34, jRGECO1a; 33, R-CaMP2; 29, GCaMP6s; 29, GCaMP6f) (f) Distribution of $\Delta F/F$ amplitude for the preferred stimulus (1210 cells, R-GECO1; 861, RCaMP1h; 1733, R-CaMP2; 1260, jRGECO1a; 1316 jRCaMP1a; 971, jRCaMP1b; 907, GCaMP6f; 672, GCaMP6s), same colors as in (e).
Figures 9A, 9B, 9C:
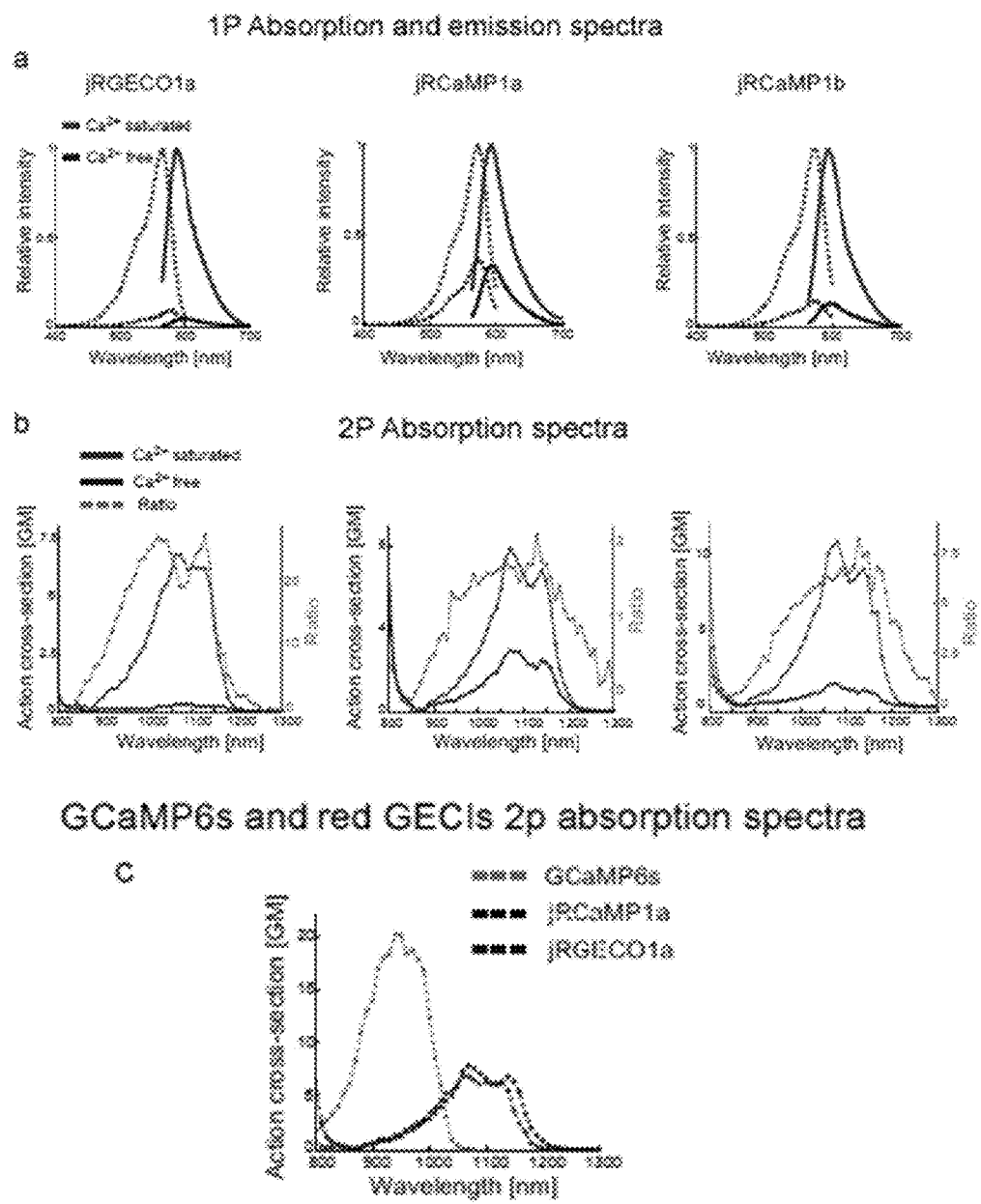
FIGS. 9A-C include absorption and emission spectra of red GECIs. (a) One-photon excitation (dashed lines) and emission (solid lines) spectra for jRGECO1a (left panel), jRCaMP1a (middle), and jRCaMP1b (right) in calcium-free (red lines) and calcium-saturated (blue lines) states; (b) Two-photon excitation spectra for jRGECO1a, jRCaMP1a, and jRCaMP1b, in calcium-free (blue) and calcium-saturated (red) states. Dashed green lines show the ratio between these two states; and (c) Two-photon excitation spectra of calcium-saturated GCaMP6s, jRCaMP1a, and jRGECO1a. Measurements were done in a purified protein assay (Methods).
Figure 13:
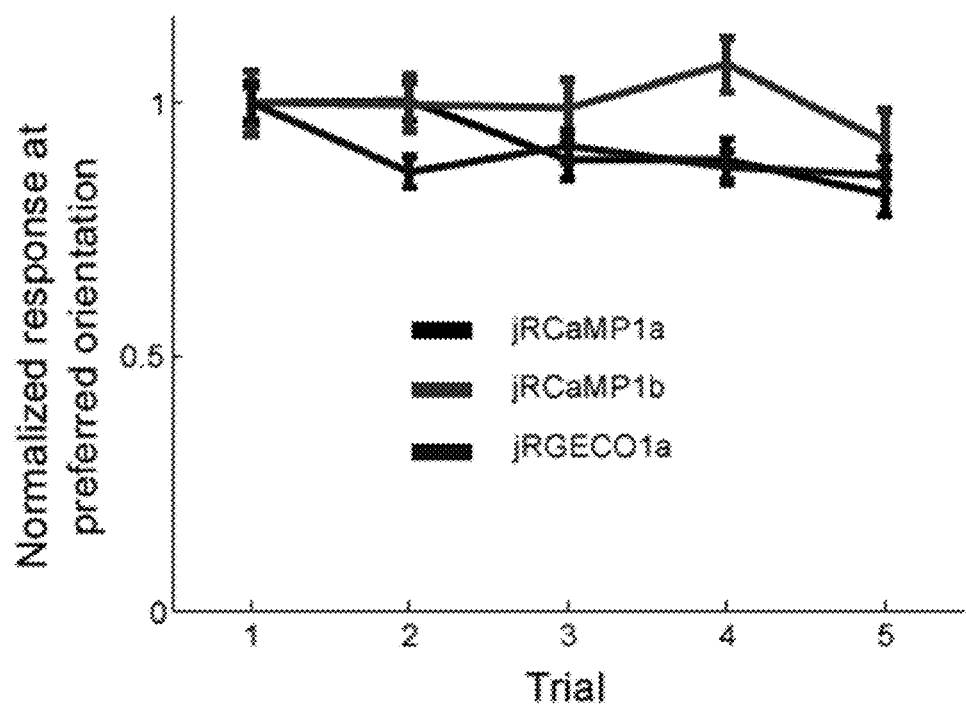
FIG. 13 includes data showing reproducible V1 response across trials. Response amplitudes of all cells, which were detected as responsive (n=308 cells, jRGECO1a; 277, jRCaMP1a; 141, jRCaMP1b), averaged and plotted against trial number. No stimulus adaptation was evident.
Figure 14:
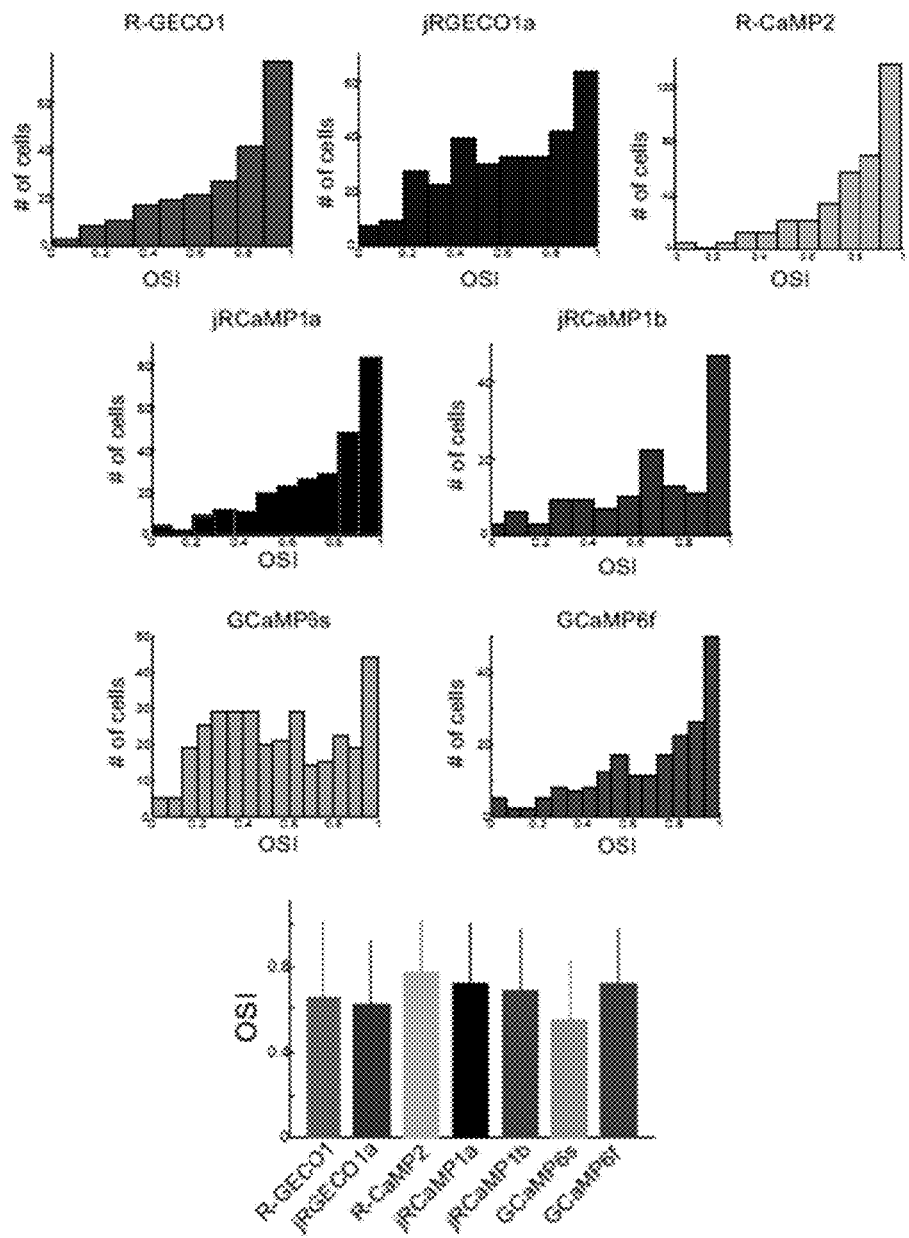
FIG. 14 is a comparison of orientation tuning in V1 neurons measured with different red GECIs. Distribution of orientation selectivity index (OSI, 3 upper rows) for all cells detected as responsive was measured using different GECIs. Bottom panel, mean±s.d for all constructs show similar tuning properties (n=238 cells, R-GECO1; 308, jRGECO1a; 386, R-CaMP2; 277, jRCaMP1a; 141, jRCaMP1b; 337, GCaMP6s; 203, GCaMP6f)).

Red Protein Calcium Indicators in Mouse V1 jRGECO1a, jRCaMP1a, jRCaMP1b, were tested, along with their parent indicators, and R-CaMP2 in the mouse primary visual cortex (V1) in vivo (FIG. 3a). The majority of V1 neurons can be driven to fire action potentials in response to drifting gratings. V1 neurons were infected with adeno-associated virus (AAV) expressing one of the red GECI variants under the human synapsin1 promoter (AAV-hsyn1-red GECI variant). Three weeks after AAV infection, L2/3 neurons showed fluorescence in the neuronal cytoplasm. Sensory stimuli consisted of moving gratings presented in eight directions to the contralateral eye. Two-photon excitation was performed with a tunable ultrafast laser (Insight DS+; Spectra-Physics) running at 1040 nm or 1100 nm (FIG. 9). Regions of interest corresponding to single neurons revealed visual stimulus-evoked fluorescence transients that were stable across trials (FIG. 13) and tuned to stimulus orientation (FIG. 3b). Orientation tuning was similar for all constructs tested (FIG. 14). Fluorescence transients tracked the dynamics of the sensory stimuli (FIG. 3b-d). mApple-based indicators tracked more faithfully than mRuby-based indicators because of their faster kinetics (signal half decay time after end of stimulus was 298±22, 331±17.9, 328±15.7, 571±45, and 500±45.5 for R-GECO1, jRGECO1a, R-CaMP2, jRCaMP1a, and jRCaMP1b respectively; Methods).

Figures 3D, 3E, 3F:
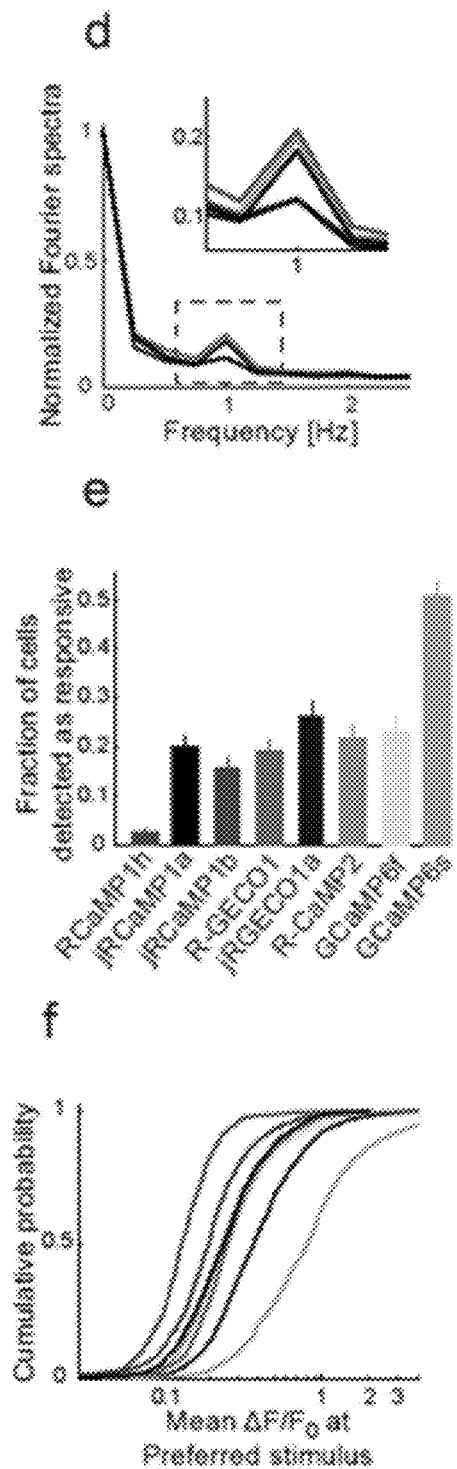

The performance of red GECIs was compared using standard metrics (Chen, Wardill et al. 2013). One measure of sensitivity is the fraction of neurons detected as responsive in the visual cortex (FIG. 3e). For jRCaMP1a and jRCaMP1b this fraction was 7.7- and 6-fold higher than for RCaMP1h ($P<10^{-6}$, Wilcoxon rank-sum test), and comparable to the widely used GCaMP6f. For jRGECO1a, the fraction was 35% higher than for R-GECO1, and higher than both R-CaMP2 and GCaMP6f, but still lower than GCaMP6s. The mean $\Delta F/F_0$ at the preferred visual stimulus (Methods) also showed enhanced sensitivity for jRCaMP1a and jRCaMP1b compared to RCaMP1h (FIG. 3f). jRGECO1a responses in vivo were larger than other red GECIs, but still smaller than GCaMP6s responses.

Figure 15:
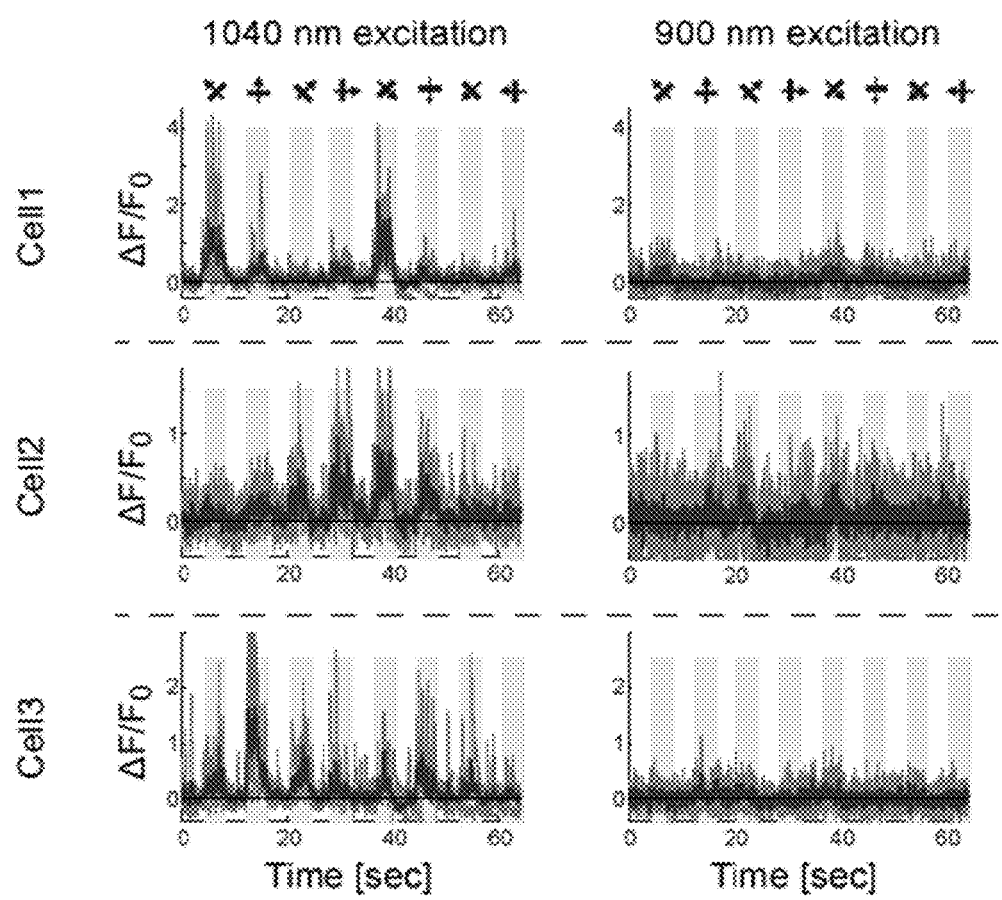
FIG. 15 includes data showing red GECIs lack of functional activity with 900 nm excitation. Three example cells' (jRGECO1a, expressed in L4 V1 neurons) functional activity for 1040 nm excitation (left) and lack of activity when excited with 900 nm (25 vs. 1 cell were detected as responsive out of 50 cells in FOV; drifting grating stimuli, Methods).
Figures 17A, 17B, 17C, 17D:
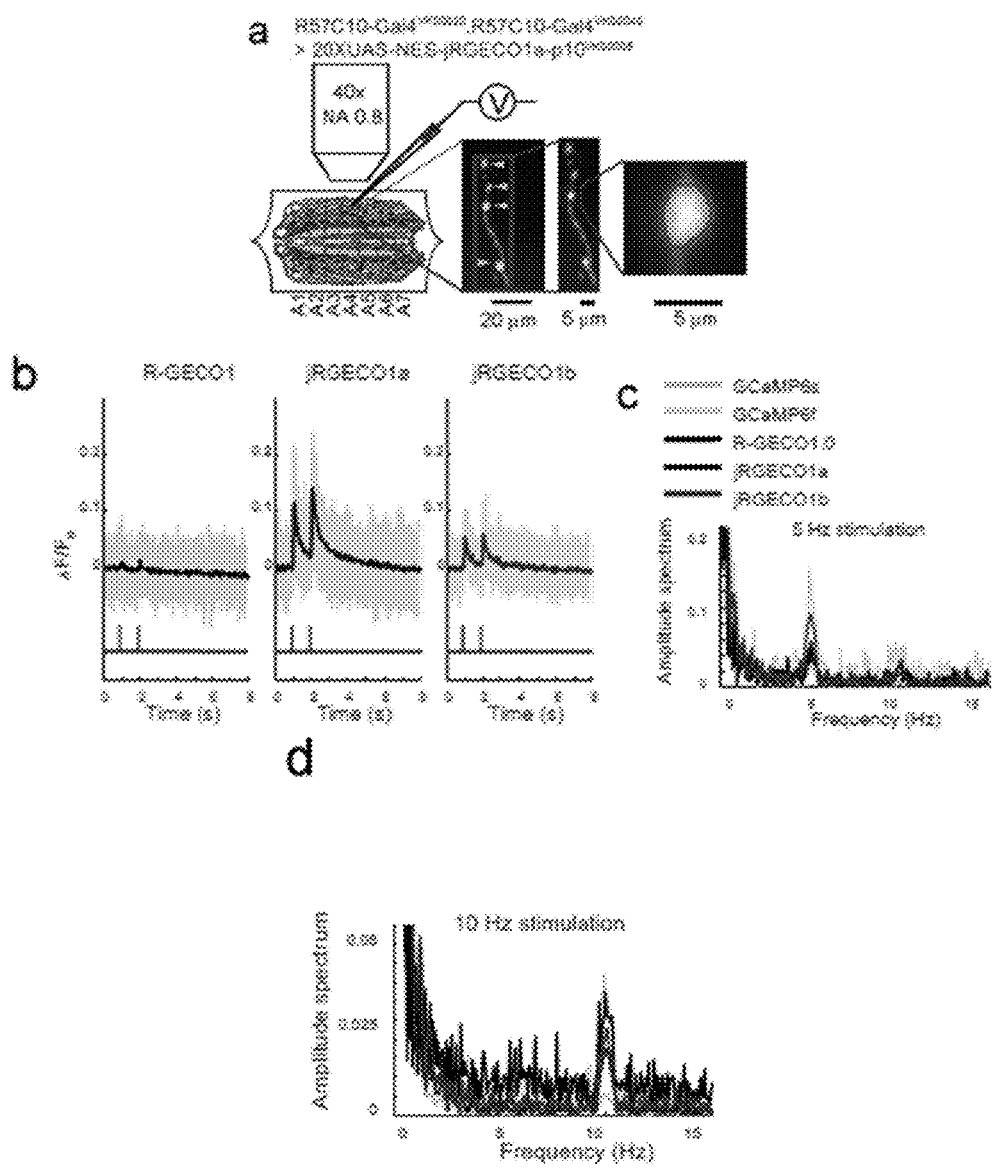
FIGS. 17A-M include data showing the imaging of activity in Drosophila larval NMJ boutons with jRGECO1a. (a) Schematic of experimental setup. Epifluorescence and high magnification $\Delta F/F_0$ images of Type 1b boutons (green arrowheads) from muscle 13 (segments A3-A5), with image segmentation ROIs superimposed (Methods); (b) Single trial and averaged fluorescence transients after 1 Hz stimulus for 2 s for R-GECO1, jRGECO1a and jRGECO1b (R-GECO1: 10 FOVs in 5 flies, 40 boutons; jRGECO1a: 12 FOVs in 7 flies, 48 boutons; jRGECO1b: 9 FOVs in 6 flies, 36 boutons. Same data set used for all other analyses); (c-d), Fourier spectra normalized to 0 Hz of fluorescence signals acquired during 5 Hz (c) and 10 Hz (d) stimulation; (e-f), $\Delta F/F_0$ (e) and SNR (f) traces (mean±s.e.m.) recorded with 1, 5, 10, 20, 40, 80 and 160 Hz stimulation for 2s (indicated by red curves at the bottom); (g-h), $\Delta F/F_0$ (g) and SNR (h) traces (mean±S.E.M.) recorded with 1 and 5 Hz stimulation for 2s (shown by red curves at the bottom, amplitude not to scale). (i-j), Comparison of $\Delta F/F_0$ traces (mean±s.e.m.) of R-GECO1 and jRGECO1 variants with 1, 5, 10 Hz (i) and 20, 40, 80 Hz (j) stimulation for 2s (shown by red curves at the bottom, amplitude not to scale); (k-l), Comparison of averaged peak $\Delta F/F_0$ responses at various frequencies (k) and peak SNR (l) (mean±s.e.m.) of GCaMP6 variants, R-GECO1 and jRGECO1 variants, with 1, 5, 10, 20, 40, 80 and 160 Hz stimulation. Note that vertical axes are log scale; and (m) Comparison of kinetics of GCaMP6 variants, R-GECO1 and jRGECO1 variants with 40 Hz stimulation. Horizontal axes are half rise time and vertical axes are half decay time.
Figures 17E, 17F:
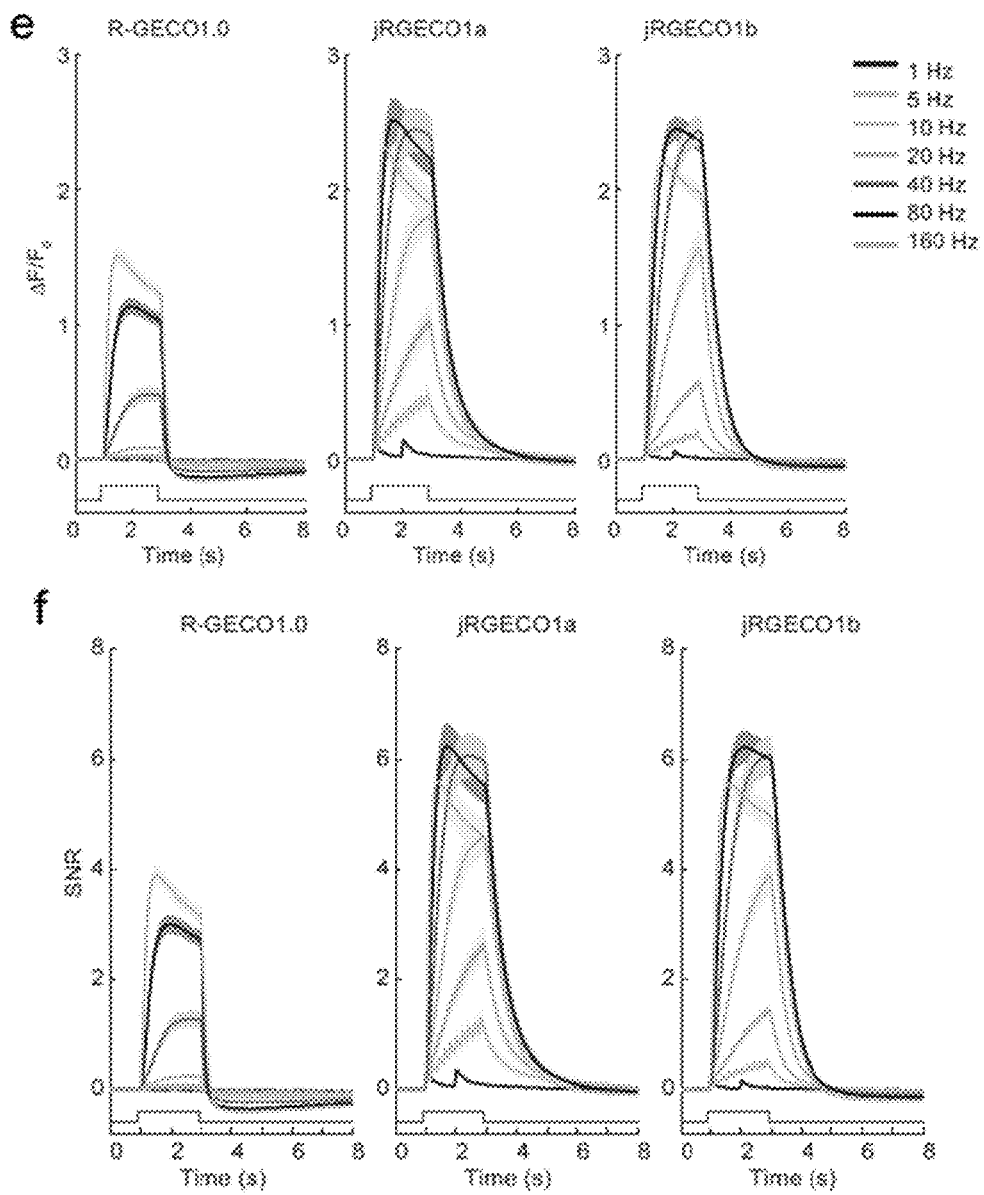
Figures 17G, 17H:
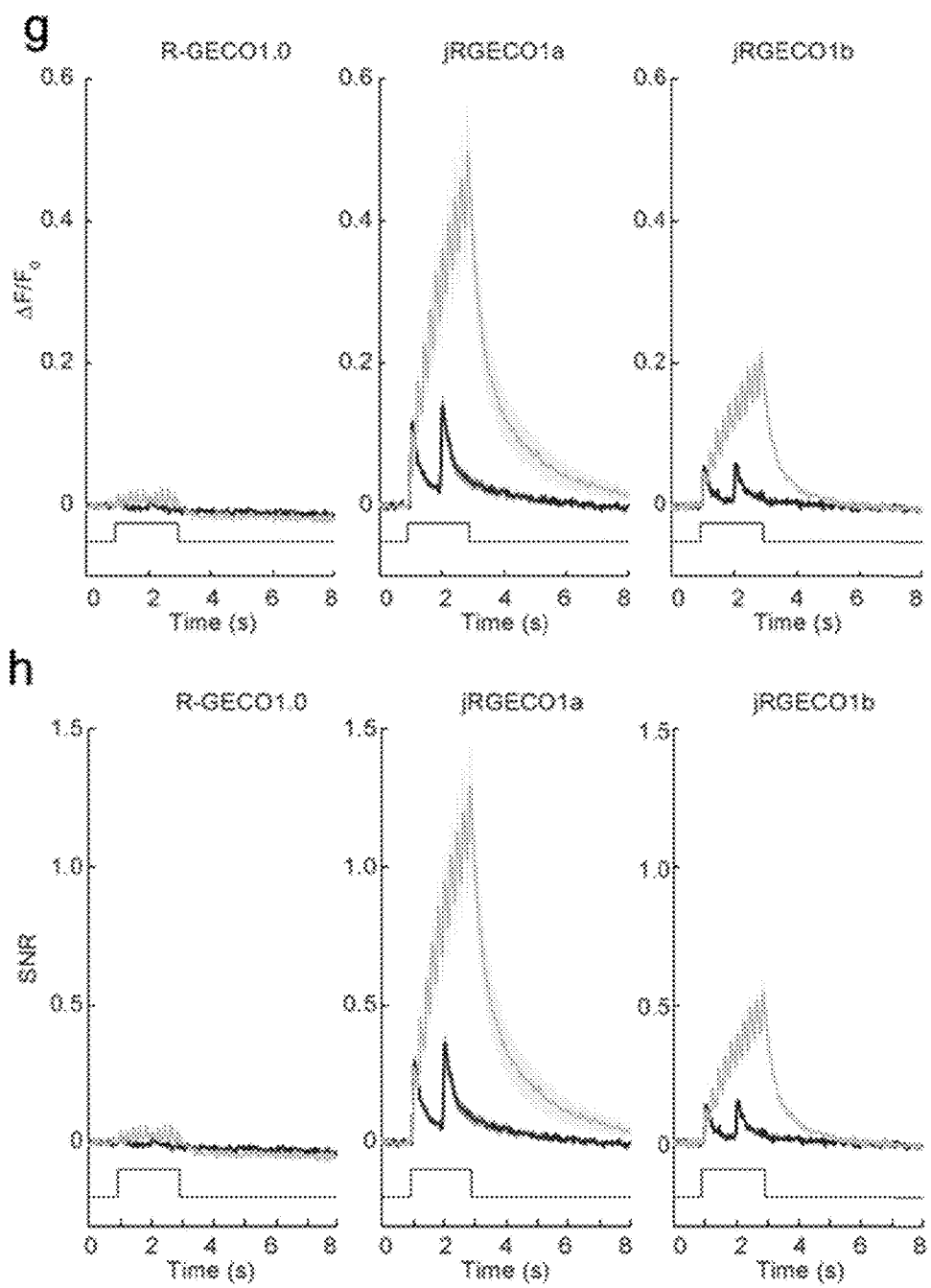
Figures 17I, 17J:
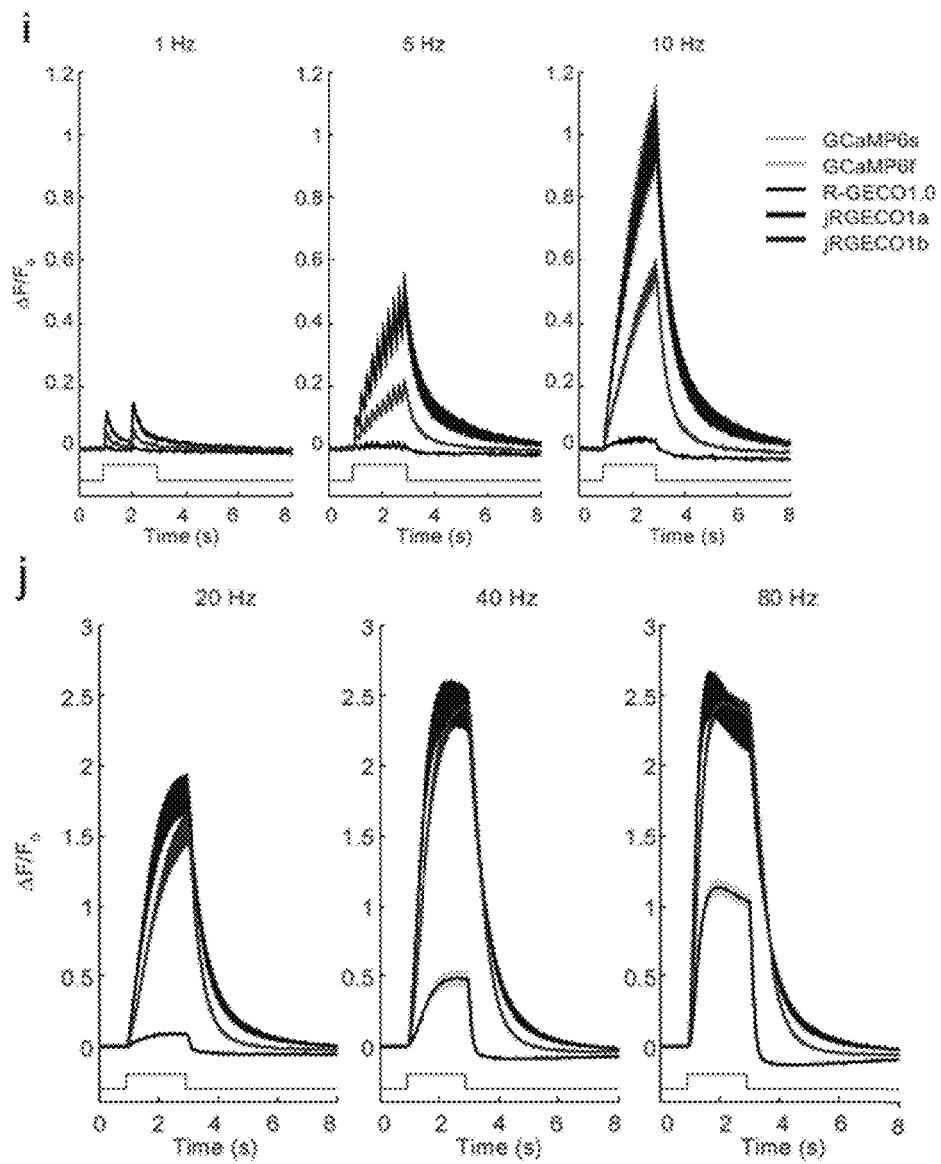
Figures 17K, 17L, 17M:
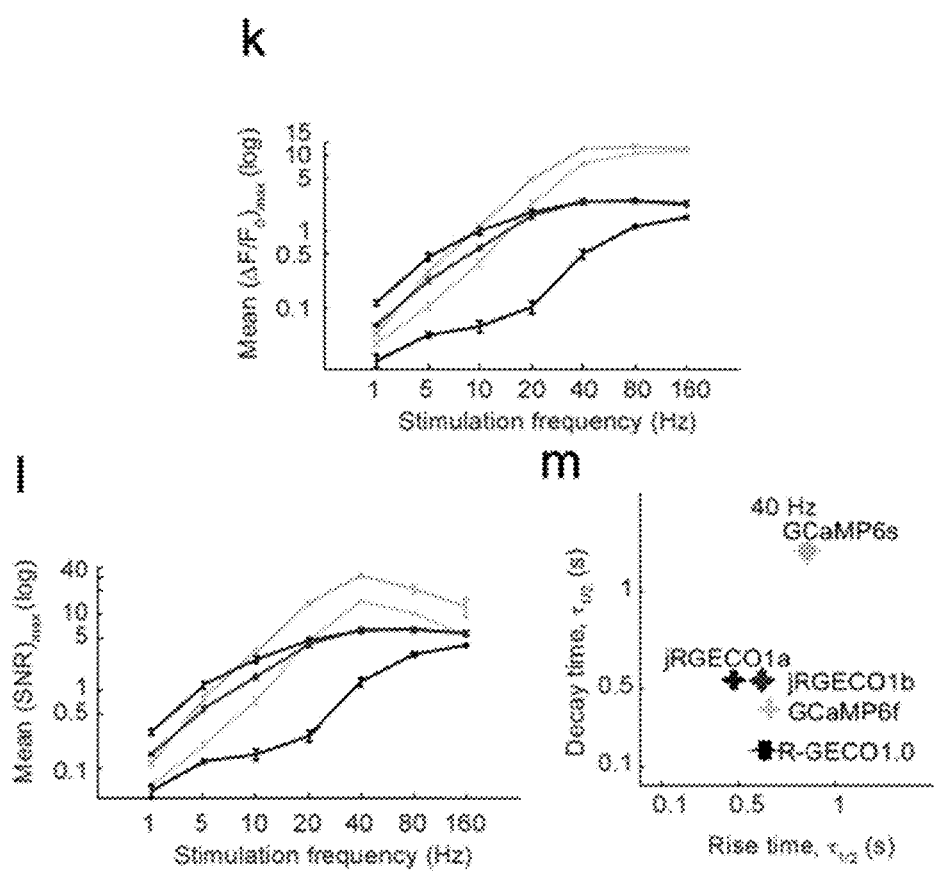
Figures 18C, 18D:
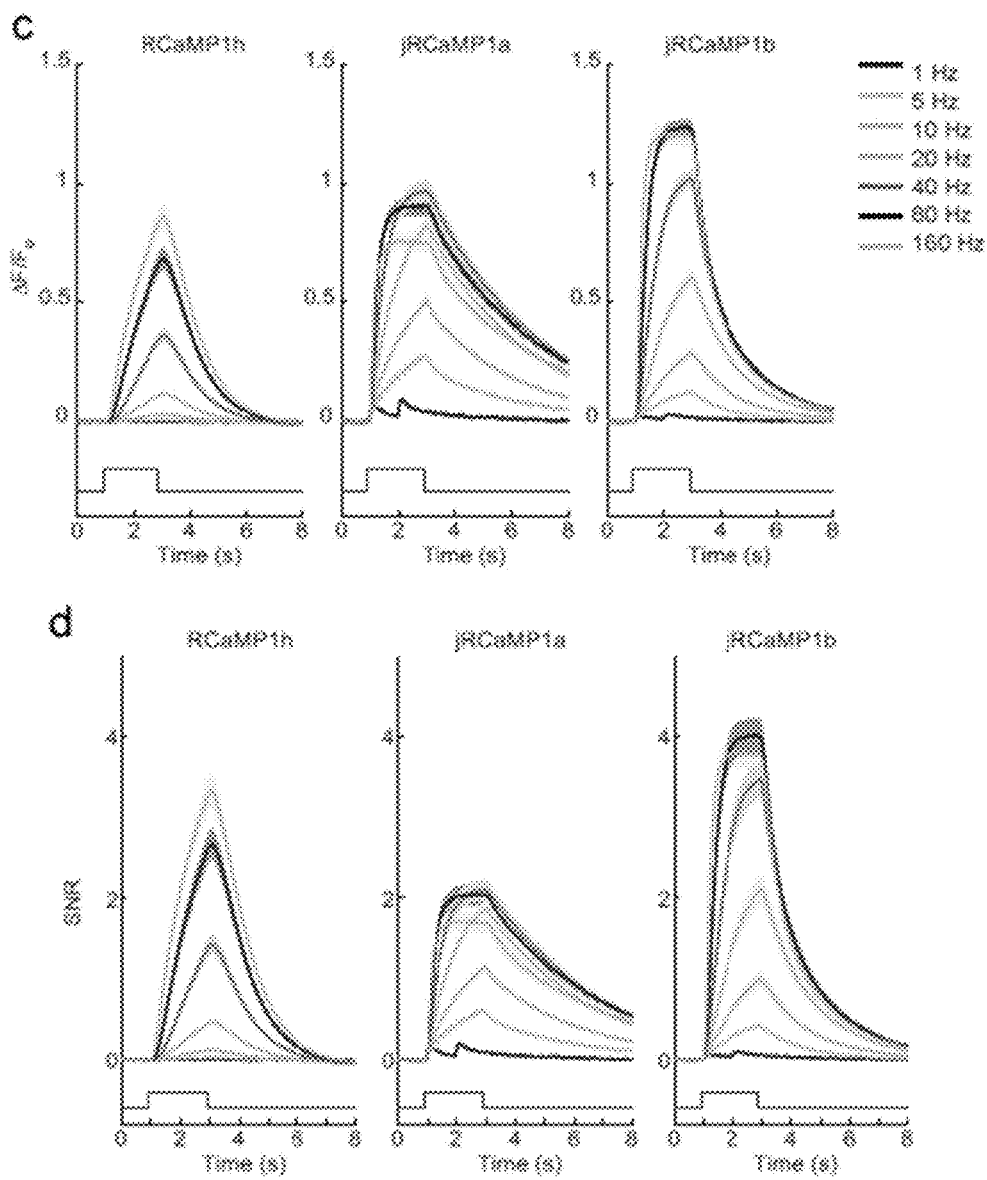
Figure 18E:
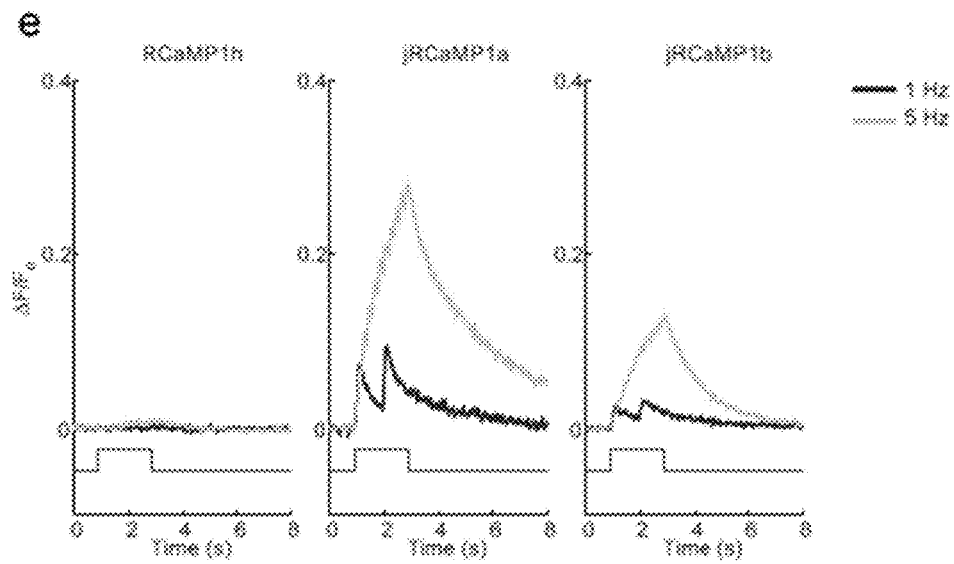
Figure 18F:
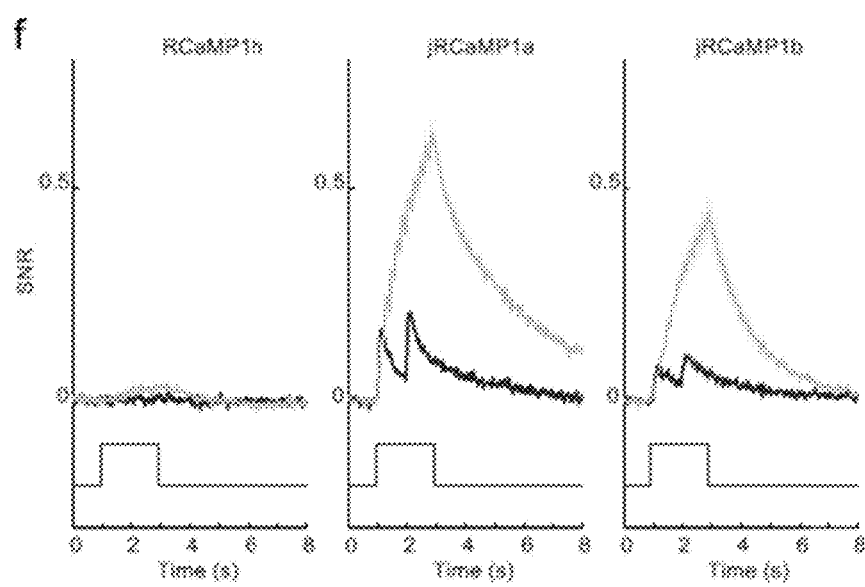
Figures 18G, 18H:
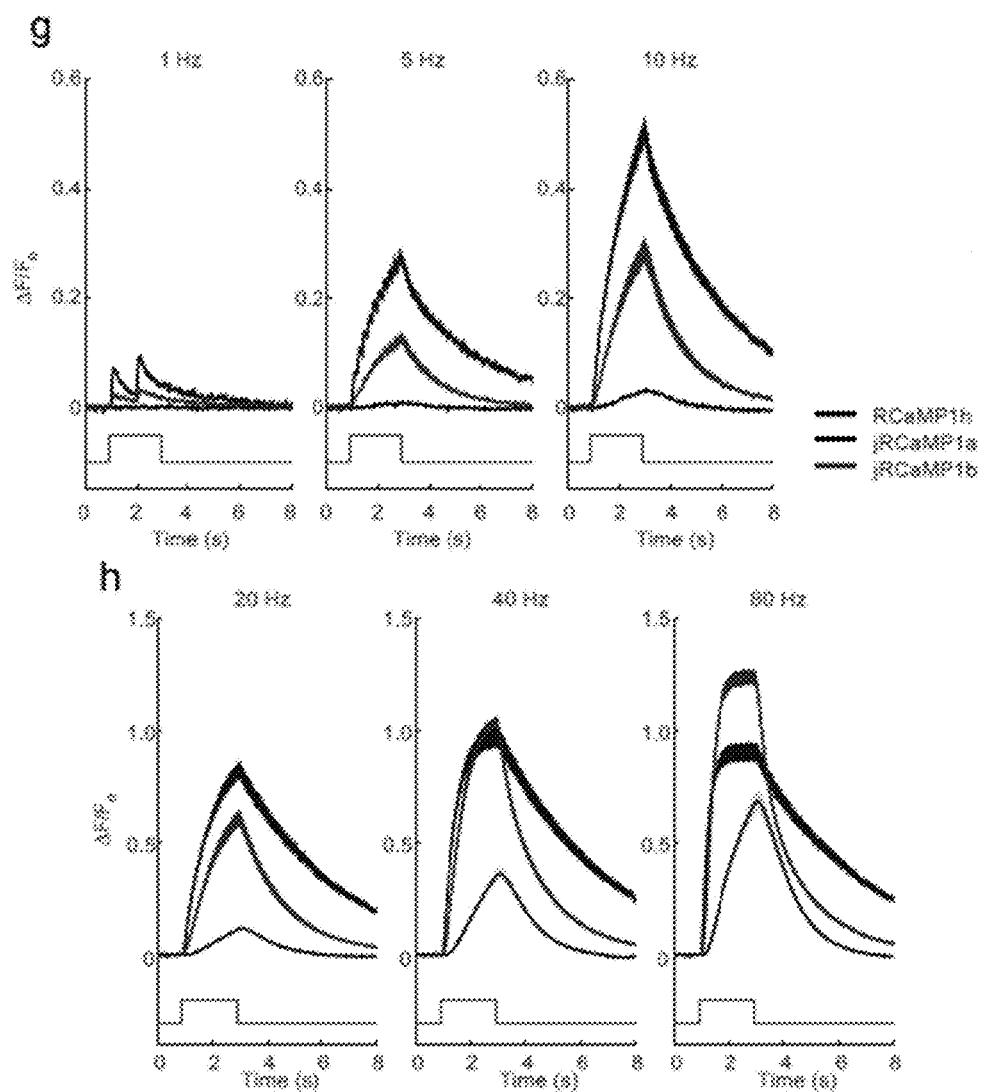
Figures 18I, 18J, 18K:
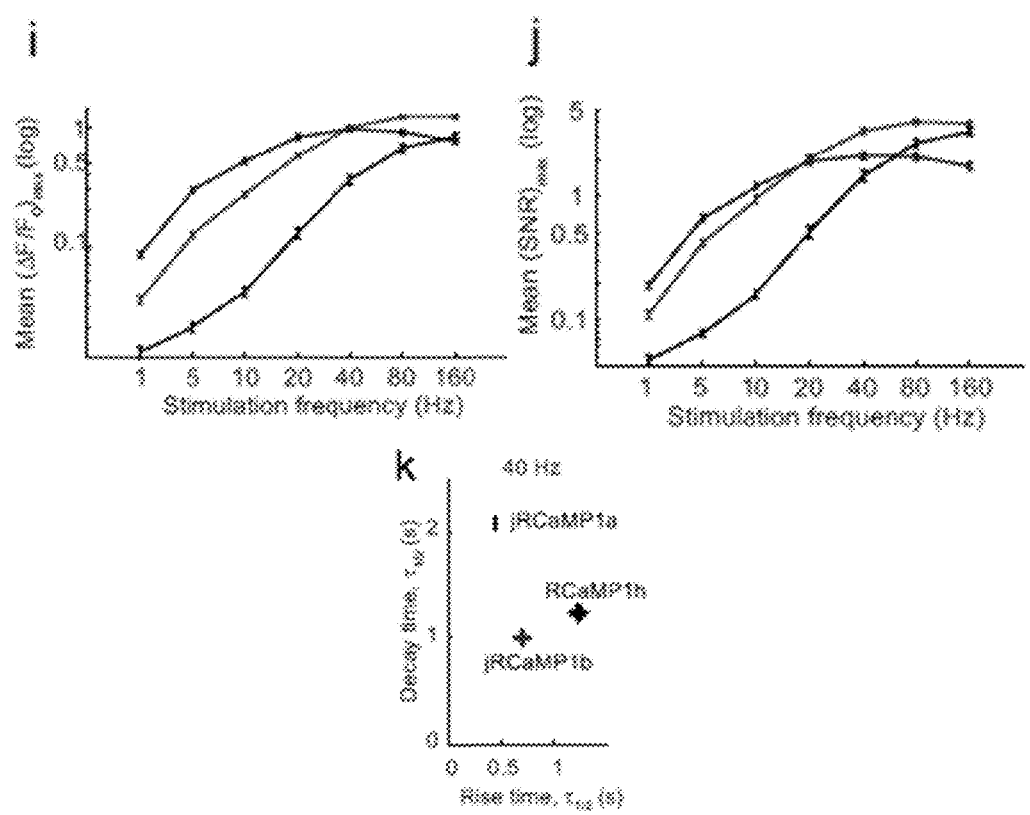
Figures 19A, 19B:
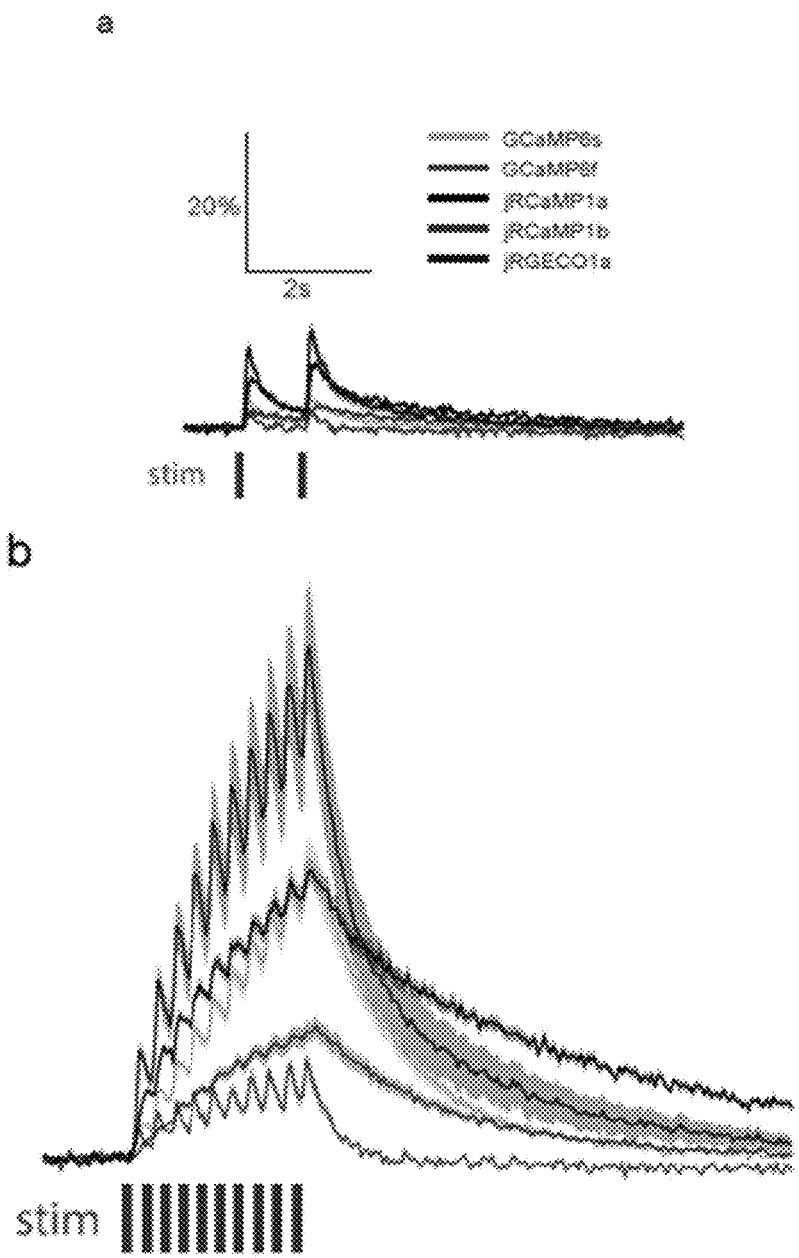
FIGS. 19A-E provide comparison data of red and green GECI activity in Drosophila larval NMJ boutons (a-b) Single trial and averaged fluorescence transients after 1 Hz (a) and 5 Hz (b) stimulus for 2 s for jRGECO1a, jRCaMP1a and jRCaMP1b (jRGECO1a: 12 FOVs in 7 flies, 48 boutons; jRCaMP1a: 11 FOVs in 7 flies, 44 boutons; jRCaMP1b: 13 FOVs in 7 flies, 52 boutons; GCaMP6s: 12 FOVs in 7 flies, 48 boutons; GCaMP6f: 12 FOVs in 7 flies. Same data set used for all other analyses); (c) Comparison of averaged peak $\Delta F/F_0$ responses with various stimulus frequencies (mean±s.e.m.) of jRGECO1a, jRCaMP1 variants and GCaMP6 variants, with 1, 5, 10, 20, 40, 80 and 160 Hz stimulation. Note that vertical axes are log scale; and (d-e), Comparison of frequency tuned averaged half decay (d) and half rise (e) (mean±s.e.m.) of jRGECO1a, jRCaMP1 variants and GCaMP6 variants, with 1, 5, 10, 20, 40, 80 and 160 Hz stimulation.
Figure 19C:
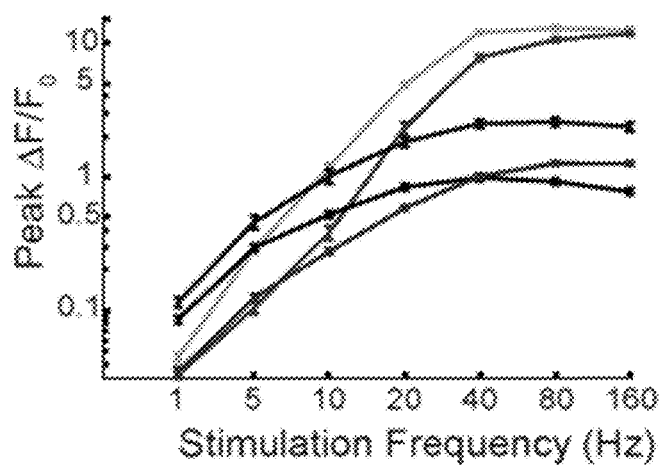
Figure 19D:
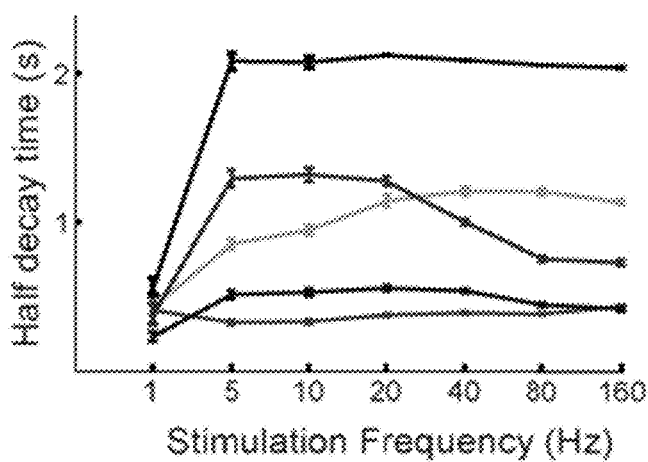
Figure 19E:
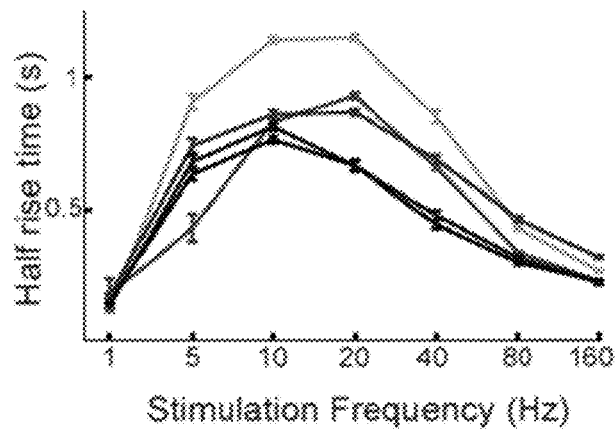

The measured jRGECO1a and jRCaMP1a responses in the visual cortex were lower than in cultured neurons (FIG. 2a, FIG. 5c) and lower than those produced by GCaMP6s (Chen, Wardill et al. 2013). Green fluorescence (500-550 nm) was noted in the in vivo images that was unevenly distributed across the cytoplasm. The green signal was visible with 900 nm excitation, but not with 1040 nm excitation, suggesting that the red GECIs partition into at least two species. Since fluorescence excited at 900 nm does not report calcium (FIG. 15), one of the species appears to contribute non-productive background fluorescence. Indeed, neurons with larger fractional fluorescence intensity at 900 nm showed lower response amplitudes (F test, p-value=0.002) (FIG. 16). These observations suggest that long-term expression can degrade jRGECO1a performance.

Imaging with red probes is less prone to scattering of excitation light and absorption of fluorescence compared with GFP-based sensors (FIG. 9). Red GECIs therefore promise deeper imaging in vivo. To estimate how fluorescence decays with imaging depth apical dendrites were imaged from layer (L) 5 neurons (FIG. 11a). An exponential decay was fitted to the fluorescence signal measured as a function of depth. Red GECI fluorescence decayed more slowly (128±29 μm; median±s.d., 19 dendrites, n=3 mice infected with RCaMP1h, R-GECO1, or jRGECO1a) than GCaMP6 fluorescence (74±15 μm median±s.d., 14 dendrites, n=2 mice infected with GCaMP6s and GCaMP6f; P<0.0001, Wilcoxon rank sum test) (FIG. 11b). For comparable conditions, imaging with red GECIs will thus add hundreds of micrometers of imaging depth compared to green GECIs.

Figures 4A, 4B, 4C, 4D:
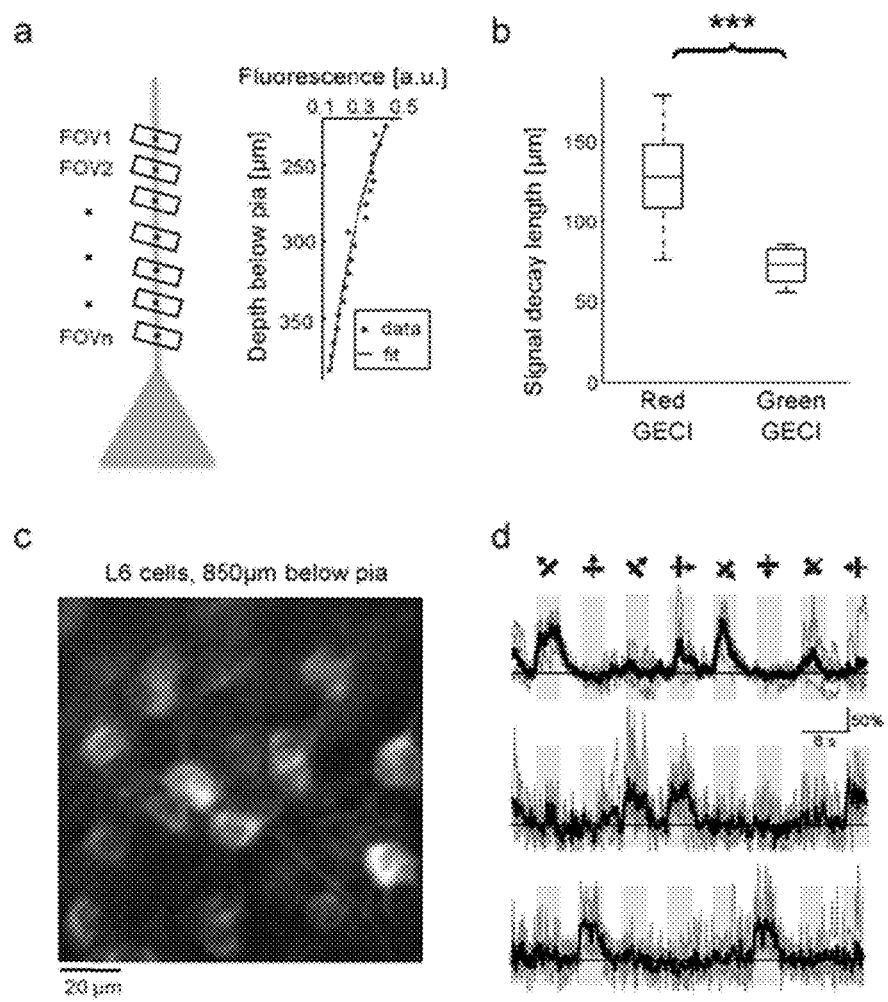
FIGS. 4A-D include deep tissue imaging using red GECIs. (a) Left, schematic of the measurement. L5 neuron apical dendrites were imaged at different depths (fields-of-view, FOVs 1-n). Right, measured brightness as a function of imaging depth. For fixed excitation light the brightness decreases as a function of imaging depth because of scattering and absorption losses. The decay was characterized by fitting an exponential function to the signal. (b) Exponential decay coefficients measured from dendrites expressing green (GCaMP6s or GCaMP6f) or red (RCaMP1h, jRCaMP1a, and jRGECO1a) GECIs. Red GECI signal decay coefficients were significantly longer than for green GECI (Wilcoxon rank sum test, P<0.0001; 3 mice and 19 dendrites for red GECIs; 2 mice and 14 dendrites for green GECIs). (c) L6 neurons, 850 μm under the pia. An NTSR1-cre mouse was infected with FLEX-hsyn-NES-jRCaMP1a AAV. (d) Example traces from three example L6 neurons. Single trials (gray) and averages of 5 trials (black) are overlaid. Eight grating motion directions are indicated by arrows and shown above traces.

For example, red GECIs facilitate imaging activity deep in L6. L6 neurons were infected by injecting AAV-hsyn1-FLEX-jRCaMP1a virus into the visual cortex of NTSR1-cre mice. Four weeks after infection orientation-tuned somatic transients were detected in L6 cells (down to 900 μm below the pia) in response to visual stimuli (FIG. 4c,d).

Relationship Between Spikes and Fluorescence Dynamics

Figures 5A, 5B, 5C, 5D, 5E, 5F, 5G:
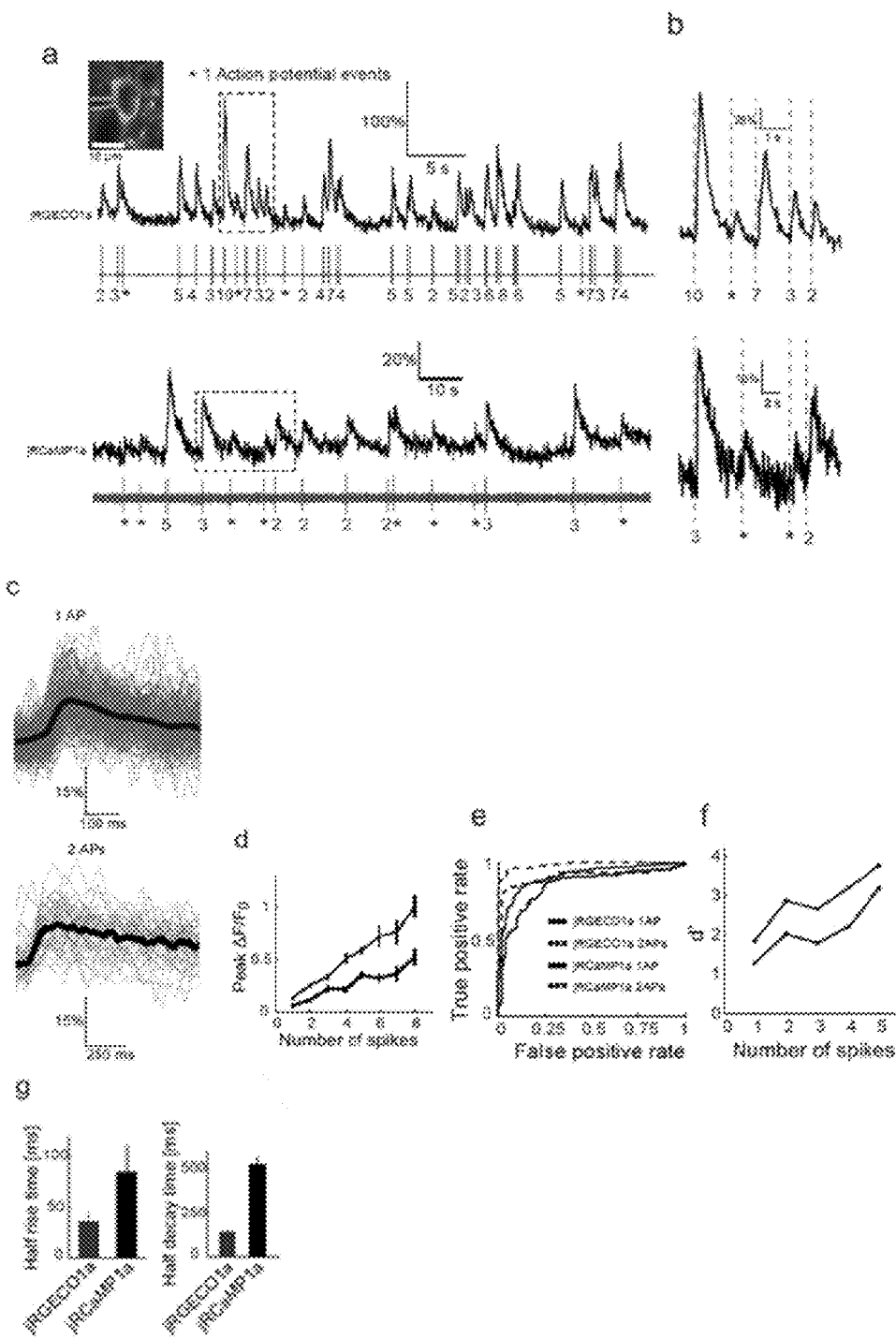
FIGS. 5A-G include combined imaging and electrophysiology in the mouse visual cortex (a) Simultaneous fluorescence dynamics and spikes measured from jRGECO1a (top, blue) and jRCaMP1a (bottom, black) expressing neurons. The number of spikes for each burst is indicated below the trace (single spikes are indicated by asterisks). Left inset, a jRCaMP1a expressing neuron with the recording pipette (green). (b) Zoomed-in view of bursts of action potentials. Top, jRGECO1a; bottom, jRCaMP1a. (c) jRGECO1a fluorescence changes in response to 1 AP (top, 215 spikes from 11 cells, n=6 mice), and jRCaMP1a fluorescence changes in response to 2 APs (bottom, 57 spikes from 10 cells, n=5 mice). Blue (top) and black (bottom) lines are the median traces. (d) Peak fluorescence change as a function of number of action potentials in a time bin (jRGECO1a: 215 1AP events; 2APs: 77 events within a 100 ms time bin; 3APs: 33, 125 ms; 4APs: 35, 150 ms; 5APS: 41, 175 ms; 6APs: 31, 200 ms; 7APs:15, 200 ms; 8APs: 17, 200 ms. jRCaMP1a: 107 1AP events; 2APs: 57, 150 ms; 3APs: 58, 200 ms; 4APs: 43, 250 ms; 5APS: 31, 300 ms; 6APs: 17, 350 ms; 7APs: 11, 350 ms; 8APs: 9, 350 ms). Error bars correspond to s.e.m. (e) Receiver operating characteristic (ROC) curve for classifying 1 and 2 APs for jRGECO1a and jRCaMP1a (jRGECO1a: 223 events of no AP firing within a 5 s bin, jRCaMP1a: 153 events of no AP firing within a 7 s bin, 1AP and 2APs data same as in d). (f) Detection sensitivity index (d') as a function of number of spikes in a time bin (same parameters as in d-e). (g) Comparison of median half decay (left) and rise (right) times of jRGECO1a and jRCaMP1a for 1AP response. Error bars correspond to s.e.m.

The relationship between somatic fluorescence changes and spiking in L2/3 cells were characterized by combining imaging with loose-seal, cell-attached recordings (FIG. 5a,b). The visual stimulus was adjusted online so that a large range of instantaneous firing rates were recorded for each cell. jRGECO1a fluorescence changes allowed relatively robust detection of activity (FIG. 5c,d). Single spikes were detected with 69.5% accuracy (5% false-positive rate, n=11 cells from 6 animals, 215 spikes) (FIG. 5e, f). Two APs in a time bin of 100 ms were detected with 94.8% accuracy (5% false-positive rate, n=11 cells from 6 animals, 77 events). Fluorescence changes of jRCaMP1a were smaller, with a detection rate for 1AP and 2AP events of 51% and 82.5% respectively (5% false-positive rate, n=10 cells from 5 animals, 107 and 57 events respectively). jRGECO1a showed higher $\Delta F/F_0$ amplitudes and better detection than jRCaMP1a over the entire range of AP bursts (FIG. 5d-f). jRGECO1a also had faster kinetics (FIG. 5g). Measured rise and decay time of jRGECO1a and jRCaMP1a were similar to GCaMP6f and GCaMP6s, respectively (Chen, Wardill et al. 2013).

Red Protein Calcium Indicators in *Drosophila*, Zebrafish, and *C. elegans*

Figures 6A, 6B, 6C, 6D:
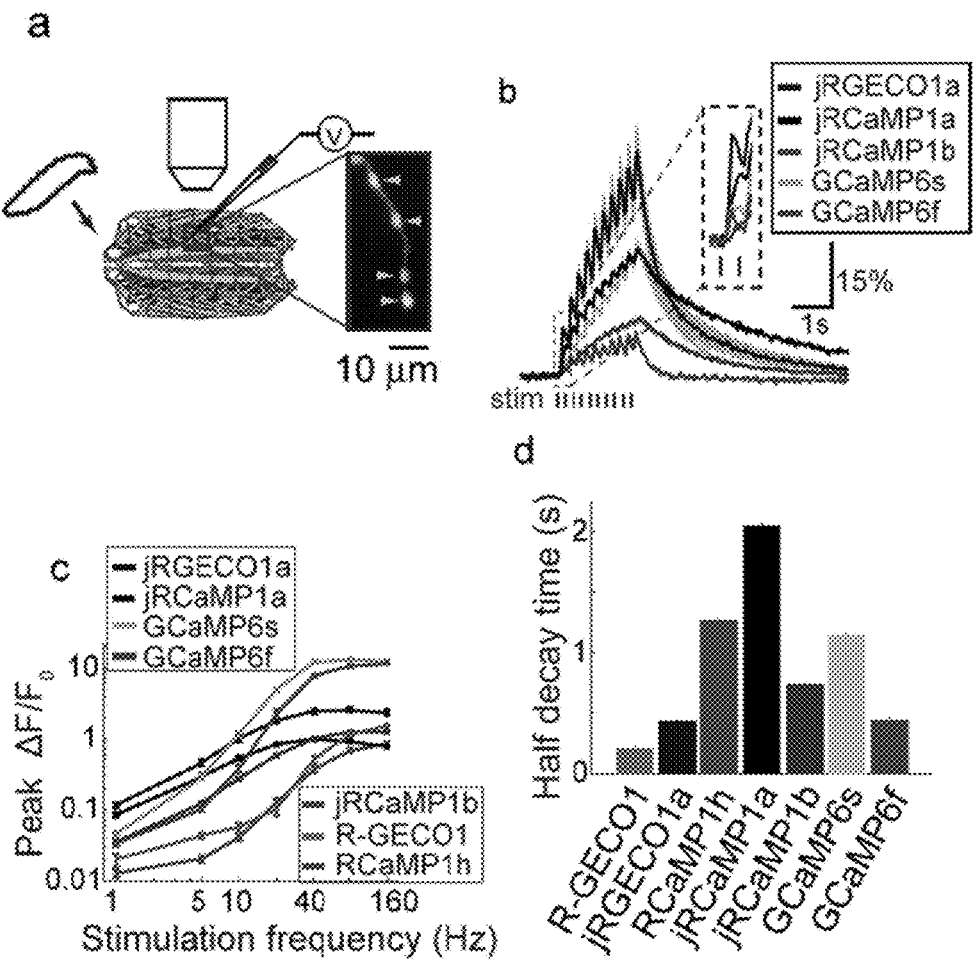
FIGS. 6A-D include data of red GECI performance in the *Drosophila* NMJ neurons (a) Schematic representation of *Drosophila* larval neuro-muscular junction (NMJ) assay. Segmented motor nerve is electrically stimulated while optically imaging calcium responses in presynaptic boutons (green arrows); (b) Response transients (mean±s.e.m.) to 5 Hz stimulation (2 s duration) for several red and green GECIs (12 FOVs for jRGECO1a; 11, jRCaMP1a; 13, jRCaMP1b; 12, GCaMP6s; 12, GCaMP6f; n=7 flies for all constructs); (c) Comparison of responses to various stimulus frequencies (peak $\Delta F/F_0$, mean±s.e.m.) of red and green GECIs for 1, 5, 10, 20, 40, 80 and 160 Hz stimulation (2 s duration). (12 FOVs for jRGECO1a; 10, R-GECO1; 11, jRCaMP1a; 13, jRCaMP1b; 10, RCaMP1h; 12, GCaMP6s; 12, GCaMP6f; n=5 flies for R-GECO1, n=7 flies for all other constructs); and (d) Half decay time (mean±s.e.m.) of red and green GECIs at 160 Hz stimulation (same FOVs and flies as in c).

Red GECIs were tested in *Drosophila*, zebrafish, and *C. elegans*. Red GECIs were expressed pan-neuronally in transgenic flies (R57C10-Gal4). Boutons were imaged in the larval neuromuscular junction (NMJ) after electrical stimulation (FIG. 6a, b; Methods). Consistent with cultured neuron data, a significant boost of single AP sensitivity was seen in jRGECO1a, jRCaMP1a, and jRCaMP1b variants compared to their parent indicators (P<0.008 for all comparisons; Wilcoxon rank sum test; FIG. 6c, FIGS. 24-25, Tables 3-5). Peak response amplitudes of jRGECO1a and jRCaMP1a outperform GCaMP6s in the 1-5 Hz stimulation range (single AP $\Delta F/F_0$ amplitude 11.6±0.9%, 8.6±0.5%, and 4.5±0.3% respectively, mean±s.e.m; FIG. 6c, FIG. 19, Table 5). The decay kinetics of jRGECO1a (half decay time at 160 Hz: 0.42±0.02s, mean±s.e.m) was similar to GCaMP6f (0.43±0.01s; FIG. 6d, FIG. 19, Table 5). The combination of high sensitivity and fast kinetics for jRGECO1a allows detection of individual spikes on top of the response envelope for stimuli up to 10 Hz (FIG. 6b, FIG. 17).

TABLE 5

GCaMP6 and red GECIs performance in *Drosophila* larval NMJ

| mean dF/F0 | stim. Frequency | GCaMP6s | GCaMP6f | jRCaMP1a | jRCaMP1b | jRGECO1a | SEM |
|---|---|---|---|---|---|---|---|
| | 1 | 0.045 | 0.034 | 0.086 | 0.035 | 0.116 | 1 |
| | 5 | 0.289 | 0.105 | 0.296 | 0.125 | 0.462 | 5 |
| | 10 | 1.168 | 0.383 | 0.526 | 0.275 | 1.015 | 10 |
| | 20 | 4.860 | 2.300 | 0.845 | 0.587 | 1.802 | 20 |
| | 40 | 12.057 | 7.794 | 0.992 | 1.011 | 2.475 | 40 |
| | 80 | 12.859 | 10.616 | 0.928 | 1.255 | 2.549 | 80 |
| | 160 | 12.240 | 11.489 | 0.780 | 1.252 | 2.348 | 160 |
| Half rise time (s) | mean | GCaMP6s | GCaMP6f | jRCaMP1a | jRCaMP1b | jRGECO1a | SEM |
| | 1 | 0.114 | 0.175 | 0.146 | 0.168 | 0.133 | 1 |
| | 5 | 0.916 | 0.431 | 0.636 | 0.746 | 0.684 | 5 |
| | 10 | 1.157 | 0.838 | 0.769 | 0.867 | 0.819 | 10 |
| | 20 | 1.166 | 0.940 | 0.669 | 0.875 | 0.669 | 20 |
| | 40 | 0.859 | 0.663 | 0.444 | 0.693 | 0.479 | 40 |
| | 80 | 0.431 | 0.337 | 0.298 | 0.464 | 0.316 | 80 |
| | 160 | 0.265 | 0.226 | 0.225 | 0.318 | 0.220 | 160 |
| Half decay time (s) | mean | GCaMP6s | GCaMP6f | jRCaMP1a | jRCaMP1b | jRGECO1a | SEM |
| | 1 | 0.440 | 0.413 | 0.573 | 0.381 | 0.232 | 1 |
| | 5 | 0.856 | 0.328 | 2.081 | 1.292 | 0.518 | 5 |
| | 10 | 0.949 | 0.334 | 2.075 | 1.320 | 0.533 | 10 |
| | 20 | 1.145 | 0.380 | 2.121 | 1.276 | 0.560 | 20 |
| | 40 | 1.208 | 0.395 | 2.088 | 1.002 | 0.542 | 40 |
| | 80 | 1.205 | 0.386 | 2.055 | 0.754 | 0.446 | 80 |
| | 160 | 1.139 | 0.434 | 2.038 | 0.729 | 0.419 | 160 |

TABLE 5-continued

GCaMP6 and red GECIs performance in *Drosophila* larval NMJ

| mean dF/F0 | stim. Frequency | GCaMP6s | GCaMP6f | jRCaMP1a | jRCaMP1b | jRGECO1a |
|---|---|---|---|---|---|---|
| | 1 | 0.003 | 0.002 | 0.005 | 0.003 | 0.009 |
| | 5 | 0.021 | 0.011 | 0.016 | 0.007 | 0.053 |
| | 10 | 0.073 | 0.048 | 0.029 | 0.013 | 0.119 |
| | 20 | 0.204 | 0.244 | 0.045 | 0.025 | 0.145 |
| | 40 | 0.338 | 0.399 | 0.051 | 0.033 | 0.174 |
| | 80 | 0.479 | 0.340 | 0.047 | 0.034 | 0.176 |
| | 160 | 0.542 | 0.342 | 0.037 | 0.042 | 0.171 |
| Half rise time (s) | mean | GCaMP6s | GCaMP6f | jRCaMP1a | jRCaMP1b | jRGECO1a |
| | 1 | 0.009 | 0.060 | 0.007 | 0.010 | 0.000 |
| | 5 | 0.028 | 0.052 | 0.024 | 0.027 | 0.026 |
| | 10 | 0.011 | 0.019 | 0.014 | 0.017 | 0.015 |
| | 20 | 0.012 | 0.012 | 0.016 | 0.012 | 0.022 |
| | 40 | 0.025 | 0.010 | 0.016 | 0.016 | 0.017 |
| | 80 | 0.007 | 0.004 | 0.009 | 0.010 | 0.009 |
| | 160 | 0.004 | 0.004 | 0.006 | 0.006 | 0.007 |
| Half decay time (s) | mean | GCaMP6s | GCaMP6f | jRCaMP1a | jRCaMP1b | jRGECO1a |
| | 1 | 0.061 | 0.093 | 0.053 | 0.072 | 0.033 |
| | 5 | 0.033 | 0.017 | 0.055 | 0.058 | 0.028 |
| | 10 | 0.031 | 0.015 | 0.033 | 0.047 | 0.025 |
| | 20 | 0.037 | 0.009 | 0.000 | 0.030 | 0.019 |
| | 40 | 0.026 | 0.008 | 0.000 | 0.020 | 0.012 |
| | 80 | 0.020 | 0.008 | 0.000 | 0.020 | 0.012 |
| | 160 | 0.014 | 0.010 | 0.008 | 0.020 | 0.015 |

TABLE 6

Comprehensive neuronal culture screening results for RCaMP1h variants

| RCaMP1h variant | # of wells | Mutations added to R-GECO1.0 |
|---|---|---|
| "RCaMP1h" | 589 | base |
| "R-CaMP2" | 9 | S38V S39K R40L R41I K42P W43S N44L K45T G47V H48I A49L R51K A52S I53M G54L L56K S57R A59F I60G 61_62insPFPVV C62S M64R A68E G71A R73K G74S Y75E T76I H77K M78K A79G K81R V82L D83K G84D L88Y S89A C90A S91E F92V V93K R97K S98A T101P 103_105delGNI K106Q M107L A109G I110A H111Y S112I S114D H115I R116K E118D R119I L120V E121S E122H S123N D124E N125D E126Y M127T F128I V130E R132C H134R V136E A137G K138R F139H V140S G141T L142G G144M G145D G146E G147L T148Y G149K S151G M152T N153G 153_166insGSLVSKGEEDNM S154A L155I N159F M162F V164L V165H L166M Q174E K176E C177I T178E N184M M187E G188A T189F M192A R193K I194L K195V I197V E198K F206W A210S T211P S212Q F213L R218K T219A F220Y Y223H K225A G226D F230Y Q233L T240R T245M R246N Y247F V252I T254H M256N T259S E262Q C265V L266F V267I H269K Q271K V272L V275T S279P N280D A282P K289M P293A D295R S296D T298L I357F K371S T373R S395G N405D E421V S424I 442_443insGGGTGGSGGGGGGEFPVKQTLNFDLLKLAGDVESNP |
| "jRCaMP1a" | 23 | T62C Y112S L298T |
| "jRCaMP1b" | 15 | T46W I60N L326M R368G |
| "206.3" | 8 | T294G |
| "206.4" | 7 | T294I |
| "206.8" | 4 | T294N |
| "206.9" | 4 | T294P |
| "206.10" | 8 | T294S |
| "206.11" | 7 | T294V |
| "206.14" | 6 | I303C |
| "206.15" | 8 | I303E |
| "206.17" | 7 | I303G |
| "206.18" | 7 | I303K |
| "206.19" | 7 | I303L |
| "206.20" | 5 | I303M |
| "206.21" | 6 | I303N |
| "206.22" | 7 | I303P |
| "206.23" | 7 | I303R |
| "206.24" | 8 | I303S |
| "206.25" | 7 | I303V |
| "206.26" | 7 | I303W |
| "206.27" | 8 | A309C |
| "206.28" | 39 | A309D |
| "206.29" | 8 | A309F |
| "206.30" | 7 | A309H |

TABLE 6-continued

Comprehensive neuronal culture screening results for RCaMP1h variants

| | | |
|---|---|---|
| "206.31" | 5 | A309K |
| "206.32" | 6 | A309M |
| "206.33" | 8 | A309P |
| "206.34" | 7 | A309Q |
| "206.35" | 7 | A309R |
| "206.36" | 28 | A309S |
| "206.38" | 7 | A309W |
| "206.39" | 7 | A309Y |
| "206.41" | 8 | I364C |
| "206.42" | 6 | I364D |
| "206.43" | 5 | I364E |
| "206.44" | 7 | I364F |
| "206.46" | 7 | I364L |
| "206.48" | 8 | I364Q |
| "206.50" | 7 | I364T |
| "206.51" | 6 | I364W |
| "206.52" | 7 | I364Y |
| "206.53" | 7 | R368F |
| "206.54" | 8 | R368M |
| "206.55" | 5 | R368N |
| "206.56" | 4 | R368P |
| "206.57" | 10 | R368Q |
| "206.58" | 10 | R368S |
| "206.59" | 7 | R368T |
| "206.60" | 7 | R368W |
| "206.61" | 4 | R368Y |
| "206.62" | 7 | T294A |
| "206.65" | 7 | T294C |
| "206.70" | 29 | I303D |
| "206.73" | 7 | I303Y |
| "206.74" | 6 | I303Q |
| "206.75" | 6 | A309I |
| "206.76" | 5 | A309L |
| "206.77" | 8 | A309E |
| "206.78" | 6 | A309N |
| "206.85" | 7 | R368L |
| "206.87" | 28 | R368G |
| "206.88" | 7 | A309T |
| "206.91" | 8 | R368I |
| "206.92" | 7 | R368K |
| "206.94" | 4 | I364G |
| "206.95" | 6 | A309G |
| "206.96" | 7 | R368H |
| "206.97" | 7 | L363T |
| "206.99" | 5 | L363R |
| "206.100" | 7 | S375I |
| "206.103" | 8 | S375P |
| "206.104" | 8 | S375Q |
| "206.106" | 5 | S375V |
| "206.107" | 8 | T373Q |
| "206.108" | 6 | T373M |
| "206.109" | 6 | T373N |
| "206.110" | 8 | T373P |
| "206.111" | 6 | T373S |
| "206.112" | 8 | T373V |
| "206.113" | 4 | T373E |
| "206.115" | 7 | T373C |
| "206.116" | 5 | T373I |
| "206.121" | 8 | T373G |
| "206.122" | 7 | T373L |
| "206.123" | 7 | T373R |
| "206.126" | 5 | S375C |
| "206.127" | 5 | S375G |
| "206.128" | 5 | S375H |
| "206.130" | 8 | S375T |
| "206.132" | 5 | L363I |
| "206.133" | 6 | L363W |
| "206.135" | 13 | Y75V |
| "206.137" | 7 | M64A |
| "206.138" | 7 | M64G |
| "206.139" | 8 | M64I |
| "206.140" | 12 | M64L |
| "206.141" | 4 | M64N |
| "206.143" | 4 | M64Q |
| "206.144" | 4 | M64R |
| "206.147" | 24 | M64C |
| "206.148" | 7 | M64D |
| "206.150" | 4 | M64H |

TABLE 6-continued

Comprehensive neuronal culture screening results for RCaMP1h variants

| | | |
|---|---|---|
| "206.152" | 8 | M64T |
| "206.153" | 4 | M64Y |
| "206.154" | 5 | Y75W |
| "206.155" | 5 | Y75A |
| "206.156" | 7 | Y75E |
| "206.157" | 31 | Y75K |
| "206.158" | 4 | L363A |
| "206.161" | 12 | T373K |
| "206.164" | 11 | A109C |
| "206.165" | 11 | A109D |
| "206.166" | 14 | A109E |
| "206.167" | 12 | A109F |
| "206.168" | 13 | A109H |
| "206.169" | 8 | A109K |
| "206.170" | 13 | A109L |
| "206.173" | 15 | A109S |
| "206.174" | 12 | A109T |
| "206.175" | 15 | A109V |
| "206.176" | 12 | A109W |
| "206.178" | 7 | E292G |
| "206.179" | 8 | E292H |
| "206.180" | 5 | E292N |
| "206.181" | 8 | E292Q |
| "206.182" | 8 | E292R |
| "206.183" | 8 | E292S |
| "206.184" | 7 | E292T |
| "206.185" | 8 | E292V |
| "206.186" | 8 | E292W |
| "206.187" | 6 | E292Y |
| "206.188" | 15 | H77Q |
| "206.190" | 8 | I110M |
| "206.193" | 5 | I110R |
| "206.194" | 5 | I110S |
| "206.195" | 6 | I110T |
| "206.196" | 6 | I110V |
| "206.197" | 6 | I110W |
| "206.200" | 6 | L298D |
| "206.201" | 7 | L298F |
| "206.203" | 8 | L298H |
| "206.206" | 43 | L298P |
| "206.207" | 8 | L298Q |
| "206.208" | 6 | L298R |
| "206.209" | 7 | L298S |
| "206.210" | 29 | L298T |
| "206.211" | 8 | L298V |
| "206.212" | 8 | L298W |
| "206.213" | 7 | L298Y |
| "206.226" | 11 | R73F |
| "206.227" | 14 | R73G |
| "206.228" | 7 | R73I |
| "206.230" | 15 | R73V |
| "206.231" | 8 | S114A |
| "206.234" | 4 | S114E |
| "206.236" | 5 | S114H |
| "206.237" | 9 | S114K |
| "206.238" | 4 | S114M |
| "206.239" | 6 | S114N |
| "206.241" | 6 | S114Q |
| "206.242" | 4 | S114R |
| "206.243" | 7 | S114T |
| "206.244" | 6 | S114V |
| "206.245" | 7 | S114W |
| "206.246" | 11 | A52G |
| "206.247" | 13 | A52Q |
| "206.249" | 7 | E292D |
| "206.250" | 4 | E292I |
| "206.252" | 5 | H77A |
| "206.253" | 10 | H77K |
| "206.254" | 7 | H77M |
| "206.255" | 7 | H77W |
| "206.256" | 42 | H77Y |
| "206.260" | 6 | P293C |
| "206.261" | 6 | P293D |
| "206.262" | 7 | P293Q |
| "206.263" | 14 | R73K |
| "206.264" | 5 | R73P |
| "206.265" | 5 | R73S |
| "206.268" | 6 | A109Y |

TABLE 6-continued

Comprehensive neuronal culture screening results for RCaMP1h variants

| | | |
|---|---|---|
| "206.269" | 5 | S114Y |
| "206.270" | 5 | A109G |
| "206.271" | 14 | A109N |
| "206.272" | 7 | E292F |
| "206.273" | 8 | E292L |
| "206.274" | 14 | H77L |
| "206.278" | 12 | R73C |
| "206.279" | 13 | R73Q |
| "206.281" | 8 | S114L |
| "206.282" | 12 | A52H |
| "206.283" | 11 | A52T |
| "206.288" | 4 | Y66Q |
| "206.292" | 8 | Y112C |
| "206.294" | 31 | Y112G |
| "206.295" | 7 | Y112I |
| "206.296" | 29 | Y112N |
| "206.297" | 7 | Y112Q |
| "206.298" | 28 | Y112S |
| "206.299" | 28 | Y112T |
| "206.300" | 7 | Y112V |
| "206.301" | 4 | Y112W |
| "206.330" | 5 | R73L |
| "206.332" | 11 | R73H |
| "206.338" | 14 | Y75G |
| "206.340" | 4 | Y75P |
| "206.341" | 14 | Y75S |
| "206.343" | 15 | Y75Q |
| "206.344" | 13 | Y75R |
| "206.346" | 8 | Y75C |
| "206.347" | 5 | L363C |
| "206.356" | 13 | E63D |
| "206.371" | 5 | A59R |
| "206.372" | 6 | A59S |
| "206.373" | 7 | A59D |
| "206.383" | 8 | A59K |
| "206.385" | 6 | A59G |
| "206.386" | 5 | A59E |
| "206.389" | 4 | W43G |
| "206.390" | 5 | W43F |
| "206.391" | 4 | W43E |
| "206.394" | 7 | W43L |
| "206.395" | 6 | W43M |
| "206.396" | 5 | W43Y |
| "206.397" | 4 | W43A |
| "206.398" | 4 | W43C |
| "206.400" | 5 | W43D |
| "206.401" | 6 | W43V |
| "206.403" | 5 | W43T |
| "206.405" | 5 | W43K |
| "206.406" | 15 | A52C |
| "206.407" | 13 | A52D |
| "206.409" | 12 | A52F |
| "206.410" | 10 | A52I |
| "206.411" | 7 | A52K |
| "206.412" | 5 | A52L |
| "206.413" | 7 | A52M |
| "206.414" | 13 | A52N |
| "206.415" | 13 | A52P |
| "206.416" | 11 | A52R |
| "206.417" | 14 | A52S |
| "206.418" | 15 | A52V |
| "206.419" | 11 | A52W |
| "206.420" | 7 | A52Y |
| "206.421" | 8 | T46A |
| "206.422" | 14 | T46E |
| "206.423" | 11 | T46F |
| "206.424" | 9 | T46G |
| "206.425" | 10 | T46K |
| "206.426" | 12 | T46L |
| "206.427" | 6 | T46M |
| "206.428" | 14 | T46P |
| "206.429" | 15 | T46Q |
| "206.430" | 26 | T46W |
| "206.431" | 11 | T46Y |
| "206.432" | 7 | H48A |
| "206.433" | 6 | H48C |
| "206.434" | 8 | H48D |
| "206.435" | 8 | H48E |

TABLE 6-continued

Comprehensive neuronal culture screening results for RCaMP1h variants

| | | |
|---|---|---|
| "206.437" | 7 | H48G |
| "206.438" | 7 | H48I |
| "206.439" | 6 | H48K |
| "206.440" | 5 | H48L |
| "206.441" | 5 | H48N |
| "206.442" | 6 | H48P |
| "206.443" | 8 | H48Q |
| "206.444" | 7 | H48R |
| "206.445" | 5 | H48S |
| "206.446" | 6 | H48T |
| "206.447" | 5 | H48V |
| "206.448" | 6 | H48W |
| "206.449" | 5 | H48Y |
| "206.450" | 6 | G47A |
| "206.451" | 7 | G47C |
| "206.453" | 5 | G47E |
| "206.454" | 7 | G47F |
| "206.455" | 6 | G47I |
| "206.457" | 21 | G47L |
| "206.460" | 8 | G47P |
| "206.461" | 8 | G47Q |
| "206.462" | 7 | G47R |
| "206.463" | 8 | G47S |
| "206.464" | 6 | G47T |
| "206.465" | 8 | G47V |
| "206.466" | 5 | G47W |
| "206.467" | 8 | G47Y |
| "206.468" | 7 | I60A |
| "206.469" | 7 | I60C |
| "206.470" | 7 | I60D |
| "206.471" | 20 | I60E |
| "206.472" | 7 | I60F |
| "206.473" | 6 | I60G |
| "206.474" | 7 | I60H |
| "206.475" | 8 | I60K |
| "206.476" | 6 | I60L |
| "206.477" | 23 | I60N |
| "206.478" | 8 | I60P |
| "206.479" | 7 | I60Q |
| "206.480" | 8 | I60R |
| "206.481" | 7 | I60S |
| "206.482" | 17 | I60T |
| "206.485" | 7 | I60Y |
| "206.487" | 7 | N61D |
| "206.493" | 4 | N61M |
| "206.495" | 7 | N61Q |
| "206.499" | 4 | N61Y |
| "206.500" | 6 | T62A |
| "206.501" | 21 | T62C |
| "206.502" | 7 | T62E |
| "206.504" | 7 | T62G |
| "206.506" | 7 | T62I |
| "206.507" | 6 | T62K |
| "206.508" | 4 | T62L |
| "206.509" | 6 | T62M |
| "206.511" | 5 | T62P |
| "206.512" | 7 | T62Q |
| "206.513" | 5 | T62R |
| "206.514" | 6 | T62V |
| "206.515" | 6 | T62W |
| "206.516" | 7 | T62Y |
| "206.517" | 10 | R73M |
| "206.518" | 7 | R73E |
| "206.519" | 13 | R73A |
| "206.520" | 13 | R73T |
| "206.521" | 6 | Y75D |
| "206.522" | 13 | Y75H |
| "206.523" | 10 | Y75I |
| "206.524" | 14 | H77E |
| "206.525" | 14 | H77F |
| "206.526" | 13 | H77S |
| "206.527" | 7 | H77I |
| "206.528" | 20 | H77C |
| "206.529" | 18 | H77G |
| "206.530" | 18 | H77T |
| "206.600" | 19 | Y66A |
| "206.603" | 5 | Y66E |
| "206.604" | 5 | Y66F |

TABLE 6-continued

Comprehensive neuronal culture screening results for RCaMP1h variants

| | | |
|---|---|---|
| "206.605" | 7 | Y66G |
| "206.606" | 7 | Y66H |
| "206.607" | 6 | Y66I |
| "206.608" | 4 | Y66K |
| "206.609" | 8 | Y66L |
| "206.610" | 8 | Y66M |
| "206.611" | 7 | Y66N |
| "206.613" | 6 | Y66R |
| "206.615" | 4 | Y66T |
| "206.617" | 5 | Y66W |
| "206.618" | 5 | V140A |
| "206.619" | 8 | V140C |
| "206.620" | 14 | V140D |
| "206.622" | 5 | V140F |
| "206.623" | 15 | V140G |
| "206.624" | 4 | V140H |
| "206.625" | 5 | V140I |
| "206.626" | 9 | V140K |
| "206.627" | 5 | V140L |
| "206.628" | 6 | V140M |
| "206.629" | 8 | V140N |
| "206.630" | 6 | V140P |
| "206.631" | 14 | V140Q |
| "206.632" | 6 | V140R |
| "206.633" | 4 | V140S |
| "206.634" | 6 | V140T |
| "206.635" | 8 | V140W |
| "206.636" | 7 | V140Y |
| "206.637" | 6 | D295A |
| "206.638" | 8 | D295C |
| "206.639" | 9 | D295E |
| "206.640" | 6 | D295F |
| "206.642" | 4 | D295H |
| "206.643" | 4 | D295I |
| "206.646" | 5 | D295M |
| "206.647" | 5 | D295N |
| "206.648" | 4 | D295P |
| "206.649" | 4 | D295Q |
| "206.650" | 4 | D295R |
| "206.651" | 5 | D295S |
| "206.652" | 4 | D295W |
| "206.653" | 4 | A367C |
| "206.654" | 4 | A367D |
| "206.655" | 4 | A367E |
| "206.656" | 4 | A367F |
| "206.659" | 5 | A367I |
| "206.662" | 5 | A367M |
| "206.666" | 5 | A367S |
| "206.667" | 4 | A367T |
| "206.668" | 5 | A367V |
| "206.669" | 4 | A367W |
| "206.670" | 5 | A367Y |
| "206.672" | 4 | S296D |
| "206.673" | 5 | S296F |
| "206.674" | 4 | S296G |
| "206.675" | 5 | S296H |
| "206.676" | 6 | S296I |
| "206.677" | 5 | S296K |
| "206.678" | 8 | S296L |
| "206.679" | 7 | S296M |
| "206.680" | 6 | S296N |
| "206.681" | 7 | S296P |
| "206.682" | 7 | S296T |
| "206.683" | 6 | S296V |
| "206.684" | 5 | S296W |
| "206.687" | 5 | F306C |
| "206.688" | 4 | F306D |
| "206.689" | 5 | F306G |
| "206.690" | 7 | F306H |
| "206.691" | 8 | F306I |
| "206.692" | 21 | R273S F306K |
| "206.693" | 7 | F306L |
| "206.694" | 7 | F306M |
| "206.695" | 4 | F306P |
| "206.696" | 8 | F306Q |
| "206.697" | 7 | F306R |
| "206.698" | 7 | F306T |
| "206.699" | 6 | F306V |

TABLE 6-continued

Comprehensive neuronal culture screening results for RCaMP1h variants

| | | |
|---|---|---|
| "206.700" | 6 | F306W |
| "206.701" | 7 | F306Y |
| "206.702" | 8 | D387C |
| "206.703" | 4 | D387E |
| "206.704" | 4 | D387F |
| "206.705" | 6 | D387H |
| "206.706" | 5 | D387K |
| "206.707" | 5 | D387M |
| "206.708" | 7 | D387R |
| "206.709" | 8 | D387S |
| "206.710" | 4 | D387T |
| "206.711" | 7 | D387V |
| "206.712" | 6 | D387W |
| "206.713" | 7 | D387Y |
| "206.714" | 7 | D389A |
| "206.715" | 7 | D389C |
| "206.716" | 7 | D389E |
| "206.717" | 8 | D389F |
| "206.718" | 8 | D389G |
| "206.719" | 5 | D389H |
| "206.720" | 7 | D389I |
| "206.721" | 6 | D389K |
| "206.722" | 6 | D389M |
| "206.723" | 5 | D389N |
| "206.724" | 4 | D389P |
| "206.725" | 6 | D389R |
| "206.726" | 7 | D389V |
| "206.727" | 8 | D389W |
| "206.728" | 6 | D389Y |
| "206.729" | 7 | D387L |
| "206.735" | 4 | V50H |
| "206.738" | 6 | V50L |
| "206.744" | 4 | V50T |
| "206.752" | 6 | R55G |
| "206.754" | 7 | R55I |
| "206.757" | 5 | R55M |
| "206.761" | 5 | R55V |
| "206.764" | 4 | L56A |
| "206.765" | 7 | L56E |
| "206.766" | 6 | L56F |
| "206.771" | 5 | L56N |
| "206.773" | 8 | L56Q |
| "206.774" | 7 | L56T |
| "206.775" | 6 | L56V |
| "206.776" | 5 | L56W |
| "206.777" | 4 | L56Y |
| "206.778" | 6 | V430H |
| "206.779" | 4 | V430P |
| "206.783" | 5 | V430T |
| "206.788" | 5 | V430R |
| "206.789" | 5 | V430C |
| "206.794" | 5 | I419V |
| "206.797" | 6 | I419M |
| "206.798" | 7 | I419Q |
| "206.800" | 4 | I419C |
| "206.801" | 6 | I419F |
| "206.802" | 4 | I419P |
| "206.805" | 7 | I419L |
| "206.806" | 6 | I419S |
| "206.807" | 5 | I419D |
| "206.808" | 5 | I419E |
| "206.809" | 7 | M418H |
| "206.810" | 5 | M418V |
| "206.811" | 6 | M418G |
| "206.812" | 6 | M418R |
| "206.814" | 5 | M418F |
| "206.815" | 5 | M418C |
| "206.816" | 5 | M418Q |
| "206.817" | 6 | M418P |
| "206.818" | 8 | M418E |
| "206.819" | 8 | M418Y |
| "206.820" | 7 | M418A |
| "206.822" | 6 | M418I |
| "206.823" | 7 | M418W |
| "206.824" | 5 | E421W |
| "206.825" | 6 | E421A |
| "206.826" | 8 | E421M |
| "206.827" | 4 | E421K |

TABLE 6-continued

Comprehensive neuronal culture screening results for RCaMP1h variants

| | | |
|---|---|---|
| "206.828" | 5 | E421L |
| "206.829" | 6 | E421V |
| "206.831" | 8 | E421I |
| "206.832" | 7 | E421G |
| "206.834" | 8 | E421S |
| "206.835" | 6 | A422K |
| "206.836" | 8 | A422R |
| "206.837" | 5 | A422W |
| "206.838" | 5 | A422F |
| "206.843" | 5 | A422I |
| "206.844" | 5 | A422V |
| "206.845" | 8 | A422S |
| "206.846" | 7 | A422E |
| "206.847" | 8 | A422P |
| "206.848" | 8 | A422Q |
| "206.849" | 8 | A422M |
| "206.850" | 7 | E417S |
| "206.851" | 7 | E417G |
| "206.852" | 4 | E417M |
| "206.853" | 5 | E417D |
| "206.854" | 5 | E417N |
| "206.855" | 4 | E417K |
| "206.856" | 5 | E417A |
| "206.858" | 7 | E417F |
| "206.859" | 8 | E417W |
| "206.860" | 7 | E417I |
| "206.861" | 5 | E417V |
| "206.862" | 8 | E417Q |
| "206.863" | 6 | E417L |
| "206.864" | 8 | D425N |
| "206.865" | 6 | D425Q |
| "206.866" | 4 | D425G |
| "206.867" | 8 | D425T |
| "206.868" | 7 | D425A |
| "206.869" | 7 | D425R |
| "206.870" | 7 | D425P |
| "206.871" | 7 | D425F |
| "206.872" | 8 | D425I |
| "206.873" | 7 | D425E |
| "206.874" | 7 | D425W |
| "206.875" | 7 | Q429D |
| "206.876" | 7 | Q429T |
| "206.879" | 7 | Q429S |
| "206.881" | 7 | Q429N |
| "206.882" | 6 | Q429K |
| "206.883" | 5 | Q429E |
| "206.884" | 4 | Q429L |
| "206.885" | 6 | Q429M |
| "206.886" | 4 | Q429I |
| "206.887" | 5 | Q429F |
| "206.888" | 5 | Q429Y |
| "206.890" | 4 | Q429H |
| "206.893" | 6 | G426F |
| "206.894" | 8 | G426M |
| "206.895" | 7 | G426T |
| "206.896" | 7 | G426K |
| "206.897" | 7 | G426I |
| "206.898" | 8 | G426D |
| "206.899" | 7 | G426N |
| "206.900" | 8 | G426Q |
| "206.901" | 8 | G426V |
| "206.902" | 7 | G426S |
| "206.903" | 8 | G426P |
| "206.904" | 8 | G426W |
| "206.905" | 7 | G426R |
| "206.906" | 6 | G426C |
| "206.907" | 4 | G426A |
| "206.908" | 6 | G426E |
| "206.910" | 5 | D427N |
| "206.911" | 6 | D427C |
| "206.912" | 4 | D427H |
| "206.914" | 5 | D427W |
| "206.915" | 7 | D427L |
| "206.916" | 4 | D427R |
| "206.917" | 4 | D427I |
| "206.919" | 7 | D427M |
| "206.920" | 7 | D427S |
| "206.921" | 5 | D427G |

TABLE 6-continued

Comprehensive neuronal culture screening results for RCaMP1h variants

| | | |
|---|---|---|
| "206.922" | 5 | D427K |
| "206.925" | 5 | V93A |
| "206.927" | 7 | V93D |
| "206.928" | 5 | V93E |
| "206.929" | 5 | V93F |
| "206.930" | 6 | V93G |
| "206.931" | 4 | V93H |
| "206.932" | 7 | V93I |
| "206.936" | 7 | V93Q |
| "206.937" | 5 | V93T |
| "206.938" | 4 | V93W |
| "206.939" | 18 | V93Y |
| "206.940" | 7 | K138C |
| "206.943" | 4 | K138G |
| "206.947" | 5 | K138M |
| "206.948" | 6 | K138N |
| "206.952" | 5 | K138Y |
| "206.953" | 6 | S279A |
| "206.960" | 5 | S279K |
| "206.961" | 5 | S279L |
| "206.962" | 4 | S279M |
| "206.964" | 4 | S279P |
| "206.965" | 5 | S279T |
| "206.969" | 8 | A351D |
| "206.970" | 9 | A351E |
| "206.971" | 8 | A351F |
| "206.972" | 7 | A351G |
| "206.973" | 7 | A351H |
| "206.974" | 8 | A351I |
| "206.975" | 9 | A351L |
| "206.976" | 8 | A351L |
| "206.977" | 7 | A351M |
| "206.979" | 4 | A351P |
| "206.980" | 6 | A351R |
| "206.981" | 8 | A351S |
| "206.982" | 6 | A351T |
| "206.983" | 10 | A351V |
| "206.984" | 7 | A351W |
| "206.985" | 7 | A351Y |
| "206.986" | 9 | S296R |
| "206.988" | 4 | I53C |
| "206.989" | 5 | I53D |
| "206.991" | 28 | I53F |
| "206.993" | 9 | I53K |
| "206.994" | 45 | I53M |
| "206.995" | 10 | I53P |
| "206.997" | 5 | I53R |
| "206.998" | 4 | I53S |
| "206.999" | 9 | I53T |
| "206.1000" | 10 | I53V |
| "206.1001" | 4 | I53Y |
| "206.1002" | 4 | G54A |
| "206.1003" | 10 | G54C |
| "206.1006" | 8 | G54F |
| "206.1007" | 4 | G54H |
| "206.1009" | 4 | G54K |
| "206.1011" | 6 | G54M |
| "206.1013" | 8 | G54R |
| "206.1014" | 5 | G54S |
| "206.1015" | 8 | G54T |
| "206.1016" | 6 | G54W |
| "206.1017" | 8 | G54Y |
| "206.1018" | 8 | S57A |
| "206.1019" | 10 | S57C |
| "206.1020" | 7 | S57D |
| "206.1021" | 10 | S57E |
| "206.1022" | 9 | S57F |
| "206.1023" | 9 | S57H |
| "206.1024" | 6 | S57I |
| "206.1025" | 8 | S57K |
| "206.1026" | 9 | S57L |
| "206.1027" | 5 | S57M |
| "206.1029" | 4 | S57R |
| "206.1030" | 4 | S57T |
| "206.1031" | 11 | S57V |
| "206.1032" | 9 | S57W |
| "206.1033" | 6 | S57Y |
| "206.1034" | 8 | S58A |

TABLE 6-continued

Comprehensive neuronal culture screening results for RCaMP1h variants

| | | |
|---|---|---|
| "206.1035" | 6 | S58C |
| "206.1036" | 4 | S58D |
| "206.1037" | 9 | S58F |
| "206.1038" | 7 | S58G |
| "206.1039" | 9 | S58I |
| "206.1040" | 9 | S58K |
| "206.1041" | 10 | S58L |
| "206.1042" | 10 | S58M |
| "206.1043" | 11 | S58N |
| "206.1044" | 9 | S58P |
| "206.1045" | 9 | S58Q |
| "206.1046" | 6 | S58R |
| "206.1047" | 10 | E417C |
| "206.1048" | 9 | E417R |
| "206.1050" | 9 | M418D |
| "206.1051" | 4 | M418L |
| "206.1052" | 4 | I419A |
| "206.1053" | 10 | I419W |
| "206.1054" | 7 | E421D |
| "206.1055" | 10 | E421N |
| "206.1056" | 10 | E421P |
| "206.1057" | 10 | E421Q |
| "206.1058" | 9 | E421T |
| "206.1059" | 9 | E421Y |
| "206.1060" | 7 | A422D |
| "206.1061" | 6 | A422G |
| "206.1062" | 6 | A422H |
| "206.1063" | 4 | A422N |
| "206.1064" | 5 | D425K |
| "206.1065" | 5 | D425L |
| "206.1066" | 5 | D425S |
| "206.1067" | 4 | G426H |
| "206.1068" | 4 | G426L |
| "206.1069" | 6 | D427A |
| "206.1070" | 5 | D427E |
| "206.1071" | 5 | D427F |
| "206.1072" | 7 | Q429G |
| "206.1074" | 5 | V430I |
| "206.1075" | 16 | Y112G L298P |
| "206.1076" | 17 | Y112G A309D |
| "206.1077" | 7 | Y112N A309P |
| "206.1081" | 21 | Y112V L298P |
| "206.1082" | 22 | Y112V A309D |
| "206.1083" | 29 | Y112V T373K |
| "206.1084" | 8 | D314A |
| "206.1085" | 7 | D314C |
| "206.1086" | 5 | D314E |
| "206.1087" | 6 | D314F |
| "206.1088" | 7 | D314G |
| "206.1089" | 6 | D314H |
| "206.1090" | 5 | D314I |
| "206.1091" | 11 | D314K |
| "206.1092" | 5 | D314L |
| "206.1093" | 8 | D314M |
| "206.1094" | 4 | D314N |
| "206.1095" | 4 | D314Q |
| "206.1096" | 4 | D314R |
| "206.1097" | 6 | D314T |
| "206.1098" | 6 | D314V |
| "206.1099" | 5 | D314W |
| "206.1100" | 5 | D314Y |
| "206.1101" | 5 | K315A |
| "206.1102" | 8 | K315C |
| "206.1103" | 9 | K315D |
| "206.1104" | 5 | K315F |
| "206.1105" | 6 | K315G |
| "206.1106" | 7 | K315H |
| "206.1107" | 6 | K315I |
| "206.1108" | 7 | K315L |
| "206.1109" | 6 | K315M |
| "206.1110" | 9 | K315P |
| "206.1111" | 6 | K315Q |
| "206.1112" | 7 | K315S |
| "206.1113" | 7 | K315T |
| "206.1114" | 4 | K315V |
| "206.1115" | 6 | K315W |
| "206.1116" | 5 | K315Y |
| "206.1117" | 7 | G317A |

TABLE 6-continued

Comprehensive neuronal culture screening results for RCaMP1h variants

| | | |
|---|---|---|
| "206.1118" | 6 | G317D |
| "206.1119" | 7 | G317E |
| "206.1120" | 7 | G317F |
| "206.1121" | 5 | G317H |
| "206.1122" | 9 | G317I |
| "206.1123" | 4 | G317K |
| "206.1124" | 7 | G317L |
| "206.1125" | 4 | G317M |
| "206.1126" | 6 | G317N |
| "206.1127" | 5 | G317P |
| "206.1128" | 11 | G317Q |
| "206.1129" | 5 | G317R |
| "206.1130" | 5 | G317T |
| "206.1131" | 6 | G317W |
| "206.1132" | 6 | G317Y |
| "206.1133" | 10 | D318A |
| "206.1134" | 4 | D318C |
| "206.1135" | 7 | D318E |
| "206.1136" | 4 | D318F |
| "206.1137" | 8 | D318G |
| "206.1138" | 9 | D318H |
| "206.1139" | 4 | D318I |
| "206.1140" | 8 | D318K |
| "206.1141" | 5 | D318L |
| "206.1142" | 5 | D318M |
| "206.1143" | 6 | D318P |
| "206.1144" | 10 | D318Q |
| "206.1145" | 10 | D318S |
| "206.1146" | 7 | D318T |
| "206.1147" | 5 | D318V |
| "206.1148" | 4 | D318W |
| "206.1149" | 4 | D318Y |
| "206.1150" | 10 | G319D |
| "206.1151" | 9 | G319E |
| "206.1153" | 6 | G319H |
| "206.1154" | 9 | G319I |
| "206.1155" | 6 | G319K |
| "206.1156" | 7 | G319L |
| "206.1157" | 7 | G319M |
| "206.1158" | 8 | G319N |
| "206.1159" | 8 | G319P |
| "206.1160" | 7 | G319Q |
| "206.1161" | 7 | G319T |
| "206.1162" | 8 | G319V |
| "206.1163" | 8 | G319W |
| "206.1164" | 8 | G319Y |
| "206.1165" | 7 | I321A |
| "206.1167" | 4 | I321D |
| "206.1168" | 8 | I321F |
| "206.1169" | 6 | I321G |
| "206.1170" | 7 | I321H |
| "206.1171" | 6 | I321K |
| "206.1172" | 7 | I321L |
| "206.1173" | 6 | I321M |
| "206.1174" | 8 | I321N |
| "206.1175" | 7 | I321P |
| "206.1176" | 5 | I321Q |
| "206.1177" | 7 | I321R |
| "206.1178" | 5 | I321S |
| "206.1179" | 7 | I321V |
| "206.1180" | 8 | I321W |
| "206.1181" | 8 | I321Y |
| "206.1182" | 7 | L326A |
| "206.1183" | 8 | L326C |
| "206.1184" | 5 | L326D |
| "206.1186" | 6 | L326F |
| "206.1187" | 7 | L326G |
| "206.1188" | 8 | L326I |
| "206.1190" | 19 | L326M |
| "206.1192" | 5 | L326P |
| "206.1194" | 8 | L326S |
| "206.1195" | 6 | L326V |
| "206.1196" | 6 | L326Y |
| "206.1197" | 5 | V329A |
| "206.1198" | 6 | V329C |
| "206.1199" | 7 | V329D |
| "206.1200" | 8 | V329E |
| "206.1202" | 6 | V329G |

TABLE 6-continued

Comprehensive neuronal culture screening results for RCaMP1h variants

| | | |
|---|---|---|
| "206.1204" | 7 | V329K |
| "206.1205" | 7 | V329M |
| "206.1206" | 5 | V329N |
| "206.1207" | 6 | V329P |
| "206.1209" | 6 | V329S |
| "206.1210" | 7 | V329T |
| "206.1211" | 6 | V329W |
| "206.1212" | 7 | V329Y |
| "206.1213" | 8 | M64C Y112N L298P |
| "206.1215" | 6 | R73F Y75K L298P A309D |
| "206.1216" | 29 | R73F Y75K L298P T373K |
| "206.1218" | 18 | Y75K L298P A309D T373K |
| "206.1219" | 18 | R73F Y75K L298P |
| "206.1220" | 20 | R73F Y75K A309D |
| "206.1221" | 22 | R73F Y75K T373K |
| "206.1222" | 21 | R73F A309D T373K |
| "206.1223" | 20 | Y75K L298P A309D |
| "206.1224" | 23 | L298P A309D T373K |
| "206.1225" | 20 | Y75K A309D T373K |
| "206.1226" | 21 | A52Y R73F |
| "206.1227" | 29 | H48G R73F |
| "206.1228" | 27 | A52Y Y75K |
| "206.1229" | 23 | H48G Y75K |
| "206.1230" | 21 | A52Y L298P |
| "206.1231" | 20 | H48G L298P |
| "206.1232" | 27 | A52Y A309D |
| "206.1233" | 29 | H48G T373K |
| "206.1234" | 27 | I60C R73F |
| "206.1235" | 52 | I60C L298P |
| "206.1236" | 25 | I60C A309D |
| "206.1240" | 5 | M64C L298P A309D |
| "206.1244" | 8 | H48G Y112G A309P |
| "206.1247" | 23 | M64C A309P |
| "206.1248" | 29 | M64C Y112G |
| "206.1249" | 23 | H48G M64C |
| "206.1250" | 40 | H77Y Y112G |
| "206.1251" | 22 | A52Y H77Y |
| "206.1252" | 25 | H48G H77Y |
| "206.1253" | 14 | L298P A309P |
| "206.1254" | 15 | R73F Y75K A309D T373K |
| "206.1255" | 17 | R73F L298P T373K |
| "206.1256" | 6 | H77Y L298P A309D |
| "206.1257" | 16 | H48G Y112N |
| "206.1258" | 23 | S58V |
| "206.1259" | 4 | S58Y |
| "206.1260" | 9 | D352A |
| "206.1261" | 8 | D352C |
| "206.1262" | 7 | D352E |
| "206.1263" | 6 | D352F |
| "206.1264" | 6 | D352G |
| "206.1265" | 7 | D352H |
| "206.1266" | 8.00 | D352K |
| "206.1267" | 8.00 | D352L |
| "206.1268" | 8.00 | D352P |
| "206.1269" | 8.00 | D352Q |
| "206.1270" | 8.00 | D352R |
| "206.1271" | 8.00 | D352S |
| "206.1272" | 8.00 | D352T |
| "206.1273" | 6.00 | D352V |
| "206.1274" | 7.00 | D352W |
| "206.1275" | 7.00 | D352Y |
| "206.1276" | 8.00 | D316A |
| "206.1277" | 7.00 | D316C |
| "206.1278" | 7.00 | D316F |
| "206.1279" | 4.00 | D316G |
| "206.1280" | 5.00 | D316H |
| "206.1281" | 5.00 | D316I |
| "206.1282" | 8.00 | D316K |
| "206.1283" | 6.00 | D316L |
| "206.1284" | 8.00 | D316M |
| "206.1285" | 8.00 | D316N |
| "206.1286" | 7.00 | D316Q |
| "206.1287" | 6.00 | D316R |
| "206.1288" | 6.00 | D316S |
| "206.1289" | 5.00 | D316V |
| "206.1290" | 6.00 | D316W |
| "206.1291" | 6.00 | D316Y |
| "206.1292" | 7.00 | E305A |

TABLE 6-continued

Comprehensive neuronal culture screening results for RCaMP1h variants

| | | |
|---|---|---|
| "206.1293" | 6.00 | E305C |
| "206.1294" | 5.00 | E305D |
| "206.1295" | 8.00 | E305F |
| "206.1296" | 7.00 | E305G |
| "206.1297" | 6.00 | E305H |
| "206.1298" | 7.00 | E305I |
| "206.1300" | 6.00 | E305M |
| "206.1301" | 7.00 | E305N |
| "206.1302" | 6.00 | E305P |
| "206.1303" | 5.00 | E305Q |
| "206.1304" | 4.00 | E305R |
| "206.1305" | 5.00 | E305S |
| "206.1306" | 4.00 | E305W |
| "206.1307" | 8.00 | E305Y |
| "206.1308" | 7.00 | A304C |
| "206.1309" | 8.00 | A304D |
| "206.1310" | 8.00 | A304E |
| "206.1311" | 8.00 | A304F |
| "206.1312" | 8.00 | A304G |
| "206.1313" | 11.00 | A304H |
| "206.1314" | 9.00 | A304K |
| "206.1315" | 10.00 | A304L |
| "206.1316" | 5.00 | A304N |
| "206.1317" | 5.00 | A304P |
| "206.1318" | 5.00 | A304R |
| "206.1319" | 4.00 | A304S |
| "206.1320" | 7.00 | A304T |
| "206.1321" | 7.00 | A304V |
| "206.1322" | 5.00 | A304Y |
| "206.1323" | 8.00 | R73F L298P A309D |
| "206.1324" | 12.00 | H48G A309D |
| "206.1325" | 10.00 | A52Y T373K |
| "206.1326" | 13.00 | I60C Y75K |
| "206.1327" | 14.00 | I60C T373K |
| "206.1329" | 10.00 | M64C H77Y L298P |
| "206.1330" | 6.00 | M64C H77Y A309D |
| "206.1334" | 12.00 | A52Y M64C |
| "206.1335" | 14.00 | H77Y A309P |
| "206.1336" | 8.00 | A52Y Y112N |
| "206.1337" | 11.00 | R73F Y112V |
| "206.1338" | 5.00 | Y75K Y112V |
| "206.1340" | 8.00 | A52Y Y112V |
| "206.1341" | 17.00 | H48G Y112V |
| "206.1343" | 19.00 | M64C Y112V |
| "206.1344" | 18.00 | H77Y Y112V |
| "206.1346" | 14.00 | T299A |
| "206.1347" | 11.00 | T299D |
| "206.1348" | 13.00 | T299E |
| "206.1349" | 11.00 | T299F |
| "206.1350" | 10.00 | T299G |
| "206.1351" | 8.00 | T299H |
| "206.1352" | 8.00 | T299L |
| "206.1353" | 29.00 | T299M |
| "206.1354" | 6.00 | T299N |
| "206.1355" | 9.00 | T299R |
| "206.1356" | 4.00 | T299V |
| "206.1357" | 4.00 | T299W |
| "206.1358" | 4.00 | T299Y |
| "206.1359" | 6.00 | E300C |
| "206.1360" | 11.00 | E300F |
| "206.1361" | 6.00 | E300H |
| "206.1362" | 8.00 | E300K |
| "206.1363" | 9.00 | E300M |
| "206.1364" | 4.00 | E300N |
| "206.1365" | 8.00 | E300P |
| "206.1370" | 5.00 | E300W |
| "206.1371" | 6.00 | E300Y |
| "206.1372" | 5.00 | E301A |
| "206.1373" | 6.00 | E301C |
| "206.1374" | 8.00 | E301D |
| "206.1375" | 4.00 | E301F |
| "206.1376" | 8.00 | E301G |
| "206.1380" | 6.00 | E301P |
| "206.1381" | 6.00 | E301Q |
| "206.1382" | 5.00 | E301R |
| "206.1383" | 5.00 | E301S |
| "206.1384" | 4.00 | E301T |
| "206.1385" | 6.00 | E301V |

TABLE 6-continued

Comprehensive neuronal culture screening results for RCaMP1h variants

| "206.1386" | 6.00 | E301W |
| "206.1387" | 7.00 | E301Y |
| "206.1388" | 7.00 | Q302C |
| "206.1389" | 5.00 | Q302E |
| "206.1390" | 6.00 | Q302F |
| "206.1392" | 6.00 | Q302H |
| "206.1393" | 7.00 | Q302I |
| "206.1394" | 5.00 | Q302K |
| "206.1397" | 5.00 | Q302N |
| "206.1398" | 4.00 | Q302P |
| "206.1401" | 4.00 | Q302T |
| "206.1403" | 8.00 | Q302W |
| "206.1404" | 6.00 | Q302Y |
| "206.1405" | 7.00 | Y75K L298P T373K |
| "206.1406" | 8.00 | H48G A52Y |
| "206.1410" | 8.00 | K106Y |
| "206.1411" | 5.00 | M107H |
| "206.1413" | 5.00 | M107T |
| "206.1414" | 5.00 | P108N |
| "206.1417" | 4.00 | P108D |
| "206.1418" | 8.00 | S375A |
| "206.1427" | 8.00 | K106G |
| "206.1429" | 7.00 | K106F |
| "206.1430" | 6.00 | K106R |
| "206.1431" | 7.00 | K106W |
| "206.1432" | 5.00 | K106M |
| "206.1434" | 7.00 | K106V |
| "206.1435" | 8.00 | M107R |
| "206.1436" | 7.00 | M107E |
| "206.1437" | 6.00 | M107Y |
| "206.1439" | 7.00 | P108H |
| "206.1441" | 9.00 | P108W |
| "206.1442" | 4.00 | P108F |
| "206.1443" | 6.00 | K106I |
| "206.1444" | 6.00 | K106P |
| "206.1457" | 14.00 | I60E T62C |
| "206.1458" | 26.00 | I60E V329F |
| "206.1459" | 14.00 | I60N T62C |
| "206.1460" | 16.00 | S58V I60T |
| "206.1461" | 15.00 | S58V R368G |
| "206.1462" | 16.00 | T46W I60N R368G |
| "206.1463" | 20.00 | T46W I60N A309S |
| "206.1464" | 15.00 | T46W I60N |
| "206.1465" | 15.00 | T46W I60T A309S |
| "206.1466" | 35.00 | T46W I60T L326M |
| "206.1467" | 16.00 | T46W S58V |
| "206.1468" | 14.00 | I60E Y112S L298T |
| "206.1469" | 16.00 | I60E Y112S T299M |
| "206.1470" | 15.00 | I60E Y112S |
| "206.1472" | 15.00 | I60E Y112T |
| "206.1473" | 13.00 | T62C Y112S R368G |
| "206.1474" | 14.00 | Y112S V329F |
| "206.1475" | 15.00 | A309S L326M |
| "206.1476" | 14.00 | I60N A309S |
| "206.1477" | 18.00 | I60N A309S R368G |
| "206.1478" | 22.00 | I60T A309S |
| "206.1479" | 15.00 | L298T T299M |
| "206.1480" | 15.00 | T46W A309S L326M |
| "206.1481" | 13.00 | T46W A309S R368G |
| "206.1482" | 19.00 | T62C T299M R368G |
| "206.1483" | 15.00 | I60N L326M |
| "206.1484" | 15.00 | L326M R368G |
| "206.1485" | 16.00 | T46W L326M |
| "206.1486" | 14.00 | T46W R368G |
| "206.1487" | 24.00 | I60E Y112T V329F |
| "206.1488" | 7.00 | T62C Y112S T299M |
| "206.1490" | 18.00 | Y112S V329F |
| "206.1491" | 16.00 | S58V A309S |
| "206.1492" | 21.00 | T46W S58V I60N A309S L326M |
| "206.1493" | 16.00 | V329F |
| "206.1494" | 16.00 | I60T R368G |
| "206.1495" | 14.00 | S58V I60N |
| "206.1496" | 14.00 | T46W I60N L326M |
| "206.1497" | 15.00 | T46W S58V A309S |
| "206.1498" | 33.00 | T46W S58V L326M |
| "206.1499" | 25.00 | I60E Y112S L298T |
| "206.1500" | 15.00 | Y112T V329F |
| "206.1501" | 10.00 | I60E T299M R368G |

TABLE 6-continued

Comprehensive neuronal culture screening results for RCaMP1h variants

| "206.1502" | 11.00 | I60N A309S L326M |
| "206.1503" | 14.00 | I60T A309S L326M |
| "206.1504" | 15.00 | S58V A309S L326M |
| "206.1505" | 14.00 | T62C L298T R368G |
| "206.1506" | 14.00 | I60T L326M |
| "206.1507" | 8.00 | S58V L326M |
| "206.1508" | 4.00 | I60E Y112S V329F |
| "206.1509" | 13.00 | I60E Y112S R368G L298T |
| "206.1510" | 23.00 | Y112T L298T V329F |
| "206.1511" | 27.00 | I60E L298T |
| "206.1512" | 16.00 | T46W A309S |
| "206.1513" | 19.00 | A309S L326M R368G |
| "206.1514" | 30.00 | I60N L326M R368G |
| "206.1515" | 15.00 | S58V L326M |
| "206.1516" | 13.00 | T46W L326M R368G |
| "206.1517" | 20.00 | T46W I60N A309S R368G |
| "206.1518" | 32.00 | T46W S58V I60T A309S L326M |
| "206.1520" | 17.00 | T46W I60T |
| "206.1522" | 16.00 | T62C Y112S L298T R368G |
| "206.1523" | 25.00 | Y112S L298T |
| "206.1524" | 16.00 | Y112T L298T |
| "206.1525" | 17.00 | A309S R368G |
| "206.1526" | 14.00 | I60E L298T V329F |
| "206.1527" | 12.00 | I60E L298T R368G |
| "206.1528" | 19.00 | L298T V329F |
| "206.1529" | 13.00 | I60N A309S L326M R368G |
| "206.1532" | 32.00 | Y112S T299M R368G |
| "206.1533" | 34.00 | I60E Y112S R368G |
| "206.1535" | 31.00 | T62C Y112S T299M R368G |
| "206.1536" | 19.00 | Y112S L298T V329F |
| "206.1537" | 22.00 | Y112S L298T R368G |
| "206.1538" | 15.00 | T46W I60N A309S L326M |

| RCaMP1h variant | 1 AP ΔF/F0 | 3 AP ΔF/F0 | 10 AP ΔF/F0 | 160 AP ΔF/F0 | Decay half time (10 AP) | F0 normalized to GFP fluoresceence |
|---|---|---|---|---|---|---|
| "RCaMP1h" | 1.00 | 1.00 | 1.00 | 1.00 | 1.00 | 1.00 |
| "R-CaMP2" | 8.69 | 9.38 | 6.98 | 0.88 | 0.40 | 1.77 |
| "jRCaMP1a" | 24.02 | 20.24 | 11.63 | 1.22 | 3.13 | 1.07 |
| "jRCaMP1b" | 12.96 | 15.82 | 14.27 | 2.31 | 1.15 | 1.48 |
| "206.3" | 0.30 | 0.65 | 0.22 | 0.04 | 0.26 | 0.61 |
| "206.4" | 1.40 | 0.71 | 0.22 | 0.03 | 1.66 | 0.67 |
| "206.8" | 1.95 | 1.07 | 0.31 | 0.01 | 0.09 | 0.86 |
| "206.9" | 3.10 | 1.53 | 0.46 | 0.02 | 0.23 | 0.74 |
| "206.10" | 0.07 | 0.12 | 0.16 | 0.43 | 0.26 | 0.85 |
| "206.11" | 1.00 | 0.64 | 0.24 | 0.03 | 0.58 | 0.76 |
| "206.14" | 0.76 | 1.13 | 1.32 | 1.02 | 0.95 | 0.91 |
| "206.15" | 1.43 | 0.95 | 0.57 | 0.48 | 0.50 | 0.76 |
| "206.17" | 3.36 | 2.33 | 1.88 | 1.11 | 0.97 | 0.64 |
| "206.18" | 1.62 | 0.75 | 0.30 | 0.19 | 0.17 | 1.70 |
| "206.19" | 0.89 | 1.36 | 1.56 | 1.03 | 1.07 | 0.73 |
| "206.20" | 1.16 | 1.46 | 1.49 | 1.47 | 0.91 | 0.68 |
| "206.21" | 0.63 | 0.39 | 0.63 | 0.66 | 0.36 | 0.67 |
| "206.22" | 0.47 | 0.65 | 0.68 | 0.94 | 0.70 | 0.24 |
| "206.23" | 0.79 | 0.68 | 0.21 | 0.24 | 0.38 | 0.96 |
| "206.24" | 1.55 | 0.84 | 0.83 | 0.81 | 0.51 | 0.94 |
| "206.25" | 1.72 | 1.38 | 1.22 | 1.07 | 1.09 | 1.12 |
| "206.26" | 3.23 | 2.72 | 2.58 | 1.33 | 1.16 | 0.93 |
| "206.27" | 0.83 | 1.01 | 1.54 | 1.36 | 1.54 | 0.71 |
| "206.28" | 2.28 | 1.99 | 2.09 | 1.27 | 0.91 | 0.66 |
| "206.29" | 2.36 | 1.79 | 1.60 | 1.37 | 0.90 | 0.70 |
| "206.30" | 1.91 | 1.18 | 0.88 | 0.63 | 0.89 | 1.12 |
| "206.31" | 1.69 | 0.99 | 0.77 | 0.43 | 0.76 | 0.87 |
| "206.32" | 1.16 | 1.79 | 1.80 | 1.55 | 0.90 | 1.02 |
| "206.33" | 1.72 | 1.31 | 1.58 | 1.22 | 0.73 | 0.89 |
| "206.34" | 2.07 | 0.80 | 0.76 | 0.67 | 0.67 | 1.00 |
| "206.35" | 2.01 | 0.87 | 0.95 | 0.58 | 0.82 | 1.38 |
| "206.36" | 0.38 | 0.89 | 1.35 | 1.29 | 0.95 | 1.07 |
| "206.38" | 2.98 | 2.91 | 2.44 | 1.05 | 1.81 | 1.01 |
| "206.39" | 3.04 | 2.30 | 1.89 | 1.07 | 0.92 | 0.89 |
| "206.41" | 0.32 | 0.50 | 0.58 | 0.70 | 0.46 | 0.97 |
| "206.42" | 1.00 | 0.45 | 0.22 | 0.19 | 0.28 | 1.07 |
| "206.43" | 0.90 | 0.68 | 0.28 | 0.09 | 0.74 | 1.63 |
| "206.44" | 1.43 | 1.10 | 0.98 | 0.81 | 0.94 | 1.23 |
| "206.46" | 0.85 | 0.69 | 0.68 | 0.89 | 0.77 | 1.08 |
| "206.48" | 0.71 | 0.59 | 0.21 | 0.46 | 0.48 | 1.33 |
| "206.50" | 1.57 | 0.78 | 0.72 | 0.71 | 0.61 | 1.25 |
| "206.51" | 3.26 | 2.63 | 1.94 | 0.89 | 0.87 | 1.33 |

TABLE 6-continued

Comprehensive neuronal culture screening results for RCaMP1h variants

| | | | | | | |
|---|---|---|---|---|---|---|
| "206.52" | 0.70 | 0.68 | 0.67 | 0.69 | 0.51 | 1.01 |
| "206.53" | 1.76 | 1.10 | 1.18 | 0.68 | 1.27 | 1.18 |
| "206.54" | 1.84 | 1.90 | 1.78 | 1.46 | 1.52 | 0.87 |
| "206.55" | 1.06 | 0.72 | 0.71 | 1.17 | 0.79 | 0.91 |
| "206.56" | 1.65 | 0.75 | 0.54 | 0.61 | 0.30 | 1.04 |
| "206.57" | 1.17 | 0.90 | 0.94 | 0.94 | 0.94 | 1.76 |
| "206.58" | 1.84 | 0.99 | 1.23 | 1.07 | 0.99 | 1.54 |
| "206.59" | 1.01 | 0.75 | 0.80 | 0.84 | 0.86 | 1.29 |
| "206.60" | 2.03 | 1.59 | 1.18 | 0.62 | 1.22 | 1.78 |
| "206.61" | 1.37 | 0.95 | 0.87 | 0.65 | 0.58 | 1.00 |
| "206.62" | 1.87 | 0.80 | 0.29 | 0.07 | 0.15 | 1.37 |
| "206.65" | 1.14 | 0.66 | 0.17 | 0.17 | 0.04 | 2.17 |
| "206.70" | 1.97 | 3.49 | 4.63 | 1.40 | 0.93 | 0.71 |
| "206.73" | 0.98 | 1.99 | 1.68 | 1.15 | 1.08 | 1.18 |
| "206.74" | 1.26 | 0.80 | 0.83 | 0.92 | 0.62 | 0.97 |
| "206.75" | 1.37 | 1.50 | 1.76 | 1.55 | 1.29 | 0.80 |
| "206.76" | 2.63 | 2.58 | 2.99 | 1.74 | 1.48 | 0.66 |
| "206.77" | 1.12 | 0.96 | 1.03 | 0.78 | 0.56 | 0.74 |
| "206.78" | 0.62 | 0.88 | 1.08 | 0.83 | 0.67 | 0.88 |
| "206.85" | 1.76 | 1.04 | 0.93 | 0.87 | 0.81 | 0.80 |
| "206.87" | 0.10 | 0.45 | 0.82 | 1.06 | 0.77 | 0.95 |
| "206.88" | 2.66 | 3.49 | 2.82 | 1.66 | 1.29 | 1.00 |
| "206.91" | 2.46 | 1.87 | 1.49 | 1.15 | 1.11 | 0.97 |
| "206.92" | 1.42 | 1.34 | 1.48 | 1.21 | 1.00 | 0.96 |
| "206.94" | 0.82 | 0.49 | 0.20 | 0.36 | 0.22 | 1.29 |
| "206.95" | 1.29 | 0.88 | 0.78 | 0.73 | 0.54 | 0.98 |
| "206.96" | 0.99 | 0.77 | 0.83 | 1.05 | 0.85 | 1.00 |
| "206.97" | 1.41 | 0.88 | 0.74 | 0.85 | 0.59 | 0.94 |
| "206.99" | 2.60 | 1.24 | 0.35 | 0.01 | 0.78 | 1.09 |
| "206.100" | 1.39 | 0.60 | 0.52 | 0.71 | 0.60 | 1.24 |
| "206.103" | 0.81 | 0.59 | 0.52 | 0.81 | 0.94 | 1.04 |
| "206.104" | 0.82 | 0.58 | 0.64 | 0.88 | 1.24 | 0.94 |
| "206.106" | 1.26 | 0.83 | 0.79 | 0.89 | 1.19 | 1.42 |
| "206.107" | 1.80 | 1.31 | 1.18 | 1.08 | 0.79 | 0.83 |
| "206.108" | 1.52 | 1.63 | 1.82 | 1.19 | 1.01 | 1.58 |
| "206.109" | 2.76 | 2.48 | 2.32 | 1.98 | 0.89 | 0.85 |
| "206.110" | 1.49 | 1.58 | 1.38 | 1.12 | 1.12 | 1.05 |
| "206.111" | 0.68 | 1.04 | 1.10 | 1.04 | 1.05 | 0.87 |
| "206.112" | 0.76 | 0.63 | 0.68 | 0.87 | 1.21 | 0.97 |
| "206.113" | 0.63 | 0.96 | 0.98 | 1.02 | 0.72 | 0.58 |
| "206.115" | 1.07 | 0.72 | 0.69 | 0.98 | 1.30 | 0.82 |
| "206.116" | 1.01 | 0.64 | 0.59 | 0.84 | 1.21 | 0.84 |
| "206.121" | 1.18 | 0.80 | 0.89 | 1.13 | 1.44 | 0.90 |
| "206.122" | 1.05 | 0.96 | 0.93 | 1.10 | 1.27 | 0.93 |
| "206.123" | 1.01 | 0.86 | 0.78 | 0.82 | 1.33 | 1.52 |
| "206.126" | 1.52 | 1.49 | 1.42 | 1.17 | 1.46 | 1.24 |
| "206.127" | 0.53 | 0.49 | 0.71 | 0.84 | 1.19 | 0.99 |
| "206.128" | 1.49 | 0.94 | 1.01 | 1.19 | 1.30 | 0.78 |
| "206.130" | 1.16 | 0.79 | 0.81 | 0.98 | 1.21 | 0.87 |
| "206.132" | 2.04 | 1.16 | 0.89 | 1.07 | 0.98 | 1.40 |
| "206.133" | 2.67 | 2.23 | 1.74 | 0.53 | 1.30 | 1.24 |
| "206.135" | 0.67 | 1.10 | 1.67 | 1.45 | 1.22 | 0.95 |
| "206.137" | 3.40 | 1.16 | 0.37 | 0.84 | 0.15 | 0.23 |
| "206.138" | 3.45 | 1.54 | 1.14 | 1.01 | 0.72 | 0.35 |
| "206.139" | 2.20 | 2.18 | 2.45 | 1.53 | 1.22 | 0.91 |
| "206.140" | 0.94 | 1.36 | 1.47 | 0.93 | 1.34 | 1.12 |
| "206.141" | 4.72 | 1.96 | 1.67 | 0.68 | 0.32 | 0.05 |
| "206.143" | 4.01 | 4.05 | 4.23 | 1.90 | 0.67 | 0.54 |
| "206.144" | 4.53 | 2.10 | 0.48 | 0.10 | 0.06 | 0.12 |
| "206.147" | 2.62 | 1.83 | 2.18 | 1.66 | 0.89 | 0.46 |
| "206.148" | 0.89 | 1.04 | 0.48 | 0.44 | 0.28 | 0.11 |
| "206.150" | 3.93 | 1.34 | 0.29 | 0.60 | 0.05 | 0.12 |
| "206.152" | 1.22 | 0.51 | 0.32 | 0.73 | 0.33 | 0.42 |
| "206.153" | 2.47 | 1.05 | 0.75 | 0.59 | 0.21 | 0.22 |
| "206.154" | 4.61 | 3.68 | 2.42 | 1.27 | 1.52 | 1.62 |
| "206.155" | 0.93 | 1.33 | 1.44 | 1.27 | 0.66 | 0.53 |
| "206.156" | 0.08 | 0.33 | 0.12 | 0.06 | 0.27 | 1.14 |
| "206.157" | 0.54 | 0.91 | 0.80 | 0.79 | 0.84 | 0.66 |
| "206.158" | 1.88 | 0.92 | 1.01 | 0.97 | 0.58 | 1.38 |
| "206.161" | 0.87 | 0.95 | 0.81 | 0.74 | 0.94 | 0.81 |
| "206.164" | 0.71 | 0.85 | 0.82 | 1.02 | 0.71 | 0.97 |
| "206.165" | 1.19 | 1.15 | 1.38 | 0.92 | 1.46 | 0.93 |
| "206.166" | 0.90 | 0.94 | 1.22 | 0.98 | 1.01 | 1.10 |
| "206.167" | 0.21 | 0.38 | 0.34 | 0.55 | 0.54 | 0.99 |
| "206.168" | 0.48 | 0.66 | 0.60 | 0.73 | 0.75 | 1.04 |
| "206.169" | 1.13 | 0.83 | 0.85 | 0.93 | 1.11 | 0.85 |
| "206.170" | 0.39 | 0.49 | 0.50 | 0.74 | 0.76 | 0.81 |
| "206.173" | 0.41 | 0.84 | 0.95 | 0.98 | 0.93 | 0.95 |

TABLE 6-continued

Comprehensive neuronal culture screening results for RCaMP1h variants

| | | | | | | |
|---|---|---|---|---|---|---|
| "206.174" | 0.82 | 1.00 | 1.02 | 0.98 | 1.01 | 0.91 |
| "206.175" | 0.39 | 0.81 | 0.90 | 0.96 | 0.78 | 0.81 |
| "206.176" | 0.56 | 0.87 | 0.92 | 0.80 | 1.29 | 0.82 |
| "206.178" | 1.47 | 0.97 | 0.79 | 0.83 | 0.83 | 0.58 |
| "206.179" | 1.30 | 1.02 | 1.03 | 0.94 | 0.80 | 0.84 |
| "206.180" | 0.44 | 0.40 | 0.72 | 0.80 | 0.52 | 0.85 |
| "206.181" | 1.30 | 0.97 | 0.77 | 1.11 | 0.71 | 0.94 |
| "206.182" | 1.10 | 0.55 | 0.39 | 0.57 | 0.85 | 0.79 |
| "206.183" | 0.85 | 0.64 | 0.23 | 0.41 | 0.45 | 0.87 |
| "206.184" | 1.39 | 0.80 | 0.45 | 0.64 | 0.61 | 0.83 |
| "206.185" | 0.72 | 0.52 | 0.31 | 0.48 | 0.52 | 0.94 |
| "206.186" | 2.29 | 1.20 | 0.86 | 0.79 | 0.77 | 0.74 |
| "206.187" | 2.03 | 1.54 | 1.36 | 1.13 | 0.99 | 0.66 |
| "206.188" | 0.80 | 0.72 | 0.77 | 1.14 | 0.73 | 0.93 |
| "206.190" | 0.11 | 0.37 | 0.91 | 0.88 | 0.59 | 0.78 |
| "206.193" | 2.54 | 0.34 | 0.12 | 0.88 | 0.08 | 0.44 |
| "206.194" | −0.40 | −0.12 | −0.12 | 0.63 | −0.01 | 0.32 |
| "206.195" | 1.26 | 0.77 | 0.38 | 1.03 | 0.34 | 0.52 |
| "206.196" | 1.48 | 0.83 | 0.45 | 0.94 | 0.91 | 0.77 |
| "206.197" | −0.07 | −0.07 | −0.02 | 0.20 | 0.02 | 0.68 |
| "206.200" | 4.04 | 3.02 | 3.19 | 1.01 | 0.73 | 0.53 |
| "206.201" | 2.04 | 1.95 | 1.65 | 1.17 | 1.05 | 1.12 |
| "206.203" | 2.01 | 1.85 | 1.58 | 1.31 | 0.72 | 0.88 |
| "206.206" | 2.49 | 2.59 | 2.56 | 1.19 | 1.48 | 0.89 |
| "206.207" | 1.65 | 1.79 | 2.37 | 1.63 | 0.70 | 0.72 |
| "206.208" | 3.26 | 2.93 | 2.04 | 0.29 | 0.89 | 0.49 |
| "206.209" | 7.89 | 6.92 | 6.65 | 1.70 | 0.87 | 0.69 |
| "206.210" | 4.40 | 5.38 | 5.70 | 1.95 | 1.09 | 0.70 |
| "206.211" | 2.35 | 1.96 | 2.77 | 1.78 | 0.76 | 1.00 |
| "206.212" | 1.31 | 1.12 | 1.21 | 1.04 | 0.72 | 0.94 |
| "206.213" | 0.60 | 0.95 | 1.21 | 0.89 | 0.66 | 0.69 |
| "206.226" | 1.75 | 0.94 | 0.57 | 0.80 | 0.61 | 0.69 |
| "206.227" | 1.91 | 2.10 | 2.48 | 1.09 | 0.69 | 0.45 |
| "206.228" | 1.52 | 0.71 | 0.53 | 0.68 | 0.65 | 0.99 |
| "206.230" | 0.68 | 0.43 | 0.42 | 0.82 | 0.59 | 1.16 |
| "206.231" | 2.53 | 2.20 | 2.16 | 1.54 | 1.15 | 1.22 |
| "206.234" | 0.63 | 0.64 | 0.74 | 1.01 | 0.63 | 0.74 |
| "206.236" | −0.05 | 0.84 | 0.93 | 0.92 | 1.80 | 0.73 |
| "206.237" | 1.89 | 1.14 | 0.76 | 0.64 | 0.91 | 0.97 |
| "206.238" | 0.21 | 0.59 | 0.75 | 1.02 | 1.22 | 0.71 |
| "206.239" | 1.00 | 1.16 | 1.38 | 1.26 | 1.00 | 0.77 |
| "206.241" | 0.07 | 0.19 | 0.21 | 0.57 | 0.63 | 0.82 |
| "206.242" | 0.42 | 0.15 | 0.09 | 0.17 | 0.06 | 0.42 |
| "206.243" | 0.68 | 0.73 | 0.85 | 1.09 | 0.70 | 0.52 |
| "206.244" | 1.12 | 0.59 | 0.53 | 0.80 | 0.65 | 0.60 |
| "206.245" | 1.01 | 1.64 | 1.47 | 1.20 | 0.99 | 0.64 |
| "206.246" | 2.21 | 1.95 | 1.94 | 1.13 | 1.28 | 0.91 |
| "206.247" | 0.55 | 0.51 | 0.40 | 0.20 | 0.67 | 0.92 |
| "206.249" | 0.15 | 0.49 | 0.58 | 0.90 | 0.62 | 0.67 |
| "206.250" | 0.25 | 0.18 | 0.07 | 0.28 | 0.07 | 0.69 |
| "206.252" | 2.39 | 1.68 | 1.97 | 1.98 | 0.66 | 0.72 |
| "206.253" | 0.41 | 0.40 | 0.31 | 0.50 | 0.54 | 1.02 |
| "206.254" | 0.54 | 0.96 | 1.22 | 1.07 | 0.59 | 0.61 |
| "206.255" | 2.35 | 1.77 | 2.16 | 1.57 | 0.68 | 0.44 |
| "206.256" | 1.79 | 2.07 | 2.12 | 1.46 | 0.97 | 0.48 |
| "206.260" | −0.21 | 0.01 | 0.05 | 0.33 | 0.05 | 0.76 |
| "206.261" | −0.60 | 0.05 | 0.07 | 0.38 | 0.05 | 0.57 |
| "206.262" | 0.09 | −0.02 | −0.01 | 0.10 | 0.04 | 1.09 |
| "206.263" | 0.38 | 0.69 | 0.77 | 0.85 | 0.82 | 1.28 |
| "206.264" | 2.84 | 1.24 | 0.72 | 0.67 | 0.17 | 0.13 |
| "206.265" | 0.71 | 0.39 | 0.56 | 0.62 | 0.37 | 0.74 |
| "206.268" | 0.66 | 0.58 | 0.59 | 0.68 | 0.96 | 0.71 |
| "206.269" | 1.81 | 2.68 | 2.29 | 2.01 | 0.95 | 0.52 |
| "206.270" | 1.25 | 0.98 | 1.32 | 1.13 | 1.42 | 0.76 |
| "206.271" | 0.94 | 0.97 | 0.88 | 0.97 | 1.09 | 0.96 |
| "206.272" | 0.60 | 1.18 | 1.12 | 1.01 | 0.74 | 0.92 |
| "206.273" | 0.09 | 0.22 | 0.25 | 0.46 | 0.53 | 1.06 |
| "206.274" | 0.48 | 0.79 | 0.86 | 0.99 | 0.81 | 0.88 |
| "206.278" | 0.28 | 0.35 | 0.39 | 0.67 | 0.49 | 0.97 |
| "206.279" | 0.15 | 0.33 | 0.35 | 0.57 | 0.53 | 0.80 |
| "206.281" | 0.09 | 0.42 | 0.38 | 0.44 | 1.04 | 1.03 |
| "206.282" | 0.31 | 0.51 | 0.29 | 0.16 | 0.36 | 0.78 |
| "206.283" | 0.94 | 1.17 | 0.93 | 0.51 | 0.76 | 1.07 |
| "206.288" | 2.03 | 0.61 | 0.96 | 0.78 | 0.43 | 0.29 |
| "206.292" | 3.20 | 2.10 | 2.34 | 1.60 | 0.69 | 0.94 |
| "206.294" | 5.16 | 2.01 | 2.15 | 1.50 | 0.64 | 0.34 |
| "206.295" | 3.94 | 3.84 | 3.63 | 1.59 | 0.88 | 0.92 |
| "206.296" | 5.97 | 4.29 | 4.13 | 1.17 | 0.95 | 0.43 |

TABLE 6-continued

Comprehensive neuronal culture screening results for RCaMP1h variants

| | | | | | | |
|---|---|---|---|---|---|---|
| "206.297" | 6.13 | 6.20 | 5.44 | 1.99 | 0.76 | 1.00 |
| "206.298" | 2.98 | 3.16 | 4.21 | 2.04 | 0.68 | 0.68 |
| "206.299" | 3.79 | 5.47 | 5.96 | 1.59 | 0.97 | 0.70 |
| "206.300" | 2.98 | 1.89 | 1.71 | 1.25 | 0.81 | 0.86 |
| "206.301" | 1.37 | 1.81 | 1.84 | 1.25 | 1.24 | 0.55 |
| "206.330" | 0.36 | 0.29 | 0.41 | 0.80 | 0.44 | 0.82 |
| "206.332" | 0.76 | 0.55 | 0.63 | 0.88 | 0.48 | 0.98 |
| "206.338" | 0.55 | 0.83 | 0.75 | 0.96 | 0.58 | 0.49 |
| "206.340" | 3.60 | 1.13 | 0.53 | 0.67 | 0.23 | 0.09 |
| "206.341" | 0.56 | 0.70 | 0.82 | 0.98 | 0.62 | 0.83 |
| "206.343" | 0.15 | 0.48 | 0.75 | 1.03 | 0.63 | 0.69 |
| "206.344" | 0.30 | 1.01 | 1.08 | 0.80 | 0.92 | 0.51 |
| "206.346" | 0.10 | 0.46 | 0.56 | 0.89 | 0.83 | 0.77 |
| "206.347" | 0.72 | 0.44 | 0.62 | 1.18 | 0.50 | 1.05 |
| "206.356" | 5.67 | 4.77 | 3.82 | 0.61 | 1.16 | 0.14 |
| "206.371" | 0.08 | 0.50 | 0.70 | 0.65 | 0.76 | 1.88 |
| "206.372" | 0.43 | 0.73 | 0.92 | 1.02 | 0.72 | 0.96 |
| "206.373" | 1.99 | 2.16 | 1.95 | 1.78 | 0.89 | 0.69 |
| "206.383" | 1.98 | 1.54 | 1.63 | 1.13 | 1.35 | 2.00 |
| "206.385" | 3.76 | 3.48 | 3.51 | 1.13 | 1.48 | 3.07 |
| "206.386" | 1.41 | 0.54 | 0.59 | 0.57 | 0.93 | 1.65 |
| "206.389" | −0.07 | 0.00 | −0.01 | 0.14 | −0.01 | 1.16 |
| "206.390" | 0.14 | 0.11 | 0.35 | 0.60 | 0.35 | 1.06 |
| "206.391" | 0.64 | −0.01 | 0.01 | 0.21 | 0.02 | 1.58 |
| "206.394" | 0.89 | 0.47 | 0.49 | 0.65 | 0.75 | 1.34 |
| "206.395" | −0.20 | −0.02 | 0.07 | 0.48 | 0.04 | 1.34 |
| "206.396" | 0.15 | 0.17 | 0.25 | 0.52 | 0.47 | 0.94 |
| "206.397" | −0.08 | −0.10 | 0.01 | 0.17 | 0.02 | 0.99 |
| "206.398" | 1.36 | 0.39 | 0.12 | 0.26 | 0.08 | 2.19 |
| "206.400" | −0.01 | −0.10 | 0.00 | 0.13 | 0.02 | 1.12 |
| "206.401" | 0.21 | 0.03 | 0.08 | 0.35 | 0.04 | 0.87 |
| "206.403" | 0.09 | −0.07 | 0.00 | 0.19 | 0.05 | 0.96 |
| "206.405" | 0.72 | 0.18 | 0.05 | 0.26 | 0.05 | 1.36 |
| "206.406" | 0.55 | 0.55 | 0.62 | 0.64 | 0.72 | 0.83 |
| "206.407" | 0.99 | 0.49 | 0.23 | 0.15 | 0.88 | 0.95 |
| "206.409" | 1.07 | 1.05 | 1.34 | 1.19 | 0.71 | 0.64 |
| "206.410" | 0.55 | 0.55 | 0.54 | 0.62 | 0.61 | 0.83 |
| "206.411" | 1.47 | 0.73 | 0.46 | 0.17 | 1.49 | 1.40 |
| "206.412" | 0.64 | 0.60 | 0.38 | 0.66 | 0.47 | 0.83 |
| "206.413" | 0.65 | 0.63 | 0.58 | 0.60 | 0.58 | 1.03 |
| "206.414" | 1.11 | 1.11 | 0.78 | 0.31 | 1.28 | 1.09 |
| "206.415" | 1.17 | 0.80 | 0.62 | 0.13 | 1.19 | 1.05 |
| "206.416" | 1.19 | 1.10 | 0.88 | 0.33 | 0.99 | 0.98 |
| "206.417" | 0.91 | 0.96 | 0.94 | 0.72 | 1.01 | 1.18 |
| "206.418" | 0.68 | 1.04 | 0.71 | 0.73 | 0.66 | 1.10 |
| "206.419" | 0.40 | 0.51 | 0.55 | 0.66 | 0.65 | 0.42 |
| "206.420" | 1.87 | 1.07 | 0.75 | 0.64 | 1.12 | 0.93 |
| "206.421" | 1.70 | 1.49 | 1.44 | 1.04 | 1.47 | 1.00 |
| "206.422" | 0.36 | 0.05 | 0.10 | 0.33 | 0.15 | 1.35 |
| "206.423" | 0.63 | 1.08 | 1.04 | 1.18 | 0.94 | 0.97 |
| "206.424" | 1.43 | 0.57 | 0.52 | 0.52 | 0.39 | 0.16 |
| "206.425" | −0.08 | −0.01 | 0.32 | 0.42 | 0.44 | 1.26 |
| "206.426" | 1.50 | 2.16 | 2.29 | 1.40 | 1.64 | 0.89 |
| "206.427" | 2.09 | 1.48 | 1.63 | 1.53 | 1.44 | 1.22 |
| "206.428" | 0.91 | 1.27 | 1.53 | 1.11 | 1.00 | 1.13 |
| "206.429" | 0.49 | 0.43 | 0.61 | 0.77 | 0.60 | 1.19 |
| "206.430" | 2.62 | 3.23 | 3.76 | 1.90 | 1.20 | 1.02 |
| "206.431" | 0.99 | 1.36 | 1.52 | 1.34 | 0.98 | 1.14 |
| "206.432" | 0.42 | 0.64 | 0.88 | 0.82 | 0.94 | 0.92 |
| "206.433" | 0.28 | 0.95 | 1.10 | 0.90 | 0.96 | 0.78 |
| "206.434" | 0.36 | 0.54 | 0.64 | 0.71 | 0.63 | 0.82 |
| "206.435" | 0.37 | 0.67 | 0.62 | 0.42 | 0.58 | 0.89 |
| "206.437" | −0.14 | 0.12 | 0.51 | 0.68 | 0.74 | 0.97 |
| "206.438" | 1.30 | 0.91 | 0.83 | 0.87 | 1.42 | 0.96 |
| "206.439" | 1.61 | 0.90 | 0.69 | 0.47 | 1.53 | 1.15 |
| "206.440" | 1.58 | 0.78 | 0.91 | 0.77 | 1.00 | 0.97 |
| "206.441" | 1.25 | 1.34 | 1.21 | 0.95 | 1.28 | 1.23 |
| "206.442" | 1.62 | 0.43 | 0.15 | 0.41 | 0.10 | 1.79 |
| "206.443" | 1.39 | 1.13 | 0.86 | 0.70 | 1.08 | 1.55 |
| "206.444" | 1.97 | 1.24 | 0.91 | 0.76 | 1.33 | 1.36 |
| "206.445" | 1.85 | 1.10 | 0.88 | 0.69 | 1.13 | 1.93 |
| "206.446" | 1.63 | 1.02 | 0.97 | 0.88 | 1.19 | 1.12 |
| "206.447" | 2.21 | 1.41 | 1.35 | 1.01 | 1.46 | 1.51 |
| "206.448" | 1.80 | 1.37 | 1.36 | 1.07 | 1.59 | 0.98 |
| "206.449" | 1.50 | 1.14 | 1.07 | 0.74 | 0.98 | 1.35 |
| "206.450" | 1.75 | 1.60 | 1.66 | 1.29 | 1.51 | 1.00 |
| "206.451" | 1.85 | 2.04 | 1.34 | 0.79 | 1.32 | 1.01 |
| "206.453" | 1.35 | 0.38 | 0.18 | 0.50 | 0.11 | 1.46 |

TABLE 6-continued

Comprehensive neuronal culture screening results for RCaMP1h variants

| | | | | | | |
|---|---|---|---|---|---|---|
| "206.454" | 3.08 | 2.81 | 2.26 | 1.45 | 1.45 | 1.50 |
| "206.455" | 2.86 | 1.96 | 1.27 | 0.88 | 2.24 | 1.34 |
| "206.457" | 0.50 | 1.39 | 1.67 | 1.33 | 1.60 | 0.88 |
| "206.460" | 0.09 | 0.10 | 0.32 | 0.46 | 0.22 | 0.99 |
| "206.461" | 0.93 | 1.22 | 1.42 | 1.15 | 1.07 | 0.98 |
| "206.462" | 2.87 | 3.31 | 2.73 | 1.71 | 1.42 | 0.83 |
| "206.463" | 0.91 | 1.42 | 1.64 | 1.33 | 1.10 | 0.91 |
| "206.464" | 0.51 | 0.86 | 1.12 | 1.03 | 0.88 | 0.85 |
| "206.465" | 2.05 | 1.96 | 1.92 | 1.39 | 1.15 | 0.70 |
| "206.466" | 2.60 | 2.71 | 2.54 | 1.58 | 1.08 | 0.67 |
| "206.467" | 3.89 | 3.33 | 2.75 | 1.55 | 1.29 | 0.68 |
| "206.468" | 8.81 | 8.39 | 6.92 | 1.46 | 0.97 | 1.02 |
| "206.469" | 6.40 | 5.85 | 5.94 | 1.71 | 1.00 | 1.00 |
| "206.470" | 12.29 | 7.29 | 6.85 | 1.41 | 0.95 | 0.69 |
| "206.471" | 2.64 | 4.91 | 6.77 | 1.79 | 1.00 | 0.71 |
| "206.472" | 0.48 | 1.00 | 1.12 | 0.48 | 1.94 | 1.99 |
| "206.473" | 5.21 | 3.89 | 3.47 | 0.58 | 1.31 | 0.95 |
| "206.474" | 9.72 | 8.32 | 6.33 | 1.56 | 1.18 | 1.40 |
| "206.475" | 5.04 | 5.32 | 5.71 | 2.13 | 0.72 | 0.83 |
| "206.476" | 1.12 | 1.01 | 1.06 | 0.96 | 0.82 | 0.94 |
| "206.477" | 1.30 | 2.04 | 3.08 | 1.50 | 0.91 | 0.99 |
| "206.478" | 6.68 | 5.66 | 5.66 | 1.15 | 1.06 | 1.29 |
| "206.479" | 4.48 | 5.85 | 6.16 | 1.51 | 0.86 | 0.85 |
| "206.480" | 4.98 | 4.74 | 4.55 | 1.54 | 0.77 | 1.15 |
| "206.481" | 6.17 | 6.06 | 5.65 | 1.21 | 0.83 | 0.87 |
| "206.482" | 1.54 | 3.34 | 4.40 | 1.83 | 0.87 | 0.92 |
| "206.485" | 2.41 | 2.48 | 2.72 | 1.44 | 1.24 | 1.21 |
| "206.487" | 4.30 | 6.98 | 7.25 | 2.36 | 1.10 | 0.82 |
| "206.493" | 9.31 | 1.82 | 1.19 | 0.23 | 1.00 | 0.19 |
| "206.495" | 6.83 | 4.75 | 3.26 | 0.59 | 2.06 | 0.56 |
| "206.499" | 12.74 | 2.11 | 1.36 | 0.13 | 1.17 | 0.34 |
| "206.500" | 2.28 | 2.88 | 2.76 | 1.68 | 0.57 | 0.79 |
| "206.501" | 0.81 | 1.56 | 2.46 | 1.82 | 0.82 | 0.64 |
| "206.502" | 0.09 | 0.30 | 0.56 | 1.06 | 0.40 | 1.21 |
| "206.504" | 6.40 | 6.27 | 8.40 | 2.41 | 0.59 | 0.42 |
| "206.506" | 1.05 | 1.07 | 1.46 | 1.51 | 0.90 | 0.60 |
| "206.507" | 0.28 | 0.78 | 0.83 | 0.49 | 0.32 | 0.49 |
| "206.508" | 1.64 | 1.99 | 1.81 | 1.49 | 0.88 | 0.61 |
| "206.509" | 4.52 | 4.72 | 4.13 | 2.10 | 0.92 | 0.96 |
| "206.511" | 1.68 | 1.39 | 1.50 | 1.10 | 0.66 | 0.30 |
| "206.512" | 0.84 | 1.13 | 1.65 | 1.72 | 0.79 | 1.32 |
| "206.513" | 1.01 | 1.35 | 1.10 | 0.37 | 0.43 | 0.49 |
| "206.514" | 1.31 | 1.29 | 1.10 | 1.70 | 0.65 | 0.82 |
| "206.515" | 1.47 | 0.73 | 0.67 | 0.16 | 0.70 | 1.72 |
| "206.516" | 2.32 | 2.27 | 2.68 | 0.75 | 1.38 | 1.56 |
| "206.517" | 0.65 | 0.50 | 0.74 | 0.98 | 0.62 | 1.07 |
| "206.518" | 0.68 | 0.30 | 0.34 | 0.45 | 0.31 | 1.22 |
| "206.519" | 0.58 | 0.59 | 0.73 | 0.73 | 0.54 | 1.06 |
| "206.520" | 0.45 | 0.39 | 0.35 | 0.68 | 0.63 | 1.09 |
| "206.521" | 0.58 | 0.48 | 0.70 | 0.83 | 0.36 | 1.36 |
| "206.522" | 0.28 | 0.57 | 0.68 | 0.77 | 0.65 | 0.99 |
| "206.523" | 2.80 | 3.80 | 4.07 | 1.79 | 1.19 | 0.88 |
| "206.524" | 1.45 | 1.54 | 2.01 | 1.45 | 0.86 | 0.65 |
| "206.525" | 2.43 | 2.79 | 2.78 | 1.48 | 1.13 | 0.88 |
| "206.526" | 1.22 | 1.12 | 1.34 | 1.15 | 0.90 | 0.90 |
| "206.527" | 1.68 | 1.96 | 1.50 | 1.17 | 0.91 | 0.97 |
| "206.528" | 1.57 | 1.87 | 2.13 | 1.41 | 1.04 | 0.98 |
| "206.529" | 1.72 | 1.98 | 2.26 | 1.91 | 0.98 | 0.71 |
| "206.530" | 0.94 | 1.09 | 1.17 | 1.18 | 0.79 | 0.69 |
| "206.600" | 2.66 | 2.36 | 2.36 | 0.88 | 0.61 | 0.51 |
| "206.603" | 2.34 | 0.86 | 0.20 | 0.27 | 0.05 | 0.63 |
| "206.604" | 1.19 | 1.03 | 0.80 | 0.66 | 0.65 | 1.28 |
| "206.605" | 3.13 | 0.87 | 1.11 | 0.63 | 0.56 | 0.26 |
| "206.606" | 2.81 | 1.17 | 1.10 | 0.89 | 0.72 | 0.63 |
| "206.607" | 1.35 | 0.92 | 0.87 | 0.65 | 0.60 | 0.72 |
| "206.608" | 2.88 | 0.93 | 0.42 | 0.52 | 0.24 | 0.71 |
| "206.609" | 1.17 | 1.18 | 1.05 | 1.09 | 0.84 | 0.48 |
| "206.610" | 1.34 | 1.41 | 1.56 | 1.19 | 0.71 | 0.43 |
| "206.611" | 4.50 | 0.75 | 0.67 | 0.46 | 0.90 | 0.29 |
| "206.613" | 3.98 | 1.25 | 0.91 | 0.82 | 0.48 | 0.41 |
| "206.615" | 1.99 | 1.08 | 0.77 | 0.62 | 0.73 | 0.69 |
| "206.617" | 3.61 | 3.52 | 3.04 | 1.15 | 1.76 | 1.27 |
| "206.618" | 3.77 | 2.16 | 1.86 | 0.57 | 1.38 | 0.98 |
| "206.619" | 3.87 | 2.56 | 2.02 | 1.01 | 1.39 | 1.27 |
| "206.620" | 4.74 | 3.27 | 2.53 | 0.75 | 1.02 | 0.23 |
| "206.622" | 3.76 | 2.89 | 2.04 | 0.98 | 0.93 | 0.98 |
| "206.623" | 4.51 | 3.38 | 2.59 | 0.86 | 0.99 | 0.28 |
| "206.624" | 3.32 | 1.36 | 1.16 | 0.81 | 0.82 | 0.21 |

TABLE 6-continued

Comprehensive neuronal culture screening results for RCaMP1h variants

| | | | | | | |
|---|---|---|---|---|---|---|
| "206.625" | 1.26 | 0.78 | 0.68 | 0.89 | 0.90 | 1.05 |
| "206.626" | 4.02 | 2.81 | 2.39 | 0.72 | 0.98 | 0.38 |
| "206.627" | 3.14 | 1.28 | 1.32 | 0.66 | 1.17 | 1.15 |
| "206.628" | 3.14 | 2.31 | 2.34 | 1.15 | 1.18 | 0.99 |
| "206.629" | 5.08 | 4.47 | 4.03 | 1.41 | 1.20 | 0.51 |
| "206.630" | 2.79 | 3.19 | 2.67 | 1.77 | 0.99 | 0.67 |
| "206.631" | 4.30 | 3.03 | 2.34 | 0.75 | 0.85 | 0.23 |
| "206.632" | 4.15 | 3.17 | 3.40 | 1.42 | 1.16 | 0.27 |
| "206.633" | 3.34 | 2.39 | 2.14 | 0.56 | 0.92 | 0.65 |
| "206.634" | 3.06 | 2.77 | 2.18 | 0.83 | 1.23 | 0.66 |
| "206.635" | 2.41 | 1.70 | 1.96 | 1.38 | 0.73 | 0.57 |
| "206.636" | 1.40 | 1.06 | 1.42 | 0.89 | 0.69 | 0.64 |
| "206.637" | 2.06 | 0.79 | 0.38 | 0.45 | 0.83 | 1.58 |
| "206.638" | 1.82 | 1.03 | 0.61 | 0.71 | 0.76 | 1.38 |
| "206.639" | 1.20 | 0.72 | 0.57 | 0.47 | 0.73 | 1.72 |
| "206.640" | 2.40 | 0.75 | 0.32 | 0.34 | 0.32 | 0.82 |
| "206.642" | 2.14 | 1.06 | 0.35 | 0.26 | 0.13 | 1.06 |
| "206.643" | 1.28 | 0.86 | 0.45 | 0.40 | 0.69 | 1.50 |
| "206.646" | 1.41 | 1.33 | 0.96 | 0.67 | 0.88 | 0.93 |
| "206.647" | 1.20 | 0.99 | 0.95 | 0.62 | 0.98 | 1.30 |
| "206.648" | 1.74 | 0.79 | 0.26 | 0.09 | 0.70 | 0.89 |
| "206.649" | 1.84 | 0.96 | 0.80 | 0.86 | 1.00 | 1.24 |
| "206.650" | 1.58 | 1.02 | 0.68 | 0.62 | 0.76 | 1.21 |
| "206.651" | 1.26 | 0.91 | 0.39 | 0.40 | 0.83 | 0.71 |
| "206.652" | 2.25 | 0.80 | 0.23 | 0.04 | 0.13 | 1.15 |
| "206.653" | 2.06 | 1.66 | 1.24 | 0.90 | 1.04 | 0.68 |
| "206.654" | 1.20 | 0.85 | 0.55 | 0.69 | 0.76 | 1.41 |
| "206.655" | 0.32 | 0.75 | 0.45 | 0.63 | 0.80 | 0.80 |
| "206.656" | 2.97 | 3.42 | 2.77 | 0.87 | 1.81 | 1.14 |
| "206.659" | 3.06 | 1.76 | 1.57 | 1.16 | 1.83 | 1.13 |
| "206.662" | 1.31 | 1.88 | 1.82 | 1.01 | 3.03 | 1.28 |
| "206.666" | 2.18 | 1.23 | 1.10 | 1.05 | 1.53 | 0.72 |
| "206.667" | 2.12 | 2.02 | 1.83 | 0.83 | 1.71 | 1.78 |
| "206.668" | 1.81 | 1.31 | 1.29 | 0.71 | 1.35 | 0.68 |
| "206.669" | 1.95 | 1.94 | 1.61 | 0.61 | 1.50 | 1.75 |
| "206.670" | 2.15 | 1.46 | 1.24 | 0.80 | 0.65 | 1.33 |
| "206.672" | 1.64 | 1.48 | 1.42 | 1.33 | 1.55 | 0.49 |
| "206.673" | 0.53 | 0.66 | 0.39 | 0.55 | 1.36 | 0.71 |
| "206.674" | 1.15 | 0.99 | 0.83 | 0.71 | 1.57 | 0.75 |
| "206.675" | 0.76 | 0.68 | 0.69 | 0.69 | 1.15 | 0.88 |
| "206.676" | 0.96 | 0.86 | 0.25 | 0.40 | 1.19 | 0.63 |
| "206.677" | 1.05 | 0.83 | 0.36 | 0.35 | 1.15 | 0.71 |
| "206.678" | 0.90 | 0.78 | 0.28 | 0.34 | 0.53 | 0.58 |
| "206.679" | 2.07 | 1.64 | 1.38 | 1.45 | 1.31 | 0.71 |
| "206.680" | 1.98 | 1.36 | 1.31 | 1.18 | 0.93 | 1.35 |
| "206.681" | 0.91 | 0.83 | 0.24 | 0.15 | 1.00 | 0.86 |
| "206.682" | 1.60 | 0.69 | 0.50 | 0.66 | 0.80 | 0.73 |
| "206.683" | 1.22 | 0.82 | 0.33 | 0.53 | 0.58 | 0.73 |
| "206.684" | 0.93 | 0.59 | 0.39 | 0.41 | 1.95 | 1.53 |
| "206.687" | 1.84 | 0.77 | 0.65 | 0.70 | 1.57 | 1.80 |
| "206.688" | 3.76 | 2.57 | 2.58 | 1.22 | 0.50 | 0.26 |
| "206.689" | 2.51 | 2.32 | 2.02 | 1.42 | 1.08 | 0.61 |
| "206.690" | 1.58 | 1.46 | 1.86 | 1.32 | 0.70 | 0.60 |
| "206.691" | 2.02 | 1.61 | 1.56 | 1.44 | 0.93 | 1.06 |
| "206.692" | 1.51 | 1.79 | 2.22 | 1.18 | 0.43 | 0.70 |
| "206.693" | 1.87 | 1.80 | 1.63 | 1.19 | 1.35 | 1.29 |
| "206.694" | 1.60 | 1.19 | 1.14 | 1.11 | 1.12 | 0.62 |
| "206.695" | 4.13 | 1.92 | 0.71 | 0.17 | 0.23 | 0.12 |
| "206.696" | 2.52 | 2.45 | 2.71 | 1.62 | 0.83 | 0.88 |
| "206.697" | 2.51 | 1.50 | 1.69 | 1.06 | 0.52 | 0.34 |
| "206.698" | 1.39 | 1.21 | 1.37 | 1.19 | 0.64 | 0.58 |
| "206.699" | 1.51 | 1.16 | 1.30 | 1.12 | 1.00 | 0.81 |
| "206.700" | 1.36 | 1.15 | 1.17 | 0.72 | 0.84 | 0.58 |
| "206.701" | 1.59 | 1.41 | 1.56 | 1.20 | 1.17 | 0.91 |
| "206.702" | 1.69 | 0.95 | 0.28 | 0.17 | 1.00 | 0.65 |
| "206.703" | 1.35 | 0.82 | 0.27 | 0.28 | 0.15 | 1.02 |
| "206.704" | 2.42 | 0.69 | 0.36 | 0.24 | 0.26 | 1.14 |
| "206.705" | 2.24 | 0.94 | 0.31 | 0.16 | 0.15 | 0.61 |
| "206.706" | 2.48 | 0.90 | 0.27 | 0.14 | 0.22 | 0.59 |
| "206.707" | 1.79 | 0.94 | 0.29 | 0.10 | 0.14 | 0.50 |
| "206.708" | 1.99 | 0.85 | 0.30 | 0.11 | 1.00 | 0.53 |
| "206.709" | 1.50 | 0.80 | 0.26 | 0.17 | 0.57 | 1.02 |
| "206.710" | 2.00 | 0.98 | 0.28 | 0.25 | 0.87 | 0.63 |
| "206.711" | 1.42 | 0.85 | 0.28 | 0.28 | 0.80 | 0.82 |
| "206.712" | 1.51 | 0.81 | 0.61 | 0.37 | 0.42 | 0.50 |
| "206.713" | 2.24 | 0.83 | 0.35 | 0.41 | 0.46 | 0.50 |
| "206.714" | 1.16 | 0.63 | 0.31 | 0.28 | 1.37 | 1.44 |
| "206.715" | 1.64 | 0.63 | 0.21 | 0.28 | 1.09 | 1.54 |

TABLE 6-continued

Comprehensive neuronal culture screening results for RCaMP1h variants

| | | | | | | |
|---|---|---|---|---|---|---|
| "206.716" | 1.48 | 0.88 | 0.27 | 0.13 | 0.42 | 0.74 |
| "206.717" | 1.58 | 1.03 | 0.31 | 0.13 | 0.29 | 0.55 |
| "206.718" | 1.86 | 1.06 | 0.32 | 0.38 | 0.24 | 0.85 |
| "206.719" | 1.24 | 0.83 | 0.27 | 0.30 | 0.14 | 0.74 |
| "206.720" | 1.62 | 0.87 | 0.27 | 0.17 | 2.96 | 0.59 |
| "206.721" | 1.54 | 0.85 | 0.27 | 0.16 | 1.00 | 0.59 |
| "206.722" | 1.05 | 0.78 | 0.26 | 0.14 | 1.00 | 0.57 |
| "206.723" | 1.14 | 0.87 | 0.34 | 0.50 | 1.42 | 0.51 |
| "206.724" | 1.64 | 0.81 | 0.25 | 0.16 | 1.00 | 0.50 |
| "206.725" | 1.56 | 0.70 | 0.27 | 0.19 | 0.18 | 0.72 |
| "206.726" | 1.07 | 0.25 | 0.11 | 0.09 | 0.11 | 0.58 |
| "206.727" | 1.21 | 0.96 | 0.30 | 0.17 | 1.00 | 0.52 |
| "206.728" | 1.26 | 0.84 | 0.28 | 0.18 | 0.73 | 0.54 |
| "206.729" | 2.28 | 0.92 | 0.29 | 0.24 | 0.78 | 0.55 |
| "206.735" | 3.24 | 1.76 | 0.55 | 0.14 | 0.26 | 0.35 |
| "206.738" | 1.80 | 1.12 | 1.06 | 1.07 | 1.49 | 0.56 |
| "206.744" | 3.75 | 1.26 | 0.40 | 0.38 | 0.09 | 0.54 |
| "206.752" | 2.89 | 1.72 | 1.65 | 0.76 | 0.89 | 0.55 |
| "206.754" | 3.97 | 2.13 | 1.64 | 1.26 | 0.85 | 0.65 |
| "206.757" | 3.06 | 1.41 | 0.62 | 0.75 | 0.20 | 0.46 |
| "206.761" | 2.17 | 1.30 | 0.71 | 0.54 | 0.43 | 0.43 |
| "206.764" | 3.56 | 2.06 | 1.95 | 1.93 | 1.15 | 1.11 |
| "206.765" | 3.20 | 2.69 | 1.89 | 1.15 | 1.26 | 0.54 |
| "206.766" | 2.99 | 2.36 | 1.85 | 1.24 | 1.05 | 0.48 |
| "206.771" | 2.72 | 1.95 | 1.90 | 1.40 | 1.48 | 0.49 |
| "206.773" | 4.11 | 3.15 | 2.83 | 1.49 | 1.37 | 0.55 |
| "206.774" | 4.23 | 3.88 | 2.76 | 0.80 | 1.61 | 0.94 |
| "206.775" | 2.34 | 2.28 | 2.46 | 1.64 | 1.53 | 1.19 |
| "206.776" | 4.29 | 2.24 | 2.22 | 2.14 | 0.93 | 0.68 |
| "206.777" | 2.33 | 1.70 | 1.29 | 0.84 | 1.20 | 0.62 |
| "206.778" | 2.52 | 0.75 | 0.22 | 0.07 | 0.07 | 0.40 |
| "206.779" | 1.49 | 0.76 | 0.61 | 0.10 | 0.12 | 0.31 |
| "206.783" | 1.62 | 0.76 | 0.14 | 0.20 | 0.09 | 0.53 |
| "206.788" | 2.26 | 0.89 | 0.42 | 0.12 | 0.15 | 0.29 |
| "206.789" | 1.42 | 0.53 | 0.60 | 0.71 | 1.02 | 0.85 |
| "206.794" | 2.15 | 1.50 | 1.38 | 1.09 | 1.16 | 1.64 |
| "206.797" | 1.71 | 0.98 | 0.76 | 0.70 | 1.51 | 0.71 |
| "206.798" | 2.56 | 0.98 | 0.26 | 0.05 | 0.07 | 0.52 |
| "206.800" | −0.63 | −0.23 | 0.00 | 0.40 | 0.03 | 0.54 |
| "206.801" | 1.13 | 0.85 | 0.72 | 0.77 | 1.00 | 1.44 |
| "206.802" | 0.64 | 0.41 | 0.51 | 0.28 | 0.15 | 0.33 |
| "206.805" | 0.65 | 0.77 | 0.56 | 0.64 | 0.86 | 1.61 |
| "206.806" | −0.55 | −0.08 | −0.03 | 0.25 | 0.02 | 0.73 |
| "206.807" | −0.65 | 0.06 | 0.08 | 0.14 | 0.08 | 0.56 |
| "206.808" | 1.83 | 0.40 | 0.26 | 0.18 | 0.18 | 0.48 |
| "206.809" | 1.42 | 0.63 | 0.24 | 0.45 | 0.28 | 1.20 |
| "206.810" | 0.92 | 0.51 | 0.56 | 0.79 | 1.09 | 1.42 |
| "206.811" | 1.42 | 0.42 | 0.17 | 0.34 | 0.09 | 0.87 |
| "206.812" | −0.64 | −0.13 | −0.03 | 0.37 | 0.02 | 0.98 |
| "206.814" | −0.54 | 0.04 | 0.36 | 0.61 | 0.50 | 0.66 |
| "206.815" | −0.70 | −0.09 | 0.42 | 0.58 | 0.14 | 0.60 |
| "206.816" | −0.99 | −0.26 | −0.05 | 0.25 | 0.07 | 0.44 |
| "206.817" | 1.39 | 0.48 | 0.48 | 0.25 | 0.35 | 0.81 |
| "206.818" | −0.71 | −0.28 | −0.05 | 0.22 | −0.02 | 0.34 |
| "206.819" | 1.20 | 0.51 | 0.52 | 0.78 | 0.92 | 1.49 |
| "206.820" | 1.40 | 0.70 | 0.49 | 0.73 | 0.72 | 1.56 |
| "206.822" | 1.21 | 1.27 | 1.51 | 1.12 | 1.31 | 1.32 |
| "206.823" | 0.02 | 0.45 | 0.62 | 0.57 | 0.41 | 0.63 |
| "206.824" | −0.64 | 0.19 | 0.53 | 0.84 | 0.43 | 0.44 |
| "206.825" | −0.18 | 0.92 | 1.18 | 1.16 | 1.04 | 1.24 |
| "206.826" | −0.53 | 0.21 | 0.73 | 1.04 | 0.53 | 0.53 |
| "206.827" | −0.24 | 0.28 | 0.87 | 0.94 | 0.60 | 0.69 |
| "206.828" | −0.82 | 0.43 | 0.93 | 1.12 | 0.73 | 0.56 |
| "206.829" | −0.14 | 0.62 | 1.06 | 1.16 | 0.91 | 0.56 |
| "206.831" | −0.23 | 0.77 | 1.36 | 1.20 | 1.15 | 0.73 |
| "206.832" | 2.61 | 2.25 | 1.84 | 0.94 | 1.15 | 1.98 |
| "206.834" | 2.76 | 2.30 | 1.66 | 1.22 | 1.33 | 1.71 |
| "206.835" | 1.65 | 0.78 | 0.73 | 0.72 | 0.86 | 0.90 |
| "206.836" | 1.56 | 0.68 | 0.41 | 0.51 | 0.63 | 0.65 |
| "206.837" | −0.07 | 0.67 | 1.11 | 0.85 | 0.57 | 0.59 |
| "206.838" | −0.38 | 0.05 | 0.24 | 0.49 | 0.13 | 0.59 |
| "206.843" | 1.32 | 0.79 | 0.76 | 0.91 | 1.01 | 1.17 |
| "206.844" | 0.28 | 0.61 | 0.93 | 0.98 | 0.53 | 0.76 |
| "206.845" | 1.10 | 0.62 | 0.42 | 0.55 | 0.75 | 0.65 |
| "206.846" | 1.77 | 0.64 | 0.22 | 0.34 | 0.84 | 0.48 |
| "206.847" | 2.01 | 0.79 | 0.47 | 0.50 | 0.68 | 0.41 |
| "206.848" | 1.62 | 0.72 | 0.43 | 0.58 | 0.50 | 0.71 |
| "206.849" | 1.02 | 0.52 | 0.44 | 0.73 | 0.74 | 0.88 |

TABLE 6-continued

Comprehensive neuronal culture screening results for RCaMP1h variants

| | | | | | | |
|---|---|---|---|---|---|---|
| "206.850" | 1.06 | 0.90 | 0.88 | 1.00 | 1.19 | 0.79 |
| "206.851" | 1.16 | 1.09 | 1.12 | 1.01 | 1.45 | 0.69 |
| "206.852" | 1.27 | 1.35 | 1.21 | 1.04 | 1.29 | 0.65 |
| "206.853" | 1.05 | 1.04 | 1.00 | 1.04 | 1.29 | 0.77 |
| "206.854" | 1.30 | 1.17 | 1.00 | 1.01 | 1.09 | 0.70 |
| "206.855" | 1.59 | 1.22 | 1.53 | 1.53 | 0.54 | 1.03 |
| "206.856" | 1.25 | 1.16 | 1.09 | 1.06 | 1.34 | 0.63 |
| "206.858" | 1.39 | 1.13 | 1.13 | 1.14 | 1.27 | 0.65 |
| "206.859" | 1.73 | 1.66 | 1.70 | 1.26 | 1.32 | 0.91 |
| "206.860" | 0.95 | 0.87 | 0.84 | 0.96 | 0.90 | 0.69 |
| "206.861" | 1.22 | 0.85 | 0.69 | 0.83 | 0.96 | 0.73 |
| "206.862" | 1.02 | 1.04 | 0.91 | 1.09 | 1.00 | 0.74 |
| "206.863" | 1.24 | 1.12 | 1.11 | 1.22 | 1.12 | 0.85 |
| "206.864" | 0.90 | 0.70 | 0.55 | 0.72 | 0.90 | 0.67 |
| "206.865" | 1.47 | 1.04 | 0.67 | 0.95 | 0.84 | 1.13 |
| "206.866" | 1.57 | 1.17 | 0.83 | 0.67 | 0.60 | 1.12 |
| "206.867" | 1.52 | 1.50 | 1.28 | 0.90 | 0.85 | 0.90 |
| "206.868" | 1.34 | 0.73 | 0.62 | 0.63 | 0.73 | 0.85 |
| "206.869" | 1.14 | 0.68 | 0.42 | 0.42 | 0.70 | 0.79 |
| "206.870" | 2.25 | 0.71 | 0.42 | 0.23 | 0.34 | 0.50 |
| "206.871" | 1.41 | 0.59 | 0.59 | 0.52 | 0.63 | 0.59 |
| "206.872" | 1.65 | 0.90 | 0.89 | 0.62 | 0.73 | 0.58 |
| "206.873" | 1.28 | 0.81 | 0.72 | 0.63 | 0.70 | 0.68 |
| "206.874" | 2.04 | 0.72 | 0.45 | 0.37 | 0.46 | 0.37 |
| "206.875" | 1.88 | 0.83 | 0.36 | 0.55 | 0.73 | 0.66 |
| "206.876" | 1.36 | 1.18 | 1.23 | 1.13 | 0.90 | 1.01 |
| "206.879" | 1.19 | 0.86 | 0.66 | 0.99 | 1.13 | 0.79 |
| "206.881" | 0.85 | 0.65 | 0.25 | 0.75 | 0.30 | 0.71 |
| "206.882" | 0.91 | 0.76 | 0.49 | 0.76 | 0.71 | 1.49 |
| "206.883" | 2.01 | 1.56 | 1.39 | 1.02 | 0.88 | 1.27 |
| "206.884" | 1.38 | 0.95 | 0.96 | 1.30 | 1.05 | 0.74 |
| "206.885" | 0.86 | 0.69 | 0.67 | 0.96 | 0.82 | 0.79 |
| "206.886" | 1.99 | 0.84 | 0.64 | 0.70 | 0.82 | 0.93 |
| "206.887" | 1.66 | 1.23 | 0.98 | 1.08 | 1.21 | 1.68 |
| "206.888" | 1.15 | 0.89 | 0.48 | 0.80 | 0.37 | 0.82 |
| "206.890" | 1.68 | 1.22 | 1.06 | 1.20 | 0.99 | 0.82 |
| "206.893" | 1.04 | 0.93 | 1.00 | 1.07 | 1.04 | 0.75 |
| "206.894" | 1.09 | 0.89 | 0.85 | 1.13 | 1.02 | 0.73 |
| "206.895" | 1.33 | 0.73 | 0.65 | 0.80 | 0.82 | 0.72 |
| "206.896" | 0.06 | 0.48 | 0.59 | 0.81 | 0.89 | 0.78 |
| "206.897" | 0.33 | 0.44 | 0.36 | 0.51 | 0.49 | 0.60 |
| "206.898" | 0.42 | 0.37 | 0.45 | 0.57 | 0.53 | 0.87 |
| "206.899" | 0.40 | 0.66 | 0.63 | 0.97 | 0.77 | 0.78 |
| "206.900" | 0.41 | 0.34 | 0.50 | 0.69 | 0.82 | 0.67 |
| "206.901" | 0.33 | 0.33 | 0.36 | 0.58 | 0.59 | 0.59 |
| "206.902" | 0.00 | 0.43 | 0.52 | 0.75 | 0.85 | 0.63 |
| "206.903" | 0.27 | 0.30 | 0.20 | 0.31 | 0.20 | 0.55 |
| "206.904" | 0.33 | 0.34 | 0.43 | 0.68 | 0.70 | 0.61 |
| "206.905" | 0.54 | 0.80 | 1.06 | 1.47 | 0.72 | 0.82 |
| "206.906" | 0.92 | 0.79 | 0.91 | 1.07 | 0.71 | 1.09 |
| "206.907" | 0.18 | 0.36 | 0.33 | 0.69 | 0.69 | 0.94 |
| "206.908" | 0.38 | 0.47 | 0.31 | 0.68 | 0.57 | 0.66 |
| "206.910" | 0.63 | 0.47 | 0.14 | 0.35 | 0.05 | 0.54 |
| "206.911" | 0.62 | 0.35 | 0.25 | 0.40 | 0.30 | 0.73 |
| "206.912" | 0.14 | 0.36 | 0.29 | 0.51 | 0.46 | 0.54 |
| "206.914" | 1.27 | 0.56 | 0.28 | 0.40 | 0.07 | 0.82 |
| "206.915" | 0.41 | 0.52 | 0.22 | 0.55 | 0.12 | 0.82 |
| "206.916" | 0.81 | 0.65 | 0.40 | 0.49 | 0.56 | 1.49 |
| "206.917" | 0.84 | 0.51 | 0.47 | 0.74 | 0.56 | 0.86 |
| "206.919" | 0.57 | 0.45 | 0.35 | 0.53 | 0.26 | 0.83 |
| "206.920" | 0.56 | 0.49 | 0.36 | 0.44 | 0.49 | 0.55 |
| "206.921" | 1.01 | 0.35 | 0.20 | 0.36 | 0.32 | 0.68 |
| "206.922" | 0.42 | 0.67 | 0.38 | 0.47 | 0.52 | 0.86 |
| "206.925" | 0.60 | 1.02 | 0.73 | 1.06 | 0.72 | 1.17 |
| "206.927" | 2.11 | 2.07 | 1.49 | 1.27 | 0.64 | 1.13 |
| "206.928" | 0.24 | 0.47 | 0.33 | 0.54 | 0.34 | 1.08 |
| "206.929" | 4.13 | 4.44 | 3.20 | 1.40 | 2.75 | 1.28 |
| "206.930" | 2.90 | 2.19 | 1.41 | 1.02 | 1.20 | 1.28 |
| "206.931" | 2.94 | 1.28 | 1.28 | 1.08 | 1.03 | 0.94 |
| "206.932" | 1.43 | 1.46 | 1.57 | 1.26 | 1.10 | 0.68 |
| "206.936" | 0.72 | 0.85 | 0.69 | 0.82 | 0.73 | 0.82 |
| "206.937" | 0.44 | 0.81 | 0.88 | 0.77 | 0.77 | 0.97 |
| "206.938" | 3.42 | 2.47 | 2.16 | 1.16 | 2.35 | 1.19 |
| "206.939" | 1.57 | 2.23 | 2.24 | 0.97 | 2.20 | 1.14 |
| "206.940" | 1.67 | 1.11 | 1.06 | 0.91 | 0.89 | 0.51 |
| "206.943" | 1.80 | 0.93 | 0.56 | 0.49 | 1.07 | 0.98 |
| "206.947" | 3.21 | 2.01 | 1.75 | 1.25 | 1.01 | 0.54 |
| "206.948" | 2.60 | 1.64 | 1.40 | 0.95 | 1.00 | 1.29 |

TABLE 6-continued

Comprehensive neuronal culture screening results for RCaMP1h variants

| | | | | | | |
|---|---|---|---|---|---|---|
| "206.952" | 1.16 | 0.80 | 0.58 | 0.84 | 0.55 | 0.40 |
| "206.953" | 1.40 | 1.13 | 0.60 | 0.82 | 0.99 | 0.56 |
| "206.960" | 1.98 | 1.23 | 1.29 | 1.24 | 0.89 | 2.23 |
| "206.961" | 1.34 | 1.22 | 0.85 | 0.87 | 1.01 | 0.95 |
| "206.962" | 1.63 | 1.68 | 1.47 | 1.08 | 1.85 | 0.80 |
| "206.964" | 2.44 | 2.12 | 1.56 | 1.28 | 1.90 | 0.99 |
| "206.965" | 1.50 | 1.42 | 1.11 | 1.07 | 2.11 | 0.54 |
| "206.969" | 0.90 | 0.64 | 0.59 | 0.57 | 1.00 | 1.04 |
| "206.970" | 0.99 | 0.77 | 0.85 | 0.75 | 1.26 | 1.14 |
| "206.971" | 0.59 | 1.04 | 1.35 | 0.99 | 3.43 | 0.98 |
| "206.972" | 0.88 | 0.60 | 0.70 | 0.59 | 1.13 | 1.07 |
| "206.973" | 1.15 | 0.97 | 0.90 | 0.78 | 0.96 | 1.00 |
| "206.974" | 2.35 | 2.12 | 1.84 | 1.27 | 2.12 | 1.00 |
| "206.975" | 1.25 | 1.66 | 2.22 | 1.21 | 2.18 | 1.10 |
| "206.976" | 3.04 | 3.21 | 2.40 | 1.18 | 1.91 | 1.46 |
| "206.977" | 1.78 | 2.07 | 1.66 | 1.13 | 2.22 | 0.68 |
| "206.979" | 1.12 | 0.67 | 0.20 | 0.07 | 0.23 | 1.50 |
| "206.980" | 2.01 | 1.38 | 1.20 | 0.64 | 0.92 | 1.34 |
| "206.981" | 1.37 | 1.00 | 0.87 | 0.77 | 0.88 | 1.07 |
| "206.982" | 1.78 | 1.26 | 0.88 | 1.08 | 0.80 | 0.94 |
| "206.983" | 0.84 | 1.44 | 1.88 | 1.15 | 1.69 | 1.06 |
| "206.984" | 4.56 | 3.50 | 2.40 | 0.95 | 2.45 | 1.82 |
| "206.985" | 3.54 | 3.13 | 1.91 | 0.96 | 1.79 | 1.19 |
| "206.986" | 0.67 | 0.63 | 0.64 | 0.75 | 1.14 | 0.79 |
| "206.988" | 1.15 | 0.74 | 0.81 | 0.32 | 0.61 | 0.88 |
| "206.989" | 1.76 | 0.84 | 0.27 | 0.05 | 0.16 | 0.37 |
| "206.991" | 3.04 | 3.43 | 3.47 | 1.62 | 1.05 | 0.84 |
| "206.993" | 1.25 | 0.54 | 0.33 | 0.07 | 0.91 | 1.09 |
| "206.994" | 2.18 | 2.43 | 2.29 | 1.06 | 1.55 | 1.10 |
| "206.995" | 1.53 | 0.91 | 0.67 | 0.10 | 1.71 | 0.60 |
| "206.997" | 1.26 | 0.29 | 0.03 | 0.02 | 0.03 | 0.62 |
| "206.998" | 1.44 | 0.54 | 0.22 | 0.09 | 0.12 | 0.70 |
| "206.999" | 0.54 | 0.18 | 0.45 | 0.17 | 0.34 | 0.64 |
| "206.1000" | 2.11 | 2.57 | 2.43 | 1.18 | 1.48 | 0.99 |
| "206.1001" | 4.09 | 1.91 | 1.49 | 0.60 | 1.74 | 0.90 |
| "206.1002" | 0.80 | 0.38 | 0.17 | 0.39 | 0.12 | 1.34 |
| "206.1003" | −0.28 | −0.04 | 0.01 | 0.40 | 0.01 | 0.68 |
| "206.1006" | 0.24 | −0.06 | 0.00 | 0.43 | 0.03 | 0.72 |
| "206.1007" | −0.28 | 0.00 | −0.01 | 0.26 | 0.00 | 0.80 |
| "206.1009" | 0.17 | −0.01 | 0.02 | 0.22 | 0.02 | 1.26 |
| "206.1011" | 0.12 | −0.06 | −0.02 | 0.41 | −0.02 | 0.40 |
| "206.1013" | −0.09 | −0.02 | 0.00 | 0.20 | 0.02 | 1.01 |
| "206.1014" | 0.20 | 0.00 | 0.00 | 0.32 | 0.03 | 0.81 |
| "206.1015" | −0.19 | −0.03 | 0.05 | 0.32 | 0.02 | 1.24 |
| "206.1016" | 0.16 | −0.04 | 0.00 | 0.32 | 0.01 | 0.54 |
| "206.1017" | 0.06 | −0.05 | 0.02 | 0.42 | 0.02 | 0.54 |
| "206.1018" | 1.16 | 1.68 | 1.82 | 1.33 | 1.10 | 1.05 |
| "206.1019" | 2.04 | 2.67 | 2.75 | 1.62 | 1.31 | 1.01 |
| "206.1020" | 1.75 | 1.04 | 0.93 | 0.56 | 0.58 | 1.02 |
| "206.1021" | 1.27 | 0.44 | 0.57 | 0.65 | 0.28 | 0.25 |
| "206.1022" | 1.07 | 1.33 | 2.11 | 1.11 | 1.08 | 0.66 |
| "206.1023" | 1.33 | 1.70 | 2.04 | 1.32 | 1.36 | 1.44 |
| "206.1024" | 1.17 | 1.15 | 0.96 | 0.88 | 0.81 | 0.65 |
| "206.1025" | 1.38 | 1.07 | 1.49 | 1.02 | 1.46 | 0.96 |
| "206.1026" | 1.05 | 0.66 | 0.78 | 0.83 | 0.84 | 0.36 |
| "206.1027" | 1.04 | 1.78 | 1.36 | 0.93 | 0.63 | 0.70 |
| "206.1029" | 1.66 | 1.55 | 1.13 | 0.91 | 1.55 | 1.24 |
| "206.1030" | 0.92 | 0.96 | 0.87 | 0.82 | 1.01 | 1.03 |
| "206.1031" | 1.24 | 1.76 | 2.56 | 1.73 | 1.34 | 0.74 |
| "206.1032" | 1.10 | 1.80 | 2.52 | 1.30 | 1.30 | 0.85 |
| "206.1033" | 1.71 | 1.76 | 1.78 | 0.91 | 1.28 | 0.90 |
| "206.1034" | 1.12 | 1.13 | 1.50 | 1.21 | 1.26 | 1.06 |
| "206.1035" | 1.86 | 1.74 | 1.39 | 0.94 | 0.89 | 1.42 |
| "206.1036" | 2.52 | 1.61 | 1.08 | 0.83 | 1.05 | 1.29 |
| "206.1037" | 1.27 | 1.48 | 2.65 | 1.56 | 1.06 | 0.74 |
| "206.1038" | 0.96 | 1.03 | 1.73 | 1.31 | 1.02 | 0.89 |
| "206.1039" | 1.78 | 1.40 | 1.94 | 1.35 | 1.13 | 0.75 |
| "206.1040" | 0.69 | 0.64 | 0.74 | 0.57 | 1.43 | 0.87 |
| "206.1041" | 1.20 | 0.72 | 0.87 | 1.04 | 1.12 | 0.65 |
| "206.1042" | 1.06 | 0.93 | 1.11 | 1.14 | 1.03 | 0.90 |
| "206.1043" | 0.58 | 0.82 | 0.88 | 0.80 | 1.16 | 1.11 |
| "206.1044" | 1.70 | 2.59 | 3.76 | 1.47 | 1.40 | 0.93 |
| "206.1045" | 0.92 | 0.71 | 1.02 | 0.90 | 0.99 | 0.75 |
| "206.1046" | 0.80 | 0.74 | 0.86 | 0.61 | 1.66 | 0.81 |
| "206.1047" | 0.65 | 0.77 | 1.28 | 1.18 | 1.31 | 0.73 |
| "206.1048" | 0.76 | 0.65 | 1.05 | 0.91 | 1.08 | 0.77 |
| "206.1050" | 1.98 | 0.56 | 0.26 | 0.33 | 0.18 | 0.42 |
| "206.1051" | 1.33 | 0.64 | 0.56 | 0.72 | 0.51 | 1.64 |

TABLE 6-continued

Comprehensive neuronal culture screening results for RCaMP1h variants

| | | | | | | |
|---|---|---|---|---|---|---|
| "206.1052" | 1.27 | 0.32 | 0.06 | 0.09 | 0.04 | 1.09 |
| "206.1053" | 1.09 | 0.58 | 0.35 | 0.34 | 0.92 | 0.64 |
| "206.1054" | 1.26 | 0.99 | 1.07 | 0.99 | 1.06 | 0.99 |
| "206.1055" | 1.52 | 0.82 | 1.00 | 0.91 | 0.87 | 1.40 |
| "206.1056" | 1.43 | 0.82 | 0.77 | 0.73 | 0.83 | 0.57 |
| "206.1057" | 0.78 | 0.91 | 1.26 | 1.22 | 1.15 | 0.89 |
| "206.1058" | 0.77 | 0.84 | 1.12 | 1.14 | 1.43 | 0.79 |
| "206.1059" | 1.44 | 1.42 | 1.84 | 1.28 | 1.61 | 0.78 |
| "206.1060" | 2.05 | 0.79 | 0.33 | 0.41 | 0.17 | 0.36 |
| "206.1061" | 1.07 | 0.63 | 0.68 | 0.77 | 0.41 | 1.08 |
| "206.1062" | 0.82 | 0.47 | 0.33 | 0.45 | 0.44 | 0.98 |
| "206.1063" | 0.91 | 0.45 | 0.22 | 0.39 | 0.25 | 0.81 |
| "206.1064" | 0.81 | 0.57 | 0.52 | 0.42 | 0.63 | 1.72 |
| "206.1065" | 1.06 | 0.38 | 0.40 | 0.43 | 0.65 | 1.54 |
| "206.1066" | 1.46 | 0.99 | 0.93 | 0.84 | 0.68 | 0.55 |
| "206.1067" | 1.21 | 0.92 | 0.82 | 0.71 | 1.02 | 1.84 |
| "206.1068" | 1.15 | 1.15 | 1.03 | 0.83 | 0.97 | 1.20 |
| "206.1069" | 0.96 | 0.56 | 0.37 | 0.38 | 0.42 | 0.96 |
| "206.1070" | 1.33 | 0.68 | 0.24 | 0.26 | 0.21 | 1.07 |
| "206.1071" | 1.38 | 0.69 | 0.55 | 0.45 | 0.49 | 0.93 |
| "206.1072" | 1.10 | 1.19 | 0.95 | 0.65 | 0.71 | 1.22 |
| "206.1074" | 0.90 | 0.70 | 0.67 | 0.62 | 0.88 | 1.43 |
| "206.1075" | 4.10 | 1.78 | 1.94 | 1.04 | 0.72 | 0.24 |
| "206.1076" | 4.73 | 1.76 | 1.89 | 0.87 | 0.37 | 0.23 |
| "206.1077" | 4.09 | 1.52 | 1.13 | 0.60 | 0.33 | 0.05 |
| "206.1081" | 2.46 | 0.89 | 0.99 | 0.65 | 0.47 | 0.51 |
| "206.1082" | 2.18 | 0.77 | 0.90 | 0.53 | 0.30 | 0.28 |
| "206.1083" | 1.46 | 0.90 | 0.85 | 0.63 | 0.69 | 0.82 |
| "206.1084" | 1.25 | 0.96 | 0.74 | 0.20 | 0.81 | 0.98 |
| "206.1085" | 1.11 | 0.93 | 0.70 | 0.27 | 0.81 | 0.85 |
| "206.1086" | 0.96 | 0.87 | 0.71 | 0.25 | 0.98 | 0.75 |
| "206.1087" | 1.42 | 1.28 | 1.06 | 0.25 | 0.87 | 0.68 |
| "206.1088" | 1.40 | 1.25 | 0.76 | 0.23 | 0.99 | 0.80 |
| "206.1089" | 0.73 | 1.00 | 0.83 | 0.27 | 1.06 | 0.80 |
| "206.1090" | 1.15 | 0.87 | 0.83 | 0.34 | 0.86 | 0.83 |
| "206.1091" | 1.76 | 0.97 | 0.94 | 0.25 | 1.12 | 0.88 |
| "206.1092" | 1.07 | 1.15 | 0.93 | 0.35 | 0.87 | 0.71 |
| "206.1093" | 1.13 | 0.84 | 0.62 | 0.19 | 0.93 | 0.88 |
| "206.1094" | 0.94 | 0.81 | 0.62 | 0.31 | 1.14 | 0.99 |
| "206.1095" | 1.33 | 1.11 | 0.70 | 0.25 | 0.84 | 0.88 |
| "206.1096" | 1.53 | 1.51 | 1.17 | 0.31 | 1.06 | 1.00 |
| "206.1097" | 1.39 | 1.07 | 0.89 | 0.33 | 0.81 | 1.03 |
| "206.1098" | 1.09 | 1.19 | 0.97 | 0.51 | 0.97 | 1.20 |
| "206.1099" | 1.43 | 1.22 | 0.86 | 0.21 | 0.84 | 0.77 |
| "206.1100" | 1.43 | 1.32 | 0.97 | 0.23 | 0.94 | 0.80 |
| "206.1101" | 1.27 | 1.46 | 1.24 | 1.08 | 1.19 | 0.75 |
| "206.1102" | 1.23 | 1.34 | 1.34 | 1.10 | 1.13 | 1.08 |
| "206.1103" | 1.43 | 0.98 | 0.86 | 0.74 | 1.07 | 0.77 |
| "206.1104" | 1.06 | 1.11 | 0.90 | 1.06 | 0.79 | 0.66 |
| "206.1105" | 2.51 | 1.86 | 1.40 | 1.15 | 0.77 | 0.71 |
| "206.1106" | 1.56 | 1.15 | 1.08 | 1.17 | 0.71 | 0.74 |
| "206.1107" | 4.17 | 2.73 | 2.17 | 1.86 | 1.08 | 0.81 |
| "206.1108" | 3.93 | 3.26 | 2.21 | 1.81 | 1.26 | 0.95 |
| "206.1109" | 1.01 | 1.27 | 1.40 | 1.12 | 1.01 | 0.86 |
| "206.1110" | 1.20 | 0.93 | 0.88 | 0.53 | 1.18 | 1.04 |
| "206.1111" | 2.77 | 2.46 | 2.17 | 1.44 | 1.08 | 1.07 |
| "206.1112" | 1.58 | 1.47 | 1.14 | 1.23 | 0.96 | 0.94 |
| "206.1113" | 1.96 | 1.51 | 1.22 | 1.13 | 0.78 | 0.88 |
| "206.1114" | 1.66 | 1.48 | 1.18 | 1.31 | 0.91 | 0.78 |
| "206.1115" | 1.98 | 1.57 | 1.12 | 0.87 | 0.75 | 0.65 |
| "206.1116" | 2.04 | 1.43 | 1.09 | 0.79 | 0.77 | 0.72 |
| "206.1117" | 1.70 | 1.09 | 1.11 | 1.11 | 1.06 | 1.09 |
| "206.1118" | 1.86 | 1.58 | 1.23 | 1.24 | 0.83 | 0.77 |
| "206.1119" | 2.36 | 2.12 | 1.57 | 1.23 | 1.06 | 1.18 |
| "206.1120" | 2.62 | 1.70 | 1.41 | 0.90 | 0.92 | 1.03 |
| "206.1121" | 3.73 | 2.93 | 2.22 | 1.70 | 0.94 | 0.99 |
| "206.1122" | 1.33 | 0.76 | 0.99 | 0.85 | 1.25 | 0.77 |
| "206.1123" | 4.66 | 2.94 | 1.67 | 1.27 | 1.16 | 0.88 |
| "206.1124" | 2.19 | 2.00 | 1.32 | 0.83 | 1.20 | 1.37 |
| "206.1125" | 1.97 | 1.54 | 1.13 | 1.09 | 0.99 | 0.68 |
| "206.1126" | 1.90 | 1.56 | 1.50 | 1.32 | 1.10 | 0.73 |
| "206.1127" | 1.90 | 1.21 | 0.66 | 0.38 | 0.87 | 0.62 |
| "206.1128" | 1.00 | 0.77 | 1.11 | 1.01 | 1.13 | 0.96 |
| "206.1129" | 2.90 | 2.49 | 1.64 | 1.00 | 1.15 | 0.99 |
| "206.1130" | 2.82 | 1.68 | 1.33 | 0.70 | 1.00 | 0.71 |
| "206.1131" | 2.24 | 1.50 | 0.99 | 0.64 | 0.80 | 0.75 |
| "206.1132" | 2.01 | 1.54 | 1.31 | 1.02 | 0.89 | 0.78 |
| "206.1133" | 1.49 | 0.88 | 0.69 | 0.34 | 0.95 | 1.01 |

TABLE 6-continued

Comprehensive neuronal culture screening results for RCaMP1h variants

| | | | | | | |
|---|---|---|---|---|---|---|
| "206.1134" | 1.94 | 1.38 | 1.00 | 0.41 | 0.87 | 1.30 |
| "206.1135" | 1.86 | 1.05 | 0.87 | 0.41 | 0.76 | 1.14 |
| "206.1136" | 2.65 | 1.83 | 1.09 | 0.38 | 0.96 | 0.97 |
| "206.1137" | 0.67 | 0.69 | 0.71 | 0.55 | 0.99 | 0.86 |
| "206.1138" | 0.80 | 0.75 | 0.83 | 0.34 | 1.07 | 1.00 |
| "206.1139" | 1.54 | 1.13 | 0.87 | 0.29 | 1.08 | 2.07 |
| "206.1140" | 0.85 | 0.88 | 0.75 | 0.39 | 0.75 | 1.12 |
| "206.1141" | 1.51 | 1.00 | 0.85 | 0.35 | 0.61 | 1.24 |
| "206.1142" | 0.37 | 0.95 | 0.87 | 0.38 | 0.68 | 0.95 |
| "206.1143" | 2.62 | 2.55 | 1.51 | 0.36 | 1.17 | 0.80 |
| "206.1144" | 1.22 | 0.72 | 0.70 | 0.37 | 0.88 | 0.80 |
| "206.1145" | 1.63 | 0.75 | 0.73 | 0.80 | 0.97 | 0.90 |
| "206.1146" | 1.53 | 0.99 | 0.97 | 0.48 | 0.84 | 1.38 |
| "206.1147" | 1.69 | 0.85 | 0.71 | 0.29 | 0.83 | 1.40 |
| "206.1148" | 1.46 | 1.27 | 0.79 | 0.29 | 0.63 | 1.44 |
| "206.1149" | 2.23 | 1.02 | 0.59 | 0.24 | 1.03 | 2.42 |
| "206.1150" | 1.63 | 0.81 | 0.91 | 0.98 | 1.16 | 0.77 |
| "206.1151" | 1.36 | 0.79 | 0.94 | 1.00 | 0.94 | 1.06 |
| "206.1153" | 1.01 | 0.75 | 0.99 | 1.01 | 0.93 | 0.86 |
| "206.1154" | 1.40 | 0.76 | 0.57 | 0.42 | 0.81 | 0.76 |
| "206.1155" | 1.86 | 1.91 | 1.88 | 1.31 | 1.04 | 1.58 |
| "206.1156" | 1.42 | 0.71 | 0.66 | 0.82 | 0.76 | 1.04 |
| "206.1157" | 0.53 | 0.57 | 0.63 | 0.78 | 0.95 | 1.21 |
| "206.1158" | 0.59 | 0.64 | 0.75 | 0.82 | 0.86 | 1.15 |
| "206.1159" | 1.50 | 0.76 | 0.70 | 0.20 | 1.12 | 0.88 |
| "206.1160" | 0.66 | 0.78 | 0.80 | 0.89 | 1.11 | 1.31 |
| "206.1161" | 0.98 | 0.72 | 0.95 | 0.88 | 1.04 | 1.05 |
| "206.1162" | 0.91 | 0.48 | 0.55 | 0.41 | 0.70 | 1.11 |
| "206.1163" | 1.03 | 0.80 | 0.81 | 0.85 | 0.84 | 1.01 |
| "206.1164" | 2.02 | 1.87 | 1.71 | 1.23 | 0.89 | 1.39 |
| "206.1165" | 2.82 | 1.81 | 1.63 | 0.78 | 0.88 | 0.91 |
| "206.1167" | 2.04 | 0.25 | 0.09 | 0.06 | 0.11 | 1.61 |
| "206.1168" | 1.59 | 1.17 | 1.44 | 0.95 | 0.83 | 1.14 |
| "206.1169" | 2.07 | 0.35 | 0.12 | 0.05 | 0.25 | 0.97 |
| "206.1170" | 1.99 | 0.51 | 0.17 | 0.08 | 1.00 | 1.11 |
| "206.1171" | 2.07 | 0.55 | 0.20 | 0.10 | 0.30 | 1.20 |
| "206.1172" | 0.83 | 0.89 | 1.05 | 1.04 | 1.07 | 0.87 |
| "206.1173" | 1.10 | 0.75 | 0.94 | 0.95 | 0.70 | 0.98 |
| "206.1174" | 1.89 | 0.50 | 0.16 | 0.04 | 0.07 | 1.03 |
| "206.1175" | 2.14 | 0.64 | 0.20 | 0.06 | 0.56 | 1.05 |
| "206.1176" | 1.68 | 0.35 | 0.14 | 0.07 | 0.19 | 1.29 |
| "206.1177" | 3.45 | 1.89 | 1.47 | 0.36 | 1.14 | 1.03 |
| "206.1178" | 1.65 | 0.58 | 0.50 | 0.40 | 0.31 | 0.85 |
| "206.1179" | 1.57 | 1.59 | 1.62 | 1.23 | 1.07 | 1.18 |
| "206.1180" | 1.53 | 0.84 | 0.83 | 0.56 | 0.81 | 0.79 |
| "206.1181" | 1.62 | 0.67 | 0.90 | 0.82 | 0.93 | 1.22 |
| "206.1182" | 1.07 | 0.90 | 0.89 | 0.46 | 0.98 | 1.05 |
| "206.1183" | 0.68 | 0.88 | 1.00 | 0.44 | 1.21 | 1.08 |
| "206.1184" | −0.48 | 0.24 | 0.06 | 0.00 | 0.03 | 0.65 |
| "206.1186" | 1.39 | 1.44 | 1.90 | 1.46 | 1.10 | 1.18 |
| "206.1187" | 1.05 | 1.41 | 1.80 | 1.33 | 1.45 | 0.98 |
| "206.1188" | 2.98 | 1.68 | 1.55 | 1.14 | 0.93 | 1.47 |
| "206.1190" | 0.13 | 0.60 | 1.02 | 1.12 | 0.94 | 0.93 |
| "206.1192" | 0.69 | 0.26 | 0.05 | 0.09 | 0.02 | 1.02 |
| "206.1194" | 1.25 | 0.46 | 0.43 | 0.19 | 0.64 | 0.83 |
| "206.1195" | 1.08 | 1.04 | 0.99 | 0.66 | 1.15 | 1.10 |
| "206.1196" | 0.65 | 0.87 | 1.42 | 1.36 | 1.17 | 0.88 |
| "206.1197" | 1.29 | 1.45 | 1.73 | 1.50 | 1.04 | 1.03 |
| "206.1198" | 2.01 | 1.76 | 1.59 | 0.99 | 0.95 | 1.04 |
| "206.1199" | 0.83 | −0.02 | 0.76 | 0.32 | 0.30 | 1.02 |
| "206.1200" | 0.04 | −0.03 | 0.00 | 0.18 | 0.01 | 1.13 |
| "206.1202" | 0.94 | 0.09 | 0.18 | 0.43 | 0.32 | 2.02 |
| "206.1204" | 1.24 | 0.13 | 0.55 | 0.65 | 0.29 | 1.12 |
| "206.1205" | 0.95 | 1.12 | 1.34 | 1.30 | 1.26 | 1.05 |
| "206.1206" | 1.50 | 0.01 | 0.11 | 0.43 | 0.07 | 0.99 |
| "206.1207" | 0.52 | −0.03 | 0.02 | 0.16 | 0.02 | 0.84 |
| "206.1209" | 1.55 | 1.29 | 1.85 | 1.15 | 0.98 | 1.03 |
| "206.1210" | 1.67 | 1.79 | 2.22 | 1.84 | 1.58 | 1.08 |
| "206.1211" | 2.97 | 2.62 | 2.40 | 0.98 | 0.97 | 1.46 |
| "206.1212" | 1.20 | 1.42 | 1.60 | 0.69 | 1.04 | 1.44 |
| "206.1213" | 3.61 | 1.22 | 0.54 | 0.17 | 0.16 | 0.07 |
| "206.1215" | 1.97 | 0.42 | 0.21 | 0.36 | 0.06 | 0.14 |
| "206.1216" | 2.08 | 1.80 | 1.47 | 0.87 | 0.81 | 0.62 |
| "206.1218" | 2.83 | 1.57 | 1.45 | 0.61 | 0.34 | 0.17 |
| "206.1219" | 1.88 | 1.40 | 1.54 | 1.03 | 0.74 | 0.53 |
| "206.1220" | 1.05 | 0.90 | 0.77 | 0.43 | 0.26 | 0.28 |
| "206.1221" | 0.51 | 0.66 | 0.26 | 0.39 | 0.26 | 0.81 |
| "206.1222" | 1.78 | 0.58 | 0.48 | 0.52 | 0.26 | 0.62 |

TABLE 6-continued

Comprehensive neuronal culture screening results for RCaMP1h variants

| | | | | | | |
|---|---|---|---|---|---|---|
| "206.1223" | 1.91 | 1.60 | 1.91 | 0.83 | 0.36 | 0.18 |
| "206.1224" | 2.27 | 1.47 | 1.45 | 0.73 | 0.50 | 0.36 |
| "206.1225" | 0.84 | 1.24 | 1.08 | 0.80 | 0.46 | 0.46 |
| "206.1226" | 1.09 | 0.76 | 0.23 | 0.26 | 0.09 | 0.61 |
| "206.1227" | 1.86 | 0.77 | 0.23 | 0.49 | 0.11 | 0.66 |
| "206.1228" | 0.75 | 0.57 | 0.20 | 0.27 | 0.09 | 0.50 |
| "206.1229" | 0.79 | 0.31 | 0.12 | 0.44 | 0.08 | 0.78 |
| "206.1230" | 1.80 | 0.94 | 1.02 | 0.54 | 0.96 | 0.97 |
| "206.1231" | 0.30 | 0.13 | 0.32 | 0.25 | 0.19 | 1.31 |
| "206.1232" | 2.08 | 0.90 | 0.94 | 0.56 | 0.35 | 0.42 |
| "206.1233" | 0.85 | 0.22 | 0.17 | 0.40 | 0.11 | 1.11 |
| "206.1234" | 2.08 | 1.46 | 2.21 | 1.06 | 0.82 | 0.71 |
| "206.1235" | 2.22 | 2.20 | 2.12 | 0.40 | 1.46 | 1.78 |
| "206.1236" | 3.91 | 3.00 | 3.05 | 0.66 | 0.64 | 0.62 |
| "206.1240" | 2.29 | 0.28 | 0.19 | 0.19 | 0.20 | 0.09 |
| "206.1244" | 4.68 | 0.39 | 0.05 | 0.35 | 0.03 | 0.25 |
| "206.1247" | 2.99 | 1.10 | 1.17 | 0.89 | 0.57 | 0.14 |
| "206.1248" | 7.64 | 1.65 | 1.95 | 0.98 | 0.51 | 0.15 |
| "206.1249" | 2.76 | 0.50 | 0.23 | 0.64 | 0.10 | 0.26 |
| "206.1250" | 4.32 | 2.59 | 3.89 | 2.72 | 0.57 | 0.18 |
| "206.1251" | 1.83 | 1.03 | 1.08 | 0.76 | 0.64 | 0.49 |
| "206.1252" | 1.09 | 0.54 | 0.80 | 0.69 | 0.39 | 0.67 |
| "206.1253" | 1.61 | 0.73 | 0.41 | 0.42 | 0.31 | 0.25 |
| "206.1254" | 1.04 | 1.01 | 0.53 | 0.40 | 0.21 | 0.30 |
| "206.1255" | 0.74 | 0.25 | 0.44 | 0.40 | 0.42 | 0.95 |
| "206.1256" | 4.79 | 1.61 | 1.64 | 0.49 | 0.15 | 0.08 |
| "206.1257" | 2.53 | 0.28 | 0.30 | 0.16 | 0.10 | 0.38 |
| "206.1258" | 0.74 | 1.45 | 1.94 | 1.36 | 1.02 | 1.08 |
| "206.1259" | 1.85 | 1.78 | 1.77 | 1.62 | 1.10 | 0.67 |
| "206.1260" | 1.44 | 0.91 | 0.83 | 0.34 | 1.08 | 0.77 |
| "206.1261" | 0.91 | 0.94 | 0.74 | 0.29 | 0.92 | 0.87 |
| "206.1262" | 0.97 | 0.96 | 0.74 | 0.33 | 0.86 | 0.85 |
| "206.1263" | 0.92 | 0.86 | 0.54 | 0.31 | 0.90 | 1.05 |
| "206.1264" | 0.98 | 1.07 | 1.12 | 0.79 | 0.99 | 0.66 |
| "206.1265" | 1.82 | 1.98 | 1.22 | 0.28 | 0.95 | 1.03 |
| "206.1266" | 2.72 | 2.56 | 1.82 | 0.58 | 1.11 | 0.86 |
| "206.1267" | 0.80 | 0.66 | 0.52 | 0.35 | 0.85 | 0.57 |
| "206.1268" | 0.64 | 0.72 | 0.62 | 0.22 | 0.99 | 0.63 |
| "206.1269" | 2.29 | 1.75 | 1.20 | 0.44 | 0.95 | 0.85 |
| "206.1270" | 1.62 | 2.54 | 1.84 | 0.48 | 1.05 | 0.85 |
| "206.1271" | 1.74 | 1.78 | 1.54 | 0.98 | 0.94 | 1.10 |
| "206.1272" | 1.43 | 1.63 | 1.54 | 0.93 | 0.84 | 0.74 |
| "206.1273" | 1.90 | 1.96 | 1.32 | 0.50 | 0.92 | 1.37 |
| "206.1274" | 0.99 | 1.05 | 0.69 | 0.36 | 0.86 | 1.11 |
| "206.1275" | 1.21 | 0.87 | 0.69 | 0.25 | 0.93 | 1.21 |
| "206.1276" | 1.50 | 1.11 | 0.85 | 0.28 | 0.92 | 1.69 |
| "206.1277" | 0.87 | 0.85 | 0.58 | 0.25 | 0.85 | 0.73 |
| "206.1278" | 1.07 | 0.73 | 0.59 | 0.22 | 1.07 | 0.76 |
| "206.1279" | 2.46 | 1.38 | 0.84 | 0.54 | 1.00 | 0.66 |
| "206.1280" | 0.50 | 0.52 | 0.44 | 0.18 | 0.86 | 0.72 |
| "206.1281" | 0.88 | 0.68 | 0.43 | 0.20 | 0.75 | 0.58 |
| "206.1282" | 0.65 | 0.57 | 0.51 | 0.18 | 0.63 | 0.86 |
| "206.1283" | 0.82 | 0.78 | 0.43 | 0.17 | 0.88 | 0.92 |
| "206.1284" | 1.01 | 0.97 | 0.73 | 0.26 | 0.86 | 1.08 |
| "206.1285" | 0.71 | 0.83 | 0.69 | 0.77 | 0.95 | 0.90 |
| "206.1286" | 1.03 | 0.68 | 0.51 | 0.23 | 0.76 | 0.91 |
| "206.1287" | 1.67 | 1.60 | 1.12 | 0.30 | 0.90 | 1.06 |
| "206.1288" | 1.56 | 1.14 | 0.74 | 0.48 | 0.83 | 1.40 |
| "206.1289" | 1.15 | 0.92 | 0.68 | 0.23 | 0.80 | 0.98 |
| "206.1290" | 0.95 | 0.70 | 0.47 | 0.18 | 0.75 | 0.80 |
| "206.1291" | 0.69 | 0.63 | 0.40 | 0.15 | 0.69 | 0.75 |
| "206.1292" | 1.22 | 1.13 | 0.99 | 0.93 | 0.90 | 0.75 |
| "206.1293" | 2.01 | 1.80 | 1.62 | 1.18 | 1.10 | 0.98 |
| "206.1294" | 0.55 | 0.80 | 0.74 | 1.01 | 0.95 | 0.92 |
| "206.1295" | 1.79 | 1.70 | 1.40 | 0.99 | 1.04 | 0.96 |
| "206.1296" | 0.88 | 0.84 | 0.77 | 1.00 | 0.85 | 0.74 |
| "206.1297" | 1.20 | 0.98 | 0.88 | 0.77 | 0.82 | 0.98 |
| "206.1298" | 1.41 | 1.56 | 1.57 | 1.02 | 1.51 | 1.04 |
| "206.1300" | 2.63 | 3.11 | 2.55 | 1.29 | 1.36 | 1.12 |
| "206.1301" | 1.09 | 1.20 | 1.26 | 1.13 | 0.78 | 0.96 |
| "206.1302" | 1.15 | 1.16 | 1.18 | 0.66 | 0.77 | 0.66 |
| "206.1303" | 1.78 | 1.38 | 1.65 | 0.89 | 0.85 | 0.82 |
| "206.1304" | 1.25 | 1.09 | 0.83 | 0.72 | 0.91 | 0.88 |
| "206.1305" | 0.80 | 1.06 | 1.35 | 0.95 | 1.45 | 0.85 |
| "206.1306" | 2.11 | 2.46 | 2.18 | 0.88 | 2.31 | 1.11 |
| "206.1307" | 1.20 | 1.24 | 1.17 | 0.84 | 0.99 | 0.78 |
| "206.1308" | 0.93 | 1.03 | 1.16 | 1.19 | 1.02 | 0.78 |
| "206.1309" | 1.03 | 1.45 | 1.46 | 1.26 | 0.93 | 0.77 |

TABLE 6-continued

Comprehensive neuronal culture screening results for RCaMP1h variants

| | | | | | | |
|---|---|---|---|---|---|---|
| "206.1310" | 0.89 | 1.07 | 1.29 | 1.23 | 1.17 | 0.75 |
| "206.1311" | 1.99 | 2.09 | 2.16 | 1.70 | 1.30 | 0.83 |
| "206.1312" | 2.11 | 2.04 | 2.00 | 1.43 | 1.19 | 1.28 |
| "206.1313" | 1.20 | 0.89 | 1.32 | 1.05 | 1.18 | 0.96 |
| "206.1314" | 0.59 | 0.79 | 0.94 | 1.04 | 1.20 | 0.99 |
| "206.1315" | 0.85 | 1.00 | 1.35 | 1.15 | 1.31 | 0.97 |
| "206.1316" | 1.00 | 0.96 | 1.14 | 1.12 | 1.00 | 0.80 |
| "206.1317" | 1.06 | 0.50 | 0.89 | 0.85 | 1.11 | 0.90 |
| "206.1318" | 0.96 | 0.79 | 0.93 | 1.03 | 1.08 | 1.01 |
| "206.1319" | 0.76 | 0.91 | 1.08 | 1.11 | 0.91 | 1.04 |
| "206.1320" | 2.73 | 2.46 | 2.04 | 1.07 | 1.16 | 1.02 |
| "206.1321" | 1.33 | 1.25 | 1.47 | 1.29 | 0.79 | 0.85 |
| "206.1322" | 0.93 | 1.18 | 0.97 | 1.18 | 1.18 | 0.91 |
| "206.1323" | 1.16 | 0.33 | 0.02 | 0.00 | 0.04 | 0.23 |
| "206.1324" | 1.96 | 0.49 | 0.22 | 0.33 | 0.08 | 0.38 |
| "206.1325" | 1.72 | 0.75 | 0.44 | 0.49 | 0.86 | 0.51 |
| "206.1326" | 2.76 | 2.19 | 2.45 | 0.77 | 1.17 | 0.56 |
| "206.1327" | 2.70 | 3.13 | 3.51 | 1.15 | 1.21 | 0.98 |
| "206.1329" | 4.04 | 1.86 | 1.67 | 0.46 | 0.31 | 0.11 |
| "206.1330" | 3.61 | 1.99 | 1.66 | 0.40 | 0.41 | 0.04 |
| "206.1334" | 4.88 | 1.12 | 0.36 | 0.43 | 0.11 | 0.21 |
| "206.1335" | 1.63 | 1.72 | 1.95 | 1.06 | 0.78 | 0.29 |
| "206.1336" | 2.67 | 0.50 | 0.43 | 0.21 | 0.17 | 0.27 |
| "206.1337" | 2.30 | 0.88 | 0.33 | 0.48 | 0.48 | 0.51 |
| "206.1338" | 2.13 | 1.05 | 0.29 | 0.10 | 0.21 | 0.54 |
| "206.1340" | 3.14 | 0.94 | 0.28 | 0.23 | 0.45 | 0.45 |
| "206.1341" | 3.16 | 0.77 | 0.23 | 0.26 | 0.23 | 0.63 |
| "206.1343" | 5.56 | 3.91 | 2.76 | 0.87 | 0.98 | 0.33 |
| "206.1344" | 3.07 | 2.35 | 3.06 | 1.65 | 0.46 | 0.58 |
| "206.1346" | 5.41 | 6.58 | 7.12 | 2.13 | 0.68 | 0.77 |
| "206.1347" | 1.12 | 1.35 | 1.60 | 1.41 | 0.67 | 0.75 |
| "206.1348" | 3.73 | 4.78 | 6.76 | 1.89 | 0.61 | 0.69 |
| "206.1349" | 2.67 | 3.65 | 4.02 | 1.80 | 0.36 | 0.60 |
| "206.1350" | 0.90 | 0.90 | 1.17 | 1.24 | 0.83 | 0.69 |
| "206.1351" | 1.32 | 1.20 | 1.51 | 1.14 | 0.90 | 0.72 |
| "206.1352" | 1.06 | 1.47 | 1.58 | 1.50 | 0.89 | 0.72 |
| "206.1353" | 0.56 | 1.38 | 2.42 | 1.71 | 0.81 | 0.81 |
| "206.1354" | 1.03 | 1.51 | 1.86 | 1.60 | 1.02 | 1.14 |
| "206.1355" | 1.34 | 1.17 | 1.57 | 1.25 | 1.01 | 0.99 |
| "206.1356" | 2.66 | 2.86 | 3.02 | 1.76 | 1.04 | 0.92 |
| "206.1357" | 8.24 | 7.92 | 6.07 | 1.47 | 1.47 | 0.56 |
| "206.1358" | 2.28 | 2.72 | 3.42 | 1.61 | 0.98 | 0.76 |
| "206.1359" | 0.88 | 1.21 | 1.26 | 1.03 | 1.30 | 1.05 |
| "206.1360" | 0.88 | 1.36 | 2.05 | 1.22 | 1.25 | 0.99 |
| "206.1361" | 0.97 | 0.96 | 1.31 | 1.11 | 1.19 | 1.04 |
| "206.1362" | 0.49 | 0.80 | 1.04 | 0.92 | 1.16 | 0.99 |
| "206.1363" | 1.14 | 1.07 | 1.35 | 1.10 | 1.27 | 1.08 |
| "206.1364" | 0.84 | 0.99 | 1.21 | 1.18 | 1.11 | 1.17 |
| "206.1365" | 1.66 | 1.52 | 1.56 | 1.33 | 1.09 | 1.14 |
| "206.1370" | 1.61 | 1.67 | 1.58 | 1.23 | 1.39 | 0.88 |
| "206.1371" | 1.12 | 1.20 | 1.52 | 1.29 | 1.34 | 1.36 |
| "206.1372" | 1.58 | 1.50 | 1.49 | 1.42 | 0.93 | 1.54 |
| "206.1373" | 1.20 | 0.95 | 1.28 | 1.26 | 1.14 | 1.24 |
| "206.1374" | 1.18 | 0.87 | 1.01 | 1.06 | 0.93 | 1.16 |
| "206.1375" | 1.00 | 1.19 | 1.53 | 1.39 | 1.06 | 1.08 |
| "206.1376" | 1.22 | 0.99 | 1.26 | 1.24 | 1.01 | 1.05 |
| "206.1380" | 1.34 | 1.54 | 1.83 | 1.18 | 0.85 | 1.59 |
| "206.1381" | 1.76 | 1.45 | 1.48 | 1.09 | 1.07 | 1.76 |
| "206.1382" | 1.15 | 1.52 | 1.59 | 1.25 | 1.35 | 1.01 |
| "206.1383" | 1.69 | 1.58 | 1.71 | 1.48 | 1.04 | 1.20 |
| "206.1384" | 0.93 | 1.11 | 1.39 | 1.47 | 1.09 | 1.00 |
| "206.1385" | 0.88 | 0.95 | 1.28 | 1.31 | 1.18 | 1.21 |
| "206.1386" | 1.93 | 1.59 | 1.98 | 1.29 | 1.15 | 1.23 |
| "206.1387" | 1.22 | 1.03 | 1.30 | 1.37 | 1.04 | 0.95 |
| "206.1388" | 1.37 | 1.49 | 1.74 | 1.40 | 0.80 | 1.18 |
| "206.1389" | 1.28 | 1.47 | 1.78 | 1.43 | 0.96 | 1.04 |
| "206.1390" | 4.94 | 3.77 | 3.84 | 1.41 | 0.82 | 0.94 |
| "206.1392" | 1.31 | 0.97 | 1.04 | 1.04 | 0.92 | 0.79 |
| "206.1393" | 1.42 | 1.08 | 1.16 | 0.95 | 1.03 | 0.89 |
| "206.1394" | 1.30 | 1.09 | 1.17 | 1.07 | 1.03 | 1.19 |
| "206.1397" | 1.55 | 1.59 | 1.49 | 1.10 | 1.13 | 1.16 |
| "206.1398" | 1.91 | 2.23 | 2.55 | 1.32 | 0.90 | 0.65 |
| "206.1401" | 1.52 | 1.13 | 1.48 | 1.05 | 0.80 | 1.05 |
| "206.1403" | 2.59 | 3.37 | 3.85 | 1.35 | 0.80 | 0.85 |
| "206.1404" | 1.91 | 2.31 | 2.62 | 1.73 | 0.80 | 0.71 |
| "206.1405" | 2.15 | 2.31 | 2.85 | 1.25 | 1.04 | 0.58 |
| "206.1406" | 1.48 | 0.17 | 0.00 | 0.05 | 0.02 | 0.98 |
| "206.1410" | 1.20 | 1.49 | 1.72 | 1.32 | 1.41 | 1.03 |

TABLE 6-continued

Comprehensive neuronal culture screening results for RCaMP1h variants

| | | | | | | |
|---|---|---|---|---|---|---|
| "206.1411" | 1.28 | 1.05 | 0.79 | 0.68 | 0.79 | 0.55 |
| "206.1413" | 0.68 | 1.06 | 1.19 | 1.16 | 1.09 | 0.76 |
| "206.1414" | 2.35 | 1.97 | 2.02 | 1.31 | 1.11 | 0.32 |
| "206.1417" | 2.97 | 1.63 | 1.48 | 0.89 | 0.68 | 0.28 |
| "206.1418" | 0.39 | 0.57 | 0.84 | 0.83 | 0.62 | 0.91 |
| "206.1427" | 0.84 | 1.56 | 1.61 | 1.13 | 1.10 | 0.85 |
| "206.1429" | 0.73 | 1.26 | 1.38 | 0.92 | 0.73 | 0.94 |
| "206.1430" | 0.54 | 0.91 | 0.97 | 1.08 | 0.88 | 0.86 |
| "206.1431" | 1.72 | 2.25 | 2.19 | 1.30 | 0.96 | 0.90 |
| "206.1432" | 0.64 | 0.71 | 0.83 | 0.94 | 0.91 | 0.83 |
| "206.1434" | 1.91 | 1.31 | 1.43 | 1.04 | 0.93 | 0.97 |
| "206.1435" | 1.34 | 1.79 | 1.61 | 1.23 | 0.78 | 0.70 |
| "206.1436" | 1.13 | 1.52 | 1.63 | 1.15 | 0.89 | 0.54 |
| "206.1437" | 1.27 | 1.74 | 1.84 | 1.14 | 0.91 | 0.92 |
| "206.1439" | 5.12 | 2.81 | 1.81 | 0.84 | 0.72 | 0.14 |
| "206.1441" | 3.26 | 1.98 | 1.99 | 1.07 | 0.95 | 0.07 |
| "206.1442" | 3.11 | 1.95 | 1.58 | 0.77 | 0.50 | 0.12 |
| "206.1443" | 0.54 | 1.25 | 1.33 | 1.06 | 0.82 | 0.98 |
| "206.1444" | 1.52 | 1.87 | 2.10 | 1.54 | 1.38 | 0.68 |
| "206.1457" | 2.08 | 4.57 | 6.73 | 1.84 | 0.79 | 0.61 |
| "206.1458" | 2.23 | 3.69 | 5.58 | 1.33 | 0.69 | 0.59 |
| "206.1459" | 2.36 | 3.33 | 4.33 | 1.47 | 0.94 | 0.65 |
| "206.1460" | 1.59 | 2.99 | 4.55 | 1.67 | 0.84 | 0.73 |
| "206.1461" | 0.25 | 0.90 | 1.63 | 1.44 | 0.79 | 1.02 |
| "206.1462" | 9.03 | 10.71 | 11.35 | 2.15 | 1.20 | 1.05 |
| "206.1463" | 10.01 | 13.07 | 14.44 | 2.63 | 1.37 | 0.97 |
| "206.1464" | 9.73 | 11.89 | 13.15 | 2.30 | 1.60 | 0.94 |
| "206.1465" | 7.71 | 10.22 | 10.30 | 2.29 | 1.27 | 0.83 |
| "206.1466" | 7.36 | 9.37 | 10.94 | 2.24 | 1.21 | 0.99 |
| "206.1467" | 1.74 | 2.72 | 3.59 | 1.90 | 1.08 | 0.93 |
| "206.1468" | 4.92 | 2.65 | 1.69 | 0.17 | 1.63 | 0.24 |
| "206.1469" | 4.16 | 2.85 | 2.56 | 0.38 | 1.09 | 0.25 |
| "206.1470" | 4.91 | 3.20 | 3.97 | 0.92 | 0.59 | 0.44 |
| "206.1472" | 3.78 | 2.87 | 3.15 | 0.56 | 0.78 | 0.51 |
| "206.1473" | 4.47 | 5.30 | 6.64 | 1.87 | 0.63 | 0.51 |
| "206.1474" | 4.69 | 3.70 | 3.76 | 0.99 | 1.93 | 0.73 |
| "206.1475" | 0.29 | 0.81 | 1.07 | 1.00 | 0.84 | 1.05 |
| "206.1476" | 1.02 | 1.47 | 2.59 | 1.85 | 0.74 | 0.67 |
| "206.1477" | 2.16 | 2.58 | 4.47 | 1.59 | 0.53 | 1.25 |
| "206.1478" | 2.31 | 3.58 | 4.86 | 2.02 | 0.71 | 1.05 |
| "206.1479" | 9.30 | 8.93 | 8.83 | 1.40 | 1.56 | 0.40 |
| "206.1480" | 3.21 | 4.11 | 4.48 | 2.31 | 1.19 | 0.90 |
| "206.1481" | 2.76 | 3.33 | 4.67 | 1.98 | 0.93 | 0.97 |
| "206.1482" | 2.25 | 2.81 | 4.80 | 1.86 | 0.63 | 0.90 |
| "206.1483" | 2.56 | 3.56 | 4.96 | 1.76 | 0.81 | 0.91 |
| "206.1484" | 0.28 | 1.01 | 1.32 | 1.26 | 0.75 | 0.79 |
| "206.1485" | 2.07 | 3.01 | 3.94 | 1.91 | 1.05 | 0.89 |
| "206.1486" | 2.58 | 3.11 | 4.20 | 1.92 | 0.98 | 0.97 |
| "206.1487" | 0.57 | 0.28 | 0.44 | 0.09 | 0.20 | 0.62 |
| "206.1489" | 6.34 | 6.55 | 7.16 | 1.10 | 1.52 | 1.48 |
| "206.1490" | 3.85 | 4.24 | 4.67 | 1.35 | 1.18 | 1.02 |
| "206.1491" | 0.52 | 1.01 | 1.58 | 1.20 | 1.02 | 1.07 |
| "206.1492" | 12.69 | 13.94 | 11.85 | 2.28 | 1.42 | 0.98 |
| "206.1493" | 0.11 | 0.81 | 1.31 | 1.17 | 0.84 | 0.71 |
| "206.1494" | 1.24 | 2.08 | 3.78 | 1.77 | 0.77 | 0.65 |
| "206.1495" | 2.89 | 4.24 | 4.97 | 1.84 | 0.80 | 1.30 |
| "206.1496" | 14.53 | 16.81 | 14.63 | 2.40 | 1.39 | 1.38 |
| "206.1497" | 1.36 | 2.30 | 2.93 | 1.69 | 0.95 | 0.76 |
| "206.1498" | 2.77 | 3.77 | 4.55 | 2.15 | 1.04 | 1.00 |
| "206.1499" | 4.61 | 2.98 | 1.80 | 0.17 | 1.68 | 0.33 |
| "206.1500" | 6.42 | 6.91 | 5.64 | 0.99 | 2.21 | 0.89 |
| "206.1501" | 6.42 | 7.67 | 6.59 | 1.07 | 1.00 | 0.42 |
| "206.1502" | 2.11 | 2.66 | 3.12 | 1.61 | 0.72 | 1.07 |
| "206.1503" | 2.04 | 2.52 | 3.49 | 1.41 | 0.72 | 1.07 |
| "206.1504" | 0.42 | 0.87 | 1.45 | 1.23 | 0.83 | 0.82 |
| "206.1505" | 8.13 | 8.39 | 8.71 | 1.89 | 1.22 | 0.73 |
| "206.1506" | 2.49 | 3.42 | 4.05 | 2.00 | 0.77 | 1.08 |
| "206.1507" | 0.71 | 1.30 | 1.25 | 1.13 | 0.96 | 1.05 |
| "206.1508" | 2.68 | 0.43 | 0.41 | 0.10 | 0.08 | 0.89 |
| "206.1509" | 2.57 | 1.62 | 0.85 | 0.06 | 0.69 | 0.18 |
| "206.1510" | 3.40 | 3.15 | 2.47 | 0.24 | 1.73 | 0.34 |
| "206.1511" | 8.92 | 7.65 | 5.41 | 0.76 | 2.53 | 0.46 |
| "206.1512" | 2.13 | 2.74 | 3.35 | 2.06 | 1.13 | 0.83 |
| "206.1513" | 0.37 | 0.60 | 1.20 | 1.06 | 0.63 | 1.00 |
| "206.1514" | 1.43 | 2.53 | 3.62 | 1.52 | 0.61 | 1.02 |
| "206.1515" | 0.40 | 0.75 | 1.20 | 1.27 | 0.94 | 0.69 |
| "206.1516" | 3.66 | 5.25 | 4.64 | 2.19 | 0.87 | 1.15 |
| "206.1517" | 13.98 | 15.26 | 12.84 | 2.38 | 1.26 | 1.44 |

TABLE 6-continued

Comprehensive neuronal culture screening results for RCaMP1h variants

| | | | | | | |
|---|---|---|---|---|---|---|
| "206.1518" | 11.94 | 14.60 | 12.63 | 1.99 | 1.33 | 0.86 |
| "206.1520" | 13.74 | 17.99 | 15.91 | 2.51 | 1.08 | 0.83 |
| "206.1522" | 20.50 | 14.58 | 8.69 | 0.89 | 2.27 | 0.62 |
| "206.1523" | 12.73 | 13.06 | 12.77 | 1.72 | 2.26 | 0.37 |
| "206.1524" | 12.81 | 12.46 | 8.80 | 0.88 | 2.23 | 0.55 |
| "206.1525" | 0.65 | 0.95 | 1.38 | 1.39 | 0.74 | 1.30 |
| "206.1526" | 7.50 | 6.56 | 4.41 | 0.42 | 1.91 | 0.26 |
| "206.1527" | 11.98 | 8.78 | 4.93 | 0.43 | 2.36 | 0.39 |
| "206.1528" | 6.84 | 7.91 | 8.90 | 2.19 | 0.99 | 0.68 |
| "206.1529" | 1.47 | 2.31 | 3.45 | 1.12 | 0.47 | 0.97 |
| "206.1532" | 4.06 | 4.00 | 4.82 | 1.27 | 0.76 | 0.57 |
| "206.1533" | 2.96 | 1.45 | 2.15 | 0.54 | 0.51 | 0.52 |
| "206.1535" | 2.91 | 3.17 | 3.35 | 0.84 | 1.04 | 0.69 |
| "206.1536" | 4.42 | 3.80 | 3.71 | 0.59 | 1.56 | 0.26 |
| "206.1537" | 9.99 | 8.92 | 7.13 | 1.22 | 2.17 | 0.35 |
| "206.1538" | 8.51 | 9.18 | 9.56 | 1.93 | 1.58 | 0.87 |

| RCaMP1h variant | 1 AP p-value | 3 AP p-value | 10 AP p-value | 160 AP p-value | Decay half time (10 AP) p-value | F0 normalized to GFP fluorescence p-value |
|---|---|---|---|---|---|---|
| "RCaMP1h" | 1.00E+00 | 1.00E+00 | 1.00E+00 | 1.00E+00 | 1.00E+00 | 1.00E+00 |
| "R-CaMP2" | 6.40E-07 | 3.05E-07 | 3.11E-07 | 1.88E-02 | 1.29E-06 | 1.96E-03 |
| "jRCaMP1a" | 4.30E-16 | 4.75E-16 | 6.14E-16 | 2.10E-03 | 3.91E-16 | 6.18E-01 |
| "jRCaMP1b" | 4.54E-11 | 4.41E-11 | 4.87E-11 | 6.52E-11 | 6.39E-03 | 1.04E-04 |
| "206.3" | 4.00E-03 | 5.08E-02 | 1.64E-06 | 1.27E-06 | 4.84E-05 | 2.80E-04 |
| "206.4" | 4.48E-01 | 7.16E-02 | 6.52E-06 | 5.75E-06 | 8.17E-01 | 2.07E-03 |
| "206.8" | 8.48E-02 | 9.31E-01 | 7.55E-04 | 5.77E-04 | 6.50E-04 | 1.97E-01 |
| "206.9" | 2.36E-03 | 6.11E-02 | 1.53E-03 | 5.90E-04 | 9.43E-02 | 4.69E-02 |
| "206.10" | 3.53E-04 | 3.09E-06 | 1.41E-06 | 3.28E-06 | 2.75E-06 | 9.85E-02 |
| "206.11" | 8.98E-01 | 1.47E-02 | 6.80E-06 | 5.75E-04 | 7.82E-03 | 4.50E-02 |
| "206.14" | 4.00E-01 | 4.56E-01 | 1.17E-01 | 6.75E-01 | 4.96E-01 | 2.39E-01 |
| "206.15" | 5.97E-02 | 4.93E-01 | 4.96E-03 | 2.99E-04 | 1.24E-05 | 2.85E-03 |
| "206.17" | 4.63E-05 | 1.24E-04 | 5.68E-04 | 6.59E-01 | 3.33E-01 | 5.40E-04 |
| "206.18" | 2.23E-02 | 1.62E-01 | 7.94E-06 | 6.80E-06 | 1.70E-02 | 7.00E-03 |
| "206.19" | 8.84E-01 | 1.27E-01 | 3.22E-02 | 8.82E-01 | 2.76E-01 | 1.94E-02 |
| "206.20" | 3.34E-01 | 9.45E-02 | 9.14E-02 | 1.56E-01 | 4.14E-01 | 3.15E-02 |
| "206.21" | 2.18E-01 | 2.84E-03 | 2.46E-03 | 1.48E-03 | 5.48E-05 | 4.46E-03 |
| "206.22" | 2.81E-01 | 1.02E-01 | 3.30E-01 | 2.72E-01 | 5.48E-04 | 5.64E-06 |
| "206.23" | 7.64E-01 | 5.90E-02 | 6.32E-06 | 6.73E-06 | 9.43E-04 | 7.51E-01 |
| "206.24" | 3.11E-02 | 5.41E-01 | 1.64E-01 | 6.22E-02 | 9.26E-04 | 2.05E-01 |
| "206.25" | 1.93E-02 | 8.99E-02 | 2.87E-01 | 5.34E-01 | 6.59E-01 | 9.45E-01 |
| "206.26" | 7.19E-05 | 2.78E-05 | 4.58E-05 | 1.79E-02 | 1.57E-01 | 1.89E-01 |
| "206.27" | 4.25E-01 | 4.61E-01 | 3.35E-03 | 1.56E-03 | 3.83E-05 | 1.00E-03 |
| "206.28" | 1.36E-11 | 2.15E-13 | 8.55E-16 | 9.22E-07 | 1.87E-03 | 2.79E-09 |
| "206.29" | 1.93E-03 | 4.22E-03 | 3.98E-03 | 6.19E-03 | 2.49E-01 | 2.17E-02 |
| "206.30" | 1.09E-02 | 1.24E-01 | 3.16E-01 | 9.49E-06 | 6.69E-02 | 5.53E-01 |
| "206.31" | 2.81E-02 | 4.40E-01 | 1.41E-01 | 2.59E-04 | 4.95E-02 | 2.98E-01 |
| "206.32" | 6.56E-01 | 5.13E-03 | 2.05E-03 | 9.31E-03 | 4.54E-01 | 7.28E-01 |
| "206.33" | 4.22E-03 | 5.41E-02 | 2.82E-03 | 8.36E-02 | 8.80E-04 | 2.42E-01 |
| "206.34" | 4.49E-03 | 2.39E-01 | 3.22E-02 | 5.63E-03 | 1.52E-03 | 4.91E-01 |
| "206.35" | 1.62E-03 | 9.02E-01 | 3.92E-01 | 1.11E-04 | 3.11E-02 | 7.26E-02 |
| "206.36" | 4.42E-03 | 4.98E-01 | 1.70E-02 | 8.53E-04 | 1.81E-01 | 1.11E-01 |
| "206.38" | 9.47E-05 | 6.25E-05 | 3.00E-05 | 6.81E-01 | 9.98E-06 | 4.50E-01 |
| "206.39" | 2.56E-04 | 4.22E-04 | 3.54E-04 | 2.54E-01 | 3.86E-01 | 5.82E-02 |
| "206.41" | 9.12E-03 | 1.69E-03 | 3.81E-04 | 9.90E-05 | 1.21E-05 | 6.10E-01 |
| "206.42" | 5.06E-01 | 6.39E-03 | 3.00E-05 | 2.64E-05 | 2.95E-03 | 9.19E-01 |
| "206.43" | 5.44E-01 | 6.98E-02 | 1.56E-04 | 1.24E-04 | 3.22E-01 | 4.73E-02 |
| "206.44" | 9.42E-02 | 6.52E-01 | 6.86E-01 | 1.27E-02 | 9.19E-01 | 2.62E-02 |
| "206.46" | 7.72E-01 | 1.89E-01 | 1.07E-01 | 2.50E-01 | 1.43E-02 | 6.13E-01 |
| "206.48" | 4.16E-01 | 6.72E-03 | 1.50E-06 | 7.21E-06 | 1.19E-03 | 6.43E-03 |
| "206.50" | 2.62E-02 | 3.45E-01 | 5.08E-03 | 2.85E-03 | 4.96E-04 | 4.69E-02 |
| "206.51" | 1.10E-03 | 6.17E-04 | 2.54E-03 | 4.59E-01 | 1.71E-01 | 1.32E-01 |
| "206.52" | 1.46E-01 | 9.59E-02 | 4.45E-02 | 3.16E-01 | 6.07E-05 | 9.23E-01 |
| "206.53" | 1.46E-01 | 3.10E-01 | 4.96E-01 | 3.28E-02 | 5.47E-03 | 1.22E-01 |
| "206.54" | 1.17E-02 | 4.36E-03 | 8.18E-03 | 1.24E-02 | 1.02E-04 | 5.10E-01 |
| "206.55" | 6.79E-01 | 2.68E-01 | 2.77E-01 | 8.30E-01 | 1.26E-01 | 7.02E-01 |
| "206.56" | 7.53E-02 | 1.38E-03 | 1.37E-03 | 3.18E-03 | 9.04E-04 | 7.35E-01 |
| "206.57" | 2.42E-01 | 7.58E-01 | 3.40E-01 | 5.98E-01 | 1.75E-01 | 7.08E-03 |
| "206.58" | 2.46E-02 | 5.73E-01 | 1.99E-01 | 6.66E-01 | 5.85E-01 | 6.28E-04 |
| "206.59" | 6.01E-01 | 5.69E-01 | 4.83E-01 | 3.16E-01 | 7.49E-02 | 2.04E-01 |
| "206.60" | 1.66E-02 | 3.10E-01 | 4.08E-01 | 3.30E-01 | 2.15E-02 | 9.94E-04 |
| "206.61" | 3.23E-01 | 9.27E-01 | 3.02E-01 | 5.87E-02 | 7.24E-02 | 8.78E-01 |
| "206.62" | 5.33E-03 | 3.08E-01 | 7.09E-06 | 5.75E-06 | 1.83E-04 | 7.23E-02 |
| "206.65" | 8.15E-01 | 6.35E-03 | 6.06E-06 | 5.75E-06 | 1.50E-02 | 3.40E-01 |
| "206.70" | 5.94E-07 | 1.56E-10 | 1.29E-12 | 4.15E-03 | 5.40E-03 | 2.65E-08 |
| "206.73" | 5.18E-01 | 6.10E-03 | 1.86E-03 | 2.20E-01 | 1.42E-01 | 2.87E-01 |

TABLE 6-continued

Comprehensive neuronal culture screening results for RCaMP1h variants

| | | | | | | |
|---|---|---|---|---|---|---|
| "206.74" | 4.06E−01 | 1.25E−01 | 5.07E−02 | 2.71E−01 | 4.21E−04 | 8.70E−01 |
| "206.75" | 1.10E−01 | 2.11E−02 | 1.32E−02 | 6.25E−03 | 9.14E−03 | 7.32E−02 |
| "206.76" | 1.95E−03 | 6.26E−04 | 2.18E−04 | 5.46E−04 | 3.36E−03 | 1.96E−03 |
| "206.77" | 3.27E−01 | 8.20E−01 | 9.55E−01 | 2.43E−01 | 2.34E−05 | 8.73E−02 |
| "206.78" | 4.10E−01 | 4.43E−01 | 6.19E−01 | 1.15E−01 | 1.44E−03 | 2.89E−01 |
| "206.85" | 2.15E−02 | 9.91E−01 | 7.07E−01 | 1.01E−01 | 1.52E−01 | 2.93E−02 |
| "206.87" | 3.80E−05 | 1.06E−04 | 1.29E−01 | 2.88E−01 | 1.45E−06 | 7.69E−01 |
| "206.88" | 1.11E−03 | 1.60E−04 | 3.36E−04 | 1.42E−04 | 8.28E−04 | 6.70E−01 |
| "206.91" | 2.69E−03 | 2.29E−02 | 9.12E−02 | 2.58E−01 | 1.43E−01 | 9.02E−01 |
| "206.92" | 3.06E−02 | 1.52E−02 | 7.30E−03 | 2.00E−01 | 6.37E−01 | 3.74E−01 |
| "206.94" | 7.91E−01 | 1.76E−02 | 6.36E−04 | 6.78E−04 | 3.65E−03 | 2.58E−01 |
| "206.95" | 2.91E−01 | 5.45E−01 | 2.39E−02 | 1.21E−02 | 1.70E−03 | 9.82E−01 |
| "206.96" | 7.17E−01 | 1.52E−01 | 2.58E−01 | 4.38E−01 | 7.67E−02 | 8.08E−01 |
| "206.97" | 2.03E−01 | 8.39E−01 | 6.59E−02 | 6.12E−02 | 9.30E−05 | 2.98E−01 |
| "206.99" | 1.81E−03 | 1.89E−01 | 2.02E−04 | 1.20E−01 | 3.08E−01 | 6.08E−01 |
| "206.100" | 5.87E−01 | 6.65E−02 | 1.16E−02 | 7.53E−04 | 2.03E−04 | 3.12E−02 |
| "206.103" | 7.75E−01 | 7.46E−03 | 1.10E−04 | 1.43E−02 | 2.44E−01 | 7.85E−01 |
| "206.104" | 3.33E−01 | 6.43E−03 | 2.97E−03 | 9.28E−02 | 3.04E−03 | 8.66E−01 |
| "206.106" | 8.36E−01 | 5.77E−01 | 2.48E−01 | 9.60E−01 | 1.02E−01 | 1.23E−02 |
| "206.107" | 1.14E−02 | 1.18E−01 | 3.82E−01 | 4.64E−01 | 2.34E−02 | 5.01E−02 |
| "206.108" | 1.79E−01 | 6.70E−02 | 3.28E−02 | 3.28E−01 | 6.62E−01 | 1.78E−02 |
| "206.109" | 3.99E−04 | 2.36E−04 | 2.52E−04 | 1.97E−04 | 5.71E−01 | 1.19E−01 |
| "206.110" | 2.11E−02 | 3.33E−03 | 9.86E−03 | 1.58E−01 | 3.20E−02 | 8.04E−01 |
| "206.111" | 5.28E−01 | 6.12E−01 | 6.54E−01 | 7.12E−01 | 7.73E−01 | 3.77E−01 |
| "206.112" | 5.85E−01 | 4.89E−02 | 1.29E−02 | 1.02E−01 | 2.54E−03 | 9.33E−01 |
| "206.113" | 2.66E−01 | 9.96E−01 | 9.03E−01 | 9.24E−01 | 3.09E−02 | 4.47E−02 |
| "206.115" | 9.52E−01 | 9.29E−01 | 1.85E−02 | 8.58E−01 | 3.19E−03 | 6.72E−02 |
| "206.116" | 9.25E−01 | 5.85E−02 | 2.51E−03 | 1.65E−01 | 6.64E−02 | 5.34E−02 |
| "206.121" | 2.55E−01 | 8.73E−01 | 9.56E−01 | 3.08E−01 | 4.54E−05 | 9.06E−01 |
| "206.122" | 1.00E+00 | 9.86E−01 | 4.37E−01 | 2.68E−01 | 6.73E−02 | 4.14E−01 |
| "206.123" | 7.77E−01 | 2.13E−01 | 9.08E−02 | 2.76E−01 | 6.78E−03 | 9.12E−04 |
| "206.126" | 1.49E−01 | 1.01E−01 | 9.04E−02 | 2.50E−01 | 1.61E−03 | 5.25E−02 |
| "206.127" | 2.22E−01 | 1.48E−02 | 1.83E−02 | 3.09E−01 | 2.16E−02 | 4.91E−01 |
| "206.128" | 1.63E−01 | 9.40E−01 | 8.48E−01 | 3.39E−01 | 2.13E−02 | 1.79E−01 |
| "206.130" | 6.14E−01 | 4.56E−01 | 1.81E−01 | 3.86E−01 | 1.03E−01 | 3.80E−01 |
| "206.132" | 9.19E−02 | 5.58E−01 | 4.23E−01 | 7.00E−01 | 5.32E−01 | 3.34E−02 |
| "206.133" | 3.78E−04 | 6.12E−03 | 4.12E−02 | 8.33E−05 | 4.04E−03 | 7.88E−02 |
| "206.135" | 5.18E−01 | 4.12E−01 | 6.94E−04 | 1.92E−05 | 7.79E−03 | 3.29E−01 |
| "206.137" | 3.64E−05 | 2.75E−01 | 2.25E−04 | 8.50E−02 | 7.80E−04 | 5.46E−06 |
| "206.138" | 6.67E−05 | 3.10E−02 | 6.93E−01 | 4.05E−01 | 9.00E−03 | 6.00E−06 |
| "206.139" | 3.50E−04 | 7.99E−05 | 8.74E−06 | 3.36E−04 | 5.07E−03 | 3.96E−01 |
| "206.140" | 9.89E−01 | 4.61E−02 | 6.50E−03 | 6.47E−01 | 6.91E−06 | 5.08E−01 |
| "206.141" | 1.16E−03 | 2.48E−02 | 3.33E−01 | 2.70E−01 | 1.08E−03 | 5.65E−04 |
| "206.143" | 1.34E−03 | 4.65E−03 | 2.09E−01 | 1.11E−01 | 6.66E−03 | 1.30E−02 |
| "206.144" | 1.46E−03 | 9.20E−03 | 4.05E−03 | 5.96E−04 | 6.23E−04 | 5.65E−04 |
| "206.147" | 2.94E−10 | 1.20E−08 | 7.52E−12 | 1.09E−09 | 5.38E−02 | 9.82E−16 |
| "206.148" | 8.91E−01 | 3.27E−01 | 8.49E−05 | 3.09E−05 | 3.27E−05 | 5.35E−06 |
| "206.150" | 2.40E−01 | 5.85E−02 | 7.87E−04 | 1.67E−02 | 2.97E−03 | 5.65E−04 |
| "206.152" | 5.04E−01 | 5.01E−04 | 5.35E−05 | 9.12E−03 | 2.95E−06 | 1.29E−05 |
| "206.153" | 5.43E−03 | 8.55E−01 | 2.52E−01 | 3.24E−03 | 7.97E−04 | 5.71E−04 |
| "206.154" | 9.23E−04 | 2.28E−03 | 1.44E−03 | 3.57E−01 | 3.09E−02 | 1.30E−02 |
| "206.155" | 6.26E−01 | 2.14E−01 | 4.25E−02 | 2.41E−01 | 4.31E−03 | 2.46E−04 |
| "206.156" | 8.49E−04 | 2.41E−04 | 5.94E−06 | 5.75E−06 | 9.55E−02 | 4.05E−02 |
| "206.157" | 2.38E−04 | 1.21E−01 | 2.11E−03 | 1.42E−04 | 2.56E−04 | 1.92E−05 |
| "206.158" | 7.43E−02 | 8.94E−01 | 8.92E−01 | 7.51E−01 | 3.61E−03 | 1.53E−02 |
| "206.161" | 8.63E−01 | 7.30E−01 | 6.61E−02 | 2.10E−01 | 1.57E−01 | 5.81E−02 |
| "206.164" | 4.79E−01 | 2.20E−01 | 1.44E−01 | 5.91E−01 | 2.34E−04 | 8.28E−01 |
| "206.165" | 8.92E−01 | 4.96E−01 | 1.17E−01 | 1.61E−01 | 1.33E−02 | 3.23E−01 |
| "206.166" | 5.21E−01 | 5.93E−01 | 2.06E−01 | 5.02E−01 | 4.61E−01 | 5.05E−01 |
| "206.167" | 1.88E−04 | 4.49E−06 | 2.68E−08 | 1.71E−07 | 2.50E−05 | 3.77E−01 |
| "206.168" | 1.51E−02 | 1.22E−02 | 1.32E−02 | 1.11E−03 | 2.05E−04 | 7.12E−01 |
| "206.169" | 3.67E−01 | 7.14E−01 | 2.70E−01 | 5.87E−01 | 4.21E−01 | 5.48E−02 |
| "206.170" | 7.48E−03 | 4.91E−04 | 1.28E−05 | 5.78E−04 | 3.76E−04 | 4.17E−03 |
| "206.173" | 7.91E−02 | 6.42E−01 | 7.87E−01 | 9.31E−01 | 6.41E−01 | 1.15E−01 |
| "206.174" | 9.70E−01 | 9.03E−01 | 9.10E−01 | 8.15E−01 | 2.22E−01 | 2.21E−01 |
| "206.175" | 1.80E−02 | 5.86E−02 | 1.04E−01 | 3.31E−01 | 1.25E−03 | 1.00E−03 |
| "206.176" | 1.89E−01 | 1.94E−01 | 1.67E−01 | 8.15E−03 | 1.41E−03 | 9.77E−03 |
| "206.178" | 8.34E−02 | 6.86E−01 | 9.55E−02 | 3.15E−02 | 7.06E−03 | 3.64E−05 |
| "206.179" | 1.09E−01 | 7.22E−01 | 6.54E−01 | 4.19E−01 | 4.69E−03 | 4.18E−02 |
| "206.180" | 1.02E−01 | 1.08E−02 | 1.10E−02 | 7.02E−02 | 4.56E−04 | 3.82E−01 |
| "206.181" | 1.34E−01 | 8.88E−01 | 1.15E−01 | 3.50E−01 | 1.52E−02 | 2.89E−01 |
| "206.182" | 6.84E−01 | 4.99E−03 | 9.90E−06 | 4.69E−05 | 1.95E−02 | 1.72E−01 |
| "206.183" | 8.18E−01 | 9.63E−03 | 1.66E−02 | 4.93E−06 | 2.03E−04 | 2.66E−01 |
| "206.184" | 8.34E−02 | 4.31E−01 | 3.36E−04 | 3.90E−03 | 5.18E−04 | 3.71E−02 |
| "206.185" | 2.34E−01 | 9.02E−04 | 2.26E−06 | 6.35E−06 | 1.53E−04 | 8.75E−01 |
| "206.186" | 1.52E−04 | 2.25E−01 | 1.03E−01 | 2.01E−02 | 3.37E−02 | 1.19E−03 |
| "206.187" | 3.98E−03 | 3.62E−02 | 1.17E−01 | 3.49E−01 | 9.51E−01 | 1.03E−02 |
| "206.188" | 2.40E−01 | 6.67E−02 | 1.03E−01 | 7.39E−01 | 2.24E−04 | 1.65E−01 |

TABLE 6-continued

Comprehensive neuronal culture screening results for RCaMP1h variants

| | | | | | | |
|---|---|---|---|---|---|---|
| "206.190" | 8.38E−03 | 4.30E−03 | 2.94E−01 | 2.20E−02 | 6.52E−05 | 1.17E−02 |
| "206.193" | 2.73E−03 | 9.36E−03 | 1.40E−04 | 5.15E−02 | 3.03E−03 | 8.81E−04 |
| "206.194" | 4.28E−04 | 1.18E−04 | 1.36E−04 | 2.80E−03 | 5.77E−04 | 1.28E−04 |
| "206.195" | 2.71E−01 | 1.26E−01 | 1.20E−04 | 8.95E−01 | 5.59E−05 | 4.45E−05 |
| "206.196" | 8.90E−02 | 3.05E−01 | 3.63E−03 | 5.64E−01 | 6.18E−01 | 5.10E−02 |
| "206.197" | 9.27E−04 | 2.82E−05 | 2.48E−05 | 2.64E−05 | 8.43E−02 | 8.15E−03 |
| "206.200" | 8.49E−05 | 8.66E−05 | 5.92E−05 | 8.12E−05 | 2.28E−02 | 3.89E−05 |
| "206.201" | 9.34E−04 | 5.86E−04 | 2.94E−03 | 2.36E−01 | 3.68E−01 | 2.02E−01 |
| "206.203" | 6.23E−03 | 1.59E−02 | 2.89E−03 | 2.59E−02 | 8.31E−03 | 9.81E−02 |
| "206.206" | 2.00E−13 | 7.64E−18 | 5.59E−21 | 2.06E−02 | 1.63E−17 | 9.34E−04 |
| "206.207" | 2.75E−02 | 1.31E−03 | 1.16E−04 | 1.02E−04 | 2.72E−03 | 3.03E−04 |
| "206.208" | 1.36E−04 | 2.52E−04 | 4.86E−04 | 2.85E−05 | 2.21E−01 | 5.40E−05 |
| "206.209" | 7.54E−06 | 6.13E−06 | 6.19E−06 | 3.64E−05 | 1.03E−01 | 4.58E−04 |
| "206.210" | 6.17E−16 | 6.65E−19 | 1.77E−19 | 2.11E−16 | 2.75E−02 | 1.01E−08 |
| "206.211" | 1.54E−03 | 7.14E−05 | 5.88E−06 | 9.32E−05 | 1.12E−02 | 5.22E−01 |
| "206.212" | 3.84E−02 | 2.26E−01 | 6.61E−02 | 4.20E−01 | 1.30E−03 | 3.95E−01 |
| "206.213" | 4.32E−01 | 9.31E−01 | 2.67E−01 | 1.73E−01 | 4.80E−04 | 1.56E−03 |
| "206.226" | 1.11E−02 | 7.14E−01 | 1.40E−04 | 2.56E−03 | 2.17E−04 | 5.52E−02 |
| "206.227" | 3.17E−05 | 3.21E−07 | 9.00E−09 | 5.94E−07 | 7.58E−06 | 2.30E−09 |
| "206.228" | 9.91E−02 | 8.19E−02 | 3.94E−04 | 2.47E−03 | 8.83E−04 | 9.00E−01 |
| "206.230" | 8.46E−02 | 9.32E−07 | 6.23E−09 | 6.82E−02 | 2.90E−07 | 2.92E−01 |
| "206.231" | 1.61E−04 | 5.90E−05 | 8.34E−05 | 9.98E−05 | 4.43E−02 | 9.08E−02 |
| "206.234" | 7.20E−01 | 2.59E−01 | 2.84E−01 | 9.43E−01 | 1.16E−02 | 1.29E−01 |
| "206.236" | 2.79E−01 | 9.00E−01 | 6.75E−01 | 5.51E−01 | 9.83E−04 | 2.42E−02 |
| "206.237" | 3.46E−02 | 9.13E−01 | 1.54E−02 | 6.41E−04 | 9.18E−01 | 3.98E−01 |
| "206.238" | 2.44E−02 | 4.53E−02 | 1.30E−01 | 8.18E−01 | 9.14E−02 | 9.68E−03 |
| "206.239" | 5.69E−01 | 3.04E−01 | 2.26E−01 | 2.23E−02 | 6.46E−01 | 6.55E−02 |
| "206.241" | 2.77E−03 | 9.19E−04 | 1.28E−04 | 2.42E−03 | 9.95E−04 | 2.03E−01 |
| "206.242" | 2.69E−01 | 4.40E−03 | 6.09E−04 | 5.90E−04 | 2.97E−03 | 1.03E−02 |
| "206.243" | 7.34E−01 | 4.77E−01 | 5.76E−01 | 1.56E−01 | 1.17E−03 | 1.05E−04 |
| "206.244" | 4.30E−01 | 4.07E−02 | 6.12E−04 | 2.39E−02 | 1.31E−01 | 1.25E−04 |
| "206.245" | 7.57E−01 | 5.15E−02 | 7.09E−02 | 2.67E−01 | 8.68E−01 | 2.36E−03 |
| "206.246" | 1.95E−04 | 1.75E−04 | 1.47E−04 | 5.03E−02 | 7.51E−05 | 4.36E−01 |
| "206.247" | 1.68E−02 | 7.80E−04 | 3.73E−09 | 7.89E−10 | 2.87E−04 | 2.06E−01 |
| "206.249" | 1.70E−02 | 1.32E−02 | 3.40E−02 | 1.49E−01 | 3.13E−04 | 2.18E−02 |
| "206.250" | 2.21E−02 | 1.75E−03 | 5.83E−04 | 6.16E−04 | 3.00E−03 | 8.29E−03 |
| "206.252" | 6.05E−03 | 1.14E−02 | 1.88E−03 | 4.03E−04 | 3.03E−02 | 1.90E−02 |
| "206.253" | 1.17E−02 | 1.23E−04 | 2.25E−07 | 1.30E−06 | 5.58E−05 | 8.36E−01 |
| "206.254" | 1.65E−01 | 4.70E−01 | 5.66E−01 | 2.98E−01 | 5.17E−04 | 4.70E−04 |
| "206.255" | 1.62E−03 | 6.95E−04 | 5.91E−05 | 4.29E−05 | 6.13E−03 | 8.19E−06 |
| "206.256" | 1.55E−07 | 1.45E−12 | 2.99E−15 | 5.91E−07 | 2.50E−01 | 3.75E−21 |
| "206.260" | 1.44E−04 | 2.62E−05 | 2.62E−05 | 3.26E−05 | 2.73E−05 | 6.77E−03 |
| "206.261" | 9.29E−05 | 3.23E−05 | 2.62E−05 | 4.31E−05 | 2.79E−05 | 7.31E−05 |
| "206.262" | 9.49E−04 | 6.00E−06 | 5.40E−05 | 5.75E−06 | 8.43E−02 | 5.67E−01 |
| "206.263" | 2.16E−02 | 1.08E−02 | 7.43E−03 | 6.07E−02 | 1.19E−03 | 2.74E−03 |
| "206.264" | 1.13E−03 | 1.32E−01 | 2.49E−02 | 2.68E−02 | 7.40E−04 | 1.17E−04 |
| "206.265" | 4.04E−01 | 1.77E−02 | 1.10E−02 | 1.81E−02 | 2.11E−04 | 9.81E−02 |
| "206.268" | 4.94E−01 | 6.31E−02 | 7.17E−03 | 1.14E−03 | 5.53E−01 | 4.16E−02 |
| "206.269" | 8.37E−02 | 9.14E−04 | 4.45E−04 | 4.32E−04 | 6.22E−01 | 2.24E−04 |
| "206.270" | 9.55E−02 | 3.07E−01 | 4.47E−02 | 3.86E−01 | 1.89E−03 | 1.21E−01 |
| "206.271" | 8.36E−01 | 7.36E−01 | 3.34E−01 | 1.43E−01 | 5.79E−01 | 1.26E−01 |
| "206.272" | 7.35E−01 | 7.16E−01 | 3.99E−01 | 8.77E−01 | 4.48E−03 | 6.91E−01 |
| "206.273" | 5.45E−04 | 1.30E−05 | 1.82E−06 | 4.46E−06 | 9.69E−06 | 7.70E−01 |
| "206.274" | 2.60E−02 | 7.44E−02 | 9.44E−02 | 3.22E−01 | 3.69E−03 | 5.38E−02 |
| "206.278" | 3.25E−03 | 7.36E−06 | 4.52E−07 | 2.42E−04 | 8.92E−08 | 5.72E−01 |
| "206.279" | 2.56E−04 | 4.79E−07 | 5.72E−09 | 4.42E−08 | 6.93E−08 | 1.43E−02 |
| "206.281" | 1.42E−03 | 1.54E−03 | 2.52E−05 | 3.18E−06 | 2.86E−01 | 5.37E−01 |
| "206.282" | 6.02E−03 | 1.17E−04 | 8.79E−09 | 3.41E−09 | 4.52E−07 | 1.09E−03 |
| "206.283" | 9.82E−01 | 6.90E−01 | 3.47E−02 | 4.70E−07 | 4.29E−03 | 8.97E−01 |
| "206.288" | 2.28E−02 | 1.22E−01 | 6.94E−01 | 1.46E−01 | 1.06E−03 | 5.90E−04 |
| "206.292" | 5.79E−05 | 2.18E−04 | 6.32E−05 | 3.67E−04 | 3.53E−04 | 8.45E−01 |
| "206.294" | 2.98E−19 | 1.47E−09 | 2.95E−12 | 2.75E−09 | 2.94E−13 | 3.30E−19 |
| "206.295" | 2.78E−05 | 2.31E−05 | 1.27E−05 | 2.39E−04 | 1.03E−01 | 2.56E−01 |
| "206.296" | 6.21E−19 | 6.71E−18 | 2.02E−17 | 1.13E−03 | 1.67E−01 | 4.42E−16 |
| "206.297" | 8.28E−06 | 6.94E−06 | 6.19E−06 | 9.95E−06 | 5.21E−03 | 8.77E−01 |
| "206.298" | 4.65E−12 | 2.99E−15 | 1.82E−18 | 5.62E−16 | 7.58E−11 | 7.66E−10 |
| "206.299" | 1.82E−15 | 1.02E−17 | 1.77E−18 | 5.96E−11 | 7.97E−01 | 1.64E−04 |
| "206.300" | 8.49E−05 | 4.51E−04 | 1.95E−03 | 4.65E−01 | 1.45E−02 | 6.65E−02 |
| "206.301" | 1.59E−02 | 1.25E−02 | 6.44E−03 | 3.54E−01 | 1.57E−01 | 1.12E−03 |
| "206.330" | 2.68E−02 | 1.11E−03 | 3.17E−04 | 4.05E−02 | 3.97E−04 | 5.44E−02 |
| "206.332" | 8.26E−01 | 3.61E−02 | 7.16E−03 | 1.28E−01 | 2.22E−07 | 7.83E−01 |
| "206.338" | 3.75E−02 | 1.44E−01 | 3.66E−02 | 3.64E−01 | 2.67E−06 | 5.58E−10 |
| "206.340" | 4.24E−03 | 9.40E−01 | 1.49E−02 | 1.25E−01 | 7.80E−04 | 5.65E−04 |
| "206.341" | 3.85E−02 | 2.70E−02 | 5.28E−02 | 9.23E−01 | 4.29E−06 | 4.97E−03 |
| "206.343" | 1.31E−06 | 3.11E−05 | 1.35E−02 | 8.25E−01 | 4.84E−08 | 1.42E−03 |
| "206.344" | 4.24E−03 | 5.47E−01 | 5.82E−01 | 1.21E−03 | 1.55E−01 | 1.13E−06 |
| "206.346" | 1.73E−03 | 1.17E−03 | 5.41E−04 | 8.47E−02 | 2.92E−02 | 5.01E−02 |
| "206.347" | 1.43E−01 | 1.64E−02 | 1.06E−01 | 7.92E−01 | 4.25E−04 | 8.53E−01 |

TABLE 6-continued

Comprehensive neuronal culture screening results for RCaMP1h variants

| | | | | | | |
|---|---|---|---|---|---|---|
| "206.356" | 3.06E−05 | 9.24E−09 | 3.16E−09 | 9.08E−07 | 3.45E−02 | 6.77E−10 |
| "206.371" | 7.96E−03 | 2.70E−02 | 3.11E−02 | 7.25E−03 | 1.87E−01 | 4.28E−04 |
| "206.372" | 1.62E−01 | 3.86E−01 | 7.88E−01 | 8.33E−01 | 6.26E−03 | 7.48E−01 |
| "206.373" | 4.43E−02 | 9.18E−03 | 6.66E−03 | 4.01E−04 | 5.26E−02 | 5.10E−02 |
| "206.383" | 1.31E−02 | 7.46E−03 | 3.35E−03 | 4.53E−01 | 5.10E−04 | 3.37E−03 |
| "206.385" | 2.57E−04 | 4.93E−05 | 3.03E−05 | 8.08E−02 | 1.35E−03 | 7.69E−05 |
| "206.386" | 4.93E−01 | 8.23E−02 | 6.29E−03 | 5.96E−04 | 2.32E−01 | 2.44E−01 |
| "206.389" | 1.18E−02 | 6.29E−04 | 5.71E−04 | 5.90E−04 | 2.84E−03 | 3.38E−01 |
| "206.390" | 4.37E−03 | 6.56E−04 | 4.32E−04 | 2.98E−03 | 4.88E−04 | 7.34E−01 |
| "206.391" | 1.38E−01 | 6.29E−04 | 5.71E−04 | 6.03E−04 | 1.46E−02 | 6.10E−03 |
| "206.394" | 2.13E−01 | 2.08E−03 | 3.14E−04 | 4.01E−04 | 7.40E−03 | 1.27E−02 |
| "206.395" | 1.63E−04 | 3.23E−05 | 2.62E−05 | 6.29E−05 | 2.79E−05 | 6.39E−03 |
| "206.396" | 7.14E−03 | 2.34E−04 | 1.54E−04 | 3.65E−04 | 3.66E−04 | 3.92E−01 |
| "206.397" | 5.57E−02 | 6.85E−04 | 5.65E−04 | 5.96E−04 | 2.81E−03 | 9.36E−01 |
| "206.398" | 8.41E−01 | 4.36E−03 | 6.03E−04 | 6.09E−04 | 3.24E−03 | 1.85E−02 |
| "206.400" | 4.52E−03 | 1.18E−04 | 1.18E−04 | 1.24E−04 | 1.46E−02 | 9.71E−02 |
| "206.401" | 3.95E−03 | 4.18E−05 | 4.10E−05 | 4.59E−05 | 1.36E−04 | 3.95E−01 |
| "206.403" | 7.96E−03 | 1.30E−04 | 1.18E−04 | 1.25E−04 | 1.50E−02 | 5.42E−01 |
| "206.405" | 7.55E−01 | 9.76E−04 | 1.26E−04 | 1.64E−04 | 2.93E−03 | 5.30E−01 |
| "206.406" | 8.33E−03 | 8.66E−04 | 6.13E−06 | 4.35E−06 | 4.95E−04 | 4.13E−02 |
| "206.407" | 5.56E−01 | 1.84E−05 | 1.65E−09 | 7.73E−10 | 1.56E−02 | 4.84E−01 |
| "206.409" | 4.48E−01 | 4.69E−01 | 6.78E−02 | 1.07E−01 | 1.93E−04 | 1.11E−04 |
| "206.410" | 7.58E−02 | 8.32E−04 | 7.01E−06 | 2.27E−04 | 1.06E−05 | 2.37E−02 |
| "206.411" | 5.73E−02 | 3.50E−01 | 7.30E−04 | 5.75E−06 | 3.78E−05 | 2.17E−02 |
| "206.412" | 2.40E−01 | 1.49E−02 | 1.54E−03 | 1.03E−03 | 2.91E−04 | 5.44E−02 |
| "206.413" | 4.74E−02 | 6.61E−03 | 4.94E−04 | 7.06E−05 | 7.81E−05 | 4.36E−01 |
| "206.414" | 5.98E−01 | 9.20E−05 | 5.78E−03 | 1.29E−05 | 2.68E−04 | 4.34E−01 |
| "206.415" | 9.65E−02 | 4.07E−01 | 1.86E−03 | 7.81E−10 | 2.77E−01 | 4.64E−01 |
| "206.416" | 6.16E−01 | 7.18E−01 | 5.11E−02 | 2.19E−08 | 6.87E−01 | 7.80E−01 |
| "206.417" | 8.41E−01 | 3.74E−01 | 8.83E−01 | 3.20E−04 | 9.56E−01 | 1.03E−01 |
| "206.418" | 6.97E−01 | 1.87E−01 | 3.72E−03 | 1.45E−04 | 1.90E−06 | 8.12E−01 |
| "206.419" | 6.68E−02 | 1.75E−04 | 2.94E−06 | 2.14E−05 | 1.25E−02 | 3.84E−08 |
| "206.420" | 6.14E−03 | 5.44E−01 | 1.89E−01 | 1.31E−03 | 2.30E−01 | 8.67E−01 |
| "206.421" | 1.46E−01 | 5.51E−02 | 1.01E−01 | 9.19E−01 | 2.38E−04 | 7.56E−01 |
| "206.422" | 6.40E−04 | 3.87E−10 | 1.84E−10 | 3.61E−10 | 6.47E−09 | 3.37E−03 |
| "206.423" | 6.56E−01 | 8.03E−01 | 3.56E−01 | 2.90E−01 | 6.13E−01 | 7.60E−01 |
| "206.424" | 1.50E−01 | 4.74E−02 | 7.08E−05 | 1.91E−05 | 4.00E−06 | 2.61E−07 |
| "206.425" | 2.90E−04 | 1.69E−07 | 1.56E−07 | 1.78E−07 | 4.16E−07 | 6.89E−03 |
| "206.426" | 6.91E−03 | 9.16E−06 | 2.23E−06 | 4.01E−04 | 2.38E−08 | 1.70E−01 |
| "206.427" | 1.07E−02 | 1.22E−02 | 1.69E−02 | 1.48E−01 | 4.40E−04 | 8.81E−02 |
| "206.428" | 8.99E−01 | 3.44E−02 | 5.77E−04 | 2.65E−01 | 9.03E−01 | 3.18E−02 |
| "206.429" | 4.15E−03 | 2.89E−05 | 1.02E−04 | 2.68E−03 | 1.10E−06 | 1.86E−02 |
| "206.430" | 1.81E−05 | 1.89E−14 | 2.37E−17 | 2.62E−15 | 5.79E−05 | 9.62E−01 |
| "206.431" | 4.11E−01 | 1.86E−02 | 1.12E−01 | 6.75E−03 | 7.26E−01 | 3.77E−01 |
| "206.432" | 1.62E−01 | 2.37E−01 | 5.76E−01 | 1.02E−02 | 5.78E−01 | 5.07E−02 |
| "206.433" | 1.98E−02 | 3.09E−01 | 9.50E−01 | 3.49E−01 | 6.48E−01 | 8.15E−03 |
| "206.434" | 2.05E−02 | 8.08E−03 | 3.78E−03 | 6.30E−04 | 3.94E−04 | 9.00E−02 |
| "206.435" | 2.39E−02 | 8.03E−02 | 5.78E−03 | 3.21E−06 | 1.63E−05 | 1.31E−01 |
| "206.437" | 2.93E−04 | 4.41E−05 | 5.36E−04 | 8.70E−04 | 1.33E−03 | 2.73E−01 |
| "206.438" | 1.67E−01 | 2.59E−01 | 9.51E−02 | 4.62E−02 | 1.53E−04 | 7.67E−01 |
| "206.439" | 3.10E−02 | 5.64E−01 | 3.12E−02 | 3.64E−04 | 4.17E−04 | 3.64E−01 |
| "206.440" | 3.75E−02 | 3.67E−01 | 3.32E−01 | 3.75E−02 | 5.41E−01 | 8.94E−01 |
| "206.441" | 8.46E−02 | 1.25E−01 | 2.33E−01 | 8.77E−01 | 3.11E−02 | 4.28E−02 |
| "206.442" | 4.96E−02 | 1.65E−03 | 2.85E−05 | 4.73E−05 | 1.68E−04 | 5.75E−04 |
| "206.443" | 1.82E−01 | 4.94E−01 | 3.10E−01 | 1.28E−04 | 3.61E−01 | 4.14E−05 |
| "206.444" | 1.24E−02 | 1.90E−01 | 7.47E−04 | 9.94E−04 | 7.71E−04 | 2.62E−03 |
| "206.445" | 1.11E−01 | 6.77E−01 | 1.58E−01 | 2.22E−03 | 7.68E−02 | 7.15E−04 |
| "206.446" | 5.98E−02 | 7.30E−01 | 6.68E−01 | 5.57E−02 | 2.20E−02 | 1.22E−01 |
| "206.447" | 2.16E−02 | 1.41E−01 | 3.92E−01 | 6.83E−01 | 2.30E−03 | 2.47E−02 |
| "206.448" | 1.55E−01 | 3.48E−02 | 1.34E−01 | 9.51E−01 | 1.71E−04 | 8.40E−01 |
| "206.449" | 2.71E−01 | 6.58E−01 | 9.94E−01 | 5.48E−01 | 9.43E−01 | 3.47E−02 |
| "206.450" | 1.99E−02 | 1.15E−02 | 4.95E−03 | 1.19E−01 | 2.04E−04 | 6.54E−01 |
| "206.451" | 3.85E−03 | 4.58E−03 | 4.27E−02 | 4.14E−01 | 1.73E−02 | 4.84E−01 |
| "206.453" | 3.14E−01 | 3.93E−03 | 1.28E−04 | 2.11E−04 | 3.28E−03 | 2.67E−02 |
| "206.454" | 5.86E−05 | 3.97E−05 | 5.80E−05 | 2.66E−02 | 8.76E−04 | 3.28E−04 |
| "206.455" | 3.61E−04 | 2.54E−03 | 1.95E−01 | 3.39E−01 | 5.25E−03 | 2.11E−02 |
| "206.457" | 8.04E−01 | 6.35E−03 | 8.30E−08 | 2.43E−05 | 2.53E−10 | 2.15E−02 |
| "206.460" | 5.24E−04 | 5.59E−05 | 3.78E−04 | 3.41E−06 | 2.26E−06 | 7.13E−01 |
| "206.461" | 5.80E−01 | 8.13E−01 | 1.30E−01 | 3.01E−01 | 2.14E−01 | 7.77E−01 |
| "206.462" | 2.43E−03 | 4.41E−05 | 1.40E−05 | 3.72E−05 | 1.88E−04 | 4.84E−02 |
| "206.463" | 6.79E−01 | 4.54E−02 | 3.01E−03 | 1.35E−02 | 2.54E−01 | 5.89E−02 |
| "206.464" | 1.04E−01 | 3.97E−01 | 5.56E−01 | 7.28E−01 | 1.32E−01 | 3.69E−02 |
| "206.465" | 5.53E−01 | 1.17E−04 | 7.27E−01 | 2.03E−01 | 1.85E−02 | 2.25E−03 |
| "206.466" | 3.00E−03 | 5.52E−04 | 2.93E−04 | 1.60E−03 | 3.75E−01 | 1.59E−03 |
| "206.467" | 8.09E−06 | 4.04E−06 | 3.48E−06 | 9.09E−04 | 2.48E−03 | 1.25E−03 |
| "206.468" | 7.39E−06 | 6.13E−06 | 6.19E−06 | 8.29E−04 | 8.59E−01 | 8.84E−01 |
| "206.469" | 8.62E−06 | 6.45E−06 | 6.19E−06 | 4.05E−05 | 4.00E−01 | 8.32E−01 |
| "206.470" | 6.00E−06 | 5.94E−06 | 6.19E−06 | 3.63E−04 | 9.73E−01 | 3.85E−03 |

TABLE 6-continued

Comprehensive neuronal culture screening results for RCaMP1h variants

| | | | | | | |
|---|---|---|---|---|---|---|
| "206.471" | 5.61E−11 | 8.10E−14 | 4.06E−14 | 1.14E−11 | 6.00E−01 | 4.37E−05 |
| "206.472" | 3.04E−01 | 5.48E−01 | 2.26E−01 | 1.90E−05 | 7.63E−06 | 1.77E−05 |
| "206.473" | 5.57E−05 | 5.46E−05 | 3.85E−05 | 3.15E−04 | 5.99E−03 | 8.91E−01 |
| "206.474" | 7.62E−06 | 6.19E−06 | 6.19E−06 | 1.22E−03 | 2.83E−02 | 3.02E−03 |
| "206.475" | 3.89E−06 | 2.55E−06 | 1.39E−06 | 9.00E−06 | 6.56E−04 | 2.47E−01 |
| "206.476" | 4.41E−01 | 7.70E−01 | 5.03E−01 | 7.90E−01 | 2.71E−02 | 2.90E−01 |
| "206.477" | 9.35E−03 | 7.13E−10 | 7.39E−15 | 1.40E−07 | 1.37E−01 | 7.08E−01 |
| "206.478" | 1.94E−06 | 1.51E−06 | 1.38E−06 | 1.39E−01 | 3.98E−01 | 2.80E−02 |
| "206.479" | 1.55E−05 | 6.59E−06 | 6.19E−06 | 7.90E−04 | 1.12E−01 | 1.40E−01 |
| "206.480" | 3.96E−06 | 2.19E−06 | 1.48E−06 | 1.33E−04 | 3.76E−03 | 6.95E−02 |
| "206.481" | 7.78E−06 | 6.45E−06 | 6.19E−06 | 1.97E−02 | 2.86E−02 | 1.41E−01 |
| "206.482" | 2.32E−04 | 2.22E−10 | 3.48E−12 | 7.45E−11 | 4.62E−03 | 1.73E−01 |
| "206.485" | 4.36E−04 | 3.88E−04 | 1.54E−04 | 8.94E−03 | 6.34E−03 | 8.11E−02 |
| "206.487" | 9.26E−04 | 6.19E−06 | 6.19E−06 | 6.73E−06 | 5.01E−01 | 9.60E−03 |
| "206.493" | 6.22E−04 | 2.11E−02 | 3.90E−02 | 5.96E−04 | 9.54E−01 | 1.57E−03 |
| "206.495" | 6.59E−06 | 1.03E−05 | 1.07E−05 | 1.20E−04 | 9.78E−06 | 1.49E−02 |
| "206.499" | 5.96E−04 | 6.05E−03 | 4.65E−01 | 5.90E−04 | 7.30E−01 | 6.09E−04 |
| "206.500" | 1.15E−01 | 1.94E−03 | 8.33E−05 | 3.45E−04 | 3.64E−04 | 3.37E−01 |
| "206.501" | 8.71E−01 | 1.29E−03 | 1.63E−09 | 3.43E−11 | 7.54E−05 | 5.61E−09 |
| "206.502" | 3.75E−02 | 5.26E−03 | 4.59E−02 | 8.60E−01 | 4.20E−05 | 4.25E−01 |
| "206.504" | 1.07E−05 | 6.32E−06 | 6.13E−06 | 6.00E−06 | 7.32E−05 | 7.16E−06 |
| "206.506" | 7.09E−01 | 6.98E−01 | 4.69E−02 | 1.08E−03 | 3.52E−01 | 4.74E−04 |
| "206.507" | 2.70E−02 | 2.63E−01 | 3.80E−01 | 1.99E−04 | 6.98E−05 | 1.21E−04 |
| "206.508" | 1.74E−01 | 1.27E−02 | 4.17E−03 | 2.23E−02 | 2.28E−01 | 3.06E−03 |
| "206.509" | 1.32E−04 | 4.64E−05 | 3.00E−05 | 9.19E−05 | 6.21E−01 | 2.64E−01 |
| "206.511" | 2.14E−02 | 4.23E−01 | 3.78E−01 | 7.40E−01 | 4.04E−03 | 1.81E−04 |
| "206.512" | 5.25E−01 | 4.38E−01 | 2.20E−02 | 2.66E−03 | 2.70E−03 | 1.77E−02 |
| "206.513" | 9.12E−01 | 2.12E−01 | 3.99E−01 | 2.67E−04 | 5.71E−04 | 9.95E−03 |
| "206.514" | 3.70E−01 | 3.24E−01 | 4.47E−01 | 8.74E−03 | 1.38E−02 | 3.18E−02 |
| "206.515" | 4.32E−01 | 4.10E−01 | 4.59E−02 | 2.67E−05 | 1.04E−01 | 3.60E−03 |
| "206.516" | 4.47E−04 | 8.41E−05 | 2.05E−05 | 9.35E−05 | 2.54E−04 | 1.37E−04 |
| "206.517" | 4.47E−01 | 6.77E−02 | 1.32E−01 | 4.21E−01 | 1.97E−05 | 1.98E−01 |
| "206.518" | 1.51E−01 | 4.66E−04 | 1.15E−05 | 1.54E−05 | 1.98E−05 | 2.26E−01 |
| "206.519" | 7.20E−02 | 4.60E−04 | 2.37E−03 | 1.72E−04 | 5.14E−08 | 6.80E−01 |
| "206.520" | 2.21E−03 | 2.59E−06 | 1.16E−08 | 4.91E−06 | 5.40E−06 | 6.33E−01 |
| "206.521" | 2.44E−01 | 1.27E−03 | 5.19E−02 | 4.31E−02 | 6.31E−05 | 1.12E−02 |
| "206.522" | 1.37E−03 | 8.46E−04 | 6.60E−03 | 3.92E−02 | 1.08E−06 | 6.09E−01 |
| "206.523" | 1.45E−05 | 2.94E−07 | 1.12E−07 | 2.09E−06 | 7.61E−03 | 4.49E−01 |
| "206.524" | 1.04E−02 | 2.89E−04 | 1.42E−07 | 4.83E−06 | 7.44E−03 | 9.73E−06 |
| "206.525" | 4.49E−07 | 2.00E−08 | 9.11E−10 | 6.26E−04 | 3.34E−02 | 1.03E−02 |
| "206.526" | 3.19E−01 | 4.32E−02 | 3.40E−03 | 4.05E−02 | 6.27E−01 | 3.07E−01 |
| "206.527" | 6.30E−02 | 3.19E−02 | 2.00E−02 | 1.56E−01 | 2.21E−01 | 6.49E−01 |
| "206.528" | 9.66E−03 | 3.18E−05 | 7.82E−08 | 1.42E−06 | 7.14E−02 | 5.06E−01 |
| "206.529" | 3.51E−04 | 1.50E−07 | 1.46E−09 | 2.24E−08 | 5.20E−01 | 5.71E−05 |
| "206.530" | 9.43E−01 | 5.17E−01 | 1.41E−01 | 1.86E−01 | 3.20E−03 | 1.71E−03 |
| "206.600" | 2.94E−08 | 2.45E−06 | 5.40E−09 | 8.03E−02 | 6.58E−06 | 2.58E−08 |
| "206.603" | 1.36E−01 | 2.82E−01 | 1.29E−04 | 1.45E−04 | 2.93E−03 | 3.32E−02 |
| "206.604" | 3.06E−01 | 7.50E−01 | 5.52E−01 | 1.04E−01 | 2.13E−02 | 2.08E−01 |
| "206.605" | 3.17E−04 | 7.32E−01 | 3.99E−01 | 1.95E−03 | 2.33E−04 | 5.88E−06 |
| "206.606" | 5.90E−03 | 2.95E−01 | 6.86E−01 | 5.32E−01 | 1.43E−02 | 1.25E−04 |
| "206.607" | 3.35E−01 | 8.66E−01 | 4.90E−01 | 8.38E−03 | 1.62E−03 | 2.46E−02 |
| "206.608" | 6.44E−03 | 3.41E−01 | 1.69E−03 | 1.56E−01 | 7.88E−04 | 8.08E−03 |
| "206.609" | 2.03E−01 | 3.88E−01 | 8.34E−01 | 8.45E−01 | 2.93E−02 | 3.85E−06 |
| "206.610" | 7.08E−02 | 9.04E−02 | 1.64E−02 | 5.22E−01 | 1.85E−03 | 6.93E−06 |
| "206.611" | 1.55E−05 | 4.10E−01 | 1.06E−01 | 1.55E−05 | 8.21E−01 | 5.88E−06 |
| "206.613" | 3.09E−03 | 4.64E−01 | 6.89E−01 | 2.04E−02 | 6.49E−03 | 3.16E−05 |
| "206.615" | 6.11E−02 | 7.20E−01 | 5.38E−01 | 7.57E−02 | 4.43E−02 | 5.58E−03 |
| "206.617" | 4.32E−04 | 2.34E−04 | 2.09E−04 | 1.92E−01 | 1.27E−03 | 8.99E−02 |
| "206.618" | 1.17E−03 | 4.95E−03 | 3.52E−03 | 8.56E−04 | 4.11E−01 | 7.42E−01 |
| "206.619" | 1.12E−05 | 1.66E−05 | 2.18E−05 | 9.04E−01 | 1.60E−03 | 2.33E−02 |
| "206.620" | 3.04E−08 | 4.44E−08 | 2.84E−07 | 1.16E−06 | 7.06E−01 | 1.77E−10 |
| "206.622" | 1.49E−03 | 7.72E−04 | 1.89E−03 | 8.81E−01 | 3.78E−01 | 6.32E−01 |
| "206.623" | 8.58E−09 | 7.25E−09 | 5.23E−08 | 2.32E−02 | 6.47E−01 | 4.54E−11 |
| "206.624" | 1.65E−03 | 1.57E−01 | 4.10E−01 | 9.71E−02 | 3.92E−01 | 5.71E−04 |
| "206.625" | 1.80E−01 | 2.42E−01 | 6.81E−01 | 8.32E−01 | 7.81E−01 | 7.94E−01 |
| "206.626" | 3.11E−06 | 9.58E−06 | 2.99E−04 | 6.39E−02 | 8.84E−01 | 4.69E−05 |
| "206.627" | 1.46E−02 | 1.17E−01 | 7.50E−01 | 1.49E−02 | 9.25E−01 | 5.33E−01 |
| "206.628" | 1.46E−03 | 1.28E−03 | 2.82E−04 | 1.22E−01 | 5.11E−02 | 7.37E−01 |
| "206.629" | 5.23E−06 | 2.21E−06 | 3.48E−06 | 4.09E−02 | 3.87E−02 | 1.91E−05 |
| "206.630" | 6.50E−04 | 2.87E−04 | 1.03E−04 | 1.14E−01 | 9.63E−01 | 1.57E−02 |
| "206.631" | 6.64E−09 | 2.35E−08 | 2.96E−08 | 8.24E−05 | 6.62E−03 | 1.71E−10 |
| "206.632" | 9.75E−05 | 1.10E−04 | 3.77E−05 | 1.03E−02 | 1.70E−01 | 2.73E−05 |
| "206.633" | 2.45E−03 | 1.32E−02 | 1.59E−02 | 2.94E−03 | 9.87E−01 | 2.80E−02 |
| "206.634" | 1.85E−04 | 1.37E−04 | 2.90E−04 | 1.47E−02 | 1.72E−02 | 3.16E−03 |
| "206.635" | 1.90E−04 | 8.59E−03 | 2.37E−04 | 5.54E−02 | 7.69E−04 | 1.83E−03 |
| "206.636" | 3.42E−02 | 4.19E−01 | 1.95E−02 | 8.98E−01 | 8.66E−03 | 4.55E−03 |
| "206.637" | 2.65E−02 | 2.49E−01 | 1.20E−04 | 5.69E−05 | 9.77E−02 | 9.92E−04 |
| "206.638" | 6.19E−03 | 9.42E−01 | 2.20E−03 | 6.16E−04 | 1.92E−01 | 5.15E−03 |

TABLE 6-continued

Comprehensive neuronal culture screening results for RCaMP1h variants

| | | | | | | |
|---|---|---|---|---|---|---|
| "206.639" | 2.81E−01 | 2.50E−02 | 1.81E−04 | 3.26E−05 | 2.78E−02 | 4.63E−04 |
| "206.640" | 4.16E−03 | 8.29E−02 | 3.62E−05 | 3.30E−05 | 3.44E−03 | 1.75E−01 |
| "206.642" | 1.20E−01 | 9.36E−01 | 8.21E−04 | 6.50E−04 | 3.50E−03 | 9.24E−01 |
| "206.643" | 3.42E−01 | 5.15E−01 | 1.46E−03 | 8.13E−04 | 1.35E−01 | 2.54E−02 |
| "206.646" | 2.75E−01 | 4.37E−01 | 5.01E−01 | 1.41E−03 | 5.97E−02 | 6.12E−01 |
| "206.647" | 5.25E−01 | 6.23E−01 | 5.15E−01 | 8.40E−04 | 5.01E−01 | 8.47E−03 |
| "206.648" | 3.56E−02 | 2.91E−01 | 6.36E−04 | 5.90E−04 | 3.05E−01 | 9.08E−01 |
| "206.649" | 4.76E−02 | 9.29E−01 | 2.07E−01 | 1.98E−01 | 6.18E−01 | 1.74E−01 |
| "206.650" | 1.22E−01 | 9.10E−01 | 5.27E−02 | 3.76E−03 | 3.68E−02 | 4.37E−01 |
| "206.651" | 6.68E−01 | 4.98E−01 | 4.03E−04 | 1.53E−04 | 9.10E−01 | 4.85E−02 |
| "206.652" | 1.32E−02 | 3.53E−01 | 6.43E−04 | 5.83E−04 | 1.64E−02 | 4.42E−01 |
| "206.653" | 3.80E−02 | 3.41E−02 | 3.06E−01 | 2.48E−01 | 4.28E−01 | 3.39E−03 |
| "206.654" | 5.20E−01 | 3.90E−01 | 1.21E−02 | 5.48E−03 | 1.88E−01 | 1.27E−01 |
| "206.655" | 1.08E−01 | 2.20E−01 | 2.65E−03 | 2.50E−02 | 3.33E−02 | 2.20E−01 |
| "206.656" | 2.16E−03 | 9.92E−01 | 1.07E−01 | 4.72E−01 | 8.31E−04 | 6.01E−01 |
| "206.659" | 2.11E−03 | 7.20E−03 | 2.19E−02 | 5.44E−01 | 6.29E−04 | 8.53E−01 |
| "206.662" | 5.06E−01 | 2.70E−02 | 3.64E−03 | 3.16E−01 | 1.17E−04 | 1.19E−01 |
| "206.666" | 2.42E−02 | 5.68E−02 | 3.82E−01 | 6.28E−01 | 1.15E−03 | 5.95E−02 |
| "206.667" | 3.13E−02 | 9.35E−03 | 1.19E−02 | 5.83E−01 | 9.24E−04 | 7.15E−02 |
| "206.668" | 6.39E−02 | 9.76E−02 | 2.62E−01 | 1.75E−02 | 2.10E−02 | 8.56E−04 |
| "206.669" | 2.60E−02 | 1.22E−02 | 4.69E−02 | 1.03E−02 | 2.93E−03 | 3.56E−03 |
| "206.670" | 1.99E−02 | 5.61E−02 | 2.16E−01 | 3.94E−02 | 2.13E−03 | 1.49E−01 |
| "206.672" | 8.33E−02 | 6.74E−02 | 1.35E−01 | 4.69E−02 | 3.22E−03 | 1.74E−03 |
| "206.673" | 2.19E−01 | 5.78E−02 | 3.08E−04 | 4.28E−04 | 5.93E−03 | 1.42E−02 |
| "206.674" | 4.27E−01 | 8.64E−01 | 4.30E−01 | 2.16E−02 | 1.17E−02 | 7.62E−02 |
| "206.675" | 6.66E−01 | 1.15E−01 | 1.02E−02 | 9.43E−03 | 4.98E−02 | 9.98E−01 |
| "206.676" | 6.49E−01 | 3.21E−01 | 3.03E−05 | 7.84E−05 | 9.19E−01 | 9.51E−04 |
| "206.677" | 5.75E−01 | 3.98E−01 | 2.04E−04 | 1.48E−04 | 5.92E−01 | 5.49E−03 |
| "206.678" | 9.61E−01 | 1.11E−01 | 2.94E−06 | 9.57E−05 | 2.74E−04 | 7.71E−06 |
| "206.679" | 9.12E−03 | 3.65E−02 | 5.25E−02 | 5.20E−02 | 9.42E−03 | 2.81E−03 |
| "206.680" | 1.28E−02 | 1.34E−01 | 5.22E−02 | 4.74E−02 | 5.73E−01 | 2.16E−02 |
| "206.681" | 6.44E−01 | 2.09E−01 | 6.59E−06 | 5.94E−06 | 1.00E+00 | 5.36E−02 |
| "206.682" | 3.06E−01 | 3.53E−01 | 1.31E−03 | 6.18E−03 | 5.15E−02 | 1.29E−02 |
| "206.683" | 4.36E−01 | 3.11E−01 | 6.04E−05 | 1.47E−04 | 1.48E−02 | 1.27E−03 |
| "206.684" | 8.18E−01 | 2.01E−02 | 3.87E−04 | 1.75E−04 | 1.21E−03 | 4.81E−01 |
| "206.687" | 3.27E−02 | 8.61E−01 | 1.45E−01 | 1.04E−01 | 2.78E−02 | 5.31E−04 |
| "206.688" | 1.65E−03 | 6.49E−03 | 3.18E−03 | 7.48E−02 | 2.04E−03 | 5.83E−04 |
| "206.689" | 1.53E−03 | 1.19E−03 | 9.94E−04 | 1.85E−02 | 1.32E−01 | 1.15E−03 |
| "206.690" | 1.13E−02 | 7.07E−03 | 4.11E−04 | 1.66E−02 | 3.84E−03 | 6.31E−05 |
| "206.691" | 1.51E−03 | 1.09E−02 | 5.72E−02 | 4.19E−02 | 3.83E−01 | 7.75E−01 |
| "206.692" | 3.21E−02 | 3.02E−04 | 9.93E−11 | 5.13E−02 | 3.04E−13 | 1.00E−05 |
| "206.693" | 4.30E−03 | 2.26E−03 | 1.27E−02 | 1.51E−01 | 2.28E−03 | 6.95E−02 |
| "206.694" | 1.75E−02 | 1.39E−01 | 5.82E−01 | 8.63E−01 | 1.96E−01 | 1.58E−04 |
| "206.695" | 2.38E−03 | 1.37E−02 | 6.28E−02 | 7.31E−01 | 1.16E−03 | 5.65E−04 |
| "206.696" | 5.33E−04 | 5.95E−05 | 1.07E−05 | 2.71E−04 | 1.46E−02 | 2.52E−02 |
| "206.697" | 5.49E−04 | 4.01E−03 | 3.51E−04 | 9.70E−01 | 2.96E−05 | 6.00E−06 |
| "206.698" | 5.45E−02 | 1.06E−01 | 7.26E−02 | 3.08E−01 | 4.06E−03 | 5.59E−05 |
| "206.699" | 4.83E−02 | 1.40E−01 | 1.37E−02 | 2.49E−01 | 8.08E−01 | 3.09E−01 |
| "206.700" | 9.88E−02 | 2.95E−01 | 4.41E−01 | 8.68E−03 | 3.20E−02 | 2.36E−04 |
| "206.701" | 2.40E−02 | 1.78E−02 | 3.38E−02 | 1.70E−01 | 4.00E−02 | 4.72E−01 |
| "206.702" | 1.79E−02 | 7.51E−01 | 1.68E−06 | 1.28E−06 | 1.00E+00 | 6.30E−04 |
| "206.703" | 6.53E−01 | 3.46E−01 | 6.50E−01 | 6.50E−01 | 9.09E−02 | 8.92E−01 |
| "206.704" | 8.08E−03 | 1.11E−01 | 3.69E−03 | 6.03E−04 | 9.14E−04 | 9.17E−01 |
| "206.705" | 1.66E−03 | 8.12E−01 | 3.62E−05 | 2.76E−05 | 9.09E−02 | 5.70E−04 |
| "206.706" | 7.25E−03 | 5.30E−01 | 1.46E−04 | 1.25E−04 | 9.31E−02 | 1.40E−03 |
| "206.707" | 6.13E−02 | 7.34E−01 | 1.59E−04 | 1.24E−04 | 8.14E−04 | 1.75E−04 |
| "206.708" | 4.71E−03 | 3.95E−01 | 7.24E−06 | 5.75E−06 | 1.00E+00 | 1.38E−05 |
| "206.709" | 4.43E−02 | 1.60E−01 | 1.53E−06 | 1.27E−06 | 7.57E−02 | 5.06E−01 |
| "206.710" | 2.61E−02 | 9.10E−01 | 6.64E−04 | 6.03E−04 | 8.40E−01 | 1.44E−02 |
| "206.711" | 1.41E−01 | 1.38E−01 | 7.54E−06 | 6.59E−06 | 8.37E−01 | 6.67E−01 |
| "206.712" | 7.44E−02 | 1.24E−01 | 3.80E−03 | 3.47E−03 | 8.20E−05 | 7.92E−05 |
| "206.713" | 9.94E−04 | 3.29E−01 | 2.38E−05 | 8.28E−06 | 1.59E−05 | 1.99E−05 |
| "206.714" | 5.15E−01 | 1.18E−02 | 1.70E−05 | 6.13E−06 | 8.81E−03 | 3.71E−02 |
| "206.715" | 7.33E−02 | 1.86E−02 | 7.01E−06 | 6.19E−06 | 9.47E−01 | 2.86E−04 |
| "206.716" | 5.36E−02 | 4.91E−01 | 7.09E−06 | 6.13E−06 | 3.94E−03 | 2.71E−03 |
| "206.717" | 4.26E−02 | 9.04E−01 | 1.88E−06 | 1.38E−06 | 1.86E−02 | 4.64E−06 |
| "206.718" | 1.85E−03 | 7.14E−01 | 2.04E−06 | 2.06E−06 | 1.76E−02 | 1.25E−01 |
| "206.719" | 9.69E−01 | 2.41E−01 | 1.40E−04 | 1.43E−04 | 9.09E−02 | 1.45E−01 |
| "206.720" | 2.88E−02 | 3.23E−01 | 7.01E−06 | 7.46E−06 | 8.43E−02 | 1.58E−04 |
| "206.721" | 7.10E−02 | 4.46E−01 | 3.06E−05 | 2.64E−05 | 1.00E+00 | 9.35E−04 |
| "206.722" | 7.43E−01 | 1.53E−01 | 2.97E−05 | 2.64E−05 | 1.00E+00 | 6.10E−05 |
| "206.723" | 5.32E−01 | 4.91E−01 | 1.96E−04 | 2.90E−04 | 1.46E−02 | 2.29E−04 |
| "206.724" | 5.99E−02 | 3.29E−01 | 6.36E−05 | 5.90E−04 | 1.00E+00 | 1.12E−03 |
| "206.725" | 1.37E−01 | 1.34E−01 | 2.94E−05 | 2.70E−05 | 9.20E−02 | 3.27E−01 |
| "206.726" | 7.46E−01 | 7.46E−05 | 5.94E−06 | 5.75E−06 | 1.60E−02 | 9.65E−05 |
| "206.727" | 2.66E−01 | 5.85E−01 | 1.64E−06 | 1.39E−06 | 1.00E+00 | 5.35E−05 |
| "206.728" | 3.14E−01 | 2.65E−01 | 3.13E−05 | 2.85E−05 | 2.34E−01 | 1.74E−04 |
| "206.729" | 1.04E−03 | 5.08E−01 | 7.09E−06 | 6.13E−06 | 3.05E−01 | 1.29E−04 |

TABLE 6-continued

Comprehensive neuronal culture screening results for RCaMP1h variants

| | | | | | | |
|---|---|---|---|---|---|---|
| "206.735" | 2.14E-03 | 1.61E-01 | 4.40E-03 | 5.90E-04 | 4.51E-03 | 1.04E-03 |
| "206.738" | 1.68E-02 | 5.47E-01 | 7.99E-01 | 7.99E-01 | 7.76E-04 | 8.33E-05 |
| "206.744" | 2.18E-03 | 3.32E-01 | 1.18E-03 | 7.39E-04 | 6.50E-04 | 3.09E-05 |
| "206.752" | 4.25E-04 | 3.50E-03 | 2.24E-03 | 8.44E-03 | 4.09E-01 | 1.01E-04 |
| "206.754" | 3.82E-05 | 5.02E-04 | 4.30E-03 | 1.78E-02 | 2.43E-02 | 9.91E-05 |
| "206.757" | 5.73E-04 | 1.59E-01 | 1.50E-01 | 3.24E-03 | 2.44E-04 | 1.75E-04 |
| "206.761" | 3.29E-03 | 1.32E-01 | 7.82E-02 | 3.14E-04 | 1.73E-03 | 1.48E-04 |
| "206.764" | 3.56E-03 | 5.58E-03 | 3.17E-02 | 1.19E-03 | 1.25E-01 | 9.29E-01 |
| "206.765" | 3.64E-05 | 7.53E-05 | 2.06E-04 | 7.16E-01 | 4.97E-03 | 2.09E-05 |
| "206.766" | 2.92E-04 | 1.14E-03 | 4.29E-03 | 1.41E-01 | 5.31E-01 | 4.98E-05 |
| "206.771" | 1.01E-03 | 4.52E-03 | 6.19E-03 | 1.12E-01 | 1.54E-03 | 1.51E-04 |
| "206.773" | 4.69E-06 | 1.24E-05 | 8.74E-06 | 9.51E-03 | 8.03E-05 | 2.14E-05 |
| "206.774" | 2.03E-05 | 1.86E-05 | 1.14E-05 | 3.74E-01 | 1.72E-05 | 4.11E-01 |
| "206.775" | 8.66E-04 | 6.34E-04 | 1.27E-04 | 4.56E-04 | 1.11E-04 | 7.67E-02 |
| "206.776" | 2.44E-04 | 5.72E-03 | 4.83E-03 | 1.16E-02 | 8.93E-01 | 2.66E-03 |
| "206.777" | 8.01E-03 | 3.46E-02 | 2.34E-01 | 2.04E-01 | 1.21E-01 | 2.55E-03 |
| "206.778" | 1.49E-03 | 2.29E-01 | 3.97E-05 | 2.62E-05 | 2.97E-05 | 3.89E-05 |
| "206.779" | 9.71E-02 | 2.52E-01 | 1.86E-02 | 5.90E-04 | 6.86E-04 | 6.03E-04 |
| "206.783" | 5.58E-02 | 5.71E-02 | 1.34E-02 | 1.25E-04 | 3.14E-03 | 1.40E-03 |
| "206.788" | 6.81E-03 | 5.16E-01 | 9.49E-04 | 1.24E-04 | 1.58E-04 | 1.24E-04 |
| "206.789" | 3.36E-01 | 3.38E-02 | 6.39E-03 | 3.52E-03 | 6.71E-01 | 2.79E-01 |
| "206.794" | 3.70E-02 | 4.19E-01 | 2.42E-01 | 6.12E-01 | 1.90E-01 | 5.32E-03 |
| "206.797" | 3.28E-02 | 9.93E-01 | 3.07E-02 | 2.67E-03 | 1.19E-03 | 2.95E-03 |
| "206.798" | 7.78E-04 | 5.51E-01 | 8.19E-06 | 5.75E-06 | 3.00E-05 | 2.62E-04 |
| "206.800" | 7.71E-04 | 6.57E-04 | 5.77E-04 | 8.75E-04 | 1.48E-02 | 1.57E-03 |
| "206.801" | 4.75E-01 | 4.41E-01 | 4.33E-02 | 2.82E-02 | 8.73E-01 | 1.88E-02 |
| "206.802" | 3.51E-01 | 2.25E-02 | 2.12E-03 | 6.22E-04 | 7.32E-04 | 6.64E-04 |
| "206.805" | 3.50E-01 | 4.50E-02 | 2.25E-04 | 3.66E-04 | 5.23E-01 | 6.73E-04 |
| "206.806" | 2.82E-05 | 2.53E-05 | 2.48E-05 | 2.79E-05 | 8.43E-02 | 9.70E-03 |
| "206.807" | 2.81E-04 | 2.54E-04 | 1.24E-04 | 1.24E-04 | 6.29E-04 | 2.67E-04 |
| "206.808" | 1.07E-02 | 4.91E-03 | 1.75E-04 | 1.28E-04 | 1.70E-04 | 7.84E-03 |
| "206.809" | 8.19E-02 | 2.57E-02 | 7.54E-06 | 7.88E-05 | 1.40E-03 | 5.75E-01 |
| "206.810" | 9.15E-01 | 1.79E-02 | 7.60E-03 | 1.97E-02 | 1.93E-01 | 2.28E-02 |
| "206.811" | 2.52E-01 | 1.88E-03 | 2.76E-05 | 3.33E-05 | 1.45E-04 | 2.54E-01 |
| "206.812" | 4.10E-05 | 2.48E-05 | 2.48E-05 | 4.14E-05 | 8.43E-02 | 6.49E-01 |
| "206.814" | 5.52E-04 | 4.32E-04 | 1.54E-03 | 7.78E-03 | 2.62E-04 | 1.13E-02 |
| "206.815" | 1.59E-04 | 1.17E-04 | 2.15E-04 | 1.30E-02 | 3.31E-04 | 7.94E-04 |
| "206.816" | 1.17E-04 | 1.30E-04 | 1.18E-04 | 3.24E-03 | 8.65E-02 | 3.17E-04 |
| "206.817" | 2.42E-01 | 7.98E-03 | 1.15E-04 | 2.91E-05 | 5.10E-05 | 6.92E-03 |
| "206.818" | 1.77E-06 | 1.58E-06 | 1.17E-06 | 2.66E-06 | 1.46E-02 | 5.88E-06 |
| "206.819" | 3.64E-01 | 1.78E-03 | 5.97E-04 | 2.82E-03 | 4.07E-01 | 4.03E-03 |
| "206.820" | 3.81E-01 | 2.74E-02 | 1.94E-04 | 5.33E-03 | 9.00E-03 | 1.81E-03 |
| "206.822" | 3.14E-01 | 4.97E-01 | 1.59E-01 | 2.73E-01 | 8.05E-03 | 1.99E-02 |
| "206.823" | 2.35E-04 | 1.54E-03 | 2.01E-03 | 4.21E-05 | 9.05E-05 | 3.45E-04 |
| "206.824" | 3.40E-04 | 5.20E-04 | 3.38E-03 | 5.78E-04 | 4.13E-04 | 9.58E-04 |
| "206.825" | 6.16E-03 | 4.70E-01 | 6.46E-01 | 2.10E-01 | 9.86E-01 | 9.55E-02 |
| "206.826" | 5.93E-04 | 8.69E-04 | 9.36E-02 | 9.28E-01 | 1.77E-03 | 3.51E-03 |
| "206.827" | 6.61E-03 | 9.93E-03 | 2.92E-01 | 6.59E-01 | 2.71E-03 | 7.10E-02 |
| "206.828" | 8.48E-04 | 3.38E-03 | 2.65E-01 | 8.75E-01 | 3.36E-02 | 8.02E-04 |
| "206.829" | 1.58E-03 | 1.06E-01 | 9.57E-01 | 8.64E-01 | 4.84E-01 | 3.15E-04 |
| "206.831" | 1.16E-03 | 3.28E-01 | 9.85E-02 | 1.91E-02 | 2.87E-01 | 6.93E-03 |
| "206.832" | 1.85E-02 | 3.44E-03 | 8.77E-02 | 1.44E-01 | 1.19E-01 | 5.04E-05 |
| "206.834" | 1.29E-04 | 1.07E-04 | 7.38E-04 | 2.75E-04 | 6.18E-04 | 7.46E-05 |
| "206.835" | 8.63E-02 | 5.25E-01 | 8.86E-02 | 4.26E-03 | 2.46E-01 | 5.23E-01 |
| "206.836" | 4.12E-02 | 1.89E-02 | 2.39E-05 | 1.07E-05 | 2.84E-03 | 3.99E-02 |
| "206.837" | 4.83E-03 | 6.32E-02 | 8.10E-01 | 8.04E-01 | 2.36E-02 | 9.67E-04 |
| "206.838" | 3.99E-04 | 1.81E-04 | 2.13E-04 | 5.32E-03 | 1.61E-04 | 3.13E-03 |
| "206.843" | 5.15E-01 | 4.34E-01 | 3.64E-01 | 1.37E-01 | 3.75E-01 | 1.26E-01 |
| "206.844" | 2.95E-02 | 4.56E-02 | 4.23E-01 | 4.16E-01 | 4.47E-04 | 1.25E-01 |
| "206.845" | 8.16E-01 | 4.71E-03 | 6.61E-06 | 2.12E-05 | 8.60E-03 | 5.85E-03 |
| "206.846" | 3.22E-02 | 3.77E-02 | 7.01E-06 | 8.62E-01 | 2.88E-01 | 1.12E-05 |
| "206.847" | 5.33E-04 | 3.92E-01 | 2.36E-05 | 5.12E-06 | 2.87E-04 | 2.42E-06 |
| "206.848" | 9.63E-03 | 8.81E-02 | 2.61E-05 | 7.33E-05 | 6.98E-06 | 4.11E-03 |
| "206.849" | 9.27E-01 | 2.07E-03 | 1.16E-05 | 7.32E-04 | 4.07E-03 | 1.43E-01 |
| "206.850" | 3.35E-02 | 9.93E-01 | 8.13E-01 | 8.42E-01 | 4.00E-02 | 4.36E-03 |
| "206.851" | 3.07E-01 | 5.60E-01 | 5.21E-01 | 9.67E-01 | 1.56E-03 | 1.18E-02 |
| "206.852" | 2.09E-01 | 1.29E-01 | 2.95E-01 | 6.18E-01 | 7.82E-02 | 7.61E-03 |
| "206.853" | 8.12E-01 | 7.85E-01 | 9.71E-01 | 6.95E-01 | 7.06E-03 | 2.34E-02 |
| "206.854" | 1.15E-01 | 5.77E-01 | 9.29E-01 | 7.46E-01 | 3.83E-01 | 3.38E-03 |
| "206.855" | 2.07E-01 | 7.96E-01 | 4.11E-01 | 1.86E-01 | 2.92E-01 | 8.27E-01 |
| "206.856" | 2.86E-01 | 2.74E-01 | 5.37E-01 | 2.21E-01 | 1.58E-02 | 2.77E-02 |
| "206.858" | 9.51E-02 | 1.91E-01 | 3.12E-01 | 2.72E-01 | 7.01E-03 | 2.77E-02 |
| "206.859" | 6.08E-03 | 2.84E-03 | 3.42E-03 | 5.28E-03 | 1.84E-04 | 2.11E-01 |
| "206.860" | 9.00E-01 | 4.94E-01 | 1.47E-01 | 7.17E-01 | 3.82E-01 | 7.12E-04 |
| "206.861" | 2.50E-01 | 6.74E-01 | 6.70E-02 | 7.95E-02 | 5.44E-01 | 5.44E-02 |
| "206.862" | 7.48E-01 | 9.14E-01 | 6.70E-01 | 6.87E-01 | 9.12E-01 | 1.10E-02 |
| "206.863" | 2.90E-01 | 3.57E-01 | 6.86E-01 | 6.55E-02 | 8.70E-02 | 1.48E-01 |
| "206.864" | 9.96E-01 | 7.58E-02 | 6.00E-03 | 2.30E-02 | 2.62E-01 | 1.86E-03 |

TABLE 6-continued

Comprehensive neuronal culture screening results for RCaMP1h variants

| | | | | | | |
|---|---|---|---|---|---|---|
| "206.865" | 7.17E−02 | 8.12E−01 | 2.80E−02 | 2.71E−01 | 3.53E−01 | 2.09E−01 |
| "206.866" | 1.71E−01 | 6.07E−01 | 2.34E−01 | 7.54E−03 | 3.54E−03 | 2.49E−01 |
| "206.867" | 3.74E−02 | 5.54E−02 | 1.74E−01 | 1.61E−01 | 1.33E−01 | 9.40E−02 |
| "206.868" | 8.83E−02 | 1.72E−01 | 5.15E−03 | 3.14E−04 | 1.41E−03 | 1.36E−01 |
| "206.869" | 5.42E−01 | 2.68E−02 | 3.64E−05 | 1.65E−05 | 3.77E−04 | 6.56E−02 |
| "206.870" | 1.07E−03 | 8.62E−02 | 6.43E−05 | 6.06E−06 | 1.47E−05 | 3.09E−05 |
| "206.871" | 9.86E−02 | 6.18E−03 | 5.06E−04 | 2.81E−05 | 2.50E−03 | 1.43E−04 |
| "206.872" | 9.63E−03 | 6.99E−01 | 3.77E−01 | 4.00E−04 | 5.40E−03 | 1.43E−05 |
| "206.873" | 1.53E−01 | 3.84E−01 | 3.98E−02 | 1.35E−04 | 4.20E−03 | 5.91E−04 |
| "206.874" | 6.35E−03 | 6.36E−02 | 2.21E−04 | 1.21E−05 | 2.34E−05 | 1.36E−05 |
| "206.875" | 6.97E−03 | 3.47E−01 | 1.34E−01 | 9.82E−05 | 7.44E−03 | 9.64E−04 |
| "206.876" | 7.19E−02 | 3.15E−01 | 2.83E−01 | 9.56E−01 | 9.88E−02 | 9.79E−01 |
| "206.879" | 2.19E−01 | 7.91E−01 | 1.56E−02 | 7.47E−01 | 4.28E−01 | 4.97E−02 |
| "206.881" | 9.37E−01 | 3.15E−02 | 5.48E−05 | 1.76E−02 | 1.77E−02 | 2.23E−02 |
| "206.882" | 8.10E−01 | 1.57E−02 | 3.09E−04 | 4.39E−03 | 5.46E−02 | 4.12E−02 |
| "206.883" | 9.15E−03 | 6.62E−02 | 6.28E−01 | 8.83E−01 | 1.12E−01 | 5.21E−01 |
| "206.884" | 1.00E−01 | 7.05E−01 | 8.62E−01 | 8.48E−02 | 8.89E−01 | 1.54E−02 |
| "206.885" | 9.63E−01 | 4.15E−01 | 2.34E−02 | 3.16E−01 | 3.12E−02 | 7.13E−02 |
| "206.886" | 1.72E−01 | 8.73E−01 | 1.87E−01 | 3.88E−02 | 5.23E−02 | 9.27E−01 |
| "206.887" | 5.99E−02 | 4.08E−01 | 7.75E−01 | 5.28E−01 | 4.57E−01 | 1.19E−03 |
| "206.888" | 6.74E−01 | 2.30E−01 | 1.56E−02 | 2.21E−01 | 8.85E−03 | 1.25E−01 |
| "206.890" | 6.11E−02 | 3.30E−01 | 9.52E−01 | 5.38E−01 | 6.23E−01 | 5.57E−02 |
| "206.893" | 6.10E−01 | 9.36E−01 | 7.66E−01 | 7.70E−01 | 5.60E−01 | 5.48E−02 |
| "206.894" | 3.71E−01 | 6.75E−01 | 4.22E−01 | 1.62E−01 | 8.63E−01 | 9.34E−03 |
| "206.895" | 2.17E−01 | 2.70E−01 | 2.13E−02 | 1.25E−01 | 1.17E−01 | 2.09E−02 |
| "206.896" | 1.12E−03 | 1.57E−03 | 4.04E−04 | 1.58E−02 | 2.39E−01 | 1.06E−02 |
| "206.897" | 1.07E−01 | 2.33E−03 | 9.30E−05 | 1.27E−01 | 9.33E−04 | 5.15E−03 |
| "206.898" | 1.15E−01 | 8.48E−03 | 6.69E−04 | 1.62E−03 | 1.02E−04 | 4.85E−01 |
| "206.899" | 6.40E−02 | 6.24E−02 | 1.53E−03 | 5.23E−01 | 6.13E−02 | 2.10E−03 |
| "206.900" | 6.31E−02 | 4.67E−04 | 1.40E−04 | 5.20E−04 | 3.85E−02 | 3.20E−03 |
| "206.901" | 1.85E−01 | 1.93E−04 | 7.33E−05 | 4.97E−04 | 2.07E−03 | 2.79E−05 |
| "206.902" | 3.22E−02 | 1.52E−03 | 8.03E−05 | 2.26E−03 | 6.43E−02 | 2.04E−04 |
| "206.903" | 7.34E−02 | 5.39E−03 | 1.79E−05 | 2.23E−06 | 1.98E−06 | 5.79E−04 |
| "206.904" | 2.76E−02 | 4.86E−03 | 5.25E−03 | 3.24E−02 | 1.58E−02 | 1.60E−02 |
| "206.905" | 9.16E−01 | 3.57E−01 | 8.42E−01 | 9.04E−02 | 1.45E−02 | 6.78E−02 |
| "206.906" | 6.96E−01 | 2.81E−01 | 2.40E−01 | 8.22E−01 | 1.33E−03 | 6.15E−01 |
| "206.907" | 6.92E−02 | 1.07E−02 | 9.61E−04 | 1.30E−02 | 1.19E−02 | 4.69E−01 |
| "206.908" | 3.98E−02 | 2.22E−03 | 8.58E−05 | 9.84E−03 | 1.75E−03 | 9.43E−04 |
| "206.910" | 1.84E−01 | 5.49E−03 | 1.28E−04 | 1.48E−04 | 2.90E−03 | 4.37E−03 |
| "206.911" | 1.47E−01 | 7.22E−04 | 3.54E−05 | 8.00E−05 | 6.06E−05 | 7.17E−02 |
| "206.912" | 1.42E−02 | 8.66E−03 | 6.85E−04 | 1.30E−03 | 1.16E−03 | 3.06E−03 |
| "206.914" | 4.32E−01 | 2.31E−02 | 1.66E−04 | 1.75E−04 | 1.40E−04 | 8.23E−02 |
| "206.915" | 4.81E−02 | 2.85E−03 | 1.18E−05 | 1.76E−04 | 1.48E−05 | 1.51E−02 |
| "206.916" | 7.44E−01 | 9.08E−02 | 1.39E−01 | 2.34E−01 | 2.23E−03 | 1.17E−02 |
| "206.917" | 8.39E−01 | 2.52E−02 | 2.57E−03 | 2.26E−02 | 1.31E−02 | 2.14E−01 |
| "206.919" | 4.50E−01 | 9.00E−03 | 1.08E−04 | 2.22E−05 | 1.48E−05 | 3.93E−01 |
| "206.920" | 1.23E−01 | 2.81E−03 | 4.72E−05 | 1.07E−05 | 6.54E−05 | 7.60E−05 |
| "206.921" | 7.55E−01 | 5.07E−03 | 1.56E−04 | 2.73E−04 | 2.20E−04 | 2.69E−03 |
| "206.922" | 2.18E−01 | 3.40E−02 | 7.72E−04 | 3.61E−04 | 2.69E−03 | 2.12E−01 |
| "206.925" | 3.67E−01 | 5.88E−01 | 1.23E−01 | 8.10E−01 | 1.11E−02 | 5.46E−01 |
| "206.927" | 6.18E−02 | 2.04E−02 | 6.78E−02 | 1.29E−01 | 3.40E−04 | 7.89E−01 |
| "206.928" | 5.28E−02 | 5.07E−03 | 1.83E−05 | 1.53E−02 | 2.23E−04 | 7.44E−01 |
| "206.929" | 4.28E−04 | 1.73E−04 | 2.62E−04 | 2.49E−02 | 1.17E−04 | 1.96E−02 |
| "206.930" | 5.26E−04 | 1.83E−03 | 4.83E−02 | 9.00E−01 | 7.86E−02 | 1.73E−02 |
| "206.931" | 8.33E−02 | 4.35E−01 | 3.77E−01 | 4.89E−01 | 9.64E−01 | 6.85E−01 |
| "206.932" | 1.10E−01 | 1.55E−02 | 7.50E−02 | 3.54E−02 | 3.61E−01 | 5.82E−04 |
| "206.936" | 4.94E−01 | 6.08E−01 | 3.00E−02 | 1.03E−01 | 7.40E−03 | 2.24E−01 |
| "206.937" | 3.71E−01 | 6.26E−01 | 7.52E−01 | 2.03E−01 | 1.88E−02 | 3.47E−01 |
| "206.938" | 1.41E−02 | 3.12E−03 | 4.40E−03 | 6.18E−01 | 5.71E−04 | 3.49E−01 |
| "206.939" | 1.99E−03 | 1.29E−08 | 6.03E−10 | 8.49E−01 | 1.21E−12 | 9.48E−02 |
| "206.940" | 2.05E−01 | 3.36E−01 | 5.35E−01 | 4.27E−01 | 8.56E−02 | 1.42E−05 |
| "206.943" | 4.63E−02 | 5.24E−01 | 1.45E−02 | 1.70E−03 | 9.05E−01 | 7.00E−01 |
| "206.947" | 1.16E−03 | 2.88E−03 | 8.47E−03 | 3.04E−02 | 4.95E−01 | 2.81E−04 |
| "206.948" | 1.16E−03 | 1.23E−02 | 4.91E−02 | 3.73E−01 | 9.91E−01 | 7.48E−02 |
| "206.952" | 2.95E−02 | 6.10E−01 | 1.40E−02 | 2.34E−01 | 4.42E−03 | 7.72E−04 |
| "206.953" | 1.48E−01 | 4.69E−01 | 1.57E−02 | 7.60E−02 | 8.12E−01 | 1.47E−02 |
| "206.960" | 9.65E−03 | 7.30E−02 | 4.12E−02 | 1.50E−01 | 4.93E−01 | 3.51E−04 |
| "206.961" | 2.31E−01 | 4.43E−01 | 7.67E−01 | 5.70E−01 | 8.46E−01 | 9.10E−01 |
| "206.962" | 1.01E−01 | 2.76E−01 | 1.44E−02 | 8.62E−01 | 7.72E−04 | 3.12E−01 |
| "206.964" | 1.13E−02 | 1.71E−02 | 6.07E−02 | 3.88E−01 | 2.32E−03 | 7.33E−01 |
| "206.965" | 1.11E−01 | 1.13E−01 | 9.33E−01 | 9.52E−01 | 1.32E−04 | 1.90E−02 |
| "206.969" | 2.87E−01 | 2.25E−02 | 5.97E−04 | 1.30E−04 | 4.89E−01 | 9.94E−01 |
| "206.970" | 5.68E−02 | 3.30E−01 | 9.19E−02 | 1.41E−01 | 4.40E−03 | 7.03E−02 |
| "206.971" | 1.84E−01 | 9.28E−01 | 7.51E−02 | 8.05E−01 | 3.10E−06 | 5.65E−01 |
| "206.972" | 7.11E−01 | 1.65E−01 | 3.28E−02 | 1.65E−04 | 1.40E−01 | 8.15E−01 |
| "206.973" | 6.76E−01 | 9.58E−01 | 3.88E−01 | 1.39E−02 | 6.69E−01 | 9.31E−01 |
| "206.974" | 3.42E−03 | 2.04E−03 | 1.38E−03 | 6.83E−02 | 2.72E−06 | 9.15E−01 |
| "206.975" | 6.23E−02 | 2.21E−04 | 1.43E−05 | 2.08E−01 | 3.08E−07 | 4.71E−01 |

TABLE 6-continued

Comprehensive neuronal culture screening results for RCaMP1h variants

| | | | | | | |
|---|---|---|---|---|---|---|
| "206.976" | 2.24E−05 | 1.02E−05 | 4.69E−05 | 1.35E−01 | 6.46E−05 | 6.54E−04 |
| "206.977" | 3.54E−03 | 7.53E−04 | 2.04E−03 | 3.28E−01 | 5.46E−06 | 1.45E−03 |
| "206.979" | 7.02E−01 | 7.29E−02 | 6.16E−04 | 5.90E−04 | 9.43E−02 | 1.27E−02 |
| "206.980" | 5.17E−03 | 2.98E−02 | 4.14E−01 | 4.99E−04 | 7.31E−01 | 1.05E−01 |
| "206.981" | 7.24E−02 | 7.97E−01 | 1.44E−01 | 2.36E−02 | 8.47E−02 | 3.09E−01 |
| "206.982" | 2.21E−02 | 2.14E−01 | 5.53E−01 | 8.44E−01 | 4.21E−02 | 5.99E−01 |
| "206.983" | 7.41E−01 | 3.79E−02 | 3.67E−04 | 1.02E−01 | 6.54E−07 | 5.03E−01 |
| "206.984" | 6.93E−05 | 6.99E−05 | 1.06E−04 | 3.08E−01 | 5.41E−06 | 2.83E−05 |
| "206.985" | 2.04E−04 | 3.51E−05 | 5.68E−04 | 5.70E−01 | 1.06E−05 | 2.60E−01 |
| "206.986" | 2.68E−01 | 5.14E−02 | 1.26E−03 | 1.08E−03 | 2.24E−02 | 1.02E−02 |
| "206.988" | 5.49E−01 | 1.27E−01 | 1.69E−01 | 6.71E−04 | 8.15E−03 | 1.93E−01 |
| "206.989" | 2.95E−02 | 2.80E−01 | 1.43E−04 | 1.22E−04 | 2.49E−04 | 3.16E−03 |
| "206.991" | 8.97E−06 | 6.78E−13 | 7.91E−18 | 3.09E−11 | 1.22E−01 | 2.42E−03 |
| "206.993" | 8.68E−02 | 1.14E−02 | 7.59E−07 | 2.83E−07 | 2.65E−01 | 5.64E−01 |
| "206.994" | 7.13E−11 | 4.12E−19 | 1.02E−21 | 7.77E−01 | 2.09E−22 | 6.75E−01 |
| "206.995" | 1.20E−02 | 8.17E−01 | 7.14E−04 | 6.39E−08 | 9.25E−05 | 6.80E−05 |
| "206.997" | 2.41E−01 | 5.68E−04 | 1.21E−04 | 1.21E−04 | 5.77E−04 | 3.68E−03 |
| "206.998" | 2.03E−01 | 2.19E−02 | 7.08E−04 | 5.90E−04 | 7.01E−04 | 5.83E−02 |
| "206.999" | 1.10E−01 | 1.98E−06 | 2.29E−04 | 2.83E−07 | 7.47E−07 | 5.35E−05 |
| "206.1000" | 5.32E−03 | 1.83E−04 | 6.48E−06 | 1.81E−01 | 1.34E−05 | 7.52E−03 |
| "206.1001" | 1.30E−03 | 1.73E−02 | 6.11E−02 | 3.90E−03 | 8.49E−04 | 4.54E−01 |
| "206.1002" | 6.66E−01 | 3.21E−03 | 6.78E−04 | 1.60E−03 | 7.08E−04 | 3.60E−01 |
| "206.1003" | 9.64E−07 | 8.60E−08 | 5.95E−08 | 2.94E−07 | 2.64E−07 | 2.45E−02 |
| "206.1006" | 2.43E−03 | 1.21E−06 | 1.24E−06 | 2.42E−06 | 1.29E−04 | 8.18E−03 |
| "206.1007" | 2.02E−03 | 6.50E−04 | 5.71E−04 | 6.16E−04 | 2.81E−03 | 1.30E−01 |
| "206.1009" | 1.32E−01 | 6.22E−04 | 5.71E−04 | 5.90E−04 | 2.84E−03 | 3.98E−01 |
| "206.1011" | 3.77E−03 | 5.63E−05 | 2.51E−05 | 4.78E−05 | 2.48E−05 | 8.84E−05 |
| "206.1013" | 3.72E−05 | 3.73E−06 | 1.19E−06 | 1.26E−06 | 2.56E−05 | 9.10E−01 |
| "206.1014" | 1.46E−02 | 1.21E−04 | 1.20E−04 | 1.45E−04 | 2.84E−03 | 8.81E−03 |
| "206.1015" | 1.53E−04 | 6.54E−06 | 1.24E−06 | 1.56E−06 | 1.30E−06 | 2.00E−01 |
| "206.1016" | 2.08E−03 | 3.30E−05 | 2.51E−05 | 3.00E−05 | 5.71E−04 | 2.38E−04 |
| "206.1017" | 3.83E−03 | 1.55E−06 | 1.23E−06 | 2.76E−06 | 5.46E−06 | 6.21E−05 |
| "206.1018" | 4.13E−01 | 3.14E−02 | 4.24E−02 | 1.06E−01 | 4.77E−01 | 7.89E−01 |
| "206.1019" | 2.13E−03 | 6.65E−06 | 2.64E−07 | 6.26E−06 | 7.58E−04 | 7.84E−01 |
| "206.1020" | 8.27E−03 | 7.57E−01 | 3.18E−01 | 1.06E−04 | 1.33E−03 | 8.34E−01 |
| "206.1021" | 5.68E−01 | 9.01E−04 | 5.17E−03 | 1.52E−04 | 7.54E−07 | 6.20E−08 |
| "206.1022" | 3.70E−01 | 3.86E−02 | 7.33E−04 | 4.72E−01 | 2.45E−01 | 3.50E−04 |
| "206.1023" | 6.28E−02 | 1.93E−03 | 2.40E−05 | 1.94E−03 | 2.53E−03 | 6.83E−04 |
| "206.1024" | 3.16E−01 | 5.89E−01 | 9.86E−01 | 5.23E−01 | 2.85E−01 | 1.33E−03 |
| "206.1025" | 5.33E−02 | 4.84E−01 | 9.69E−01 | 8.96E−01 | 3.87E−05 | 9.51E−01 |
| "206.1026" | 5.51E−01 | 2.67E−02 | 7.56E−02 | 2.01E−02 | 2.36E−01 | 3.56E−07 |
| "206.1027" | 2.22E−01 | 1.12E−01 | 4.96E−01 | 6.60E−01 | 1.01E−02 | 2.44E−03 |
| "206.1029" | 1.28E−01 | 1.99E−01 | 5.69E−01 | 2.34E−01 | 3.58E−03 | 1.34E−01 |
| "206.1030" | 9.38E−01 | 7.86E−01 | 8.07E−01 | 1.94E−01 | 9.68E−01 | 8.27E−01 |
| "206.1031" | 7.28E−02 | 1.59E−04 | 1.03E−07 | 9.78E−06 | 5.27E−04 | 4.79E−03 |
| "206.1032" | 7.18E−02 | 2.55E−03 | 1.89E−06 | 1.36E−02 | 9.86E−04 | 3.06E−01 |
| "206.1033" | 2.05E−02 | 7.54E−03 | 5.29E−03 | 6.14E−01 | 8.79E−02 | 2.37E−01 |
| "206.1034" | 2.88E−01 | 4.71E−01 | 1.62E−02 | 9.32E−02 | 4.23E−03 | 9.20E−01 |
| "206.1035" | 4.09E−02 | 6.66E−02 | 1.84E−01 | 6.37E−01 | 9.11E−02 | 2.90E−02 |
| "206.1036" | 2.35E−02 | 1.52E−01 | 6.07E−01 | 1.22E−01 | 3.60E−01 | 3.97E−02 |
| "206.1037" | 2.54E−01 | 2.09E−03 | 1.48E−06 | 1.75E−05 | 4.03E−01 | 4.32E−03 |
| "206.1038" | 7.44E−01 | 4.81E−01 | 1.84E−01 | 1.04E−01 | 9.31E−01 | 6.38E−01 |
| "206.1039" | 2.92E−02 | 6.45E−02 | 5.58E−02 | 3.07E−01 | 7.75E−02 | 3.66E−03 |
| "206.1040" | 3.33E−01 | 7.13E−03 | 6.02E−03 | 8.99E−06 | 5.94E−04 | 2.21E−02 |
| "206.1041" | 2.64E−01 | 1.71E−01 | 3.53E−01 | 9.90E−01 | 2.79E−01 | 5.69E−06 |
| "206.1042" | 9.29E−01 | 8.72E−01 | 6.39E−01 | 6.44E−01 | 8.19E−01 | 7.70E−02 |
| "206.1043" | 1.90E−01 | 2.80E−01 | 1.27E−01 | 1.48E−02 | 3.50E−01 | 1.66E−01 |
| "206.1044" | 1.76E−03 | 7.23E−06 | 4.19E−07 | 9.03E−05 | 5.53E−05 | 1.68E−01 |
| "206.1045" | 6.34E−01 | 1.58E−01 | 4.53E−01 | 1.72E−01 | 7.45E−01 | 1.16E−02 |
| "206.1046" | 3.65E−01 | 9.08E−02 | 1.85E−01 | 4.06E−04 | 1.03E−04 | 1.57E−01 |
| "206.1047" | 1.66E−01 | 3.37E−01 | 2.21E−01 | 1.05E−01 | 1.81E−02 | 1.89E−02 |
| "206.1048" | 4.28E−01 | 4.03E−02 | 8.38E−01 | 3.56E−01 | 7.55E−01 | 2.29E−02 |
| "206.1050" | 2.30E−03 | 1.05E−03 | 3.52E−07 | 3.94E−07 | 2.13E−06 | 8.64E−07 |
| "206.1051" | 2.44E−01 | 3.79E−01 | 7.06E−02 | 2.30E−02 | 3.16E−02 | 2.89E−03 |
| "206.1052" | 5.73E−02 | 5.33E−03 | 5.90E−04 | 5.90E−04 | 5.84E−04 | 4.78E−01 |
| "206.1053" | 4.95E−01 | 4.72E−03 | 3.82E−07 | 1.00E−07 | 1.24E−01 | 7.84E−06 |
| "206.1054" | 2.55E−01 | 9.03E−01 | 8.82E−01 | 8.98E−01 | 8.84E−01 | 7.91E−01 |
| "206.1055" | 7.67E−02 | 3.79E−01 | 9.48E−01 | 6.16E−02 | 1.12E−01 | 4.79E−02 |
| "206.1056" | 5.18E−02 | 9.05E−02 | 1.52E−02 | 1.29E−01 | 1.09E−02 | 4.16E−04 |
| "206.1057" | 8.04E−01 | 6.10E−01 | 1.82E−01 | 9.74E−02 | 2.29E−02 | 1.09E−01 |
| "206.1058" | 7.77E−01 | 2.21E−01 | 7.88E−01 | 3.12E−01 | 2.47E−05 | 1.97E−02 |
| "206.1059" | 5.55E−02 | 5.64E−03 | 1.62E−03 | 1.55E−01 | 5.60E−06 | 4.48E−03 |
| "206.1060" | 2.42E−03 | 1.52E−01 | 1.16E−03 | 9.17E−06 | 1.49E−03 | 1.93E−05 |
| "206.1061" | 9.82E−01 | 2.01E−02 | 1.11E−02 | 8.50E−03 | 2.79E−04 | 8.83E−01 |
| "206.1062" | 6.93E−01 | 2.15E−03 | 5.46E−05 | 6.35E−05 | 1.54E−04 | 7.83E−01 |
| "206.1063" | 9.03E−01 | 1.85E−02 | 6.64E−04 | 8.30E−04 | 8.49E−04 | 5.64E−02 |
| "206.1064" | 6.15E−01 | 4.18E−02 | 7.72E−04 | 1.96E−04 | 2.64E−03 | 4.31E−02 |
| "206.1065" | 8.14E−01 | 3.47E−03 | 1.67E−03 | 2.20E−04 | 2.36E−03 | 3.61E−02 |

TABLE 6-continued

Comprehensive neuronal culture screening results for RCaMP1h variants

| | | | | | | |
|---|---|---|---|---|---|---|
| "206.1066" | 5.68E−02 | 6.62E−01 | 6.10E−01 | 2.13E−02 | 3.59E−03 | 7.37E−03 |
| "206.1067" | 5.71E−01 | 9.15E−01 | 5.22E−01 | 1.47E−01 | 6.16E−01 | 3.80E−03 |
| "206.1068" | 6.43E−01 | 7.91E−01 | 8.27E−01 | 1.04E−01 | 9.92E−01 | 3.74E−01 |
| "206.1069" | 8.63E−01 | 1.37E−02 | 8.66E−05 | 4.23E−05 | 6.98E−05 | 7.57E−01 |
| "206.1070" | 2.07E−01 | 2.58E−02 | 2.78E−04 | 1.30E−04 | 2.03E−04 | 2.43E−01 |
| "206.1071" | 3.41E−01 | 1.97E−01 | 3.93E−04 | 3.91E−04 | 7.55E−04 | 9.73E−01 |
| "206.1072" | 8.99E−02 | 5.47E−01 | 8.95E−01 | 3.90E−03 | 5.90E−04 | 2.33E−01 |
| "206.1074" | 9.69E−01 | 2.07E−01 | 4.02E−02 | 7.72E−03 | 4.98E−01 | 2.44E−02 |
| "206.1075" | 2.39E−10 | 4.55E−04 | 9.59E−06 | 3.49E−01 | 1.81E−03 | 9.23E−12 |
| "206.1076" | 1.25E−11 | 1.87E−02 | 1.17E−05 | 9.67E−02 | 2.83E−10 | 3.88E−12 |
| "206.1077" | 1.58E−05 | 1.94E−02 | 4.74E−01 | 7.32E−05 | 1.18E−03 | 5.35E−06 |
| "206.1081" | 1.31E−09 | 4.48E−01 | 8.65E−01 | 1.90E−08 | 3.04E−13 | 4.50E−12 |
| "206.1082" | 6.86E−08 | 5.74E−03 | 1.16E−01 | 8.61E−11 | 2.94E−14 | 2.11E−15 |
| "206.1083" | 1.64E−04 | 4.17E−01 | 5.83E−02 | 8.50E−12 | 1.28E−11 | 7.02E−04 |
| "206.1084" | 2.00E−01 | 7.59E−01 | 3.24E−02 | 1.28E−06 | 1.08E−02 | 9.99E−01 |
| "206.1085" | 6.51E−01 | 9.58E−01 | 5.59E−02 | 6.19E−06 | 4.94E−02 | 2.13E−01 |
| "206.1086" | 8.02E−01 | 6.28E−01 | 2.85E−02 | 1.30E−04 | 5.78E−01 | 2.01E−01 |
| "206.1087" | 5.57E−02 | 1.71E−01 | 7.75E−01 | 2.76E−05 | 7.69E−02 | 1.11E−02 |
| "206.1088" | 1.19E−01 | 3.51E−01 | 1.67E−01 | 5.88E−06 | 8.61E−01 | 2.72E−02 |
| "206.1089" | 8.44E−01 | 9.69E−01 | 2.01E−01 | 2.94E−01 | 8.25E−01 | 1.04E−01 |
| "206.1090" | 4.25E−01 | 6.15E−01 | 1.36E−01 | 1.96E−04 | 1.73E−01 | 1.62E−02 |
| "206.1091" | 4.97E−02 | 7.80E−01 | 3.56E−01 | 1.61E−08 | 7.07E−02 | 3.83E−02 |
| "206.1092" | 4.85E−01 | 2.94E−01 | 7.61E−01 | 1.45E−04 | 2.68E−01 | 1.47E−02 |
| "206.1093" | 5.30E−01 | 3.64E−01 | 7.32E−04 | 1.27E−06 | 6.98E−01 | 8.85E−02 |
| "206.1094" | 8.30E−01 | 7.82E−01 | 1.50E−01 | 6.71E−04 | 4.69E−01 | 6.40E−01 |
| "206.1095" | 2.84E−01 | 9.17E−01 | 4.47E−02 | 6.22E−04 | 1.20E−01 | 2.27E−01 |
| "206.1096" | 1.14E−01 | 1.53E−01 | 8.36E−01 | 6.16E−04 | 3.90E−01 | 9.99E−01 |
| "206.1097" | 1.26E−01 | 6.93E−01 | 2.75E−01 | 3.33E−05 | 2.33E−02 | 7.28E−01 |
| "206.1098" | 5.51E−01 | 4.15E−01 | 7.75E−01 | 7.54E−05 | 4.73E−01 | 3.64E−01 |
| "206.1099" | 1.29E−01 | 2.11E−01 | 2.76E−01 | 1.24E−04 | 2.85E−01 | 5.34E−02 |
| "206.1100" | 1.26E−01 | 1.81E−01 | 6.15E−01 | 1.26E−04 | 2.58E−01 | 7.39E−02 |
| "206.1101" | 2.42E−01 | 2.57E−01 | 5.95E−01 | 3.33E−01 | 3.07E−02 | 7.56E−02 |
| "206.1102" | 2.75E−01 | 1.18E−01 | 1.29E−01 | 8.02E−01 | 7.05E−02 | 3.05E−01 |
| "206.1103" | 1.80E−01 | 6.90E−01 | 1.49E−01 | 1.42E−02 | 4.95E−01 | 1.06E−01 |
| "206.1104" | 6.12E−01 | 8.20E−01 | 5.83E−01 | 8.77E−01 | 4.43E−02 | 3.05E−03 |
| "206.1105" | 4.80E−03 | 1.48E−01 | 3.43E−01 | 5.90E−02 | 2.33E−02 | 2.04E−03 |
| "206.1106" | 4.22E−02 | 2.19E−01 | 7.64E−01 | 1.90E−01 | 1.17E−02 | 4.61E−03 |
| "206.1107" | 2.15E−03 | 1.80E−03 | 2.08E−03 | 3.64E−04 | 6.16E−01 | 1.39E−02 |
| "206.1108" | 4.67E−05 | 2.50E−05 | 3.28E−05 | 1.97E−05 | 1.90E−03 | 7.14E−01 |
| "206.1109" | 3.44E−01 | 3.55E−01 | 5.54E−01 | 8.22E−01 | 8.19E−01 | 2.30E−01 |
| "206.1110" | 5.10E−01 | 4.14E−01 | 1.69E−01 | 1.09E−05 | 1.03E−02 | 9.35E−01 |
| "206.1111" | 1.76E−03 | 3.72E−03 | 2.54E−02 | 5.57E−02 | 6.18E−01 | 2.05E−01 |
| "206.1112" | 1.67E−02 | 4.40E−02 | 7.71E−01 | 1.47E−01 | 8.47E−01 | 9.63E−01 |
| "206.1113" | 4.43E−03 | 8.83E−03 | 9.64E−01 | 2.55E−01 | 6.15E−02 | 8.23E−02 |
| "206.1114" | 4.66E−02 | 1.87E−01 | 8.94E−01 | 1.59E−01 | 2.67E−01 | 1.29E−01 |
| "206.1115" | 1.19E−02 | 4.88E−02 | 3.28E−01 | 2.05E−01 | 7.03E−03 | 3.77E−03 |
| "206.1116" | 8.09E−03 | 1.25E−01 | 9.33E−01 | 4.59E−02 | 8.17E−02 | 4.25E−02 |
| "206.1117" | 3.69E−02 | 2.26E−01 | 6.10E−01 | 2.05E−01 | 5.29E−01 | 7.01E−01 |
| "206.1118" | 1.28E−02 | 1.99E−02 | 3.46E−01 | 3.60E−02 | 1.81E−01 | 2.37E−02 |
| "206.1119" | 6.01E−04 | 8.63E−04 | 3.56E−02 | 2.36E−01 | 1.91E−01 | 3.84E−01 |
| "206.1120" | 5.63E−03 | 1.45E−02 | 1.94E−01 | 5.44E−01 | 1.62E−01 | 8.51E−01 |
| "206.1121" | 5.41E−01 | 6.14E−01 | 1.57E−03 | 5.10E−01 | 4.51E−01 | 7.38E−01 |
| "206.1122" | 9.88E−02 | 7.88E−01 | 9.94E−01 | 2.40E−02 | 4.57E−03 | 3.42E−03 |
| "206.1123" | 2.14E−03 | 5.38E−03 | 1.36E−01 | 2.40E−01 | 9.03E−02 | 4.27E−01 |
| "206.1124" | 1.08E−03 | 5.63E−03 | 1.02E−01 | 2.29E−01 | 8.01E−02 | 1.43E−02 |
| "206.1125" | 6.32E−02 | 1.35E−01 | 4.30E−01 | 3.60E−02 | 5.98E−01 | 1.63E−02 |
| "206.1126" | 6.48E−03 | 9.57E−03 | 1.26E−02 | 5.54E−02 | 1.03E−01 | 1.28E−01 |
| "206.1127" | 1.69E−02 | 6.47E−01 | 2.58E−02 | 1.75E−04 | 5.35E−01 | 3.05E−03 |
| "206.1128" | 6.41E−01 | 4.79E−01 | 4.37E−01 | 7.94E−01 | 3.82E−02 | 7.61E−01 |
| "206.1129" | 2.32E−03 | 2.11E−03 | 1.28E−01 | 9.94E−01 | 2.60E−01 | 8.92E−01 |
| "206.1130" | 2.44E−03 | 6.39E−02 | 5.18E−01 | 1.43E−02 | 7.13E−01 | 4.37E−03 |
| "206.1131" | 2.58E−03 | 7.63E−02 | 9.63E−01 | 2.56E−02 | 4.46E−02 | 2.67E−02 |
| "206.1132" | 4.87E−03 | 2.72E−02 | 1.37E−01 | 9.08E−01 | 2.74E−01 | 1.43E−02 |
| "206.1133" | 3.34E−02 | 5.84E−01 | 1.72E−02 | 8.78E−08 | 2.34E−01 | 8.63E−01 |
| "206.1134" | 2.82E−01 | 2.29E−01 | 6.70E−01 | 8.21E−06 | 2.04E−01 | 4.00E−01 |
| "206.1135" | 1.54E−02 | 6.01E−01 | 1.57E−01 | 1.06E−05 | 6.65E−03 | 7.34E−01 |
| "206.1136" | 3.66E−03 | 1.32E−02 | 6.66E−01 | 7.31E−04 | 5.52E−01 | 8.52E−01 |
| "206.1137" | 6.31E−01 | 6.08E−02 | 1.99E−02 | 2.45E−05 | 9.33E−01 | 1.94E−01 |
| "206.1138" | 6.04E−01 | 6.76E−02 | 2.85E−02 | 4.02E−07 | 2.93E−01 | 8.84E−01 |
| "206.1139" | 1.48E−01 | 5.07E−01 | 3.14E−01 | 6.22E−04 | 2.83E−01 | 9.51E−04 |
| "206.1140" | 5.84E−01 | 2.29E−01 | 5.38E−02 | 2.35E−06 | 4.43E−03 | 5.95E−01 |
| "206.1141" | 1.95E−01 | 8.88E−01 | 1.15E−01 | 1.48E−04 | 3.41E−03 | 8.80E−02 |
| "206.1142" | 5.21E−01 | 9.15E−01 | 3.07E−01 | 1.56E−01 | 6.89E−03 | 8.51E−01 |
| "206.1143" | 1.99E−02 | 4.66E−03 | 8.55E−02 | 3.47E−05 | 5.28E−02 | 3.43E−02 |
| "206.1144" | 1.41E−01 | 2.04E−01 | 7.90E−03 | 9.05E−08 | 1.85E−01 | 2.71E−01 |
| "206.1145" | 4.00E−02 | 5.05E−02 | 1.63E−02 | 1.52E−02 | 3.11E−01 | 3.77E−01 |
| "206.1146" | 4.59E−02 | 8.91E−01 | 4.95E−01 | 2.40E−05 | 4.46E−01 | 8.55E−03 |
| "206.1147" | 5.88E−02 | 5.28E−01 | 8.94E−02 | 1.36E−04 | 2.95E−01 | 1.12E−01 |

TABLE 6-continued

Comprehensive neuronal culture screening results for RCaMP1h variants

| | | | | | | |
|---|---|---|---|---|---|---|
| "206.1148" | 1.20E−01 | 2.99E−01 | 1.73E−01 | 6.22E−04 | 6.43E−03 | 1.18E−01 |
| "206.1149" | 3.36E−02 | 6.11E−01 | 6.44E−02 | 6.16E−04 | 8.77E−01 | 2.14E−03 |
| "206.1150" | 1.58E−02 | 1.59E−01 | 2.68E−01 | 1.83E−01 | 9.23E−02 | 2.87E−01 |
| "206.1151" | 2.59E−01 | 3.06E−01 | 2.97E−01 | 5.04E−01 | 9.29E−01 | 2.16E−01 |
| "206.1153" | 3.90E−01 | 7.32E−01 | 6.68E−01 | 8.51E−01 | 7.27E−01 | 3.19E−01 |
| "206.1154" | 1.24E−01 | 1.31E−01 | 1.21E−01 | 1.60E−06 | 7.21E−02 | 1.36E−03 |
| "206.1155" | 2.07E−02 | 4.36E−03 | 2.15E−03 | 2.85E−02 | 5.49E−01 | 1.05E−02 |
| "206.1156" | 1.32E−01 | 2.62E−01 | 1.56E−02 | 1.27E−01 | 1.92E−03 | 2.72E−01 |
| "206.1157" | 1.04E−01 | 2.40E−02 | 6.52E−03 | 2.19E−02 | 3.70E−01 | 9.64E−02 |
| "206.1158" | 4.03E−01 | 7.92E−02 | 4.89E−02 | 4.39E−02 | 1.97E−01 | 1.87E−01 |
| "206.1159" | 5.05E−02 | 2.86E−01 | 1.29E−02 | 1.28E−06 | 1.06E−01 | 1.11E−01 |
| "206.1160" | 3.36E−01 | 1.16E−01 | 1.25E−01 | 2.55E−01 | 7.02E−01 | 5.76E−02 |
| "206.1161" | 7.49E−01 | 1.04E−01 | 4.08E−01 | 1.45E−01 | 8.11E−01 | 7.04E−01 |
| "206.1162" | 8.79E−01 | 9.75E−03 | 5.62E−04 | 4.51E−06 | 9.26E−04 | 6.39E−01 |
| "206.1163" | 3.49E−01 | 4.42E−01 | 2.97E−01 | 5.28E−02 | 6.99E−02 | 9.14E−01 |
| "206.1164" | 1.04E−03 | 5.75E−04 | 8.38E−04 | 5.15E−01 | 1.48E−01 | 1.12E−03 |
| "206.1165" | 7.96E−05 | 9.71E−04 | 3.59E−03 | 2.28E−02 | 8.04E−01 | 1.76E−01 |
| "206.1167" | 5.76E−02 | 2.08E−03 | 5.96E−04 | 5.90E−04 | 7.08E−04 | 2.95E−02 |
| "206.1168" | 3.47E−02 | 2.00E−01 | 1.32E−02 | 4.58E−01 | 3.27E−02 | 2.21E−01 |
| "206.1169" | 4.10E−03 | 1.24E−03 | 2.82E−05 | 2.64E−05 | 2.44E−04 | 6.82E−01 |
| "206.1170" | 4.07E−03 | 1.19E−02 | 2.83E−05 | 5.75E−06 | 6.03E−01 | 2.07E−01 |
| "206.1171" | 3.31E−03 | 9.44E−03 | 7.17E−05 | 2.64E−05 | 4.70E−05 | 1.46E−01 |
| "206.1172" | 9.09E−01 | 7.54E−01 | 4.53E−01 | 7.44E−01 | 2.98E−01 | 1.88E−01 |
| "206.1173" | 5.26E−01 | 2.63E−01 | 6.32E−01 | 3.45E−01 | 3.49E−03 | 5.42E−01 |
| "206.1174" | 4.99E−03 | 9.63E−03 | 1.51E−06 | 1.27E−06 | 1.77E−04 | 7.55E−01 |
| "206.1175" | 1.46E−03 | 1.47E−02 | 8.11E−06 | 5.75E−06 | 7.87E−03 | 9.58E−01 |
| "206.1176" | 4.67E−02 | 1.07E−03 | 1.33E−04 | 1.24E−04 | 1.93E−04 | 1.06E−01 |
| "206.1177" | 1.24E−04 | 2.92E−03 | 2.83E−02 | 7.46E−06 | 2.39E−01 | 3.81E−01 |
| "206.1178" | 1.96E−01 | 2.01E−02 | 1.01E−02 | 1.63E−04 | 9.63E−04 | 1.42E−01 |
| "206.1179" | 7.51E−02 | 9.29E−02 | 8.83E−03 | 8.87E−02 | 8.52E−02 | 1.50E−02 |
| "206.1180" | 3.03E−02 | 9.89E−01 | 4.62E−01 | 1.66E−05 | 9.05E−03 | 3.97E−02 |
| "206.1181" | 3.49E−02 | 2.84E−01 | 9.53E−01 | 7.46E−03 | 1.66E−01 | 1.22E−01 |
| "206.1182" | 7.32E−01 | 6.21E−01 | 6.32E−01 | 1.43E−05 | 9.96E−01 | 9.91E−01 |
| "206.1183" | 3.44E−01 | 4.66E−01 | 5.64E−01 | 3.18E−06 | 3.49E−02 | 1.39E−01 |
| "206.1184" | 2.11E−02 | 9.32E−04 | 1.25E−04 | 1.18E−04 | 1.18E−04 | 7.03E−03 |
| "206.1186" | 2.62E−01 | 1.12E−01 | 4.91E−03 | 8.62E−03 | 4.30E−01 | 8.99E−02 |
| "206.1187" | 3.06E−01 | 6.56E−02 | 7.84E−04 | 1.34E−02 | 3.26E−04 | 5.96E−01 |
| "206.1188" | 5.58E−04 | 2.28E−03 | 6.27E−03 | 3.30E−01 | 3.09E−01 | 4.25E−03 |
| "206.1190" | 1.11E−02 | 4.38E−02 | 9.59E−01 | 3.52E−02 | 1.85E−01 | 5.50E−01 |
| "206.1192" | 6.28E−01 | 4.81E−04 | 1.24E−04 | 1.22E−04 | 1.18E−04 | 8.00E−01 |
| "206.1194" | 2.87E−01 | 1.77E−02 | 6.35E−04 | 1.38E−06 | 5.23E−03 | 1.64E−02 |
| "206.1195" | 6.60E−01 | 6.44E−01 | 8.38E−01 | 2.37E−02 | 1.91E−01 | 4.78E−01 |
| "206.1196" | 2.43E−01 | 6.34E−01 | 2.89E−02 | 2.52E−02 | 7.58E−02 | 1.84E−01 |
| "206.1197" | 1.55E−01 | 1.47E−01 | 2.20E−02 | 2.42E−01 | 7.19E−01 | 4.45E−01 |
| "206.1198" | 1.51E−01 | 1.77E−01 | 1.64E−01 | 8.12E−01 | 9.46E−01 | 5.09E−01 |
| "206.1199" | 7.14E−01 | 5.18E−05 | 2.28E−01 | 1.36E−05 | 1.66E−05 | 7.24E−01 |
| "206.1200" | 6.11E−03 | 1.44E−06 | 1.88E−06 | 1.31E−06 | 1.33E−04 | 7.47E−01 |
| "206.1202" | 7.05E−02 | 9.85E−05 | 1.39E−04 | 1.10E−04 | 1.22E−04 | 8.81E−04 |
| "206.1204" | 2.26E−01 | 2.98E−05 | 1.88E−03 | 6.80E−05 | 1.22E−05 | 9.02E−01 |
| "206.1205" | 8.91E−01 | 2.55E−01 | 5.53E−02 | 5.07E−02 | 1.68E−02 | 3.27E−01 |
| "206.1206" | 4.91E−01 | 1.68E−04 | 1.26E−04 | 1.84E−04 | 1.39E−04 | 8.36E−01 |
| "206.1207" | 3.27E−01 | 3.06E−05 | 2.56E−05 | 2.64E−05 | 5.71E−04 | 6.52E−02 |
| "206.1209" | 4.46E−02 | 6.65E−01 | 3.88E−02 | 3.86E−05 | 8.53E−01 | 5.63E−01 |
| "206.1210" | 1.62E−02 | 8.56E−04 | 2.73E−05 | 3.86E−05 | 2.21E−04 | 1.69E−01 |
| "206.1211" | 6.85E−04 | 2.17E−04 | 1.47E−04 | 5.34E−01 | 8.66E−01 | 7.98E−03 |
| "206.1212" | 2.15E−01 | 5.61E−02 | 4.04E−01 | 7.30E−03 | 2.49E−01 | 1.03E−02 |
| "206.1213" | 2.86E−05 | 1.96E−01 | 1.17E−02 | 1.38E−06 | 2.17E−06 | 1.17E−06 |
| "206.1215" | 2.90E−02 | 9.64E−03 | 1.80E−04 | 3.89E−05 | 1.33E−04 | 2.48E−05 |
| "206.1216" | 2.72E−09 | 5.20E−07 | 2.33E−05 | 1.30E−03 | 2.84E−06 | 1.76E−11 |
| "206.1218" | 5.54E−07 | 5.65E−05 | 1.75E−02 | 8.03E−04 | 4.71E−12 | 4.90E−13 |
| "206.1219" | 3.66E−05 | 2.99E−03 | 1.30E−03 | 5.36E−01 | 4.16E−04 | 7.46E−09 |
| "206.1220" | 3.33E−01 | 4.12E−01 | 2.99E−03 | 2.76E−12 | 1.72E−13 | 1.39E−13 |
| "206.1221" | 3.22E−03 | 2.59E−04 | 1.11E−14 | 6.53E−14 | 5.30E−11 | 4.36E−04 |
| "206.1222" | 3.05E−05 | 1.79E−03 | 3.03E−09 | 1.28E−11 | 4.90E−12 | 8.07E−08 |
| "206.1223" | 3.64E−06 | 3.36E−05 | 5.12E−06 | 1.52E−13 | 5.77E−13 | 2.81E−14 |
| "206.1224" | 2.26E−08 | 2.82E−04 | 4.14E−06 | 9.98E−06 | 1.09E−12 | 1.64E−15 |
| "206.1225" | 8.15E−01 | 9.33E−02 | 3.09E−01 | 2.43E−03 | 2.86E−11 | 3.18E−13 |
| "206.1226" | 1.06E−01 | 2.92E−02 | 1.69E−13 | 2.49E−14 | 4.62E−12 | 2.06E−07 |
| "206.1227" | 6.71E−05 | 3.50E−03 | 6.90E−17 | 8.69E−17 | 1.91E−11 | 1.29E−11 |
| "206.1228" | 3.75E−02 | 1.43E−06 | 1.59E−15 | 3.77E−18 | 1.59E−12 | 8.68E−16 |
| "206.1229" | 4.66E−02 | 7.67E−11 | 5.40E−16 | 4.55E−14 | 4.54E−09 | 3.80E−06 |
| "206.1230" | 1.74E−05 | 5.81E−01 | 7.61E−01 | 1.66E−08 | 3.51E−01 | 9.28E−01 |
| "206.1231" | 1.87E−04 | 4.72E−11 | 1.06E−11 | 3.79E−14 | 4.03E−13 | 5.10E−04 |
| "206.1232" | 2.99E−10 | 7.41E−01 | 7.86E−01 | 1.64E−13 | 4.79E−17 | 5.24E−18 |
| "206.1233" | 1.83E−01 | 3.21E−14 | 1.82E−19 | 1.54E−18 | 4.48E−14 | 3.47E−02 |
| "206.1234" | 2.96E−07 | 4.00E−06 | 3.57E−11 | 8.46E−01 | 1.63E−04 | 4.69E−09 |
| "206.1235" | 5.35E−12 | 2.92E−19 | 1.04E−22 | 4.41E−31 | 2.19E−21 | 1.17E−20 |
| "206.1236" | 3.51E−14 | 1.73E−13 | 1.72E−15 | 1.72E−06 | 3.75E−09 | 8.44E−12 |

TABLE 6-continued

Comprehensive neuronal culture screening results for RCaMP1h variants

| | | | | | | |
|---|---|---|---|---|---|---|
| "206.1240" | 7.69E−02 | 8.74E−03 | 8.40E−04 | 1.24E−04 | 1.51E−04 | 1.17E−04 |
| "206.1244" | 1.99E−04 | 2.20E−04 | 1.28E−06 | 4.88E−06 | 5.77E−04 | 1.19E−06 |
| "206.1247" | 4.89E−11 | 9.43E−01 | 4.52E−01 | 3.77E−02 | 3.44E−11 | 3.93E−16 |
| "206.1248" | 3.49E−19 | 1.15E−06 | 9.10E−08 | 5.42E−01 | 1.03E−15 | 9.76E−20 |
| "206.1249" | 1.78E−08 | 1.93E−08 | 4.00E−12 | 6.27E−07 | 3.07E−12 | 4.99E−16 |
| "206.1250" | 1.24E−18 | 9.70E−18 | 3.97E−25 | 2.95E−19 | 3.08E−17 | 3.66E−26 |
| "206.1251" | 1.38E−05 | 3.66E−01 | 4.71E−01 | 1.21E−05 | 3.93E−08 | 7.45E−14 |
| "206.1252" | 1.81E−01 | 8.26E−07 | 1.06E−03 | 1.33E−09 | 1.18E−13 | 6.58E−10 |
| "206.1253" | 1.13E−01 | 1.02E−01 | 2.63E−06 | 1.78E−09 | 3.48E−09 | 1.75E−10 |
| "206.1254" | 3.46E−01 | 3.52E−01 | 4.13E−07 | 1.31E−10 | 4.38E−10 | 4.64E−11 |
| "206.1255" | 4.18E−01 | 1.60E−07 | 1.76E−06 | 2.30E−11 | 9.64E−11 | 1.60E−01 |
| "206.1256" | 1.25E−04 | 1.18E−02 | 5.73E−03 | 1.83E−04 | 3.78E−05 | 2.48E−05 |
| "206.1257" | 8.21E−06 | 2.84E−08 | 6.79E−11 | 1.01E−11 | 6.48E−11 | 1.24E−11 |
| "206.1258" | 9.70E−01 | 1.84E−03 | 2.61E−07 | 2.20E−06 | 4.63E−01 | 6.37E−01 |
| "206.1259" | 7.57E−02 | 2.13E−02 | 1.53E−02 | 1.05E−02 | 1.92E−01 | 1.83E−02 |
| "206.1260" | 1.75E−01 | 4.80E−01 | 6.28E−02 | 4.54E−07 | 6.11E−01 | 6.20E−02 |
| "206.1261" | 7.06E−01 | 4.22E−01 | 2.62E−02 | 1.47E−06 | 5.02E−01 | 3.14E−01 |
| "206.1262" | 6.18E−01 | 5.23E−01 | 1.14E−02 | 6.73E−06 | 2.91E−02 | 5.10E−02 |
| "206.1263" | 9.19E−01 | 5.66E−01 | 3.09E−03 | 3.26E−05 | 6.55E−01 | 8.53E−01 |
| "206.1264" | 4.20E−01 | 4.15E−01 | 6.91E−01 | 1.58E−01 | 8.77E−01 | 1.29E−02 |
| "206.1265" | 1.15E−02 | 2.66E−03 | 3.24E−01 | 6.13E−06 | 6.66E−01 | 9.89E−01 |
| "206.1266" | 0.00 | 0.00 | 0.00 | 0.00 | 0.30 | 0.12 |
| "206.1267" | 0.97 | 0.09 | 0.00 | 0.00 | 0.16 | 0.00 |
| "206.1268" | 0.53 | 0.40 | 0.02 | 0.00 | 0.54 | 0.01 |
| "206.1269" | 0.00 | 0.01 | 0.20 | 0.00 | 0.37 | 0.15 |
| "206.1270" | 0.01 | 0.00 | 0.00 | 0.00 | 0.44 | 0.05 |
| "206.1271" | 0.04 | 0.01 | 0.02 | 0.92 | 0.58 | 0.58 |
| "206.1272" | 0.03 | 0.00 | 0.02 | 0.37 | 0.08 | 0.02 |
| "206.1273" | 0.02 | 0.00 | 0.13 | 0.00 | 0.54 | 0.02 |
| "206.1274" | 0.94 | 0.95 | 0.00 | 0.00 | 0.55 | 0.67 |
| "206.1275" | 0.50 | 0.70 | 0.01 | 0.00 | 0.27 | 0.14 |
| "206.1276" | 0.09 | 0.38 | 0.09 | 0.00 | 0.60 | 0.00 |
| "206.1277" | 0.86 | 0.27 | 0.00 | 0.00 | 0.20 | 0.05 |
| "206.1278" | 0.76 | 0.31 | 0.01 | 0.00 | 0.25 | 0.23 |
| "206.1279" | 0.02 | 0.09 | 0.37 | 0.00 | 0.96 | 0.01 |
| "206.1280" | 0.10 | 0.01 | 0.00 | 0.00 | 0.10 | 0.10 |
| "206.1281" | 0.50 | 0.07 | 0.00 | 0.00 | 0.01 | 0.02 |
| "206.1282" | 0.47 | 0.02 | 0.00 | 0.00 | 0.00 | 0.07 |
| "206.1283" | 0.43 | 0.10 | 0.00 | 0.00 | 0.15 | 0.34 |
| "206.1284" | 0.60 | 0.94 | 0.06 | 0.00 | 0.39 | 0.48 |
| "206.1285" | 0.50 | 0.51 | 0.03 | 0.00 | 0.57 | 0.57 |
| "206.1286" | 0.87 | 0.06 | 0.00 | 0.00 | 0.00 | 0.16 |
| "206.1287" | 0.03 | 0.02 | 0.94 | 0.00 | 0.19 | 0.82 |
| "206.1288" | 0.21 | 0.51 | 0.07 | 0.00 | 0.37 | 0.01 |
| "206.1289" | 0.19 | 0.95 | 0.02 | 0.00 | 0.04 | 0.96 |
| "206.1290" | 0.77 | 0.25 | 0.00 | 0.00 | 0.01 | 0.01 |
| "206.1291" | 0.64 | 0.12 | 0.00 | 0.00 | 0.01 | 0.06 |
| "206.1292" | 0.32 | 0.45 | 0.72 | 0.25 | 0.44 | 0.13 |
| "206.1293" | 0.01 | 0.01 | 0.02 | 0.26 | 0.36 | 0.60 |
| "206.1294" | 0.17 | 0.22 | 0.11 | 0.77 | 0.69 | 0.12 |
| "206.1295" | 0.02 | 0.01 | 0.12 | 0.49 | 0.50 | 0.39 |
| "206.1296" | 0.79 | 0.82 | 0.21 | 0.70 | 0.13 | 0.04 |
| "206.1297" | 0.33 | 0.72 | 0.58 | 0.08 | 0.02 | 0.69 |
| "206.1298" | 0.08 | 0.01 | 0.01 | 0.85 | 0.00 | 0.99 |
| "206.1300" | 0.00 | 0.00 | 0.00 | 0.04 | 0.01 | 0.88 |
| "206.1301" | 0.58 | 0.41 | 0.41 | 0.80 | 0.21 | 0.96 |
| "206.1302" | 0.40 | 0.21 | 0.34 | 0.00 | 0.04 | 0.00 |
| "206.1303" | 0.07 | 0.22 | 0.19 | 0.36 | 0.02 | 0.03 |
| "206.1304" | 0.63 | 0.90 | 0.28 | 0.01 | 0.56 | 0.50 |
| "206.1305" | 0.66 | 0.45 | 0.20 | 0.79 | 0.00 | 0.30 |
| "206.1306" | 0.01 | 0.00 | 0.00 | 0.73 | 0.00 | 0.91 |
| "206.1307" | 0.36 | 0.12 | 0.20 | 0.18 | 0.43 | 0.01 |
| "206.1308" | 0.62 | 0.75 | 0.25 | 0.07 | 0.95 | 0.02 |
| "206.1309" | 0.48 | 0.16 | 0.06 | 0.04 | 0.94 | 0.03 |
| "206.1310" | 0.84 | 0.49 | 0.24 | 0.04 | 0.09 | 0.00 |
| "206.1311" | 0.01 | 0.00 | 0.00 | 0.00 | 0.00 | 0.08 |
| "206.1312" | 0.01 | 0.00 | 0.00 | 0.01 | 0.07 | 0.03 |
| "206.1313" | 0.48 | 0.98 | 0.03 | 0.74 | 0.00 | 0.29 |
| "206.1314" | 0.34 | 0.08 | 0.40 | 0.61 | 0.00 | 0.72 |
| "206.1315" | 0.55 | 0.89 | 0.03 | 0.19 | 0.00 | 0.98 |
| "206.1316" | 0.80 | 0.91 | 0.26 | 0.19 | 0.66 | 0.06 |
| "206.1317" | 0.49 | 0.03 | 0.57 | 0.34 | 0.39 | 0.21 |
| "206.1318" | 0.89 | 0.35 | 0.84 | 0.79 | 0.38 | 0.76 |
| "206.1319" | 0.59 | 0.73 | 0.57 | 0.32 | 0.62 | 0.94 |
| "206.1320" | 0.00 | 0.00 | 0.00 | 0.18 | 0.16 | 0.45 |
| "206.1321" | 0.32 | 0.19 | 0.10 | 0.12 | 0.48 | 0.36 |
| "206.1322" | 0.72 | 0.50 | 0.62 | 0.18 | 0.24 | 0.68 |
| "206.1323" | 0.96 | 0.00 | 0.00 | 0.00 | 0.00 | 0.00 |

TABLE 6-continued

Comprehensive neuronal culture screening results for RCaMP1h variants

| | | | | | | |
|---|---|---|---|---|---|---|
| "206.1324" | 0.00 | 0.00 | 0.00 | 0.00 | 0.00 | 0.00 |
| "206.1325" | 0.09 | 0.02 | 0.00 | 0.00 | 0.25 | 0.00 |
| "206.1326" | 0.00 | 0.00 | 0.00 | 0.03 | 0.01 | 0.00 |
| "206.1327" | 0.00 | 0.00 | 0.00 | 0.29 | 0.00 | 0.68 |
| "206.1329" | 0.00 | 0.01 | 0.01 | 0.00 | 0.00 | 0.00 |
| "206.1330" | 0.00 | 0.00 | 0.08 | 0.00 | 0.00 | 0.00 |
| "206.1334" | 0.00 | 0.81 | 0.00 | 0.00 | 0.00 | 0.00 |
| "206.1335" | 0.00 | 0.00 | 0.00 | 0.96 | 0.00 | 0.00 |
| "206.1336" | 0.00 | 0.01 | 0.00 | 0.00 | 0.00 | 0.00 |
| "206.1337" | 0.00 | 0.62 | 0.00 | 0.00 | 0.00 | 0.00 |
| "206.1338" | 0.03 | 0.96 | 0.00 | 0.00 | 0.02 | 0.00 |
| "206.1340" | 0.00 | 0.68 | 0.00 | 0.00 | 0.04 | 0.00 |
| "206.1341" | 0.00 | 0.27 | 0.00 | 0.00 | 0.00 | 0.00 |
| "206.1343" | 0.00 | 0.00 | 0.00 | 0.76 | 0.35 | 0.00 |
| "206.1344" | 0.00 | 0.00 | 0.00 | 0.00 | 0.00 | 0.00 |
| "206.1346" | 0.00 | 0.00 | 0.00 | 0.00 | 0.00 | 0.00 |
| "206.1347" | 0.06 | 0.02 | 0.00 | 0.00 | 0.02 | 0.02 |
| "206.1348" | 0.00 | 0.00 | 0.00 | 0.00 | 0.00 | 0.00 |
| "206.1349" | 0.00 | 0.00 | 0.00 | 0.00 | 0.00 | 0.00 |
| "206.1350" | 0.16 | 0.35 | 0.07 | 0.01 | 0.00 | 0.00 |
| "206.1351" | 0.12 | 0.12 | 0.01 | 0.30 | 0.13 | 0.00 |
| "206.1352" | 0.23 | 0.02 | 0.00 | 0.00 | 0.04 | 0.00 |
| "206.1353" | 0.91 | 0.00 | 0.00 | 0.00 | 0.00 | 0.00 |
| "206.1354" | 0.32 | 0.04 | 0.02 | 0.02 | 0.41 | 0.17 |
| "206.1355" | 0.19 | 0.13 | 0.00 | 0.02 | 0.56 | 0.35 |
| "206.1356" | 0.00 | 0.00 | 0.00 | 0.00 | 0.77 | 0.30 |
| "206.1357" | 0.00 | 0.00 | 0.00 | 0.02 | 0.00 | 0.00 |
| "206.1358" | 0.02 | 0.01 | 0.00 | 0.01 | 0.71 | 0.03 |
| "206.1359" | 0.86 | 0.28 | 0.16 | 0.83 | 0.01 | 0.68 |
| "206.1360" | 0.67 | 0.01 | 0.00 | 0.02 | 0.00 | 0.61 |
| "206.1361" | 0.69 | 0.93 | 0.06 | 0.13 | 0.01 | 0.70 |
| "206.1362" | 0.16 | 0.10 | 0.84 | 0.41 | 0.12 | 0.73 |
| "206.1363" | 0.91 | 0.84 | 0.06 | 0.18 | 0.00 | 0.97 |
| "206.1364" | 0.88 | 0.77 | 0.53 | 0.29 | 0.45 | 0.53 |
| "206.1365" | 0.01 | 0.04 | 0.05 | 0.01 | 0.49 | 0.22 |
| "206.1370" | 0.07 | 0.02 | 0.01 | 0.03 | 0.00 | 0.63 |
| "206.1371" | 0.64 | 0.44 | 0.08 | 0.32 | 0.00 | 0.09 |
| "206.1372" | 0.14 | 0.33 | 0.05 | 0.03 | 0.75 | 0.00 |
| "206.1373" | 0.62 | 0.74 | 0.39 | 0.13 | 0.18 | 0.12 |
| "206.1374" | 0.55 | 0.32 | 1.00 | 0.95 | 0.23 | 0.05 |
| "206.1375" | 0.91 | 0.48 | 0.07 | 0.06 | 0.79 | 0.83 |
| "206.1376" | 0.42 | 0.99 | 0.21 | 0.37 | 0.40 | 0.34 |
| "206.1380" | 0.11 | 0.16 | 0.01 | 0.28 | 0.19 | 0.00 |
| "206.1381" | 0.06 | 0.04 | 0.03 | 0.47 | 0.27 | 0.00 |
| "206.1382" | 0.65 | 0.02 | 0.01 | 0.13 | 0.05 | 0.19 |
| "206.1383" | 0.27 | 0.11 | 0.01 | 0.07 | 0.50 | 0.19 |
| "206.1384" | 0.88 | 0.46 | 0.10 | 0.06 | 0.50 | 0.68 |
| "206.1385" | 0.83 | 0.77 | 0.10 | 0.02 | 0.05 | 0.06 |
| "206.1386" | 0.01 | 0.02 | 0.01 | 0.08 | 0.11 | 0.25 |
| "206.1387" | 0.24 | 0.27 | 0.10 | 0.02 | 0.90 | 0.76 |
| "206.1388" | 0.09 | 0.01 | 0.00 | 0.03 | 0.03 | 0.60 |
| "206.1389" | 0.43 | 0.07 | 0.00 | 0.01 | 0.68 | 0.93 |
| "206.1390" | 0.00 | 0.00 | 0.00 | 0.06 | 0.04 | 0.48 |
| "206.1392" | 0.15 | 0.58 | 0.62 | 0.60 | 0.42 | 0.11 |
| "206.1393" | 0.06 | 0.48 | 0.30 | 0.38 | 0.68 | 0.06 |
| "206.1394" | 0.29 | 0.58 | 0.82 | 0.60 | 0.78 | 0.15 |
| "206.1397" | 0.09 | 0.07 | 0.04 | 0.89 | 0.12 | 0.29 |
| "206.1398" | 0.04 | 0.01 | 0.00 | 0.11 | 0.69 | 0.00 |
| "206.1401" | 0.17 | 0.26 | 0.05 | 0.70 | 0.07 | 0.74 |
| "206.1403" | 0.00 | 0.00 | 0.00 | 0.01 | 0.01 | 0.05 |
| "206.1404" | 0.01 | 0.00 | 0.00 | 0.00 | 0.01 | 0.01 |
| "206.1405" | 0.00 | 0.00 | 0.00 | 0.06 | 0.84 | 0.00 |
| "206.1406" | 0.10 | 0.00 | 0.00 | 0.00 | 0.00 | 0.19 |
| "206.1410" | 0.47 | 0.03 | 0.01 | 0.05 | 0.00 | 0.96 |
| "206.1411" | 0.35 | 0.86 | 0.15 | 0.01 | 0.05 | 0.01 |
| "206.1413" | 0.60 | 0.85 | 0.35 | 0.25 | 0.08 | 0.22 |
| "206.1414" | 0.00 | 0.00 | 0.00 | 0.67 | 0.15 | 0.00 |
| "206.1417" | 0.00 | 0.03 | 0.10 | 0.16 | 0.04 | 0.00 |
| "206.1418" | 0.04 | 0.04 | 0.03 | 0.05 | 0.00 | 0.27 |
| "206.1427" | 0.87 | 0.01 | 0.00 | 0.11 | 0.29 | 0.19 |
| "206.1429" | 0.39 | 0.33 | 0.32 | 0.48 | 0.01 | 0.22 |
| "206.1430" | 0.25 | 0.52 | 0.68 | 0.46 | 0.25 | 0.21 |
| "206.1431" | 0.03 | 0.00 | 0.00 | 0.21 | 0.42 | 0.25 |
| "206.1432" | 0.31 | 0.15 | 0.50 | 0.32 | 0.77 | 0.24 |
| "206.1434" | 0.16 | 0.11 | 0.05 | 0.95 | 0.58 | 0.88 |
| "206.1435" | 0.25 | 0.01 | 0.01 | 0.10 | 0.04 | 0.00 |
| "206.1436" | 0.31 | 0.02 | 0.05 | 0.57 | 0.02 | 0.00 |
| "206.1437" | 0.73 | 0.11 | 0.10 | 0.55 | 0.26 | 0.17 |

TABLE 6-continued

Comprehensive neuronal culture screening results for RCaMP1h variants

| | | | | | | |
|---|---|---|---|---|---|---|
| "206.1439" | 0.00 | 0.00 | 0.00 | 0.18 | 0.00 | 0.00 |
| "206.1441" | 0.00 | 0.00 | 0.00 | 0.75 | 0.05 | 0.00 |
| "206.1442" | 0.01 | 0.01 | 0.03 | 0.04 | 0.01 | 0.00 |
| "206.1443" | 0.18 | 0.48 | 0.46 | 0.97 | 0.02 | 0.89 |
| "206.1444" | 0.07 | 0.01 | 0.00 | 0.00 | 0.00 | 0.00 |
| "206.1457" | 0.00 | 0.00 | 0.00 | 0.00 | 0.00 | 0.00 |
| "206.1458" | 0.00 | 0.00 | 0.00 | 0.00 | 0.00 | 0.00 |
| "206.1459" | 0.00 | 0.00 | 0.00 | 0.00 | 0.15 | 0.00 |
| "206.1460" | 0.00 | 0.00 | 0.00 | 0.00 | 0.01 | 0.00 |
| "206.1461" | 0.00 | 0.13 | 0.00 | 0.00 | 0.00 | 0.28 |
| "206.1462" | 0.00 | 0.00 | 0.00 | 0.00 | 0.00 | 0.74 |
| "206.1463" | 0.00 | 0.00 | 0.00 | 0.00 | 0.00 | 0.30 |
| "206.1464" | 0.00 | 0.00 | 0.00 | 0.00 | 0.00 | 0.75 |
| "206.1465" | 0.00 | 0.00 | 0.00 | 0.00 | 0.00 | 0.24 |
| "206.1466" | 0.00 | 0.00 | 0.00 | 0.00 | 0.00 | 0.75 |
| "206.1467" | 0.00 | 0.00 | 0.00 | 0.00 | 0.05 | 0.29 |
| "206.1468" | 0.00 | 0.00 | 0.00 | 0.00 | 0.00 | 0.00 |
| "206.1469" | 0.00 | 0.00 | 0.00 | 0.00 | 0.32 | 0.00 |
| "206.1470" | 0.00 | 0.00 | 0.00 | 0.15 | 0.00 | 0.00 |
| "206.1472" | 0.00 | 0.00 | 0.00 | 0.00 | 0.00 | 0.00 |
| "206.1473" | 0.00 | 0.00 | 0.00 | 0.00 | 0.00 | 0.00 |
| "206.1474" | 0.00 | 0.00 | 0.00 | 0.80 | 0.00 | 0.00 |
| "206.1475" | 0.00 | 0.01 | 0.56 | 0.54 | 0.01 | 0.62 |
| "206.1476" | 0.47 | 0.00 | 0.00 | 0.00 | 0.00 | 0.00 |
| "206.1477" | 0.00 | 0.00 | 0.00 | 0.00 | 0.00 | 0.22 |
| "206.1478" | 0.00 | 0.00 | 0.00 | 0.00 | 0.00 | 0.90 |
| "206.1479" | 0.00 | 0.00 | 0.00 | 0.00 | 0.00 | 0.00 |
| "206.1480" | 0.00 | 0.00 | 0.00 | 0.00 | 0.00 | 0.21 |
| "206.1481" | 0.00 | 0.00 | 0.00 | 0.00 | 0.35 | 0.37 |
| "206.1482" | 0.00 | 0.00 | 0.00 | 0.00 | 0.00 | 0.14 |
| "206.1483" | 0.00 | 0.00 | 0.00 | 0.00 | 0.00 | 0.47 |
| "206.1484" | 0.00 | 0.35 | 0.11 | 0.00 | 0.00 | 0.18 |
| "206.1485" | 0.00 | 0.00 | 0.00 | 0.00 | 0.19 | 0.37 |
| "206.1486" | 0.00 | 0.00 | 0.00 | 0.00 | 0.98 | 0.58 |
| "206.1487" | 0.00 | 0.00 | 0.00 | 0.00 | 0.00 | 0.00 |
| "206.1489" | 0.00 | 0.00 | 0.00 | 0.94 | 0.00 | 0.00 |
| "206.1490" | 0.00 | 0.00 | 0.00 | 0.00 | 0.00 | 0.71 |
| "206.1491" | 0.02 | 0.69 | 0.00 | 0.00 | 0.61 | 0.60 |
| "206.1492" | 0.00 | 0.00 | 0.00 | 0.00 | 0.00 | 0.25 |
| "206.1493" | 0.00 | 0.27 | 0.09 | 0.13 | 0.00 | 0.00 |
| "206.1494" | 0.19 | 0.00 | 0.00 | 0.00 | 0.00 | 0.00 |
| "206.1495" | 0.00 | 0.00 | 0.00 | 0.00 | 0.00 | 0.01 |
| "206.1496" | 0.00 | 0.00 | 0.00 | 0.00 | 0.00 | 0.02 |
| "206.1497" | 0.03 | 0.00 | 0.00 | 0.00 | 0.19 | 0.00 |
| "206.1498" | 0.00 | 0.00 | 0.00 | 0.00 | 0.47 | 0.90 |
| "206.1499" | 0.00 | 0.00 | 0.00 | 0.00 | 0.00 | 0.00 |
| "206.1500" | 0.00 | 0.00 | 0.00 | 0.79 | 0.00 | 0.04 |
| "206.1501" | 0.00 | 0.00 | 0.00 | 0.49 | 0.56 | 0.00 |
| "206.1502" | 0.00 | 0.00 | 0.00 | 0.00 | 0.00 | 0.96 |
| "206.1503" | 0.00 | 0.00 | 0.00 | 0.01 | 0.00 | 0.75 |
| "206.1504" | 0.01 | 0.57 | 0.01 | 0.01 | 0.01 | 0.13 |
| "206.1505" | 0.00 | 0.00 | 0.00 | 0.00 | 0.00 | 0.00 |
| "206.1506" | 0.00 | 0.00 | 0.00 | 0.00 | 0.00 | 0.99 |
| "206.1507" | 0.55 | 0.37 | 0.24 | 0.61 | 0.39 | 0.67 |
| "206.1508" | 0.01 | 0.01 | 0.00 | 0.00 | 0.00 | 0.30 |
| "206.1509" | 0.00 | 0.00 | 0.14 | 0.00 | 0.00 | 0.00 |
| "206.1510" | 0.00 | 0.00 | 0.00 | 0.00 | 0.00 | 0.00 |
| "206.1511" | 0.00 | 0.00 | 0.00 | 0.00 | 0.00 | 0.00 |
| "206.1512" | 0.00 | 0.00 | 0.00 | 0.00 | 0.02 | 0.09 |
| "206.1513" | 0.00 | 0.00 | 0.33 | 0.45 | 0.00 | 0.90 |
| "206.1514" | 0.00 | 0.00 | 0.00 | 0.00 | 0.00 | 0.35 |
| "206.1515" | 0.01 | 0.19 | 0.02 | 0.02 | 0.10 | 0.00 |
| "206.1516" | 0.00 | 0.00 | 0.00 | 0.00 | 0.10 | 0.93 |
| "206.1517" | 0.00 | 0.00 | 0.00 | 0.00 | 0.00 | 0.00 |
| "206.1518" | 0.00 | 0.00 | 0.00 | 0.00 | 0.00 | 0.00 |
| "206.1520" | 0.00 | 0.00 | 0.00 | 0.00 | 0.10 | 0.00 |
| "206.1522" | 0.00 | 0.00 | 0.00 | 0.02 | 0.00 | 0.00 |
| "206.1523" | 0.00 | 0.00 | 0.00 | 0.00 | 0.00 | 0.00 |
| "206.1524" | 0.00 | 0.00 | 0.00 | 0.02 | 0.00 | 0.00 |
| "206.1525" | 0.18 | 0.38 | 0.03 | 0.00 | 0.00 | 0.05 |
| "206.1526" | 0.00 | 0.00 | 0.00 | 0.00 | 0.00 | 0.00 |
| "206.1527" | 0.00 | 0.00 | 0.00 | 0.00 | 0.00 | 0.00 |
| "206.1528" | 0.00 | 0.00 | 0.00 | 0.00 | 0.87 | 0.00 |
| "206.1529" | 0.06 | 0.00 | 0.00 | 0.11 | 0.00 | 0.40 |
| "206.1532" | 0.00 | 0.00 | 0.00 | 0.00 | 0.00 | 0.00 |
| "206.1533" | 0.00 | 0.00 | 0.00 | 0.00 | 0.00 | 0.00 |
| "206.1535" | 0.00 | 0.00 | 0.00 | 0.00 | 0.14 | 0.00 |
| "206.1536" | 0.00 | 0.00 | 0.00 | 0.00 | 0.00 | 0.00 |

TABLE 6-continued

| Comprehensive neuronal culture screening results for RCaMP1h variants | | | | | | |
|---|---|---|---|---|---|---|
| "206.1537" | 0.00 | 0.00 | 0.00 | 0.01 | 0.00 | 0.00 |
| "206.1538" | 0.00 | 0.00 | 0.00 | 0.00 | 0.00 | 0.12 |

TABLE 7

Comprehensive neuronal culture screening results for R-GECO1.0 variants

| R-GECO1.0 variant | Number of wells | Mutations added to R-GECO1.0 |
|---|---|---|
| "R-GECO1.0" | 526 | base |
| "R-CaMP2" | 9 | S38V S39K R40L R41I K42P W43S N44L K45T A46T G47V H48I A49L R51K A52S I53M G54L L56K S57R 58_59insFGNPF V173L K204V T206V F222L T373I N380S D381Y T382R R393G 451_452insGGGTGGSGGGGGGEFPVKQTLNFDLLKLAGDVESNP |
| "jRGECO1a" | 13 | Q306D M339F |
| "jRGECO1b" | 28 | I109K R131C L321C |
| "106.13" | 6 | T303M |
| "106.16" | 8 | A318C |
| "106.19" | 8 | A318F |
| "106.22" | 6 | A318I |
| "106.23" | 4 | A318K |
| "106.25" | 10 | A318M |
| "106.27" | 6 | A318P |
| "106.30" | 29 | A318S |
| "106.31" | 7 | A318T |
| "106.32" | 6 | A318V |
| "106.37" | 7 | I312D |
| "106.38" | 8 | I312E |
| "106.39" | 6 | I312F |
| "106.40" | 7 | I312G |
| "106.42" | 7 | I312K |
| "106.43" | 9 | I312L |
| "106.44" | 11 | I312M |
| "106.46" | 4 | I312P |
| "106.48" | 4 | I312R |
| "106.50" | 6 | I312T |
| "106.58" | 4 | D305G |
| "106.62" | 9 | D305L |
| "106.65" | 4 | D305P |
| "106.68" | 7 | D305S |
| "106.69" | 4 | D305T |
| "106.88" | 5 | A52T |
| "106.91" | 6 | A52Y |
| "106.97" | 5 | T303R |
| "106.103" | 5 | A349E |
| "106.104" | 4 | A349F |
| "106.109" | 7 | A349L |
| "106.112" | 7 | A349P |
| "106.113" | 6 | A349Q |
| "106.119" | 5 | A349Y |
| "106.121" | 5 | D353C |
| "106.150" | 7 | E357S |
| "106.155" | 6 | N356C |
| "106.156" | 7 | N356D |
| "106.158" | 5 | N356F |
| "106.162" | 5 | N356M |
| "106.173" | 5 | A360F |
| "106.174" | 7 | A360G |
| "106.176" | 4 | A360K |
| "106.178" | 7 | A360P |
| "106.181" | 5 | A360T |
| "106.182" | 6 | A360V |
| "106.183" | 5 | A360W |
| "106.185" | 5 | G362A |
| "106.186" | 7 | G362C |
| "106.188" | 5 | G362F |
| "106.189" | 7 | G362H |
| "106.190" | 5 | G362I |
| "106.191" | 7 | G362K |
| "106.192" | 5 | G362L |
| "106.194" | 5 | G362N |
| "106.195" | 4 | G362P |
| "106.197" | 5 | G362R |
| "106.212" | 5 | R377Q |

TABLE 7-continued

Comprehensive neuronal culture screening results for R-GECO1.0 variants

| | | |
|---|---|---|
| "106.213" | 5 | R377S |
| "106.216" | 6 | R377W |
| "106.217" | 4 | R377Y |
| "106.220" | 6 | K378D |
| "106.221" | 7 | K378E |
| "106.222" | 4 | K378F |
| "106.228" | 4 | K378P |
| "106.230" | 6 | K378S |
| "106.238" | 5 | M379G |
| "106.239" | 7 | M379H |
| "106.240" | 6 | M379I |
| "106.241" | 4 | M379K |
| "106.242" | 5 | M379L |
| "106.243" | 6 | M379N |
| "106.246" | 7 | M379S |
| "106.247" | 6 | M379T |
| "106.248" | 5 | M379V |
| "106.249" | 7 | M379W |
| "106.250" | 5 | M379Y |
| "106.253" | 4 | S58E |
| "106.256" | 6 | S58M |
| "106.260" | 4 | S58R |
| "106.261" | 5 | S58W |
| "106.267" | 4 | P59N |
| "106.273" | 6 | V60Q |
| "106.279" | 7 | V61I |
| "106.289" | 5 | S62A |
| "106.293" | 6 | S62H |
| "106.294" | 5 | S62M |
| "106.295" | 4 | S62R |
| "106.296" | 4 | S62T |
| "106.322" | 5 | I76W |
| "106.323" | 4 | I76Y |
| "106.327" | 4 | K78G |
| "106.341" | 7 | R81A |
| "106.344" | 6 | R81E |
| "106.345" | 7 | R81F |
| "106.347" | 6 | R81I |
| "106.348" | 5 | R81K |
| "106.349" | 4 | R81L |
| "106.351" | 5 | R81N |
| "106.364" | 4 | H87K |
| "106.365" | 6 | H87L |
| "106.367" | 5 | H87Q |
| "106.369" | 4 | H87S |
| "106.370" | 5 | H87T |
| "106.371" | 7 | H87V |
| "106.372" | 12 | H87W |
| "106.374" | 7 | T373C |
| "106.375" | 5 | T373D |
| "106.379" | 4 | T373H |
| "106.389" | 5 | T373W |
| "106.403" | 5 | W43G |
| "106.404" | 5 | W43A |
| "106.405" | 7 | W43L |
| "106.408" | 8 | W43F |
| "106.410" | 8 | D359Y |
| "106.411" | 5 | D359F |
| "106.415" | 5 | D359A |
| "106.422" | 6 | S74G |
| "106.427" | 6 | A90G |
| "106.433" | 6 | A90S |
| "106.438" | 6 | A90C |
| "106.439" | 26 | D359N |
| "106.440" | 7 | D359M |
| "106.444" | 4 | D359T |
| "106.448" | 4 | D361V |
| "106.449" | 6 | D361S |
| "106.450" | 4 | D361W |
| "106.453" | 5 | D361Q |
| "106.457" | 8 | D361T |
| "106.459" | 4 | D361P |
| "106.460" | 5 | D361N |
| "106.461" | 6 | D361C |
| "106.462" | 6 | D361F |
| "106.463" | 5 | D361R |
| "106.475" | 25 | M375W |
| "106.479" | 14 | M375F |

TABLE 7-continued

Comprehensive neuronal culture screening results for R-GECO1.0 variants

| | | |
|---|---|---|
| "106.483" | 5 | N380T |
| "106.487" | 4 | N380V |
| "106.494" | 7 | N380I |
| "106.496" | 15 | N380G |
| "106.501" | 5 | N380P |
| "106.511" | 4 | D383G |
| "106.520" | 7 | D383Q |
| "106.521" | 4 | E387Q |
| "106.524" | 4 | E387S |
| "106.525" | 5 | E387W |
| "106.526" | 6 | E387A |
| "106.527" | 5 | E387F |
| "106.528" | 5 | E387M |
| "106.531" | 6 | E387T |
| "106.532" | 6 | E387I |
| "106.533" | 4 | E387K |
| "106.537" | 6 | E387N |
| "106.545" | 7 | S74A |
| "106.555" | 4 | G79W |
| "106.560" | 6 | G79E |
| "106.561" | 7 | G79Q |
| "106.562" | 7 | G79A |
| "106.563" | 6 | A90I |
| "106.569" | 9 | T303F |
| "106.570" | 11 | A349T |
| "106.600" | 16 | M298W |
| "106.601" | 10 | M298P |
| "106.602" | 8 | G299F |
| "106.603" | 4 | G299I |
| "106.604" | 35 | M298L |
| "106.605" | 12 | M298D |
| "106.606" | 12 | M298S |
| "106.607" | 7 | G299A |
| "106.608" | 6 | G299W |
| "106.609" | 15 | M298Y |
| "106.610" | 6 | G299R |
| "106.611" | 16 | M298Q |
| "106.612" | 12 | M298K |
| "106.613" | 7 | G299S |
| "106.614" | 8 | G299N |
| "106.615" | 12 | M298F |
| "106.616" | 16 | M298I |
| "106.617" | 15 | M298V |
| "106.618" | 14 | M298T |
| "106.619" | 15 | M298C |
| "106.620" | 7 | G299C |
| "106.622" | 15 | M298N |
| "106.623" | 14 | M298H |
| "106.624" | 15 | M298E |
| "106.625" | 15 | M298G |
| "106.626" | 16 | M298R |
| "106.627" | 7 | R304W |
| "106.628" | 6 | R304E |
| "106.629" | 4 | R304M |
| "106.630" | 6 | G299E |
| "106.631" | 8 | G299H |
| "106.632" | 8 | R304I |
| "106.633" | 8 | R304P |
| "106.634" | 8 | G299Y |
| "106.635" | 8 | R304S |
| "106.636" | 7 | R304G |
| "106.637" | 8 | R304H |
| "106.638" | 8 | R304F |
| "106.639" | 7 | G299M |
| "106.640" | 4 | R304N |
| "106.641" | 6 | R304Y |
| "106.642" | 4 | G299D |
| "106.643" | 7 | G299K |
| "106.644" | 7 | R304T |
| "106.645" | 8 | R304V |
| "106.646" | 8 | R304A |
| "106.648" | 7 | G299V |
| "106.649" | 6 | G299Q |
| "106.650" | 7 | A302H |
| "106.651" | 7 | A302D |
| "106.652" | 26 | A302F |
| "106.653" | 4 | A302V |
| "106.654" | 5 | A302M |

TABLE 7-continued

Comprehensive neuronal culture screening results for R-GECO1.0 variants

| | | |
|---|---|---|
| "106.655" | 7 | A302R |
| "106.656" | 8 | A302E |
| "106.657" | 8 | A302S |
| "106.658" | 7 | A302Q |
| "106.659" | 7 | A302K |
| "106.660" | 8 | A302C |
| "106.661" | 8 | A302G |
| "106.662" | 7 | A302I |
| "106.663" | 5 | A302N |
| "106.665" | 4 | A302Y |
| "106.666" | 4 | A302L |
| "106.667" | 5 | R304L |
| "106.668" | 6 | R304Q |
| "106.669" | 7 | T308E |
| "106.670" | 6 | T308C |
| "106.671" | 7 | T308G |
| "106.672" | 7 | T308P |
| "106.673" | 5 | T308Q |
| "106.674" | 6 | R304C |
| "106.683" | 7 | R304K |
| "106.686" | 5 | T308Y |
| "106.688" | 4 | E301P |
| "106.690" | 5 | E301Q |
| "106.691" | 5 | T308R |
| "106.692" | 5 | E301I |
| "106.693" | 4 | E301F |
| "106.694" | 5 | E301V |
| "106.695" | 5 | E301R |
| "106.697" | 4 | E301N |
| "106.698" | 6 | E301M |
| "106.699" | 7 | E301A |
| "106.700" | 6 | E301D |
| "106.701" | 8 | E301K |
| "106.702" | 7 | E301H |
| "106.703" | 7 | E301L |
| "106.704" | 7 | E301T |
| "106.705" | 8 | E301C |
| "106.706" | 6 | E301G |
| "106.707" | 8 | E317V |
| "106.708" | 8 | E317T |
| "106.709" | 6 | E317F |
| "106.710" | 6 | E317D |
| "106.711" | 6 | E317Q |
| "106.712" | 13 | L321W |
| "106.714" | 5 | E317N |
| "106.715" | 6 | E317R |
| "106.716" | 8 | E317G |
| "106.717" | 15 | L321F |
| "106.718" | 14 | L321A |
| "106.719" | 11 | L321Q |
| "106.720" | 7 | E317W |
| "106.721" | 8 | E317I |
| "106.722" | 8 | E317Y |
| "106.723" | 8 | E317H |
| "106.724" | 16 | L321V |
| "106.725" | 12 | L321N |
| "106.726" | 8 | E317M |
| "106.727" | 9 | L321G |
| "106.728" | 17 | L321Y |
| "106.729" | 7 | E317K |
| "106.730" | 5 | E317A |
| "106.731" | 10 | L321R |
| "106.732" | 7 | E317C |
| "106.733" | 15 | L321I |
| "106.734" | 7 | I330F |
| "106.735" | 8 | I330T |
| "106.736" | 12 | L321M |
| "106.738" | 12 | L321H |
| "106.739" | 4 | I330P |
| "106.740" | 6 | I330M |
| "106.741" | 14 | L321T |
| "106.742" | 33 | L321C |
| "106.744" | 10 | L321D |
| "106.745" | 13 | L321S |
| "106.747" | 4 | I330L |
| "106.748" | 8 | L321K |
| "106.749" | 5 | I330K |
| "106.750" | 7 | I330C |

TABLE 7-continued

Comprehensive neuronal culture screening results for R-GECO1.0 variants

| | | |
|---|---|---|
| "106.751" | 7 | I330R |
| "106.752" | 7 | I330V |
| "106.753" | 7 | I330S |
| "106.754" | 7 | L321E |
| "106.755" | 7 | I330D |
| "106.756" | 6 | L335T |
| "106.757" | 4 | I330H |
| "106.758" | 4 | I330A |
| "106.759" | 6 | L335H |
| "106.760" | 5 | L335P |
| "106.761" | 4 | L335R |
| "106.762" | 7 | L335K |
| "106.763" | 7 | L335V |
| "106.764" | 6 | L335Q |
| "106.765" | 6 | L335F |
| "106.766" | 7 | I330N |
| "106.767" | 7 | I330N |
| "106.768" | 8 | L335N |
| "106.769" | 6 | L335D |
| "106.770" | 6 | L335G |
| "106.771" | 8 | L335A |
| "106.772" | 4 | L335S |
| "106.773" | 7 | L335M |
| "106.774" | 8 | L335I |
| "106.775" | 5 | M339K |
| "106.776" | 8 | M339L |
| "106.777" | 7 | M339D |
| "106.778" | 5 | M339Q |
| "106.779" | 8 | M339G |
| "106.780" | 6 | M339P |
| "106.781" | 8 | M339A |
| "106.782" | 7 | M339E |
| "106.783" | 22 | M339F |
| "106.784" | 5 | L335E |
| "106.785" | 7 | M339R |
| "106.786" | 6 | M339W |
| "106.787" | 6 | M339T |
| "106.792" | 8 | M339N |
| "106.793" | 9 | K42A |
| "106.794" | 10 | K42Q |
| "106.795" | 12 | K42W |
| "106.796" | 7 | K42V |
| "106.798" | 9 | K42T |
| "106.799" | 10 | K42E |
| "106.800" | 10 | K42I |
| "106.801" | 10 | K42H |
| "106.802" | 13 | K42G |
| "106.803" | 8 | K42Y |
| "106.804" | 11 | K42N |
| "106.805" | 13 | K42L |
| "106.806" | 16 | K42P |
| "106.807" | 10 | K42D |
| "106.808" | 10 | K42F |
| "106.810" | 8 | M354I |
| "106.811" | 7 | M354T |
| "106.812" | 6 | M354V |
| "106.813" | 4 | M354C |
| "106.814" | 7 | M354S |
| "106.815" | 7 | M354F |
| "106.816" | 4 | M354P |
| "106.817" | 6 | M354Q |
| "106.818" | 7 | M354K |
| "106.819" | 28 | M354G |
| "106.822" | 4 | M354L |
| "106.823" | 7 | M354E |
| "106.824" | 6 | M354R |
| "106.825" | 8 | M354N |
| "106.826" | 8 | M354W |
| "108.830" | 5 | T138L |
| "108.831" | 7 | I109W |
| "108.832" | 5 | I109P |
| "108.833" | 4 | I109E |
| "108.837" | 6 | I109T |
| "108.838" | 23 | I109K |
| "108.839" | 17 | I109M |
| "108.840" | 6 | I109D |
| "108.841" | 7 | I109Q |
| "108.842" | 8 | I109N |
| "108.843" | 7 | I109C |

TABLE 7-continued

Comprehensive neuronal culture screening results for R-GECO1.0 variants

| | | |
|---|---|---|
| "108.844" | 5 | I109Y |
| "108.845" | 5 | I109V |
| "108.847" | 5 | I109R |
| "108.849" | 8 | D111M |
| "108.850" | 98 | D111L |
| "108.852" | 5 | D111W |
| "108.853" | 5 | D111H |
| "108.854" | 5 | D111F |
| "108.858" | 4 | D111Q |
| "108.859" | 5 | D111N |
| "108.878" | 4 | K113Q |
| "108.890" | 4 | K113D |
| "108.893" | 4 | K113F |
| "108.901" | 5 | L114M |
| "108.914" | 6 | D115E |
| "108.915" | 5 | D115Q |
| "108.916" | 6 | D115S |
| "108.917" | 4 | D115N |
| "108.921" | 5 | D115K |
| "108.922" | 6 | D115C |
| "108.923" | 5 | D115A |
| "108.924" | 8 | D115L |
| "108.925" | 7 | D115Y |
| "108.926" | 6 | D115F |
| "108.927" | 7 | D115I |
| "108.928" | 7 | D115T |
| "108.929" | 7 | D115W |
| "108.930" | 7 | D115H |
| "106.933" | 4 | E133W |
| "106.934" | 6 | R135M |
| "106.938" | 4 | R135S |
| "106.941" | 5 | R135W |
| "106.942" | 7 | R135Y |
| "106.943" | 7 | K231A |
| "106.944" | 7 | K231C |
| "106.945" | 7 | K231D |
| "106.946" | 6 | K231F |
| "106.947" | 5 | K231G |
| "106.948" | 7 | K231H |
| "106.949" | 5 | K231I |
| "106.950" | 6 | K231L |
| "106.951" | 8 | K231M |
| "106.957" | 5 | K231V |
| "106.1000" | 6 | D305V D353G N356G E357A N380T |
| "106.1001" | 7 | D305V D353G N356G E357A |
| "106.1003" | 10 | D305V N356G E357A N380T |
| "106.1004" | 9 | D353G N356G E357A N380T |
| "106.1005" | 6 | D305V D353G N356G |
| "106.1006" | 9 | D305V D353G E357A |
| "106.1007" | 26 | D305V D353G N380T |
| "106.1008" | 9 | D305V N356G N380T |
| "106.1009" | 10 | D305V E357A N380T |
| "106.1010" | 7 | D353G E357A N380T |
| "106.1011" | 10 | D305V D353G E357A N380G |
| "106.1012" | 10 | D305V D353G N380G |
| "106.1013" | 6 | D353G N356G N380G |
| "106.1014" | 7 | N356G E357A N380G |
| "106.1015" | 4 | A349N M375F |
| "106.1018" | 6 | A52L D353G |
| "106.1020" | 7 | A52L E357A |
| "106.1021" | 7 | A349N D353G |
| "106.1022" | 7 | A349N N356G |
| "106.1023" | 9 | A349N E357A |
| "106.1024" | 9 | D305V M375F |
| "106.1025" | 12 | D353G M375F |
| "106.1027" | 11 | E357A M375F |
| "106.1028" | 10 | M375F N380T |
| "106.1029" | 7 | A52L N380G |
| "106.1030" | 12 | A349N N380G |
| "106.1031" | 12 | M375F N380G |
| "106.1032" | 8 | D305V D353G E357A N380T |
| "106.1033" | 8 | D353G N356G E357A |
| "106.1034" | 8 | D353G N356G N380T |
| "106.1035" | 8 | N356G E357A N380T |
| "106.1036" | 8 | D305V D353G N356G E357A N380G |
| "106.1037" | 15 | D305V D353G N356G N380G |
| "106.1038" | 25 | D305V N356G E357A N380G |
| "106.1039" | 4 | D353G N356G E357A N380G |

TABLE 7-continued

Comprehensive neuronal culture screening results for R-GECO1.0 variants

| | | |
|---|---|---|
| "106.1040" | 8 | D305V N356G N380G |
| "106.1041" | 6 | D305V E357A N380G |
| "106.1042" | 5 | D353G E357A N380G |
| "106.1043" | 7 | A52L A349N M375F |
| "106.1044" | 6 | A52L A349N |
| "106.1046" | 5 | A349N N380T |
| "106.1048" | 29 | E314D |
| "106.1053" | 7 | D305V N356G E357A |
| "106.1054" | 13 | A52L N380T |
| "108.1057" | 4 | C129W |
| "108.1058" | 6 | C129S |
| "108.1066" | 5 | C129M |
| "108.1069" | 5 | C129H |
| "108.1071" | 5 | C129N |
| "108.1072" | 5 | S137M |
| "108.1073" | 6 | S137F |
| "108.1074" | 7 | S137Y |
| "108.1078" | 5 | S137R |
| "108.1079" | 7 | S137T |
| "108.1080" | 4 | S137K |
| "108.1082" | 7 | S137A |
| "108.1083" | 6 | S137W |
| "108.1084" | 6 | S137V |
| "108.1086" | 4 | S137Q |
| "108.1103" | 6 | T138A |
| "106.1104" | 7 | K45S |
| "106.1105" | 5 | K45N |
| "106.1106" | 7 | K45H |
| "106.1107" | 6 | K45G |
| "106.1108" | 4 | K45W |
| "106.1109" | 5 | K45R |
| "106.1110" | 7 | K45Q |
| "106.1113" | 4 | K45F |
| "106.1114" | 8 | K45V |
| "106.1115" | 4 | K45E |
| "106.1116" | 8 | K45A |
| "106.1117" | 6 | K45L |
| "106.1118" | 6 | K45P |
| "106.1119" | 11 | K45Y |
| "106.1120" | 6 | K45I |
| "106.1121" | 5 | K45C |
| "106.1122" | 5 | H48I |
| "106.1123" | 4 | H48T |
| "106.1124" | 5 | H48V |
| "106.1125" | 26 | H48R |
| "106.1126" | 21 | H48W |
| "106.1128" | 4 | H48N |
| "106.1129" | 6 | H48G |
| "106.1130" | 5 | H48Y |
| "106.1131" | 7 | H48Q |
| "106.1135" | 4 | H48D |
| "106.1136" | 4 | H48S |
| "106.1139" | 5 | A49W |
| "106.1140" | 5 | A49C |
| "106.1144" | 4 | A49S |
| "106.1145" | 7 | A49P |
| "106.1163" | 7 | Q306V |
| "106.1164" | 5 | Q306T |
| "106.1165" | 5 | Q306Y |
| "106.1166" | 8 | Q306W |
| "106.1167" | 6 | Q306K |
| "106.1168" | 6 | Q306G |
| "106.1169" | 8 | Q306L |
| "106.1170" | 28 | Q306D |
| "106.1175" | 4 | Q306M |
| "106.1176" | 7 | Q306C |
| "106.1177" | 5 | L307K |
| "106.1178" | 5 | L307A |
| "106.1179" | 4 | L307F |
| "106.1180" | 5 | L307V |
| "106.1181" | 5 | L307Y |
| "106.1183" | 7 | L307N |
| "106.1185" | 8 | L307S |
| "106.1186" | 4 | L307T |
| "106.1187" | 4 | L307P |
| "106.1189" | 4 | L307E |
| "106.1193" | 7 | L307M |
| "106.1195" | 7 | L307Q |

TABLE 7-continued

Comprehensive neuronal culture screening results for R-GECO1.0 variants

| | | |
|---|---|---|
| "106.1196" | 7 | D363Y |
| "106.1197" | 7 | D363G |
| "106.1202" | 4 | D363M |
| "106.1203" | 7 | D363F |
| "106.1205" | 5 | D363H |
| "106.1209" | 5 | D363V |
| "106.1212" | 6 | H182L |
| "106.1215" | 11 | R131A |
| "106.1216" | 37 | R131C |
| "106.1217" | 5 | R131D |
| "106.1218" | 8 | R131E |
| "106.1219" | 12 | R131F |
| "106.1220" | 7 | R131G |
| "106.1221" | 9 | R131H |
| "106.1222" | 8 | R131I |
| "106.1223" | 10 | R131K |
| "106.1224" | 14 | R131L |
| "106.1225" | 12 | R131M |
| "106.1226" | 10 | R131N |
| "106.1228" | 15 | R131Q |
| "106.1229" | 15 | R131S |
| "106.1230" | 12 | R131T |
| "106.1231" | 16 | R131V |
| "106.1232" | 14 | R131W |
| "106.1233" | 11 | R131Y |
| "106.1235" | 4 | E133C |
| "106.1237" | 5 | E133F |
| "106.1238" | 7 | E133G |
| "106.1241" | 5 | E133K |
| "106.1244" | 8 | E133N |
| "106.1246" | 7 | E133Q |
| "106.1247" | 6 | E133R |
| "106.1248" | 5 | E133S |
| "106.1249" | 7 | E133V |
| "106.1250" | 14 | E133Y |
| "106.1251" | 30 | R135A |
| "106.1252" | 7 | R135C |
| "106.1253" | 5 | R135D |
| "106.1254" | 7 | R135E |
| "106.1255" | 7 | R135F |
| "106.1256" | 7 | R135G |
| "106.1257" | 5 | R135H |
| "106.1258" | 6 | R135I |
| "106.1259" | 8 | R135K |
| "106.1260" | 6 | R135L |
| "106.1261" | 6 | K231E |
| "106.1262" | 5 | K231T |
| "106.1264" | 4 | E133T |
| "106.1265" | 12 | K73C |
| "106.1267" | 8 | K73E |
| "106.1272" | 10 | K73M |
| "106.1274" | 12 | K73Q |
| "106.1275" | 6 | K73R |
| "106.1277" | 5 | K73T |
| "106.1278" | 8 | K73W |
| "106.1282" | 34 | K73V |
| "106.1284" | 6 | E158A |
| "106.1285" | 8 | E158D |
| "106.1286" | 4 | E158F |
| "106.1287" | 7 | E158G |
| "106.1288" | 6 | E158I |
| "106.1289" | 6 | E158K |
| "106.1290" | 7 | E158L |
| "106.1292" | 7 | E158N |
| "106.1293" | 8 | E158P |
| "106.1294" | 7 | E158R |
| "106.1295" | 4 | E158S |
| "106.1296" | 5 | E158T |
| "106.1297" | 8 | E158V |
| "106.1298" | 8 | E158W |
| "106.1300" | 6 | E158C |
| "106.1301" | 6 | E158H |
| "106.1302" | 5 | E158Q |
| "106.1303" | 6 | I165A |
| "106.1304" | 7 | I165C |
| "106.1305" | 5 | I165D |
| "106.1307" | 5 | I165F |
| "106.1309" | 6 | I165H |

TABLE 7-continued

Comprehensive neuronal culture screening results for R-GECO1.0 variants

| | | |
|---|---|---|
| "106.1310" | 4 | I165K |
| "106.1312" | 7 | I165P |
| "106.1315" | 7 | I165V |
| "106.1316" | 6 | I165W |
| "106.1318" | 4 | I165N |
| "106.1319" | 4 | I165R |
| "106.1320" | 7 | I165T |
| "106.1327" | 6 | F222L |
| "106.1333" | 5 | F222V |
| "106.1357" | 6 | F240W |
| "106.1358" | 6 | F240Y |
| "106.1360" | 5 | I230C |
| "106.1368" | 4 | I230M |
| "106.1377" | 4 | L408C |
| "106.1386" | 4 | L408W |
| "106.1387" | 4 | E386A |
| "106.1388" | 7 | E386C |
| "106.1389" | 6 | E386D |
| "106.1390" | 5 | E386F |
| "106.1391" | 5 | E386G |
| "106.1392" | 6 | E386H |
| "106.1393" | 7 | E386I |
| "106.1396" | 6 | E386M |
| "106.1397" | 6 | E386P |
| "106.1399" | 7 | E386R |
| "106.1400" | 5 | E386S |
| "106.1401" | 7 | E386T |
| "106.1402" | 8 | E386V |
| "106.1403" | 6 | E386W |
| "106.1404" | 6 | E386Y |
| "106.1405" | 6 | A391H |
| "106.1406" | 6 | A391D |
| "106.1407" | 7 | A391W |
| "106.1409" | 7 | A391M |
| "106.1423" | 4 | A391P |
| "106.1424" | 5 | K397F |
| "106.1425" | 5 | K397I |
| "106.1426" | 6 | K397M |
| "106.1427" | 6 | K397W |
| "106.1429" | 6 | K397H |
| "106.1430" | 8 | K397C |
| "106.1431" | 8 | K397D |
| "106.1432" | 7 | K397P |
| "106.1433" | 5 | K397N |
| "106.1434" | 8 | K397R |
| "106.1435" | 6 | K397A |
| "106.1438" | 4 | K397L |
| "106.1439" | 4 | K397G |
| "106.1440" | 5 | K397E |
| "106.1442" | 6 | L56W |
| "106.1443" | 4 | R393G |
| "106.1444" | 4 | R393I |
| "106.1445" | 7 | R393T |
| "106.1446" | 5 | R393E |
| "106.1447" | 8 | R393H |
| "106.1448" | 5 | R393V |
| "106.1449" | 5 | R393C |
| "106.1450" | 5 | R393N |
| "106.1451" | 5 | R393P |
| "106.1452" | 7 | R393W |
| "106.1453" | 8 | R393A |
| "106.1454" | 4 | R393L |
| "106.1456" | 5 | R393D |
| "106.1458" | 5 | R393S |
| "106.1459" | 4 | R393Q |
| "106.1460" | 4 | R393M |
| "106.1461" | 4 | R393K |
| "106.1507" | 6 | V173A |
| "106.1510" | 4 | M175C |
| "106.1513" | 6 | M175T |
| "106.1514" | 4 | M175Q |
| "106.1515" | 7 | M175A |
| "106.1516" | 7 | M175F |
| "106.1517" | 4 | M175I |
| "106.1519" | 4 | I262M |
| "106.1520" | 8 | I262A |
| "106.1524" | 4 | I262L |
| "106.1527" | 4 | I262F |

TABLE 7-continued

Comprehensive neuronal culture screening results for R-GECO1.0 variants

| | | |
|---|---|---|
| "106.1529" | 8 | I262V |
| "106.1533" | 7 | I262T |
| "106.1534" | 7 | I262C |
| "106.1536" | 6 | N265A |
| "106.1537" | 4 | N265S |
| "106.1538" | 7 | N265Y |
| "106.1539" | 5 | N265G |
| "106.1540" | 5 | N265M |
| "106.1541" | 5 | N265K |
| "106.1542" | 6 | N265Q |
| "106.1544" | 6 | N265T |
| "106.1545" | 8 | N265C |
| "106.1546" | 6 | N265F |
| "106.1547" | 5 | N265V |
| "106.1549" | 4 | N265I |
| "106.1551" | 6 | N265R |
| "106.1553" | 6 | S268A |
| "106.1561" | 5 | S268T |
| "106.1572" | 4 | M412P |
| "106.1576" | 7 | M412Y |
| "106.1577" | 6 | M412Q |
| "106.1578" | 5 | M412H |
| "106.1579" | 4 | M412I |
| "106.1580" | 7 | M412R |
| "106.1581" | 6 | M412C |
| "106.1582" | 6 | M412A |
| "106.1583" | 8 | M412L |
| "106.1584" | 7 | M412N |
| "106.1585" | 8 | M412E |
| "106.1586" | 7 | M412V |
| "106.1587" | 4 | L415E |
| "106.1588" | 5 | L415Y |
| "106.1589" | 4 | L415A |
| "106.1590" | 5 | L415G |
| "106.1591" | 5 | L415M |
| "106.1592" | 4 | L415W |
| "106.1593" | 4 | L415R |
| "106.1595" | 5 | L415F |
| "106.1596" | 6 | L415D |
| "106.1598" | 4 | L415Q |
| "106.1599" | 8 | L415S |
| "106.1600" | 6 | L415V |
| "106.1601" | 8 | L415N |
| "106.1602" | 8 | L415H |
| "106.1603" | 8 | L415C |
| "106.1604" | 6 | L415P |
| "106.1605" | 6 | L415I |
| "106.1606" | 5 | M427P |
| "106.1607" | 5 | M427H |
| "106.1608" | 7 | M427I |
| "106.1609" | 5 | M427A |
| "106.1610" | 6 | M427D |
| "106.1611" | 7 | M427F |
| "106.1624" | 20 | H48R D111L D305V N356G E357A N380G |
| "106.1625" | 12 | H48W D111L |
| "106.1626" | 7 | H48W D111L D359N |
| "106.1627" | 7 | H48W D111L M375W |
| "106.1628" | 13 | H48W D111L R135A |
| "106.1629" | 18 | K73V I109K M298L |
| "106.1630" | 11 | K73V I109K M354G |
| "106.1631" | 31 | I109M D111L |
| "106.1632" | 6 | I109M D111L R135A |
| "106.1633" | 5 | I109M D111L M375W |
| "106.1634" | 7 | H48W I109M D111L |
| "106.1635" | 5 | H48W I109M D111L M375W |
| "106.1636" | 26 | H48R I109M D111L |
| "106.1637" | 13 | H48R I109M D111L D305V N356G E357A N380G |
| "106.1638" | 8 | H48R I109M D111L R135A |
| "106.1639" | 7 | H48R I109M D111L D359N |
| "106.1640" | 8 | K73V I109K L321C M354G |
| "106.1641" | 8 | I109K M298L L321C M375F |
| "106.1642" | 7 | I109K M298L L321C M354G |
| "106.1643" | 7 | D111L D305V N356G E357A D359N N380G |
| "106.1644" | 8 | I109M D111L D305V N356G E357A M375W N380G |
| "106.1645" | 6 | A318S M339F |
| "106.1646" | 7 | E314D M375W |
| "106.1647" | 18 | Q306D A318S M354G |
| "106.1648" | 22 | R131C E314D M375W |

TABLE 7-continued

Comprehensive neuronal culture screening results for R-GECO1.0 variants

| | | |
|---|---|---|
| "106.1649" | 5 | K73V L321C |
| "106.1650" | 8 | K73V L321C M375F |
| "106.1651" | 6 | K73V L321C M354G |
| "106.1652" | 7 | M298L L321C M354G |
| "106.1653" | 6 | A302F A318S M375F |
| "106.1654" | 6 | I109K L321C M375W |
| "106.1655" | 18 | D305V M339F D353G N380T |
| "106.1656" | 20 | H48R D111L |
| "106.1657" | 7 | H48R I109K L321C |
| "106.1658" | 6 | K73V I109K L321C M375F |
| "106.1659" | 28 | K73V I109K M298L L321C M375F |
| "106.1660" | 7 | I109M D111L R135A M375W |
| "106.1661" | 8 | H48W D111L R135A M375W |
| "106.1662" | 30 | A302F A318S |
| "106.1663" | 7 | A302F M339F |
| "106.1664" | 7 | A302F D305V D353G N380T |
| "106.1665" | 7 | A302F Q306D |
| "106.1666" | 6 | A302F Q306D M375F |
| "106.1667" | 4 | A302F Q306D M354G |
| "106.1668" | 13 | D305V Q306D D353G N380T |
| "106.1669" | 8 | M298L L321C |
| "106.1671" | 5 | H48R R131C E314D |
| "106.1672" | 7 | H48R R131C L321C |
| "106.1673" | 7 | K73V M298L |
| "106.1674" | 8 | K73V M298L L321C |
| "106.1675" | 4 | I109K R131C |
| "106.1676" | 7 | I109K R131C M375W |
| "106.1677" | 7 | D111L R135A |
| "106.1678" | 5 | D111L R135A D359N |
| "106.1679" | 6 | D111L R135A M375W |
| "106.1680" | 7 | I109K M298L |
| "106.1681" | 7 | I109K M298L M375F |
| "106.1682" | 11 | I109K M298L L321C |
| "106.1683" | 7 | A302F D305V D353G M375F N380T |
| "106.1684" | 7 | D111L R135A D359N M375W |
| "106.1685" | 12 | D305V A318S D353G M354G N380T |
| "106.1686" | 7 | I109K R131C L321C M375W |
| "106.1687" | 7 | D111L D305V N356G E357A D359N M375W N380G |
| "106.1688" | 7 | A302F D305V D353G M354G N380T |
| "106.1689" | 6 | Q306D A318S M375F |
| "106.1690" | 8 | K73V M298L L321C M354G |
| "106.1691" | 8 | D305V M339F D353G M354G N380T |
| "106.1692" | 6 | H48R R131C E314D M375W |
| "106.1693" | 7 | M298L L321C M375F |
| "106.1694" | 7 | A302F A318S M354G |
| "106.1695" | 7 | D111L D359N M375W |
| "106.1696" | 12 | K73V I109K L321C |
| "106.1697" | 8 | H48R D111L R135A D359N |
| "106.1698" | 5 | Q306D A318S |
| "106.1699" | 6 | R131C M375W |
| "106.1700" | 6 | H48R R131C |
| "106.1701" | 7 | K73V M298L M354G |
| "106.1702" | 15 | D111L R135A D305V N356G E357A N380G |
| "106.1703" | 7 | I109K M298L M354G |
| "106.1704" | 7 | D111L R135A D305V N356G E357A M375W N380G |
| "106.1705" | 7 | K73V M298L L321C M375F |
| "106.1706" | 7 | D305V M339F D353G M375F N380T |
| "106.1707" | 7 | D305V A318S D353G M375F N380T |
| "106.1708" | 6 | K73V I109K M298L M375F |
| "106.1709" | 8 | R131C E314D |
| "106.1710" | 7 | R131C L321C |
| "106.1711" | 6 | K73V M298L M375F |
| "106.1712" | 8 | D305V Q306D D353G M375F N380T |
| "106.1713" | 8 | H48R D111L D359N |
| "106.1714" | 14 | H48R D111L R135A |
| "106.1715" | 15 | H48R I109K R131C |
| "106.1716" | 14 | K73V I109K |
| "106.1717" | 13 | I109K L321C |
| "106.1718" | 15 | K73V I109K M375F |
| "106.1719" | 14 | D111L D359N |
| "106.1720" | 13 | K73V I109K M298L M354G |
| "106.1722" | 12 | I109M D111L D359N |
| "106.1723" | 11 | H48W D111L D305V N356G E357A N380G |
| "106.1724" | 16 | I109M D111L D305V N356G E357A N380G |
| "106.1725" | 18 | D111L D305V N356G E357A N380G |
| "106.1726" | 12 | H48R I109K R131C L321C |
| "106.1727" | 13 | K73V I109K M298L L321C |
| "106.1728" | 18 | K73V I109K M298L L321C M354G |

TABLE 7-continued

Comprehensive neuronal culture screening results for R-GECO1.0 variants

| | | |
|---|---|---|
| "106.1729" | 15 | H48R D111L D305V N356G E357A D359N N380G |
| "106.1730" | 15 | D111L D305V N356G E357A M375W N380G |
| "106.1731" | 15 | H48R E314D |
| "106.1732" | 7 | R131C L321C M375W |
| "106.1733" | 30 | D305V A318S D353G N380T |
| "106.1734" | 11 | Q306D M339F M375F |
| "106.1735" | 15 | Q306D M339F M354G |
| "106.1736" | 12 | A318S M339F M375F |
| "106.1737" | 10 | A318S M339F M354G |
| "106.1738" | 14 | A302F M339F M375F |
| "106.1739" | 16 | A302F M339F M354G |
| "106.1740" | 14 | H48R D111L R135A D305V N356G E357A N380G |
| "106.1741" | 20 | H48W D111L D305V N356G E357A M375W N380G |
| "106.1742" | 21 | I109M D111L D359N M375W |
| "106.1744" | 35 | D305V Q306D D353G M354G N380T |

| R-GECO1.0 variant | 1 AP $\Delta F/F_0$ | 3 AP $\Delta F/F_0$ | 10 AP $\Delta F/F_0$ | 160 AP $\Delta F/F_0$ | Decay half time (10 AP) | $F_0$ normalized to GFP fluorescence |
|---|---|---|---|---|---|---|
| "R-GECO1.0" | 1.00 | 1.00 | 1.00 | 1.00 | 1.00 | 1.00 |
| "R-CaMP2" | 1.31 | 1.40 | 0.94 | 0.39 | 0.70 | 3.35 |
| "jRGECO1a" | 8.57 | 6.07 | 3.41 | 1.10 | 1.05 | 0.77 |
| "jRGECO1b" | 1.14 | 1.47 | 1.68 | 1.06 | 0.88 | 0.82 |
| "106.13" | 0.72 | 0.62 | 0.62 | 0.90 | 1.20 | 0.93 |
| "106.16" | 1.79 | 2.28 | 2.05 | 0.91 | 0.84 | 1.06 |
| "106.19" | 0.48 | 0.36 | 0.41 | 0.33 | 0.57 | 0.70 |
| "106.22" | 1.78 | 2.01 | 1.67 | 0.66 | 0.56 | 0.97 |
| "106.23" | 0.27 | 0.08 | 0.07 | 0.07 | 0.22 | 0.61 |
| "106.25" | 1.08 | 1.61 | 1.19 | 0.56 | 0.45 | 0.74 |
| "106.27" | 0.53 | 0.49 | 0.57 | 0.63 | 0.79 | 0.53 |
| "106.30" | 2.04 | 2.26 | 2.15 | 1.15 | 0.86 | 0.95 |
| "106.31" | 2.06 | 2.52 | 2.37 | 1.16 | 0.81 | 0.92 |
| "106.32" | 2.64 | 3.21 | 2.87 | 1.27 | 1.06 | 0.70 |
| "106.37" | 0.28 | 0.46 | 0.68 | 0.59 | 0.55 | 0.46 |
| "106.38" | 0.76 | 0.99 | 0.97 | 0.79 | 0.80 | 0.74 |
| "106.39" | 0.40 | 0.35 | 0.35 | 0.33 | 0.43 | 0.63 |
| "106.40" | 0.51 | 0.48 | 0.48 | 0.55 | 0.56 | 0.50 |
| "106.42" | 0.50 | 0.51 | 0.72 | 0.82 | 0.76 | 0.86 |
| "106.43" | 0.44 | 0.36 | 0.50 | 0.58 | 0.55 | 0.77 |
| "106.44" | 0.71 | 0.87 | 0.93 | 0.86 | 0.82 | 0.72 |
| "106.46" | 0.39 | 0.20 | 0.22 | 0.25 | 0.49 | 0.40 |
| "106.48" | 0.39 | 0.55 | 0.66 | 0.75 | 0.75 | 0.82 |
| "106.50" | 1.54 | 1.72 | 1.54 | 1.20 | 0.77 | 0.72 |
| "106.58" | 0.87 | 1.00 | 0.91 | 0.80 | 0.64 | 1.05 |
| "106.62" | 0.57 | 0.68 | 0.68 | 0.66 | 0.83 | 1.08 |
| "106.65" | 0.42 | 0.23 | 0.08 | 0.09 | 0.28 | 0.51 |
| "106.68" | 0.62 | 0.64 | 0.71 | 0.67 | 0.83 | 1.20 |
| "106.69" | 3.38 | 2.31 | 1.66 | 1.07 | 0.83 | 1.00 |
| "106.88" | 0.20 | 0.09 | 0.17 | 0.29 | 0.26 | 1.23 |
| "106.91" | 0.22 | 0.09 | 0.07 | 0.10 | 0.16 | 1.00 |
| "106.97" | 1.78 | 1.60 | 1.26 | 1.05 | 0.80 | 0.83 |
| "106.103" | 2.38 | 1.61 | 1.43 | 0.84 | 1.26 | 4.66 |
| "106.104" | 0.96 | 0.98 | 0.95 | 0.96 | 0.62 | 0.96 |
| "106.109" | 0.58 | 0.60 | 0.58 | 0.58 | 0.98 | 1.26 |
| "106.112" | 0.71 | 0.71 | 0.71 | 0.64 | 0.83 | 1.38 |
| "106.113" | 2.00 | 1.77 | 1.45 | 1.07 | 0.79 | 0.90 |
| "106.119" | 2.85 | 2.11 | 2.14 | 1.78 | 0.87 | 0.81 |
| "106.121" | 2.15 | 1.71 | 1.34 | 0.80 | 1.45 | 0.92 |
| "106.150" | 2.52 | 1.66 | 1.22 | 0.73 | 1.38 | 1.01 |
| "106.155" | 0.69 | 0.77 | 0.70 | 0.60 | 0.66 | 0.85 |
| "106.156" | 0.84 | 0.98 | 0.62 | 0.56 | 0.67 | 0.79 |
| "106.158" | 0.61 | 0.51 | 0.52 | 0.56 | 0.67 | 0.87 |
| "106.162" | 0.67 | 0.86 | 0.79 | 0.70 | 0.69 | 1.00 |
| "106.173" | 1.21 | 1.20 | 1.00 | 0.76 | 1.06 | 0.96 |
| "106.174" | 0.40 | 0.44 | 0.47 | 0.63 | 0.67 | 1.11 |
| "106.176" | 0.93 | 0.85 | 0.71 | 0.84 | 0.73 | 1.28 |
| "106.178" | 0.13 | 0.09 | 0.05 | 0.08 | 0.27 | 0.72 |
| "106.181" | 0.91 | 0.80 | 0.95 | 0.94 | 0.96 | 0.81 |
| "106.182" | 1.25 | 1.28 | 0.92 | 0.88 | 0.96 | 0.79 |
| "106.183" | 1.16 | 0.89 | 0.89 | 0.95 | 0.94 | 0.73 |
| "106.185" | 0.75 | 0.63 | 0.65 | 1.02 | 0.58 | 0.84 |
| "106.186" | 1.63 | 1.20 | 1.19 | 1.43 | 0.77 | 0.88 |
| "106.188" | 0.29 | 0.35 | 0.36 | 0.40 | 0.45 | 0.56 |
| "106.189" | 0.56 | 0.57 | 0.58 | 0.64 | 0.69 | 0.80 |
| "106.190" | 0.11 | 0.16 | 0.19 | 0.27 | 0.32 | 0.82 |
| "106.191" | 0.77 | 0.73 | 0.70 | 0.78 | 0.96 | 0.89 |
| "106.192" | 0.57 | 0.41 | 0.50 | 0.58 | 0.55 | 0.80 |

TABLE 7-continued

Comprehensive neuronal culture screening results for R-GECO1.0 variants

| | | | | | | |
|---|---|---|---|---|---|---|
| "106.194" | 0.72 | 0.56 | 0.58 | 0.94 | 0.61 | 0.98 |
| "106.195" | 0.13 | 0.06 | 0.05 | 0.08 | 0.24 | 0.90 |
| "106.197" | 0.80 | 0.76 | 0.69 | 0.79 | 0.84 | 0.87 |
| "106.212" | 0.51 | 0.58 | 0.55 | 0.71 | 0.53 | 0.72 |
| "106.213" | 0.28 | 0.24 | 0.31 | 0.38 | 0.26 | 0.82 |
| "106.216" | 0.94 | 0.88 | 0.74 | 0.64 | 0.78 | 0.93 |
| "106.217" | 0.50 | 0.39 | 0.35 | 0.40 | 0.41 | 0.76 |
| "106.220" | 1.29 | 1.09 | 0.78 | 0.51 | 0.61 | 0.82 |
| "106.221" | 2.19 | 2.08 | 1.39 | 0.80 | 0.93 | 0.70 |
| "106.222" | 0.13 | 0.21 | 0.24 | 0.33 | 0.33 | 0.87 |
| "106.228" | 2.02 | 1.47 | 1.06 | 0.53 | 0.69 | 0.81 |
| "106.230" | 2.01 | 1.94 | 1.39 | 0.82 | 1.06 | 0.93 |
| "106.238" | 0.68 | 0.70 | 0.68 | 0.53 | 0.43 | 1.04 |
| "106.239" | 0.75 | 0.71 | 0.61 | 0.51 | 0.50 | 0.94 |
| "106.240" | 1.37 | 1.25 | 0.92 | 1.49 | 0.63 | 0.60 |
| "106.241" | 0.96 | 1.03 | 0.97 | 0.87 | 0.67 | 1.22 |
| "106.242" | 0.90 | 0.76 | 0.71 | 0.67 | 0.94 | 1.16 |
| "106.243" | 0.85 | 0.89 | 0.80 | 0.68 | 0.50 | 0.94 |
| "106.246" | 0.72 | 0.86 | 0.82 | 0.59 | 0.52 | 1.06 |
| "106.247" | 1.03 | 1.17 | 1.01 | 0.71 | 0.66 | 0.97 |
| "106.248" | 0.76 | 0.75 | 0.81 | 0.77 | 0.71 | 1.12 |
| "106.249" | 0.35 | 0.43 | 0.56 | 0.43 | 0.40 | 1.39 |
| "106.250" | 0.93 | 1.05 | 0.87 | 0.85 | 0.89 | 1.29 |
| "106.253" | 0.71 | 0.88 | 0.82 | 0.61 | 0.49 | 1.53 |
| "106.256" | 1.15 | 1.25 | 1.14 | 0.69 | 0.84 | 1.30 |
| "106.260" | 2.62 | 1.65 | 0.87 | 0.34 | 1.51 | 2.52 |
| "106.261" | 0.63 | 0.58 | 0.58 | 0.49 | 0.69 | 1.36 |
| "106.267" | 0.21 | 0.26 | 0.30 | 0.34 | 0.45 | 0.82 |
| "106.273" | 2.20 | 1.72 | 1.17 | 0.62 | 1.18 | 1.55 |
| "106.279" | 0.35 | 0.33 | 0.39 | 0.50 | 0.55 | 0.99 |
| "106.289" | 1.81 | 1.46 | 1.12 | 0.94 | 1.05 | 1.23 |
| "106.293" | 0.76 | 0.78 | 0.78 | 0.70 | 0.70 | 1.19 |
| "106.294" | −0.01 | 0.13 | 0.15 | 0.21 | 0.42 | 0.93 |
| "106.295" | 0.08 | 0.11 | 0.08 | 0.08 | 0.30 | 0.98 |
| "106.296" | 0.41 | 0.43 | 0.40 | 0.39 | 0.76 | 0.98 |
| "106.322" | 1.44 | 0.82 | 0.63 | 0.58 | 1.79 | 1.48 |
| "106.323" | 0.38 | 0.39 | 0.40 | 0.39 | 0.65 | 1.40 |
| "106.327" | 0.25 | 0.19 | 0.04 | 0.05 | 0.04 | 0.19 |
| "106.341" | 2.48 | 2.07 | 1.39 | 1.12 | 1.05 | 1.10 |
| "106.344" | 1.55 | 1.12 | 0.76 | 0.65 | 0.79 | 0.23 |
| "106.345" | 1.30 | 1.21 | 0.85 | 0.92 | 0.93 | 0.57 |
| "106.347" | 0.63 | 0.60 | 0.43 | 0.55 | 0.80 | 0.86 |
| "106.348" | 0.83 | 0.70 | 0.72 | 0.85 | 0.82 | 0.94 |
| "106.349" | 3.10 | 2.47 | 1.92 | 1.25 | 1.09 | 0.63 |
| "106.351" | 0.96 | 1.09 | 0.71 | 0.71 | 0.86 | 0.46 |
| "106.364" | 0.37 | 0.25 | 0.17 | 0.25 | 0.35 | 0.81 |
| "106.365" | 0.58 | 0.42 | 0.33 | 0.43 | 0.63 | 0.91 |
| "106.367" | 0.90 | 0.76 | 0.71 | 0.68 | 0.70 | 0.82 |
| "106.369" | 1.00 | 0.98 | 0.75 | 0.75 | 0.80 | 0.81 |
| "106.370" | 0.96 | 0.54 | 0.45 | 0.55 | 0.73 | 0.68 |
| "106.371" | 0.46 | 0.45 | 0.30 | 0.36 | 0.52 | 0.69 |
| "106.372" | 0.31 | 0.36 | 0.34 | 0.52 | 0.69 | 0.75 |
| "106.374" | 3.92 | 2.83 | 1.72 | 1.19 | 1.15 | 1.03 |
| "106.375" | 2.87 | 2.17 | 1.79 | 1.13 | 0.96 | 0.89 |
| "106.379" | 1.82 | 1.71 | 1.44 | 1.17 | 0.75 | 1.19 |
| "106.389" | 1.10 | 1.50 | 1.42 | 1.08 | 0.92 | 1.15 |
| "106.403" | 0.08 | 0.04 | 0.09 | 0.12 | 0.35 | 0.64 |
| "106.404" | 0.15 | 0.15 | 0.22 | 0.29 | 0.51 | 0.61 |
| "106.405" | 0.43 | 0.55 | 0.54 | 0.45 | 0.76 | 0.55 |
| "106.408" | 0.50 | 0.58 | 0.61 | 0.58 | 0.65 | 0.66 |
| "106.410" | 0.40 | 0.27 | 0.22 | 0.16 | 0.50 | 0.91 |
| "106.411" | 0.31 | 0.52 | 0.38 | 0.24 | 0.59 | 0.94 |
| "106.415" | 1.55 | 1.20 | 0.82 | 0.49 | 1.33 | 0.91 |
| "106.422" | 2.01 | 1.92 | 1.50 | 0.92 | 1.10 | 0.95 |
| "106.427" | 3.86 | 2.56 | 1.75 | 1.10 | 0.98 | 0.88 |
| "106.433" | 1.69 | 1.60 | 1.47 | 1.18 | 1.02 | 0.89 |
| "106.438" | 1.63 | 1.58 | 1.15 | 1.05 | 0.85 | 1.42 |
| "106.439" | 1.49 | 1.30 | 0.96 | 0.58 | 1.17 | 1.19 |
| "106.440" | 1.57 | 1.11 | 0.65 | 0.51 | 0.88 | 1.42 |
| "106.444" | 1.48 | 1.07 | 0.78 | 0.46 | 1.70 | 1.18 |
| "106.448" | 2.09 | 1.45 | 1.07 | 0.79 | 0.75 | 1.25 |
| "106.449" | 2.84 | 2.09 | 1.46 | 1.07 | 0.91 | 1.53 |
| "106.450" | 0.70 | 0.55 | 0.38 | 0.33 | 0.58 | 0.88 |
| "106.453" | 0.88 | 0.70 | 0.50 | 0.40 | 0.73 | 1.60 |
| "106.457" | 2.63 | 2.03 | 1.45 | 1.02 | 1.05 | 1.41 |
| "106.459" | 0.25 | 0.17 | 0.14 | 0.14 | 0.30 | 0.78 |
| "106.460" | 1.09 | 1.12 | 0.98 | 0.89 | 1.14 | 0.80 |
| "106.461" | 0.22 | 0.26 | 0.23 | 0.24 | 0.51 | 0.82 |

TABLE 7-continued

Comprehensive neuronal culture screening results for R-GECO1.0 variants

| | | | | | | |
|---|---|---|---|---|---|---|
| "106.462" | 0.35 | 0.19 | 0.22 | 0.29 | 0.71 | 0.74 |
| "106.463" | 0.22 | 0.24 | 0.25 | 0.33 | 0.59 | 1.01 |
| "106.475" | 0.14 | 0.33 | 0.51 | 0.44 | 0.23 | 0.80 |
| "106.479" | 0.34 | 0.48 | 0.60 | 0.46 | 0.30 | 0.90 |
| "106.483" | 1.80 | 1.71 | 1.60 | 1.03 | 1.07 | 1.08 |
| "106.487" | 0.98 | 0.99 | 0.99 | 1.04 | 0.53 | 1.48 |
| "106.494" | 1.44 | 1.42 | 1.40 | 1.25 | 0.67 | 1.18 |
| "106.496" | 0.59 | 0.62 | 0.74 | 0.68 | 0.65 | 0.94 |
| "106.501" | 0.69 | 0.66 | 0.64 | 0.61 | 0.54 | 0.82 |
| "106.511" | 0.07 | 0.10 | 0.25 | 0.43 | 0.36 | 0.78 |
| "106.520" | 0.68 | 0.66 | 0.56 | 0.71 | 0.89 | 1.28 |
| "106.521" | 0.33 | 0.19 | 0.13 | 0.25 | 0.24 | 0.96 |
| "106.524" | 0.32 | 0.24 | 0.29 | 0.32 | 0.35 | 1.48 |
| "106.525" | 0.27 | 0.29 | 0.25 | 0.34 | 0.38 | 1.50 |
| "106.526" | 0.07 | 0.10 | 0.12 | 0.25 | 0.41 | 0.99 |
| "106.527" | 0.21 | 0.14 | 0.19 | 0.26 | 0.63 | 0.93 |
| "106.528" | 0.22 | 0.18 | 0.21 | 0.27 | 0.53 | 0.79 |
| "106.531" | 0.33 | 0.21 | 0.21 | 0.22 | 0.28 | 1.06 |
| "106.532" | 0.26 | 0.24 | 0.29 | 0.32 | 0.43 | 0.83 |
| "106.533" | 0.49 | 0.42 | 0.28 | 0.21 | 0.43 | 0.79 |
| "106.537" | 0.17 | 0.17 | 0.18 | 0.17 | 0.40 | 1.12 |
| "106.545" | 0.66 | 0.64 | 0.55 | 0.60 | 0.81 | 0.65 |
| "106.555" | 0.28 | 0.29 | 0.24 | 0.37 | 0.43 | 0.70 |
| "106.560" | 0.50 | 0.38 | 0.27 | 0.35 | 0.51 | 0.67 |
| "106.561" | 0.29 | 0.29 | 0.19 | 0.45 | 0.57 | 0.86 |
| "106.562" | 0.73 | 0.43 | 0.40 | 0.55 | 0.92 | 0.83 |
| "106.563" | 3.86 | 2.64 | 1.47 | 0.73 | 2.09 | 0.98 |
| "106.569" | 0.43 | 0.46 | 0.53 | 0.83 | 1.13 | 0.93 |
| "106.570" | 0.82 | 1.01 | 0.96 | 0.94 | 0.92 | 1.16 |
| "106.600" | 0.64 | 0.66 | 0.70 | 0.79 | 1.04 | 0.97 |
| "106.601" | 0.93 | 0.59 | 0.54 | 0.62 | 1.01 | 0.16 |
| "106.602" | 0.39 | 0.30 | 0.37 | 0.59 | 0.59 | 0.75 |
| "106.603" | 0.41 | 0.38 | 0.37 | 0.47 | 0.55 | 0.23 |
| "106.604" | 0.57 | 0.71 | 0.84 | 0.98 | 0.92 | 1.13 |
| "106.605" | 1.66 | 1.42 | 1.14 | 1.08 | 1.52 | 1.21 |
| "106.606" | 1.02 | 0.91 | 0.87 | 0.74 | 1.23 | 1.06 |
| "106.607" | 1.18 | 1.04 | 0.92 | 0.89 | 1.17 | 0.59 |
| "106.608" | 0.23 | 0.26 | 0.33 | 0.65 | 0.72 | 0.47 |
| "106.609" | 0.36 | 0.43 | 0.50 | 0.66 | 0.82 | 0.95 |
| "106.610" | 0.54 | 0.52 | 0.45 | 0.56 | 1.08 | 0.90 |
| "106.611" | 0.61 | 0.63 | 0.65 | 0.80 | 0.94 | 1.16 |
| "106.612" | 0.75 | 0.76 | 0.77 | 0.79 | 0.87 | 0.95 |
| "106.613" | 0.72 | 0.68 | 0.63 | 0.72 | 0.87 | 0.56 |
| "106.614" | 0.96 | 0.90 | 0.88 | 1.14 | 0.80 | 0.49 |
| "106.615" | 0.61 | 0.61 | 0.61 | 0.84 | 0.80 | 0.89 |
| "106.616" | 1.83 | 1.49 | 1.48 | 1.37 | 1.25 | 1.10 |
| "106.617" | 1.86 | 2.11 | 1.76 | 1.31 | 1.39 | 0.83 |
| "106.618" | 1.01 | 0.95 | 0.94 | 0.96 | 1.21 | 1.09 |
| "106.619" | 0.87 | 0.89 | 0.80 | 0.90 | 1.16 | 0.92 |
| "106.620" | 0.69 | 0.69 | 0.69 | 0.99 | 1.16 | 0.60 |
| "106.622" | 1.05 | 0.91 | 0.83 | 0.92 | 1.11 | 0.95 |
| "106.623" | 0.79 | 0.87 | 0.86 | 0.94 | 1.06 | 0.89 |
| "106.624" | 0.63 | 0.60 | 0.59 | 0.88 | 1.16 | 0.95 |
| "106.625" | 0.79 | 0.90 | 0.89 | 0.90 | 1.04 | 0.89 |
| "106.626" | 1.03 | 1.03 | 1.08 | 0.99 | 0.96 | 0.83 |
| "106.627" | 0.55 | 0.65 | 0.76 | 0.64 | 0.60 | 0.62 |
| "106.628" | 0.53 | 0.40 | 0.37 | 0.68 | 0.40 | 0.38 |
| "106.629" | 1.86 | 1.90 | 1.72 | 1.40 | 0.76 | 0.65 |
| "106.630" | 1.33 | 1.06 | 0.93 | 0.72 | 0.92 | 0.45 |
| "106.631" | 0.70 | 0.64 | 0.61 | 0.78 | 1.04 | 0.63 |
| "106.632" | 0.55 | 0.57 | 0.60 | 0.57 | 0.63 | 0.59 |
| "106.633" | 0.21 | 0.19 | 0.24 | 0.34 | 0.49 | 0.69 |
| "106.634" | 0.59 | 0.66 | 0.78 | 1.07 | 0.77 | 0.57 |
| "106.635" | 0.32 | 0.38 | 0.38 | 0.42 | 0.67 | 0.68 |
| "106.636" | 0.15 | 0.15 | 0.20 | 0.32 | 0.39 | 0.58 |
| "106.637" | 0.41 | 0.37 | 0.37 | 0.51 | 0.54 | 0.55 |
| "106.638" | 0.39 | 0.32 | 0.36 | 0.48 | 0.51 | 0.58 |
| "106.639" | 0.97 | 0.82 | 0.66 | 0.96 | 1.02 | 0.46 |
| "106.640" | 0.87 | 0.73 | 0.72 | 0.96 | 0.59 | 0.51 |
| "106.641" | 1.92 | 1.71 | 1.43 | 1.15 | 0.96 | 0.75 |
| "106.642" | 1.01 | 0.73 | 0.75 | 0.66 | 0.63 | 0.34 |
| "106.643" | 1.18 | 0.94 | 0.70 | 0.37 | 1.05 | 0.82 |
| "106.644" | 0.47 | 0.48 | 0.48 | 0.55 | 0.70 | 0.77 |
| "106.645" | 0.64 | 0.62 | 0.66 | 0.61 | 0.57 | 0.78 |
| "106.646" | 0.22 | 0.29 | 0.33 | 0.37 | 0.43 | 0.68 |
| "106.648" | 0.48 | 0.35 | 0.42 | 0.55 | 0.72 | 0.37 |
| "106.649" | 0.75 | 0.71 | 0.65 | 0.73 | 0.84 | 0.51 |
| "106.650" | 1.83 | 1.33 | 0.96 | 0.81 | 1.57 | 0.71 |

TABLE 7-continued

Comprehensive neuronal culture screening results for R-GECO1.0 variants

| | | | | | | |
|---|---|---|---|---|---|---|
| "106.651" | 0.53 | 0.43 | 0.39 | 0.50 | 1.01 | 0.49 |
| "106.652" | 3.18 | 2.07 | 1.25 | 0.59 | 2.27 | 1.27 |
| "106.653" | 0.76 | 0.90 | 0.87 | 1.01 | 1.17 | 1.26 |
| "106.654" | 0.34 | 0.44 | 0.59 | 0.74 | 0.67 | 0.85 |
| "106.655" | 0.30 | 0.42 | 0.54 | 0.66 | 0.64 | 1.17 |
| "106.656" | 0.21 | 0.28 | 0.37 | 0.56 | 0.68 | 1.00 |
| "106.657" | 0.57 | 0.72 | 0.82 | 0.92 | 0.97 | 1.21 |
| "106.658" | 0.72 | 0.96 | 1.00 | 1.10 | 0.76 | 0.87 |
| "106.659" | 0.31 | 0.30 | 0.40 | 0.50 | 0.54 | 1.36 |
| "106.660" | 1.07 | 1.14 | 1.17 | 1.04 | 1.17 | 1.42 |
| "106.661" | 0.35 | 0.39 | 0.48 | 0.72 | 0.83 | 1.27 |
| "106.662" | 1.27 | 1.16 | 1.24 | 1.19 | 1.15 | 1.05 |
| "106.663" | 0.37 | 0.39 | 0.57 | 0.87 | 0.77 | 1.29 |
| "106.665" | 2.24 | 1.31 | 0.90 | 0.68 | 2.65 | 0.49 |
| "106.666" | 1.03 | 0.91 | 0.93 | 1.43 | 1.08 | 0.32 |
| "106.667" | 0.45 | 0.40 | 0.33 | 0.69 | 0.84 | 0.36 |
| "106.668" | 0.35 | 0.36 | 0.38 | 0.77 | 1.02 | 0.41 |
| "106.669" | 0.39 | 0.51 | 0.46 | 0.88 | 1.16 | 0.44 |
| "106.670" | 0.76 | 0.61 | 0.53 | 0.82 | 1.33 | 0.60 |
| "106.671" | 0.82 | 0.68 | 0.58 | 0.62 | 1.29 | 0.69 |
| "106.672" | 0.32 | 0.27 | 0.27 | 0.44 | 0.78 | 0.56 |
| "106.673" | 0.78 | 0.61 | 0.52 | 0.81 | 1.05 | 0.46 |
| "106.674" | 0.59 | 0.57 | 0.66 | 0.66 | 0.71 | 1.38 |
| "106.683" | 0.14 | 0.21 | 0.28 | 0.43 | 0.66 | 1.42 |
| "106.686" | 0.52 | 0.31 | 0.19 | 0.30 | 1.22 | 1.06 |
| "106.688" | 0.55 | 0.41 | 0.40 | 0.45 | 0.74 | 0.15 |
| "106.690" | 0.13 | 0.11 | 0.14 | 0.29 | 0.37 | 0.81 |
| "106.691" | 0.37 | 0.32 | 0.28 | 0.40 | 0.87 | 0.95 |
| "106.692" | 0.11 | 0.06 | 0.11 | 0.25 | 0.31 | 0.53 |
| "106.693" | 0.07 | 0.05 | 0.06 | 0.15 | 0.31 | 0.53 |
| "106.694" | 0.12 | 0.11 | 0.15 | 0.31 | 0.36 | 0.60 |
| "106.695" | 0.09 | 0.06 | 0.06 | 0.10 | 0.18 | 0.82 |
| "106.697" | 0.19 | 0.06 | 0.07 | 0.17 | 0.35 | 0.20 |
| "106.698" | 0.27 | 0.16 | 0.21 | 0.38 | 0.46 | 0.50 |
| "106.699" | 0.16 | 0.13 | 0.16 | 0.26 | 0.29 | 0.73 |
| "106.700" | 0.38 | 0.29 | 0.35 | 0.39 | 0.58 | 0.39 |
| "106.701" | 0.10 | 0.05 | 0.06 | 0.13 | 0.44 | 0.62 |
| "106.702" | 0.10 | 0.11 | 0.13 | 0.25 | 0.37 | 0.40 |
| "106.703" | 0.12 | 0.08 | 0.08 | 0.12 | 0.26 | 0.42 |
| "106.704" | 0.14 | 0.10 | 0.14 | 0.26 | 0.36 | 0.46 |
| "106.705" | 0.09 | 0.06 | 0.10 | 0.22 | 0.35 | 0.59 |
| "106.706" | 0.29 | 0.18 | 0.14 | 0.25 | 0.36 | 0.33 |
| "106.707" | 0.26 | 0.30 | 0.39 | 0.40 | 0.40 | 0.87 |
| "106.708" | 0.12 | 0.22 | 0.30 | 0.38 | 0.40 | 0.90 |
| "106.709" | 0.38 | 0.36 | 0.43 | 0.68 | 0.36 | 0.59 |
| "106.710" | 0.88 | 0.71 | 0.69 | 0.76 | 0.99 | 0.63 |
| "106.711" | 0.38 | 0.30 | 0.35 | 0.58 | 0.64 | 0.52 |
| "106.712" | 0.22 | 0.30 | 0.40 | 0.41 | 0.41 | 0.76 |
| "106.714" | 0.15 | 0.19 | 0.24 | 0.40 | 0.45 | 0.50 |
| "106.715" | 0.17 | 0.21 | 0.27 | 0.43 | 0.53 | 0.66 |
| "106.716" | 0.44 | 0.43 | 0.45 | 0.66 | 0.98 | 0.63 |
| "106.717" | 0.56 | 0.67 | 0.77 | 0.69 | 0.50 | 1.12 |
| "106.718" | 0.48 | 0.41 | 0.49 | 0.97 | 0.74 | 0.75 |
| "106.719" | 0.29 | 0.20 | 0.20 | 0.28 | 0.51 | 1.16 |
| "106.720" | 0.27 | 0.41 | 0.53 | 0.64 | 0.58 | 0.68 |
| "106.721" | 0.22 | 0.31 | 0.36 | 0.39 | 0.41 | 0.69 |
| "106.722" | 0.17 | 0.22 | 0.28 | 0.43 | 0.49 | 0.63 |
| "106.723" | 0.20 | 0.33 | 0.37 | 0.50 | 0.66 | 0.74 |
| "106.724" | 1.68 | 1.69 | 1.46 | 1.03 | 1.11 | 0.93 |
| "106.725" | 0.21 | 0.09 | 0.15 | 0.21 | 0.25 | 1.12 |
| "106.726" | 0.50 | 0.60 | 0.63 | 0.59 | 0.59 | 0.59 |
| "106.727" | 0.25 | 0.21 | 0.28 | 0.31 | 0.33 | 1.25 |
| "106.728" | 0.78 | 0.93 | 1.15 | 0.95 | 0.79 | 1.28 |
| "106.729" | 0.17 | 0.16 | 0.32 | 0.48 | 0.29 | 1.10 |
| "106.730" | 0.34 | 0.30 | 0.43 | 0.65 | 0.82 | 1.19 |
| "106.731" | 0.25 | 0.12 | 0.04 | 0.13 | 0.18 | 0.95 |
| "106.732" | 0.69 | 0.76 | 0.75 | 0.74 | 0.67 | 0.82 |
| "106.733" | 2.08 | 1.87 | 1.36 | 1.02 | 1.24 | 1.10 |
| "106.734" | 0.20 | 0.16 | 0.19 | 0.20 | 0.24 | 0.40 |
| "106.735" | 1.07 | 1.06 | 0.98 | 0.71 | 0.43 | 0.36 |
| "106.736" | 0.60 | 0.67 | 0.74 | 0.76 | 0.65 | 1.24 |
| "106.738" | 0.20 | 0.13 | 0.19 | 0.24 | 0.23 | 1.16 |
| "106.739" | 0.29 | 0.10 | 0.03 | 0.02 | 0.43 | 0.89 |
| "106.740" | 0.25 | 0.28 | 0.38 | 0.35 | 0.40 | 0.57 |
| "106.741" | 0.24 | 0.28 | 0.32 | 0.53 | 0.51 | 1.01 |
| "106.742" | 0.76 | 0.84 | 0.96 | 0.98 | 0.89 | 1.26 |
| "106.744" | 0.28 | 0.13 | 0.08 | 0.16 | 0.32 | 0.77 |
| "106.745" | 0.27 | 0.27 | 0.29 | 0.35 | 0.39 | 0.81 |

TABLE 7-continued

Comprehensive neuronal culture screening results for R-GECO1.0 variants

| | | | | | | |
|---|---|---|---|---|---|---|
| "106.747" | 0.32 | 0.31 | 0.35 | 0.36 | 0.35 | 0.50 |
| "106.748" | 0.28 | 0.09 | 0.05 | 0.08 | 0.19 | 1.22 |
| "106.749" | 0.37 | 0.22 | 0.11 | 0.07 | 0.55 | 0.33 |
| "106.750" | 0.42 | 0.57 | 0.57 | 0.70 | 0.62 | 1.62 |
| "106.751" | 0.24 | 0.08 | 0.05 | 0.05 | 0.53 | 1.10 |
| "106.752" | 0.82 | 0.99 | 0.97 | 0.64 | 1.49 | 1.98 |
| "106.753" | 0.17 | 0.31 | 0.42 | 0.39 | 0.23 | 1.05 |
| "106.754" | 0.13 | 0.04 | 0.02 | 0.05 | 0.11 | 1.38 |
| "106.755" | 0.28 | 0.13 | 0.08 | 0.06 | 0.78 | 0.47 |
| "106.756" | 0.36 | 0.21 | 0.31 | 0.41 | 0.28 | 0.45 |
| "106.757" | 0.57 | 0.21 | 0.07 | 0.01 | 0.25 | 0.59 |
| "106.758" | 0.95 | 0.92 | 0.85 | 0.59 | 0.27 | 0.62 |
| "106.759" | 0.45 | 0.28 | 0.31 | 0.24 | 0.30 | 0.38 |
| "106.760" | 0.37 | 0.18 | 0.09 | 0.13 | 0.80 | 0.36 |
| "106.761" | 0.36 | 0.22 | 0.06 | 0.07 | 0.34 | 0.28 |
| "106.762" | 0.43 | 0.20 | 0.08 | 0.15 | 0.71 | 0.27 |
| "106.763" | 0.87 | 0.72 | 0.67 | 0.62 | 0.45 | 0.35 |
| "106.764" | 0.43 | 0.16 | 0.12 | 0.23 | 0.25 | 0.21 |
| "106.765" | 1.26 | 1.29 | 0.99 | 0.76 | 0.30 | 0.41 |
| "106.767" | 0.29 | 0.12 | 0.04 | 0.03 | 0.15 | 0.33 |
| "106.768" | 0.34 | 0.16 | 0.07 | 0.10 | 0.38 | 0.17 |
| "106.769" | 0.46 | 0.17 | 0.06 | 0.07 | 0.22 | 0.25 |
| "106.770" | 0.30 | 0.13 | 0.09 | 0.19 | 0.37 | 0.26 |
| "106.771" | 1.18 | 1.18 | 1.01 | 1.16 | 0.58 | 0.46 |
| "106.772" | 0.42 | 0.30 | 0.34 | 0.33 | 0.35 | 0.43 |
| "106.773" | 0.86 | 0.85 | 0.86 | 0.63 | 0.47 | 0.53 |
| "106.774" | 1.40 | 1.45 | 1.26 | 0.86 | 0.50 | 0.63 |
| "106.775" | 2.19 | 1.72 | 1.36 | 0.69 | 0.59 | 0.41 |
| "106.776" | 0.78 | 0.77 | 0.74 | 1.14 | 1.09 | 0.85 |
| "106.777" | 0.35 | 0.18 | 0.20 | 0.22 | 0.33 | 0.29 |
| "106.778" | 1.03 | 0.76 | 0.69 | 0.42 | 0.30 | 0.32 |
| "106.779" | 1.08 | 1.23 | 0.89 | 0.62 | 0.37 | 0.31 |
| "106.780" | 0.46 | 0.39 | 0.32 | 0.27 | 0.31 | 0.30 |
| "106.781" | 2.18 | 2.02 | 1.65 | 1.08 | 0.61 | 0.45 |
| "106.782" | 0.48 | 0.64 | 0.75 | 0.63 | 0.31 | 0.28 |
| "106.783" | 5.05 | 4.11 | 3.03 | 1.12 | 1.18 | 0.90 |
| "106.784" | 0.36 | 0.11 | 0.05 | 0.07 | 0.37 | 0.63 |
| "106.785" | 0.88 | 0.91 | 0.87 | 0.46 | 0.39 | 0.88 |
| "106.786" | 1.63 | 2.37 | 1.86 | 0.72 | 0.48 | 1.25 |
| "106.787" | 1.07 | 1.22 | 1.27 | 0.74 | 0.51 | 0.71 |
| "106.792" | 0.47 | 0.57 | 0.58 | 0.51 | 0.33 | 0.27 |
| "106.793" | 0.44 | 0.50 | 0.54 | 0.74 | 0.82 | 0.56 |
| "106.794" | 0.68 | 0.83 | 0.72 | 0.82 | 0.88 | 0.48 |
| "106.795" | 0.83 | 0.70 | 0.70 | 0.83 | 0.68 | 0.68 |
| "106.796" | 1.34 | 1.30 | 1.06 | 1.31 | 1.18 | 0.57 |
| "106.798" | 0.44 | 0.59 | 0.74 | 0.95 | 0.94 | 0.59 |
| "106.799" | 0.29 | 0.55 | 0.47 | 0.76 | 1.25 | 0.59 |
| "106.800" | 0.62 | 0.76 | 0.80 | 0.99 | 0.92 | 0.58 |
| "106.801" | 1.12 | 1.16 | 1.09 | 1.18 | 1.02 | 0.74 |
| "106.802" | 0.34 | 0.39 | 0.40 | 0.69 | 0.88 | 0.52 |
| "106.803" | 1.59 | 1.50 | 1.27 | 1.42 | 1.01 | 0.61 |
| "106.804" | 0.51 | 0.57 | 0.72 | 0.93 | 1.18 | 0.68 |
| "106.805" | 1.25 | 1.09 | 0.92 | 1.30 | 1.12 | 0.87 |
| "106.806" | 0.36 | 0.47 | 0.56 | 0.74 | 0.94 | 0.55 |
| "106.807" | 0.26 | 0.42 | 0.56 | 0.92 | 0.70 | 0.46 |
| "106.808" | 1.87 | 1.79 | 1.55 | 1.28 | 1.19 | 0.69 |
| "106.810" | 0.55 | 0.78 | 0.86 | 0.61 | 0.50 | 0.91 |
| "106.811" | 0.69 | 0.83 | 0.81 | 0.39 | 0.42 | 0.57 |
| "106.812" | 0.36 | 0.57 | 0.66 | 0.47 | 0.33 | 0.62 |
| "106.813" | −0.03 | 0.07 | 0.19 | 0.35 | 0.33 | 0.86 |
| "106.814" | 0.19 | 0.41 | 0.43 | 0.41 | 0.36 | 0.59 |
| "106.815" | 0.37 | 0.52 | 0.50 | 0.49 | 0.59 | 0.56 |
| "106.816" | 0.16 | 0.26 | 0.15 | 0.11 | 0.48 | 0.40 |
| "106.817" | 0.81 | 0.98 | 0.81 | 0.62 | 0.42 | 0.58 |
| "106.818" | 1.33 | 1.23 | 1.10 | 0.59 | 0.54 | 0.42 |
| "106.819" | 0.53 | 0.72 | 0.62 | 0.45 | 0.29 | 0.75 |
| "106.822" | 0.39 | 0.34 | 0.39 | 0.41 | 0.53 | 0.79 |
| "106.823" | 0.58 | 0.70 | 0.49 | 0.49 | 0.29 | 0.63 |
| "106.824" | 0.93 | 1.05 | 1.00 | 0.43 | 0.45 | 0.65 |
| "106.825" | 0.48 | 0.54 | 0.53 | 0.51 | 0.28 | 0.60 |
| "106.826" | 1.09 | 1.15 | 0.87 | 0.58 | 0.65 | 0.70 |
| "108.830" | 0.58 | 0.59 | 0.63 | 0.82 | 1.01 | 0.86 |
| "108.831" | 1.10 | 0.92 | 0.84 | 0.77 | 1.15 | 0.88 |
| "108.832" | 2.70 | 1.45 | 0.81 | 0.36 | 2.14 | 0.30 |
| "108.833" | 1.49 | 1.22 | 0.87 | 0.69 | 2.03 | 1.05 |
| "108.837" | 0.94 | 0.80 | 0.71 | 0.89 | 0.96 | 0.64 |
| "108.838" | 2.82 | 2.95 | 2.46 | 1.12 | 1.17 | 1.16 |
| "108.839" | 1.30 | 1.60 | 1.47 | 1.12 | 1.44 | 1.19 |

TABLE 7-continued

Comprehensive neuronal culture screening results for R-GECO1.0 variants

| | | | | | | |
|---|---|---|---|---|---|---|
| "108.840" | 2.45 | 1.46 | 0.87 | 0.36 | 2.66 | 2.92 |
| "108.841" | 1.12 | 0.97 | 0.92 | 0.78 | 0.97 | 0.94 |
| "108.842" | 3.12 | 2.21 | 1.33 | 0.61 | 2.11 | 1.51 |
| "108.843" | 2.10 | 1.64 | 1.21 | 0.81 | 1.77 | 1.01 |
| "108.844" | 2.11 | 1.56 | 1.13 | 0.95 | 1.74 | 1.04 |
| "108.845" | 1.23 | 1.01 | 0.92 | 0.76 | 1.12 | 0.84 |
| "108.847" | 1.22 | 1.07 | 0.84 | 0.64 | 0.92 | 0.85 |
| "108.849" | 3.31 | 2.13 | 1.23 | 0.56 | 2.74 | 1.55 |
| "108.850" | 2.50 | 1.85 | 1.20 | 0.61 | 2.48 | 1.73 |
| "108.852" | 1.97 | 1.49 | 1.05 | 0.84 | 1.82 | 1.11 |
| "108.853" | 3.10 | 2.09 | 1.38 | 0.67 | 2.62 | 1.57 |
| "108.854" | 2.24 | 1.56 | 1.05 | 0.69 | 2.78 | 0.89 |
| "108.858" | 3.92 | 2.58 | 1.31 | 0.62 | 2.65 | 1.49 |
| "108.859" | 3.56 | 2.55 | 1.54 | 0.86 | 1.94 | 1.24 |
| "108.878" | 0.68 | 0.74 | 0.81 | 0.85 | 0.64 | 0.84 |
| "108.890" | 0.56 | 0.66 | 0.52 | 0.59 | 0.92 | 1.01 |
| "108.893" | 1.05 | 0.80 | 1.02 | 1.29 | 0.61 | 0.58 |
| "108.901" | 1.27 | 1.48 | 1.43 | 0.94 | 0.85 | 0.79 |
| "108.914" | 0.59 | 0.67 | 0.70 | 0.63 | 0.99 | 1.39 |
| "108.915" | 0.91 | 0.90 | 0.80 | 0.64 | 1.13 | 1.84 |
| "108.916" | 1.01 | 1.01 | 0.94 | 0.55 | 1.08 | 1.59 |
| "108.917" | 1.21 | 0.87 | 0.78 | 0.44 | 1.10 | 1.60 |
| "108.921" | 0.97 | 0.90 | 0.69 | 0.34 | 1.36 | 2.22 |
| "108.922" | 0.83 | 0.83 | 0.56 | 0.43 | 1.10 | 1.77 |
| "108.923" | 0.79 | 0.75 | 0.59 | 0.43 | 0.97 | 1.35 |
| "108.924" | 0.74 | 0.83 | 0.67 | 0.45 | 1.23 | 1.40 |
| "108.925" | 1.15 | 1.05 | 0.88 | 0.57 | 1.27 | 1.50 |
| "108.926" | 0.89 | 0.92 | 0.78 | 0.51 | 1.09 | 1.53 |
| "108.927" | 0.64 | 0.59 | 0.52 | 0.39 | 1.04 | 1.79 |
| "108.928" | 0.80 | 0.74 | 0.67 | 0.44 | 1.17 | 1.53 |
| "108.929" | 1.28 | 1.13 | 0.88 | 0.76 | 1.09 | 1.35 |
| "108.930" | 1.04 | 1.04 | 0.89 | 0.51 | 1.28 | 1.61 |
| "106.933" | 0.32 | 0.26 | 0.25 | 0.34 | 0.58 | 0.81 |
| "106.934" | 1.56 | 1.06 | 0.56 | 0.37 | 1.92 | 1.60 |
| "106.938" | 1.29 | 1.12 | 0.70 | 0.70 | 1.69 | 0.93 |
| "106.941" | 0.83 | 0.71 | 0.55 | 0.47 | 1.77 | 1.23 |
| "106.942" | 1.81 | 1.20 | 0.89 | 0.66 | 2.07 | 1.09 |
| "106.943" | 0.66 | 0.75 | 0.54 | 0.67 | 1.05 | 0.76 |
| "106.944" | 0.45 | 0.52 | 0.40 | 0.39 | 0.78 | 0.99 |
| "106.945" | 0.16 | 0.26 | 0.29 | 0.42 | 0.62 | 0.51 |
| "106.946" | 0.23 | 0.28 | 0.34 | 0.58 | 0.73 | 0.91 |
| "106.947" | 0.49 | 0.54 | 0.54 | 0.82 | 0.83 | 0.50 |
| "106.948" | 0.37 | 0.42 | 0.46 | 0.59 | 0.90 | 1.05 |
| "106.949" | 0.56 | 0.36 | 0.39 | 0.41 | 0.59 | 0.43 |
| "106.950" | 0.28 | 0.49 | 0.57 | 0.59 | 0.71 | 0.75 |
| "106.951" | 0.40 | 0.46 | 0.46 | 0.48 | 0.71 | 0.93 |
| "106.957" | 0.62 | 0.62 | 0.69 | 0.64 | 0.72 | 0.43 |
| "106.1000" | 3.01 | 2.42 | 1.07 | 0.37 | 1.90 | 2.03 |
| "106.1001" | 3.84 | 2.39 | 0.96 | 0.46 | 1.82 | 1.84 |
| "106.1003" | 4.65 | 2.98 | 1.62 | 0.54 | 1.88 | 1.33 |
| "106.1004" | 3.11 | 2.17 | 1.35 | 0.53 | 1.59 | 1.39 |
| "106.1005" | 3.15 | 2.05 | 1.36 | 0.79 | 0.93 | 1.01 |
| "106.1006" | 5.03 | 2.86 | 1.53 | 0.60 | 1.90 | 1.23 |
| "106.1007" | 3.81 | 3.85 | 2.37 | 0.93 | 1.26 | 1.27 |
| "106.1008" | 2.10 | 1.42 | 1.01 | 0.57 | 0.82 | 0.95 |
| "106.1009" | 4.67 | 2.76 | 1.35 | 0.57 | 1.57 | 1.29 |
| "106.1010" | 3.64 | 1.97 | 1.22 | 0.54 | 1.56 | 1.12 |
| "106.1011" | 6.59 | 3.71 | 1.79 | 0.61 | 1.54 | 1.32 |
| "106.1012" | 3.57 | 2.78 | 1.72 | 0.80 | 0.74 | 1.03 |
| "106.1013" | 3.47 | 2.74 | 1.83 | 0.85 | 0.69 | 0.89 |
| "106.1014" | 2.67 | 2.41 | 1.75 | 0.66 | 1.14 | 1.05 |
| "106.1015" | 0.61 | 0.73 | 0.53 | 0.37 | 0.25 | 0.63 |
| "106.1018" | 1.61 | 1.40 | 0.95 | 0.58 | 0.33 | 0.85 |
| "106.1020" | 1.75 | 2.15 | 1.40 | 0.87 | 0.68 | 0.85 |
| "106.1021" | 2.15 | 1.42 | 1.15 | 0.82 | 0.76 | 1.04 |
| "106.1022" | 1.26 | 1.20 | 0.90 | 0.91 | 0.80 | 0.81 |
| "106.1023" | 1.94 | 1.85 | 1.19 | 0.78 | 1.32 | 0.92 |
| "106.1024" | 0.98 | 0.87 | 0.78 | 0.53 | 0.43 | 0.78 |
| "106.1025" | 1.03 | 1.13 | 0.99 | 0.67 | 0.37 | 0.70 |
| "106.1027" | 2.40 | 2.04 | 1.42 | 0.66 | 0.54 | 0.87 |
| "106.1028" | 1.14 | 1.27 | 1.04 | 0.57 | 0.35 | 0.92 |
| "106.1029" | 0.29 | 0.22 | 0.24 | 0.19 | 0.21 | 0.84 |
| "106.1030" | 1.36 | 1.19 | 1.20 | 0.82 | 0.66 | 0.75 |
| "106.1031" | 0.97 | 0.81 | 0.76 | 0.48 | 0.30 | 0.77 |
| "106.1032" | 4.53 | 2.74 | 1.23 | 0.47 | 2.28 | 1.68 |
| "106.1033" | 5.57 | 3.80 | 2.05 | 0.73 | 1.60 | 1.38 |
| "106.1034" | 3.21 | 2.93 | 1.92 | 0.87 | 1.14 | 0.96 |
| "106.1035" | 5.43 | 3.32 | 1.95 | 0.69 | 1.62 | 1.26 |

TABLE 7-continued

Comprehensive neuronal culture screening results for R-GECO1.0 variants

| | | | | | | |
|---|---|---|---|---|---|---|
| "106.1036" | 5.73 | 3.50 | 1.71 | 0.56 | 1.31 | 1.63 |
| "106.1037" | 4.45 | 3.20 | 1.61 | 0.71 | 0.87 | 1.17 |
| "106.1038" | 4.11 | 3.70 | 2.29 | 0.78 | 1.43 | 1.48 |
| "106.1039" | 7.39 | 4.71 | 2.34 | 0.84 | 1.23 | 1.59 |
| "106.1040" | 3.91 | 3.15 | 1.99 | 0.88 | 0.73 | 1.34 |
| "106.1041" | 3.71 | 2.55 | 1.67 | 0.72 | 1.09 | 1.27 |
| "106.1042" | 4.27 | 3.05 | 1.66 | 0.72 | 1.46 | 1.31 |
| "106.1043" | 0.52 | 0.43 | 0.42 | 0.26 | 0.23 | 0.77 |
| "106.1044" | 0.41 | 0.40 | 0.43 | 0.30 | 0.30 | 0.98 |
| "106.1046" | 1.28 | 1.15 | 1.16 | 0.80 | 0.94 | 1.13 |
| "106.1048" | 1.38 | 1.66 | 1.62 | 0.97 | 0.78 | 1.17 |
| "106.1053" | 5.55 | 3.54 | 1.79 | 0.69 | 1.89 | 1.40 |
| "106.1054" | 0.61 | 0.62 | 0.66 | 0.51 | 0.37 | 0.80 |
| "108.1057" | 0.70 | 0.81 | 0.71 | 1.02 | 1.09 | 1.04 |
| "108.1058" | 0.97 | 0.78 | 0.75 | 0.89 | 0.87 | 0.70 |
| "108.1066" | 0.71 | 0.73 | 0.78 | 0.88 | 0.66 | 1.13 |
| "108.1069" | 0.83 | 0.71 | 0.73 | 0.74 | 0.89 | 1.13 |
| "108.1071" | 0.75 | 0.56 | 0.63 | 0.88 | 0.69 | 1.13 |
| "108.1072" | 0.98 | 0.98 | 0.89 | 0.78 | 0.83 | 1.03 |
| "108.1073" | 0.67 | 0.71 | 0.67 | 0.85 | 0.74 | 0.84 |
| "108.1074" | 1.33 | 1.51 | 1.19 | 0.95 | 0.81 | 1.01 |
| "108.1078" | 2.15 | 1.82 | 1.68 | 1.10 | 0.90 | 1.30 |
| "108.1079" | 1.16 | 1.08 | 0.88 | 0.85 | 0.84 | 1.02 |
| "108.1080" | 1.11 | 0.90 | 0.89 | 0.94 | 0.67 | 1.18 |
| "108.1082" | 0.73 | 0.62 | 0.70 | 0.96 | 0.84 | 1.10 |
| "108.1083" | 1.27 | 1.43 | 1.03 | 0.90 | 0.69 | 0.97 |
| "108.1084" | 0.80 | 0.78 | 0.77 | 0.85 | 0.69 | 1.21 |
| "108.1086" | 1.46 | 1.96 | 1.34 | 0.93 | 0.78 | 0.99 |
| "108.1103" | 0.71 | 0.73 | 0.64 | 0.76 | 0.81 | 1.05 |
| "106.1104" | 0.32 | 0.36 | 0.44 | 0.58 | 0.51 | 0.96 |
| "106.1105" | 0.09 | 0.12 | 0.16 | 0.41 | 0.30 | 1.05 |
| "106.1106" | 0.09 | 0.12 | 0.21 | 0.40 | 0.44 | 1.09 |
| "106.1107" | 0.15 | 0.12 | 0.27 | 0.42 | 0.38 | 0.79 |
| "106.1108" | 0.06 | 0.08 | 0.15 | 0.18 | 0.24 | 1.44 |
| "106.1109" | 0.88 | 1.03 | 0.90 | 0.84 | 0.69 | 1.51 |
| "106.1110" | 0.66 | 0.50 | 0.56 | 0.57 | 0.40 | 1.27 |
| "106.1113" | 0.41 | 0.26 | 0.41 | 0.44 | 0.34 | 1.24 |
| "106.1114" | 3.29 | 2.26 | 1.31 | 0.72 | 2.52 | 1.78 |
| "106.1115" | −0.01 | 0.09 | 0.16 | 0.22 | 0.24 | 1.54 |
| "106.1116" | 0.81 | 0.76 | 0.71 | 0.78 | 0.69 | 1.08 |
| "106.1117" | 0.92 | 0.99 | 0.83 | 0.73 | 1.03 | 1.25 |
| "106.1118" | 0.63 | 0.58 | 0.56 | 0.61 | 0.93 | 0.72 |
| "106.1119" | 0.25 | 0.40 | 0.49 | 0.59 | 0.77 | 1.13 |
| "106.1120" | 2.78 | 2.04 | 1.40 | 0.78 | 2.44 | 1.54 |
| "106.1121" | 0.38 | 0.55 | 0.54 | 0.52 | 0.84 | 1.17 |
| "106.1122" | 3.21 | 2.51 | 1.54 | 0.88 | 0.91 | 1.31 |
| "106.1123" | 4.30 | 3.85 | 2.23 | 1.37 | 0.84 | 0.97 |
| "106.1124" | 2.81 | 2.31 | 1.62 | 0.90 | 0.77 | 1.63 |
| "106.1125" | 0.10 | 0.17 | 0.29 | 0.33 | 0.29 | 1.45 |
| "106.1126" | 2.08 | 1.67 | 1.42 | 0.81 | 1.24 | 1.51 |
| "106.1128" | 0.82 | 1.17 | 1.12 | 1.00 | 0.79 | 1.72 |
| "106.1129" | 0.90 | 1.19 | 0.99 | 0.96 | 0.51 | 0.95 |
| "106.1130" | 0.66 | 0.77 | 0.50 | 0.74 | 0.72 | 1.48 |
| "106.1131" | 0.76 | 0.68 | 0.73 | 0.67 | 0.47 | 1.28 |
| "106.1135" | 0.22 | 0.25 | 0.29 | 0.40 | 0.64 | 0.82 |
| "106.1136" | 0.71 | 0.55 | 0.68 | 0.59 | 0.66 | 1.05 |
| "106.1139" | 0.21 | 0.08 | 0.15 | 0.15 | 0.23 | 1.06 |
| "106.1140" | 0.51 | 0.61 | 0.47 | 0.45 | 1.23 | 0.61 |
| "106.1144" | 0.15 | 0.19 | 0.34 | 0.51 | 0.47 | 1.27 |
| "106.1145" | 0.48 | 0.19 | 0.24 | 0.39 | 0.73 | 0.79 |
| "106.1163" | 1.03 | 0.78 | 0.65 | 0.63 | 0.88 | 1.02 |
| "106.1164" | 0.75 | 0.78 | 0.75 | 0.75 | 0.76 | 0.90 |
| "106.1165" | 0.90 | 0.51 | 0.42 | 0.58 | 0.79 | 1.03 |
| "106.1166" | 0.27 | 0.30 | 0.36 | 0.57 | 0.73 | 0.88 |
| "106.1167" | 0.95 | 0.95 | 0.70 | 0.75 | 0.78 | 0.93 |
| "106.1168" | 0.41 | 0.49 | 0.50 | 0.51 | 0.54 | 1.04 |
| "106.1169" | 0.62 | 0.60 | 0.52 | 0.70 | 1.00 | 1.10 |
| "106.1170" | 0.60 | 0.81 | 0.92 | 0.88 | 0.86 | 0.95 |
| "106.1175" | 0.80 | 0.80 | 0.79 | 0.61 | 0.98 | 0.98 |
| "106.1176" | 0.49 | 0.60 | 0.64 | 0.60 | 0.81 | 1.01 |
| "106.1177" | 0.28 | 0.18 | 0.15 | 0.26 | 0.41 | 1.23 |
| "106.1178" | 0.26 | 0.18 | 0.22 | 0.29 | 0.42 | 1.41 |
| "106.1179" | 0.14 | 0.17 | 0.24 | 0.43 | 0.45 | 1.21 |
| "106.1180" | 0.86 | 0.88 | 0.75 | 0.74 | 1.04 | 1.61 |
| "106.1181" | 0.21 | 0.31 | 0.33 | 0.41 | 0.51 | 1.08 |
| "106.1183" | 0.27 | 0.19 | 0.12 | 0.17 | 0.86 | 1.56 |
| "106.1185" | 0.22 | 0.08 | 0.07 | 0.15 | 0.46 | 1.27 |
| "106.1186" | 0.21 | 0.12 | 0.08 | 0.14 | 0.72 | 2.30 |

TABLE 7-continued

Comprehensive neuronal culture screening results for R-GECO1.0 variants

| | | | | | | |
|---|---|---|---|---|---|---|
| "106.1187" | 0.40 | 0.31 | 0.26 | 0.32 | 0.58 | 1.56 |
| "106.1189" | 0.35 | 0.20 | 0.10 | 0.08 | 1.34 | 1.32 |
| "106.1193" | 0.83 | 0.98 | 1.00 | 0.73 | 0.64 | 1.20 |
| "106.1195" | 1.00 | 0.66 | 0.46 | 0.56 | 0.97 | 1.17 |
| "106.1196" | 0.48 | 0.39 | 0.35 | 0.23 | 0.53 | 1.49 |
| "106.1197" | 0.33 | 0.36 | 0.36 | 0.38 | 0.60 | 1.21 |
| "106.1202" | 0.28 | 0.34 | 0.28 | 0.26 | 0.46 | 1.00 |
| "106.1203" | 0.14 | 0.16 | 0.16 | 0.18 | 0.39 | 1.40 |
| "106.1205" | 0.26 | 0.18 | 0.21 | 0.16 | 0.48 | 1.43 |
| "106.1209" | 0.10 | 0.12 | 0.15 | 0.16 | 0.34 | 1.42 |
| "106.1212" | 0.93 | 0.94 | 0.78 | 0.65 | 0.92 | 1.47 |
| "106.1215" | 1.07 | 0.73 | 0.74 | 1.00 | 0.95 | 1.08 |
| "106.1216" | 0.39 | 0.51 | 0.60 | 0.85 | 0.87 | 1.02 |
| "106.1217" | 1.16 | 1.10 | 0.97 | 0.88 | 0.72 | 0.38 |
| "106.1218" | 0.70 | 0.60 | 0.67 | 1.02 | 0.76 | 0.75 |
| "106.1219" | 0.61 | 0.59 | 0.56 | 0.77 | 0.75 | 0.92 |
| "106.1220" | 0.48 | 0.55 | 0.81 | 1.01 | 0.80 | 0.70 |
| "106.1221" | 0.76 | 0.88 | 1.09 | 1.17 | 0.90 | 1.18 |
| "106.1222" | 1.38 | 1.26 | 1.20 | 1.28 | 0.89 | 0.99 |
| "106.1223" | 0.94 | 1.21 | 1.11 | 0.99 | 1.04 | 1.40 |
| "106.1224" | 0.69 | 0.77 | 0.92 | 0.84 | 0.94 | 0.88 |
| "106.1225" | 0.56 | 0.69 | 0.85 | 0.93 | 0.92 | 1.35 |
| "106.1226" | 0.78 | 1.15 | 1.30 | 1.12 | 0.87 | 1.15 |
| "106.1228" | 0.81 | 1.02 | 1.15 | 1.07 | 0.87 | 1.00 |
| "106.1229" | 0.78 | 0.62 | 0.76 | 0.89 | 0.94 | 1.26 |
| "106.1230" | 0.54 | 0.74 | 0.81 | 0.90 | 0.97 | 1.53 |
| "106.1231" | 0.57 | 0.76 | 0.83 | 1.04 | 0.86 | 1.24 |
| "106.1232" | 0.36 | 0.34 | 0.50 | 0.66 | 0.79 | 1.26 |
| "106.1233" | 0.49 | 0.46 | 0.61 | 0.67 | 0.73 | 1.00 |
| "106.1235" | 2.95 | 2.74 | 2.05 | 1.71 | 1.11 | 1.02 |
| "106.1237" | 1.31 | 1.08 | 0.90 | 0.73 | 1.38 | 1.62 |
| "106.1238" | 1.67 | 1.43 | 1.22 | 1.10 | 1.16 | 1.21 |
| "106.1241" | 2.29 | 2.13 | 1.66 | 0.87 | 1.06 | 2.11 |
| "106.1244" | 1.58 | 1.57 | 1.32 | 1.03 | 0.78 | 1.32 |
| "106.1246" | 1.33 | 1.40 | 1.09 | 0.70 | 1.13 | 1.82 |
| "106.1247" | 2.24 | 1.90 | 1.24 | 0.75 | 1.42 | 1.79 |
| "106.1248" | 1.58 | 1.42 | 0.89 | 0.82 | 1.28 | 2.36 |
| "106.1249" | 2.37 | 1.97 | 1.30 | 0.83 | 1.01 | 1.70 |
| "106.1250" | 1.61 | 1.86 | 1.47 | 1.14 | 1.25 | 1.27 |
| "106.1251" | 2.06 | 1.76 | 1.30 | 0.92 | 1.92 | 0.89 |
| "106.1252" | 3.87 | 3.08 | 1.71 | 1.14 | 1.95 | 1.12 |
| "106.1253" | 3.62 | 1.90 | 1.23 | 0.70 | 2.38 | 0.61 |
| "106.1254" | 2.52 | 1.70 | 1.09 | 0.67 | 1.55 | 0.37 |
| "106.1255" | 3.01 | 1.87 | 1.06 | 0.47 | 2.56 | 1.56 |
| "106.1256" | 1.52 | 1.50 | 1.11 | 0.78 | 2.03 | 0.87 |
| "106.1257" | 1.79 | 1.53 | 0.88 | 0.50 | 2.15 | 1.77 |
| "106.1258" | 2.25 | 1.90 | 1.40 | 1.05 | 2.04 | 0.78 |
| "106.1259" | 1.51 | 1.51 | 1.22 | 0.77 | 1.32 | 1.36 |
| "106.1260" | 2.17 | 1.63 | 1.09 | 0.63 | 2.54 | 1.16 |
| "106.1261" | 0.93 | 0.74 | 0.72 | 0.95 | 1.04 | 0.62 |
| "106.1262" | 1.07 | 1.01 | 0.96 | 0.81 | 0.92 | 0.65 |
| "106.1264" | 0.98 | 0.98 | 1.00 | 0.90 | 0.87 | 1.81 |
| "106.1265" | 1.24 | 1.35 | 1.38 | 1.14 | 1.21 | 1.24 |
| "106.1267" | 1.41 | 1.53 | 1.09 | 0.96 | 1.07 | 0.65 |
| "106.1272" | 0.86 | 1.17 | 1.17 | 1.11 | 0.95 | 0.95 |
| "106.1274" | 2.21 | 2.26 | 1.98 | 1.43 | 1.15 | 0.92 |
| "106.1275" | 1.40 | 1.67 | 1.56 | 1.15 | 1.07 | 1.05 |
| "106.1277" | 1.19 | 1.44 | 1.38 | 1.24 | 0.98 | 0.92 |
| "106.1278" | 1.15 | 1.47 | 1.56 | 1.27 | 1.10 | 0.77 |
| "106.1282" | 0.80 | 0.88 | 1.24 | 1.17 | 0.92 | 0.77 |
| "106.1284" | 0.53 | 0.65 | 0.66 | 0.66 | 1.01 | 1.35 |
| "106.1285" | 1.72 | 1.70 | 1.25 | 0.97 | 1.21 | 0.93 |
| "106.1286" | 2.46 | 2.15 | 1.62 | 0.97 | 1.44 | 1.08 |
| "106.1287" | 0.56 | 0.77 | 0.86 | 0.67 | 1.06 | 1.68 |
| "106.1288" | 0.53 | 0.60 | 0.60 | 0.69 | 0.96 | 1.40 |
| "106.1289" | 0.51 | 0.58 | 0.58 | 0.73 | 1.12 | 0.97 |
| "106.1290" | 0.66 | 0.97 | 0.74 | 0.68 | 1.05 | 1.17 |
| "106.1292" | 1.24 | 1.38 | 1.07 | 0.84 | 1.17 | 0.95 |
| "106.1293" | 0.74 | 1.03 | 0.94 | 0.81 | 1.04 | 1.02 |
| "106.1294" | 1.23 | 1.88 | 1.70 | 1.26 | 1.24 | 0.76 |
| "106.1295" | 2.51 | 2.47 | 1.82 | 1.22 | 1.27 | 0.79 |
| "106.1296" | 2.82 | 2.05 | 1.51 | 1.32 | 1.12 | 0.97 |
| "106.1297" | 1.51 | 1.33 | 1.16 | 0.88 | 1.18 | 1.05 |
| "106.1298" | 0.97 | 0.92 | 0.93 | 0.81 | 1.09 | 1.11 |
| "106.1300" | 1.34 | 1.76 | 1.53 | 1.32 | 1.15 | 0.70 |
| "106.1301" | 1.16 | 1.60 | 1.31 | 0.88 | 1.29 | 1.19 |
| "106.1302" | 0.94 | 1.25 | 1.10 | 0.97 | 0.95 | 1.03 |
| "106.1303" | 1.11 | 1.09 | 0.83 | 0.70 | 0.95 | 0.20 |

TABLE 7-continued

Comprehensive neuronal culture screening results for R-GECO1.0 variants

| | | | | | | |
|---|---|---|---|---|---|---|
| "106.1304" | 1.40 | 1.66 | 1.26 | 1.06 | 1.02 | 0.95 |
| "106.1305" | 1.12 | 1.28 | 1.29 | 1.08 | 0.91 | 0.34 |
| "106.1307" | 1.12 | 1.12 | 0.91 | 1.01 | 0.86 | 0.40 |
| "106.1309" | 0.62 | 0.69 | 0.56 | 0.49 | 0.97 | 0.29 |
| "106.1310" | 1.21 | 0.96 | 0.86 | 0.64 | 0.96 | 0.14 |
| "106.1312" | 0.49 | 0.75 | 0.55 | 0.52 | 1.16 | 0.32 |
| "106.1315" | 0.75 | 0.82 | 0.82 | 0.75 | 1.30 | 1.30 |
| "106.1316" | 0.71 | 0.58 | 0.43 | 0.47 | 1.01 | 0.18 |
| "106.1318" | 0.68 | 0.67 | 0.61 | 0.59 | 1.08 | 0.32 |
| "106.1319" | 0.50 | 0.41 | 0.33 | 0.20 | 0.81 | 0.16 |
| "106.1320" | 0.88 | 1.02 | 1.12 | 0.96 | 1.11 | 0.76 |
| "106.1327" | 0.31 | 0.51 | 0.73 | 0.89 | 0.83 | 1.01 |
| "106.1333" | 0.43 | 0.33 | 0.40 | 0.67 | 0.67 | 0.77 |
| "106.1357" | 1.32 | 1.41 | 1.46 | 1.56 | 0.69 | 0.55 |
| "106.1358" | 2.49 | 2.82 | 2.15 | 1.94 | 0.93 | 0.75 |
| "106.1360" | 1.09 | 1.29 | 1.07 | 1.94 | 0.99 | 0.50 |
| "106.1368" | 2.79 | 2.65 | 1.88 | 1.22 | 1.88 | 1.18 |
| "106.1377" | 0.96 | 1.59 | 1.47 | 1.21 | 1.43 | 1.69 |
| "106.1386" | 0.54 | 0.46 | 0.70 | 1.11 | 0.77 | 0.61 |
| "106.1387" | 0.57 | 0.66 | 0.77 | 0.87 | 1.00 | 1.51 |
| "106.1388" | 0.43 | 0.55 | 0.74 | 0.90 | 0.92 | 1.38 |
| "106.1389" | 0.56 | 0.80 | 0.98 | 0.95 | 1.03 | 1.29 |
| "106.1390" | 0.36 | 0.42 | 0.63 | 1.00 | 0.83 | 1.27 |
| "106.1391" | 0.25 | 0.49 | 0.60 | 0.73 | 0.85 | 1.42 |
| "106.1392" | 0.94 | 1.58 | 1.53 | 1.09 | 1.15 | 1.29 |
| "106.1393" | 0.59 | 0.69 | 0.87 | 1.10 | 1.13 | 1.20 |
| "106.1396" | 1.05 | 1.47 | 1.40 | 1.73 | 1.40 | 1.16 |
| "106.1397" | 0.15 | 0.41 | 0.57 | 0.89 | 0.50 | 0.83 |
| "106.1399" | 1.09 | 1.31 | 1.16 | 1.11 | 1.32 | 1.42 |
| "106.1400" | 0.34 | 0.49 | 0.70 | 0.85 | 0.82 | 1.21 |
| "106.1401" | 0.44 | 0.62 | 0.84 | 0.93 | 0.90 | 1.36 |
| "106.1402" | 0.24 | 0.44 | 0.64 | 0.87 | 0.90 | 1.36 |
| "106.1403" | 0.33 | 0.55 | 0.76 | 0.91 | 0.93 | 1.15 |
| "106.1404" | 0.41 | 0.62 | 0.84 | 0.83 | 0.86 | 1.66 |
| "106.1405" | 0.17 | 0.07 | 0.17 | 0.29 | 0.37 | 0.63 |
| "106.1406" | 0.09 | 0.03 | 0.05 | 0.39 | 0.16 | 0.68 |
| "106.1407" | 0.14 | 0.10 | 0.18 | 0.23 | 0.39 | 1.33 |
| "106.1409" | 1.16 | 1.38 | 1.40 | 0.99 | 1.31 | 1.28 |
| "106.1423" | 0.14 | 0.13 | 0.22 | 0.42 | 0.39 | 0.76 |
| "106.1424" | 0.57 | 0.75 | 0.64 | 0.72 | 1.08 | 1.17 |
| "106.1425" | 0.63 | 0.73 | 0.80 | 0.77 | 1.00 | 1.35 |
| "106.1426" | 0.52 | 0.71 | 0.71 | 0.78 | 1.19 | 1.47 |
| "106.1427" | 0.44 | 0.43 | 0.43 | 0.69 | 0.99 | 1.02 |
| "106.1429" | 0.46 | 0.78 | 0.90 | 0.88 | 1.12 | 1.10 |
| "106.1430" | 0.57 | 0.71 | 0.78 | 0.81 | 1.17 | 1.27 |
| "106.1431" | 0.09 | 0.29 | 0.53 | 0.73 | 0.94 | 0.98 |
| "106.1432" | 0.77 | 1.24 | 1.43 | 1.20 | 1.35 | 0.96 |
| "106.1433" | 0.63 | 0.90 | 1.07 | 1.14 | 0.76 | 0.69 |
| "106.1434" | 1.96 | 1.74 | 1.27 | 0.98 | 1.55 | 2.16 |
| "106.1435" | 0.92 | 0.78 | 0.72 | 0.95 | 1.20 | 1.40 |
| "106.1438" | 0.71 | 0.78 | 0.68 | 0.86 | 1.16 | 1.54 |
| "106.1439" | 1.16 | 1.16 | 0.81 | 1.18 | 1.36 | 0.84 |
| "106.1440" | 1.07 | 1.27 | 1.30 | 1.35 | 1.19 | 1.24 |
| "106.1442" | 0.81 | 0.60 | 0.41 | 0.27 | 0.64 | 1.22 |
| "106.1443" | 3.52 | 2.95 | 2.01 | 1.36 | 1.10 | 1.36 |
| "106.1444" | 3.01 | 2.43 | 1.67 | 1.25 | 0.93 | 0.65 |
| "106.1445" | 1.93 | 2.14 | 1.84 | 1.42 | 1.05 | 1.30 |
| "106.1446" | 1.54 | 1.43 | 1.62 | 1.24 | 0.91 | 1.24 |
| "106.1447" | 2.42 | 2.17 | 1.88 | 1.39 | 1.14 | 1.04 |
| "106.1448" | 2.85 | 2.82 | 2.36 | 1.40 | 0.92 | 0.78 |
| "106.1449" | 1.07 | 1.12 | 1.01 | 0.99 | 1.14 | 1.04 |
| "106.1450" | 1.01 | 1.10 | 0.91 | 0.92 | 0.84 | 1.26 |
| "106.1451" | 0.18 | 0.40 | 0.47 | 0.75 | 0.65 | 0.72 |
| "106.1452" | 0.33 | 0.31 | 0.42 | 0.91 | 0.73 | 0.76 |
| "106.1453" | 0.95 | 1.18 | 1.08 | 1.01 | 0.97 | 1.00 |
| "106.1454" | 1.60 | 1.70 | 1.28 | 1.34 | 1.04 | 0.87 |
| "106.1456" | 1.28 | 1.49 | 1.37 | 1.27 | 1.04 | 1.06 |
| "106.1458" | 3.48 | 2.97 | 2.43 | 1.50 | 0.96 | 1.15 |
| "106.1459" | 1.41 | 1.50 | 1.50 | 1.34 | 1.02 | 1.19 |
| "106.1460" | 0.90 | 0.95 | 0.97 | 0.85 | 0.91 | 0.88 |
| "106.1461" | 2.57 | 2.07 | 2.05 | 1.52 | 1.20 | 1.30 |
| "106.1507" | 1.40 | 1.55 | 1.76 | 1.02 | 1.15 | 0.83 |
| "106.1510" | 0.56 | 0.72 | 0.93 | 0.93 | 1.13 | 1.21 |
| "106.1513" | 0.76 | 1.11 | 1.31 | 1.05 | 1.05 | 0.58 |
| "106.1514" | 0.54 | 0.43 | 0.39 | 0.38 | 0.89 | 0.11 |
| "106.1515" | 0.55 | 0.86 | 0.98 | 0.96 | 1.09 | 1.38 |
| "106.1516" | 0.73 | 0.76 | 0.90 | 1.01 | 0.95 | 0.65 |
| "106.1517" | 0.92 | 1.03 | 1.14 | 0.97 | 1.00 | 0.24 |

TABLE 7-continued

Comprehensive neuronal culture screening results for R-GECO1.0 variants

| | | | | | | |
|---|---|---|---|---|---|---|
| "106.1519" | 0.96 | 1.55 | 1.56 | 0.96 | 1.07 | 1.16 |
| "106.1520" | 1.09 | 1.17 | 1.16 | 0.88 | 1.24 | 0.74 |
| "106.1524" | 0.32 | 0.52 | 0.64 | 0.77 | 1.02 | 1.16 |
| "106.1527" | 0.38 | 0.59 | 0.62 | 0.73 | 0.89 | 0.33 |
| "106.1529" | 0.80 | 0.88 | 0.91 | 0.81 | 1.04 | 1.29 |
| "106.1533" | 1.09 | 1.36 | 1.27 | 0.88 | 1.14 | 0.60 |
| "106.1534" | 0.73 | 0.91 | 0.91 | 0.81 | 1.19 | 1.52 |
| "106.1536" | 0.53 | 0.63 | 0.78 | 0.76 | 1.17 | 1.39 |
| "106.1537" | 0.57 | 0.71 | 0.78 | 0.79 | 1.01 | 1.67 |
| "106.1538" | 0.50 | 0.66 | 0.69 | 0.78 | 1.05 | 1.54 |
| "106.1539" | 0.55 | 0.76 | 0.94 | 0.83 | 1.02 | 1.72 |
| "106.1540" | 0.39 | 0.57 | 0.71 | 0.78 | 0.89 | 1.41 |
| "106.1541" | 0.39 | 0.59 | 0.63 | 0.78 | 0.86 | 1.63 |
| "106.1542" | 1.53 | 2.12 | 1.93 | 1.24 | 1.19 | 0.88 |
| "106.1544" | 0.48 | 0.58 | 0.65 | 0.66 | 1.15 | 1.59 |
| "106.1545" | 0.46 | 0.58 | 0.74 | 0.78 | 1.09 | 1.46 |
| "106.1546" | 0.43 | 0.63 | 0.76 | 0.68 | 1.07 | 2.07 |
| "106.1547" | 0.51 | 0.59 | 0.79 | 0.93 | 0.98 | 1.17 |
| "106.1549" | 0.55 | 0.72 | 0.88 | 0.88 | 1.04 | 1.41 |
| "106.1551" | 0.54 | 0.68 | 0.86 | 0.79 | 1.03 | 1.53 |
| "106.1553" | 0.70 | 0.88 | 0.93 | 0.73 | 1.13 | 0.30 |
| "106.1561" | 0.31 | 0.39 | 0.53 | 0.70 | 0.90 | 1.03 |
| "106.1572" | 0.04 | 0.07 | 0.16 | 0.32 | 0.60 | 0.73 |
| "106.1576" | 0.72 | 0.91 | 1.21 | 1.02 | 1.27 | 0.89 |
| "106.1577" | 0.15 | 0.13 | 0.26 | 0.61 | 0.76 | 1.01 |
| "106.1578" | 0.14 | 0.15 | 0.28 | 0.57 | 0.65 | 0.71 |
| "106.1579" | 0.33 | 0.35 | 0.64 | 0.87 | 1.05 | 0.95 |
| "106.1580" | 0.14 | 0.10 | 0.22 | 0.56 | 0.70 | 0.78 |
| "106.1581" | 0.28 | 0.44 | 0.55 | 0.80 | 1.11 | 1.00 |
| "106.1582" | 0.16 | 0.17 | 0.32 | 0.60 | 0.79 | 0.80 |
| "106.1583" | 0.20 | 0.31 | 0.51 | 0.85 | 0.95 | 1.47 |
| "106.1584" | 0.10 | 0.09 | 0.22 | 0.65 | 0.88 | 0.70 |
| "106.1585" | 0.14 | 0.09 | 0.18 | 0.50 | 0.77 | 0.74 |
| "106.1586" | 0.13 | 0.23 | 0.52 | 0.78 | 1.04 | 0.94 |
| "106.1587" | 0.29 | 0.14 | 0.19 | 0.26 | 0.26 | 0.59 |
| "106.1588" | 0.16 | 0.20 | 0.28 | 0.37 | 0.28 | 0.78 |
| "106.1589" | 0.17 | 0.05 | 0.15 | 0.26 | 0.30 | 1.09 |
| "106.1590" | 0.18 | 0.11 | 0.15 | 0.19 | 0.27 | 0.61 |
| "106.1591" | 0.22 | 0.39 | 0.70 | 0.77 | 0.69 | 1.24 |
| "106.1592" | 0.35 | 0.42 | 0.69 | 0.79 | 0.74 | 0.86 |
| "106.1593" | 0.18 | 0.09 | 0.10 | 0.15 | 0.21 | 0.63 |
| "106.1595" | 0.34 | 0.43 | 0.57 | 0.76 | 1.02 | 1.22 |
| "106.1596" | 0.13 | 0.10 | 0.20 | 0.35 | 0.40 | 0.84 |
| "106.1598" | 0.11 | 0.04 | 0.06 | 0.14 | 0.12 | 1.02 |
| "106.1599" | 0.15 | 0.15 | 0.33 | 0.31 | 0.25 | 0.69 |
| "106.1600" | 0.37 | 0.64 | 0.84 | 0.84 | 0.65 | 0.78 |
| "106.1601" | 0.08 | 0.07 | 0.16 | 0.31 | 0.24 | 0.61 |
| "106.1602" | 0.16 | 0.06 | 0.11 | 0.21 | 0.15 | 0.67 |
| "106.1603" | 0.11 | 0.19 | 0.40 | 0.50 | 0.37 | 0.91 |
| "106.1604" | 0.12 | 0.07 | 0.24 | 0.44 | 0.43 | 0.77 |
| "106.1605" | 0.23 | 0.28 | 0.46 | 0.55 | 0.61 | 1.16 |
| "106.1606" | 0.16 | 0.05 | 0.08 | 0.16 | 0.47 | 0.66 |
| "106.1607" | 0.09 | 0.18 | 0.44 | 0.82 | 0.86 | 0.68 |
| "106.1608" | 0.38 | 0.64 | 1.01 | 1.09 | 1.26 | 0.52 |
| "106.1609" | 0.26 | 0.52 | 0.82 | 0.98 | 1.26 | 0.66 |
| "106.1610" | 0.14 | 0.07 | 0.14 | 0.35 | 0.73 | 0.72 |
| "106.1611" | 0.19 | 0.32 | 0.65 | 0.81 | 0.82 | 0.44 |
| "106.1624" | 3.51 | 3.49 | 2.16 | 0.70 | 0.72 | 2.40 |
| "106.1625" | 2.64 | 1.52 | 0.64 | 0.22 | 2.97 | 4.26 |
| "106.1626" | 0.07 | 0.22 | 0.16 | 0.06 | 1.17 | 5.44 |
| "106.1627" | 1.78 | 1.91 | 1.38 | 0.74 | 0.86 | 1.48 |
| "106.1628" | 4.43 | 2.52 | 1.08 | 0.37 | 3.42 | 2.72 |
| "106.1629" | 2.50 | 2.25 | 1.93 | 1.26 | 1.02 | 0.98 |
| "106.1630" | 1.06 | 1.35 | 1.29 | 0.57 | 0.26 | 0.46 |
| "106.1631" | 3.55 | 2.72 | 1.56 | 0.66 | 2.31 | 1.97 |
| "106.1632" | 3.41 | 2.90 | 2.12 | 1.02 | 2.00 | 1.46 |
| "106.1633" | 1.44 | 1.18 | 1.20 | 1.01 | 0.73 | 0.96 |
| "106.1634" | 3.14 | 1.80 | 0.80 | 0.25 | 3.04 | 4.24 |
| "106.1635" | 1.87 | 2.24 | 1.96 | 0.85 | 0.89 | 1.77 |
| "106.1636" | 0.89 | 0.84 | 0.88 | 0.80 | 0.75 | 1.77 |
| "106.1637" | 2.34 | 2.40 | 1.97 | 0.66 | 0.60 | 2.25 |
| "106.1638" | 0.51 | 0.79 | 0.90 | 0.90 | 0.69 | 1.38 |
| "106.1639" | 1.29 | 1.24 | 0.96 | 0.40 | 0.84 | 2.29 |
| "106.1640" | 0.71 | 0.95 | 1.01 | 0.52 | 0.31 | 0.50 |
| "106.1641" | 0.38 | 0.63 | 0.84 | 0.51 | 0.30 | 1.11 |
| "106.1642" | 0.82 | 1.34 | 1.42 | 0.51 | 0.26 | 0.86 |
| "106.1643" | 2.95 | 1.96 | 0.89 | 0.25 | 1.79 | 3.26 |
| "106.1644" | 2.66 | 2.99 | 2.08 | 0.74 | 0.94 | 1.37 |

TABLE 7-continued

Comprehensive neuronal culture screening results for R-GECO1.0 variants

| | | | | | | |
|---|---|---|---|---|---|---|
| "106.1645" | 4.39 | 4.38 | 2.95 | 0.94 | 0.99 | 0.67 |
| "106.1646" | 0.45 | 0.62 | 0.72 | 0.47 | 0.25 | 0.64 |
| "106.1647" | 0.19 | 0.28 | 0.43 | 0.36 | 0.23 | 0.49 |
| "106.1648" | 0.24 | 0.27 | 0.41 | 0.37 | 0.25 | 0.53 |
| "106.1649" | 0.78 | 0.77 | 0.90 | 1.22 | 0.66 | 0.66 |
| "106.1650" | 0.21 | 0.36 | 0.50 | 0.61 | 0.27 | 0.62 |
| "106.1651" | 0.31 | 0.49 | 0.45 | 0.36 | 0.26 | 0.49 |
| "106.1652" | 0.30 | 0.41 | 0.55 | 0.39 | 0.23 | 0.59 |
| "106.1653" | 1.33 | 1.41 | 1.13 | 0.53 | 0.65 | 0.57 |
| "106.1654" | 0.24 | 0.36 | 0.50 | 0.53 | 0.29 | 0.73 |
| "106.1655" | 6.71 | 4.89 | 2.28 | 0.58 | 1.75 | 1.72 |
| "106.1656" | 0.54 | 0.73 | 0.72 | 0.69 | 0.77 | 1.71 |
| "106.1657" | 0.70 | 1.11 | 1.24 | 0.92 | 0.40 | 1.26 |
| "106.1658" | 1.34 | 1.58 | 1.63 | 1.30 | 0.39 | 0.44 |
| "106.1659" | 0.47 | 0.62 | 0.78 | 0.60 | 0.32 | 0.59 |
| "106.1660" | 0.44 | 0.60 | 0.69 | 0.69 | 0.46 | 0.61 |
| "106.1661" | 0.55 | 0.73 | 0.79 | 0.63 | 0.58 | 0.83 |
| "106.1662" | 3.29 | 2.37 | 1.32 | 0.47 | 1.61 | 0.82 |
| "106.1663" | 2.78 | 1.78 | 0.89 | 0.29 | 1.80 | 1.00 |
| "106.1664" | 2.43 | 1.66 | 0.74 | 0.21 | 1.46 | 1.75 |
| "106.1665" | 4.74 | 3.10 | 1.51 | 0.51 | 2.20 | 0.88 |
| "106.1666" | 1.58 | 1.31 | 1.31 | 0.51 | 0.74 | 0.51 |
| "106.1667" | 1.44 | 1.27 | 0.84 | 0.25 | 0.52 | 0.57 |
| "106.1668" | 4.75 | 4.10 | 3.12 | 1.16 | 1.22 | 1.00 |
| "106.1669" | 1.73 | 1.91 | 1.75 | 1.49 | 0.68 | 0.79 |
| "106.1671" | 0.48 | 0.75 | 0.83 | 0.70 | 0.29 | 0.93 |
| "106.1672" | 0.15 | 0.19 | 0.24 | 0.39 | 0.28 | 1.07 |
| "106.1673" | 0.39 | 0.56 | 0.73 | 1.13 | 0.66 | 0.58 |
| "106.1674" | 0.80 | 0.84 | 1.02 | 1.16 | 0.66 | 0.80 |
| "106.1675" | 0.78 | 0.69 | 0.76 | 0.83 | 0.86 | 0.59 |
| "106.1676" | 0.29 | 0.65 | 0.82 | 0.54 | 0.24 | 0.64 |
| "106.1677" | 1.88 | 1.51 | 1.06 | 0.99 | 2.06 | 1.01 |
| "106.1678" | 1.45 | 1.17 | 0.72 | 0.38 | 2.10 | 1.62 |
| "106.1679" | 0.98 | 1.29 | 1.34 | 0.85 | 0.54 | 0.73 |
| "106.1680" | 1.51 | 1.52 | 1.30 | 1.00 | 0.88 | 1.13 |
| "106.1681" | 0.46 | 0.64 | 0.72 | 0.66 | 0.30 | 0.77 |
| "106.1682" | 1.34 | 1.38 | 1.47 | 0.85 | 0.81 | 0.99 |
| "106.1683" | 5.77 | 3.80 | 1.71 | 0.40 | 1.24 | 0.78 |
| "106.1684" | 1.32 | 1.07 | 0.74 | 0.36 | 0.35 | 0.62 |
| "106.1685" | 1.27 | 1.32 | 1.01 | 0.50 | 0.35 | 0.67 |
| "106.1686" | 0.28 | 0.45 | 0.60 | 0.48 | 0.27 | 0.56 |
| "106.1687" | 1.31 | 1.38 | 1.09 | 0.56 | 0.58 | 1.03 |
| "106.1688" | 0.13 | 0.19 | 0.17 | 0.06 | 0.44 | 1.45 |
| "106.1689" | 0.96 | 1.29 | 1.21 | 0.76 | 0.27 | 0.45 |
| "106.1690" | 0.17 | 0.31 | 0.39 | 0.38 | 0.21 | 0.34 |
| "106.1691" | 0.81 | 0.80 | 0.64 | 0.33 | 0.45 | 0.81 |
| "106.1692" | 0.09 | 0.17 | 0.23 | 0.22 | 0.19 | 0.53 |
| "106.1693" | 0.68 | 0.86 | 0.99 | 0.59 | 0.24 | 0.61 |
| "106.1694" | 3.16 | 3.15 | 1.68 | 0.45 | 0.58 | 0.44 |
| "106.1695" | 1.08 | 1.01 | 0.91 | 0.46 | 0.46 | 0.63 |
| "106.1696" | 3.11 | 2.89 | 2.37 | 1.40 | 0.87 | 0.80 |
| "106.1697" | 0.87 | 0.80 | 0.60 | 0.40 | 0.63 | 1.12 |
| "106.1698" | 1.74 | 2.52 | 2.56 | 1.00 | 0.77 | 0.63 |
| "106.1699" | 0.22 | 0.31 | 0.39 | 0.29 | 0.21 | 0.47 |
| "106.1700" | 0.28 | 0.34 | 0.40 | 0.34 | 0.28 | 1.08 |
| "106.1701" | 0.16 | 0.32 | 0.48 | 0.41 | 0.23 | 0.42 |
| "106.1702" | 5.51 | 3.12 | 1.43 | 0.43 | 2.24 | 2.59 |
| "106.1703" | 2.02 | 2.71 | 1.82 | 0.84 | 0.36 | 0.54 |
| "106.1704" | 3.11 | 3.19 | 2.29 | 0.90 | 0.98 | 1.28 |
| "106.1705" | 0.26 | 0.39 | 0.59 | 0.48 | 0.26 | 0.67 |
| "106.1706" | 1.88 | 2.43 | 2.28 | 0.84 | 0.64 | 0.99 |
| "106.1707" | 1.27 | 1.93 | 2.08 | 0.81 | 0.55 | 0.73 |
| "106.1708" | 0.43 | 0.66 | 0.93 | 0.66 | 0.31 | 0.74 |
| "106.1709" | 0.79 | 0.92 | 1.13 | 0.98 | 0.81 | 1.02 |
| "106.1710" | 0.47 | 0.76 | 0.89 | 0.96 | 0.80 | 1.06 |
| "106.1711" | 0.63 | 0.97 | 1.22 | 0.71 | 0.30 | 0.86 |
| "106.1712" | 1.84 | 2.67 | 2.47 | 0.88 | 0.58 | 0.92 |
| "106.1713" | 0.98 | 0.85 | 0.74 | 0.45 | 0.93 | 1.70 |
| "106.1714" | 0.40 | 0.53 | 0.68 | 0.72 | 0.69 | 1.38 |
| "106.1715" | 0.24 | 0.38 | 0.52 | 0.37 | 0.34 | 1.23 |
| "106.1716" | 2.09 | 2.36 | 1.80 | 1.44 | 1.18 | 0.83 |
| "106.1717" | 1.66 | 1.64 | 1.34 | 0.91 | 1.06 | 1.20 |
| "106.1718" | 0.75 | 0.99 | 0.96 | 0.68 | 0.38 | 0.71 |
| "106.1719" | 1.22 | 0.92 | 0.49 | 0.20 | 2.40 | 2.70 |
| "106.1720" | 0.45 | 0.51 | 0.60 | 0.49 | 0.27 | 0.43 |
| "106.1722" | 1.96 | 1.34 | 0.70 | 0.26 | 2.24 | 2.04 |
| "106.1723" | 0.57 | 0.55 | 0.29 | 0.10 | 1.48 | 4.40 |
| "106.1724" | 3.61 | 2.39 | 1.10 | 0.33 | 1.86 | 1.98 |

TABLE 7-continued

Comprehensive neuronal culture screening results for R-GECO1.0 variants

| | | | | | | |
|---|---|---|---|---|---|---|
| "106.1725" | 3.96 | 2.19 | 0.92 | 0.27 | 2.21 | 2.77 |
| "106.1726" | 0.48 | 0.64 | 0.72 | 0.61 | 0.29 | 1.36 |
| "106.1727" | 2.05 | 1.99 | 1.69 | 1.10 | 0.87 | 0.82 |
| "106.1728" | 1.12 | 1.41 | 1.16 | 0.65 | 0.30 | 0.46 |
| "106.1729" | 2.11 | 1.75 | 1.04 | 0.38 | 0.51 | 2.01 |
| "106.1730" | 3.03 | 2.78 | 1.91 | 0.71 | 1.10 | 1.45 |
| "106.1731" | 0.19 | 0.31 | 0.39 | 0.39 | 0.29 | 1.13 |
| "106.1732" | 0.16 | 0.16 | 0.29 | 0.26 | 0.20 | 0.58 |
| "106.1733" | 4.04 | 3.69 | 2.45 | 0.83 | 1.32 | 0.97 |
| "106.1734" | 1.46 | 2.21 | 1.97 | 0.90 | 0.33 | 0.65 |
| "106.1735" | 0.65 | 0.76 | 0.69 | 0.32 | 0.25 | 0.56 |
| "106.1736" | 0.86 | 1.06 | 1.19 | 0.69 | 0.27 | 0.57 |
| "106.1737" | 0.19 | 0.29 | 0.44 | 0.45 | 0.21 | 0.56 |
| "106.1738" | 1.13 | 0.99 | 0.79 | 0.36 | 0.85 | 0.78 |
| "106.1739" | 1.74 | 1.37 | 0.86 | 0.26 | 0.73 | 0.61 |
| "106.1740" | 2.19 | 2.30 | 1.69 | 0.74 | 0.62 | 1.45 |
| "106.1741" | 2.25 | 1.82 | 1.22 | 0.45 | 1.07 | 1.52 |
| "106.1742" | 0.65 | 0.58 | 0.57 | 0.30 | 0.46 | 1.04 |
| "106.1744" | 0.83 | 0.79 | 0.65 | 0.32 | 0.44 | 0.96 |

| R-GECO1.0 variant | 1 AP p-value | 3 AP p-value | 10 AP p-value | 160 AP p-value | Decay half time (10 AP) p-value | $F_0$ normalized to GFP fluorescence p-value |
|---|---|---|---|---|---|---|
| "R-GECO1.0" | 1.00E+00 | 1.00E+00 | 1.00E+00 | 1.00E+00 | 1.00E+00 | 1.00E+00 |
| "R-CaMP2" | 2.91E-01 | 1.50E-01 | 4.37E-01 | 1.50E-06 | 1.27E-04 | 2.80E-06 |
| "jRGECO1a" | 2.32E-09 | 1.67E-09 | 3.81E-09 | 4.75E-09 | 3.17E-01 | 2.30E-02 |
| "jRGECO1b" | 4.46E-02 | 5.14E-04 | 1.44E-04 | 5.36E-01 | 3.58E-03 | 2.35E-03 |
| "106.13" | 4.80E-01 | 1.98E-01 | 9.32E-02 | 4.60E-01 | 3.81E-02 | 3.32E-01 |
| "106.16" | 2.14E-03 | 2.20E-04 | 1.18E-04 | 9.13E-01 | 1.76E-02 | 8.65E-01 |
| "106.19" | 7.74E-03 | 9.11E-04 | 2.56E-04 | 4.56E-06 | 1.71E-06 | 5.78E-03 |
| "106.22" | 3.25E-02 | 1.15E-02 | 4.95E-02 | 7.00E-02 | 4.06E-05 | 4.44E-01 |
| "106.23" | 1.34E-03 | 5.69E-04 | 5.69E-04 | 5.76E-04 | 5.69E-04 | 1.07E-02 |
| "106.25" | 5.42E-01 | 5.73E-01 | 7.97E-01 | 5.71E-04 | 2.36E-07 | 6.83E-02 |
| "106.27" | 3.02E-01 | 1.75E-01 | 1.64E-01 | 2.18E-02 | 1.60E-01 | 1.04E-04 |
| "106.30" | 1.66E-07 | 1.94E-09 | 2.04E-10 | 1.22E-01 | 5.65E-05 | 3.87E-01 |
| "106.31" | 4.14E-03 | 5.81E-04 | 2.60E-04 | 3.09E-01 | 5.39E-03 | 5.15E-01 |
| "106.32" | 7.53E-04 | 2.62E-04 | 1.52E-03 | 4.98E-01 | 7.64E-01 | 6.26E-03 |
| "106.37" | 1.81E-04 | 2.85E-03 | 2.15E-02 | 7.98E-01 | 5.44E-06 | 9.44E-05 |
| "106.38" | 4.58E-01 | 6.67E-01 | 6.03E-01 | 5.18E-02 | 2.62E-03 | 4.28E-03 |
| "106.39" | 2.51E-03 | 7.59E-05 | 7.18E-05 | 1.25E-04 | 3.04E-05 | 1.84E-03 |
| "106.40" | 5.17E-02 | 2.63E-02 | 2.24E-02 | 2.88E-03 | 9.50E-06 | 1.83E-04 |
| "106.42" | 4.29E-02 | 6.75E-03 | 5.29E-03 | 8.90E-02 | 6.97E-04 | 2.22E-02 |
| "106.43" | 3.87E-02 | 1.40E-02 | 2.77E-02 | 2.04E-03 | 4.93E-07 | 1.07E-01 |
| "106.44" | 5.46E-01 | 6.85E-01 | 7.78E-01 | 3.88E-01 | 3.02E-03 | 1.44E-03 |
| "106.46" | 1.33E-02 | 6.81E-04 | 7.32E-04 | 8.34E-04 | 5.69E-04 | 2.01E-03 |
| "106.48" | 5.05E-03 | 1.67E-02 | 4.37E-02 | 9.11E-02 | 2.29E-03 | 2.82E-01 |
| "106.50" | 3.09E-01 | 1.34E-01 | 6.59E-02 | 3.22E-01 | 1.99E-02 | 7.18E-03 |
| "106.58" | 6.01E-01 | 5.32E-01 | 6.43E-01 | 5.17E-01 | 9.38E-04 | 9.96E-01 |
| "106.62" | 5.61E-02 | 3.28E-02 | 1.40E-02 | 8.16E-03 | 3.10E-04 | 3.86E-01 |
| "106.65" | 8.37E-03 | 7.15E-04 | 5.69E-04 | 5.69E-04 | 5.69E-04 | 2.26E-02 |
| "106.68" | 1.30E-01 | 6.03E-02 | 6.52E-02 | 5.15E-03 | 6.85E-03 | 4.32E-02 |
| "106.69" | 1.28E-01 | 2.48E-01 | 3.09E-01 | 9.10E-01 | 5.06E-02 | 9.18E-01 |
| "106.88" | 2.07E-03 | 1.13E-03 | 5.40E-04 | 2.56E-04 | 1.18E-04 | 1.47E-01 |
| "106.91" | 1.27E-04 | 2.58E-05 | 2.61E-05 | 2.61E-05 | 2.52E-05 | 6.09E-01 |
| "106.97" | 3.22E-02 | 1.09E-01 | 5.09E-01 | 8.41E-01 | 4.29E-02 | 2.37E-01 |
| "106.103" | 1.56E-01 | 6.47E-01 | 8.02E-01 | 3.85E-01 | 5.38E-03 | 1.67E-04 |
| "106.104" | 6.15E-01 | 7.05E-01 | 9.65E-01 | 6.24E-01 | 7.77E-04 | 7.47E-01 |
| "106.109" | 1.35E-02 | 2.55E-03 | 1.51E-03 | 2.70E-04 | 6.56E-01 | 1.90E-01 |
| "106.112" | 3.13E-01 | 1.35E-01 | 1.20E-01 | 1.30E-01 | 9.59E-02 | 3.46E-02 |
| "106.113" | 7.07E-03 | 1.16E-02 | 2.04E-02 | 4.59E-01 | 5.67E-02 | 4.28E-01 |
| "106.119" | 4.32E-03 | 8.29E-03 | 3.29E-02 | 4.11E-02 | 8.80E-02 | 1.20E-01 |
| "106.121" | 3.77E-02 | 9.54E-02 | 2.77E-01 | 1.40E-01 | 1.26E-03 | 2.63E-01 |
| "106.150" | 1.38E-03 | 1.25E-02 | 2.25E-01 | 1.19E-01 | 4.09E-02 | 9.60E-01 |
| "106.155" | 2.49E-01 | 1.16E-01 | 3.73E-02 | 6.63E-03 | 6.34E-05 | 3.29E-01 |
| "106.156" | 7.30E-01 | 6.20E-01 | 1.41E-01 | 1.33E-02 | 3.92E-05 | 9.76E-02 |
| "106.158" | 6.11E-02 | 2.24E-02 | 2.72E-03 | 2.75E-03 | 2.91E-03 | 2.98E-01 |
| "106.162" | 6.20E-01 | 7.00E-01 | 2.00E-01 | 5.03E-02 | 3.59E-04 | 6.15E-01 |
| "106.173" | 1.51E-01 | 3.84E-01 | 5.73E-01 | 4.30E-01 | 4.92E-01 | 7.69E-01 |
| "106.174" | 2.27E-02 | 1.19E-02 | 3.60E-03 | 1.67E-02 | 4.79E-04 | 5.10E-01 |
| "106.176" | 5.79E-01 | 2.45E-01 | 1.34E-01 | 2.04E-01 | 5.26E-03 | 2.09E-01 |
| "106.178" | 1.51E-05 | 5.84E-06 | 5.57E-06 | 5.57E-06 | 5.44E-06 | 7.91E-01 |
| "106.181" | 6.55E-01 | 7.53E-01 | 6.94E-01 | 8.46E-01 | 2.78E-01 | 1.47E-01 |
| "106.182" | 5.45E-01 | 6.53E-01 | 4.24E-01 | 2.18E-01 | 8.84E-01 | 3.99E-02 |
| "106.183" | 5.73E-01 | 8.75E-01 | 4.85E-01 | 7.29E-01 | 3.46E-01 | 1.03E-02 |
| "106.185" | 2.23E-01 | 1.84E-01 | 1.45E-01 | 9.29E-01 | 1.18E-04 | 1.06E-01 |
| "106.186" | 8.85E-02 | 4.52E-01 | 3.04E-01 | 3.23E-02 | 7.90E-04 | 6.59E-01 |

TABLE 7-continued

Comprehensive neuronal culture screening results for R-GECO1.0 variants

| | | | | | | |
|---|---|---|---|---|---|---|
| "106.188" | 5.52E−04 | 2.77E−04 | 3.75E−04 | 1.36E−03 | 1.18E−04 | 3.33E−03 |
| "106.189" | 9.61E−02 | 4.39E−02 | 1.66E−02 | 5.17E−02 | 7.10E−04 | 1.90E−02 |
| "106.190" | 9.21E−04 | 3.00E−04 | 3.03E−04 | 1.86E−02 | 1.18E−04 | 1.06E−01 |
| "106.191" | 7.96E−01 | 3.00E−01 | 2.01E−01 | 1.26E−01 | 9.77E−01 | 4.06E−01 |
| "106.192" | 1.60E−02 | 5.83E−04 | 1.48E−03 | 6.15E−03 | 1.75E−04 | 7.10E−02 |
| "106.194" | 8.86E−02 | 2.88E−02 | 3.99E−02 | 8.18E−01 | 1.23E−04 | 4.27E−01 |
| "106.195" | 1.27E−03 | 5.69E−04 | 5.69E−04 | 5.69E−04 | 5.69E−04 | 4.15E−01 |
| "106.197" | 5.95E−01 | 1.56E−01 | 6.61E−02 | 2.63E−01 | 4.17E−02 | 8.86E−02 |
| "106.212" | 5.83E−02 | 4.76E−02 | 5.64E−02 | 1.64E−01 | 1.81E−04 | 1.50E−02 |
| "106.213" | 1.01E−03 | 6.56E−04 | 1.01E−03 | 1.82E−03 | 1.18E−04 | 9.71E−02 |
| "106.216" | 7.42E−01 | 4.15E−01 | 1.79E−01 | 7.07E−01 | 4.70E−01 | 4.28E−01 |
| "106.217" | 2.02E−02 | 3.87E−03 | 1.57E−03 | 1.45E−03 | 5.69E−04 | 7.87E−02 |
| "106.220" | 5.02E−01 | 9.80E−01 | 1.02E−01 | 3.46E−03 | 2.61E−05 | 1.59E−01 |
| "106.221" | 9.39E−03 | 2.82E−01 | 2.28E−01 | 2.67E−01 | 2.09E−01 | 2.67E−03 |
| "106.222" | 1.27E−03 | 1.57E−03 | 1.52E−03 | 1.68E−03 | 5.69E−04 | 6.81E−01 |
| "106.228" | 3.20E−02 | 1.44E−01 | 7.05E−01 | 4.56E−03 | 5.59E−03 | 1.12E−01 |
| "106.230" | 2.44E−03 | 9.76E−03 | 1.47E−01 | 6.03E−01 | 6.05E−01 | 4.97E−01 |
| "106.238" | 5.49E−02 | 1.11E−01 | 5.60E−02 | 1.77E−03 | 1.18E−04 | 6.43E−01 |
| "106.239" | 5.34E−01 | 1.32E−01 | 7.67E−02 | 6.96E−01 | 5.44E−06 | 4.13E−01 |
| "106.240" | 5.89E−01 | 9.31E−01 | 2.20E−01 | 1.47E−01 | 2.90E−05 | 8.96E−04 |
| "106.241" | 9.99E−01 | 7.77E−01 | 7.97E−01 | 4.48E−01 | 2.01E−03 | 2.30E−01 |
| "106.242" | 5.89E−01 | 2.58E−01 | 1.21E−01 | 4.60E−02 | 2.55E−01 | 1.59E−01 |
| "106.243" | 4.27E−01 | 5.12E−01 | 2.71E−01 | 2.14E−01 | 2.52E−05 | 9.75E−01 |
| "106.246" | 5.86E−01 | 6.77E−01 | 6.15E−01 | 1.23E−02 | 5.44E−06 | 8.15E−01 |
| "106.247" | 6.84E−01 | 7.00E−01 | 9.90E−01 | 8.96E−02 | 8.58E−05 | 9.20E−01 |
| "106.248" | 7.15E−01 | 5.34E−01 | 5.61E−01 | 3.05E−01 | 2.83E−03 | 3.33E−01 |
| "106.249" | 1.92E−04 | 1.25E−04 | 3.66E−04 | 4.27E−05 | 5.44E−06 | 1.19E−02 |
| "106.250" | 7.29E−01 | 8.96E−01 | 5.07E−01 | 1.85E−01 | 3.26E−01 | 7.77E−02 |
| "106.253" | 2.83E−01 | 4.31E−01 | 2.94E−01 | 1.92E−01 | 5.90E−04 | 1.38E−02 |
| "106.256" | 1.91E−01 | 2.67E−01 | 4.72E−01 | 6.67E−02 | 7.73E−02 | 8.33E−02 |
| "106.260" | 5.42E−03 | 5.93E−02 | 6.38E−01 | 1.14E−03 | 1.15E−02 | 7.96E−04 |
| "106.261" | 1.43E−01 | 7.91E−02 | 2.16E−02 | 1.99E−03 | 2.71E−04 | 9.65E−02 |
| "106.267" | 3.10E−03 | 1.47E−03 | 8.15E−04 | 1.24E−03 | 5.69E−04 | 8.74E−02 |
| "106.273" | 8.16E−03 | 4.33E−02 | 6.74E−01 | 4.74E−03 | 3.14E−02 | 2.53E−03 |
| "106.279" | 3.11E−04 | 5.99E−05 | 3.00E−05 | 4.66E−04 | 5.44E−06 | 5.54E−01 |
| "106.289" | 1.47E−01 | 5.11E−01 | 8.75E−01 | 5.28E−01 | 7.35E−01 | 2.70E−01 |
| "106.293" | 1.66E−01 | 2.51E−01 | 1.57E−01 | 1.74E−02 | 5.00E−05 | 2.43E−01 |
| "106.294" | 1.18E−04 | 1.21E−04 | 1.29E−04 | 1.47E−04 | 1.18E−04 | 9.73E−01 |
| "106.295" | 5.83E−04 | 5.69E−04 | 5.69E−04 | 5.69E−04 | 5.69E−04 | 8.35E−01 |
| "106.296" | 1.99E−02 | 5.82E−03 | 1.94E−03 | 1.49E−03 | 1.25E−02 | 9.07E−01 |
| "106.322" | 8.97E−02 | 7.82E−01 | 4.79E−02 | 2.20E−03 | 3.00E−04 | 3.02E−03 |
| "106.323" | 4.66E−03 | 1.72E−03 | 2.22E−03 | 1.39E−03 | 2.70E−03 | 1.41E−01 |
| "106.327" | 9.31E−03 | 8.54E−04 | 5.69E−04 | 5.69E−04 | 2.82E−03 | 5.69E−04 |
| "106.341" | 1.67E−03 | 7.71E−03 | 8.53E−02 | 2.74E−01 | 3.29E−01 | 6.74E−01 |
| "106.344" | 2.14E−01 | 8.46E−01 | 2.66E−01 | 6.11E−03 | 1.99E−03 | 2.52E−05 |
| "106.345" | 2.15E−01 | 2.16E−01 | 7.96E−01 | 4.88E−01 | 1.47E−01 | 3.98E−04 |
| "106.347" | 1.92E−02 | 5.59E−03 | 4.04E−04 | 1.42E−03 | 2.49E−03 | 9.69E−02 |
| "106.348" | 7.60E−01 | 5.09E−01 | 2.73E−01 | 2.99E−01 | 4.76E−02 | 9.96E−01 |
| "106.349" | 7.60E−03 | 3.20E−02 | 9.18E−02 | 4.46E−01 | 3.10E−01 | 1.99E−02 |
| "106.351" | 8.59E−01 | 6.34E−01 | 1.00E−01 | 1.26E−01 | 3.22E−02 | 1.57E−04 |
| "106.364" | 5.05E−03 | 7.59E−04 | 6.12E−04 | 7.77E−04 | 5.69E−04 | 1.58E−01 |
| "106.365" | 2.55E−02 | 2.67E−03 | 2.94E−04 | 2.76E−03 | 4.56E−05 | 2.69E−01 |
| "106.367" | 9.68E−01 | 3.19E−01 | 2.29E−01 | 1.11E−01 | 1.56E−02 | 8.32E−02 |
| "106.369" | 9.49E−01 | 7.30E−01 | 1.74E−01 | 1.39E−01 | 1.00E−02 | 1.93E−01 |
| "106.370" | 5.69E−01 | 4.92E−02 | 2.12E−03 | 2.62E−03 | 3.14E−04 | 2.77E−02 |
| "106.371" | 1.80E−03 | 2.67E−04 | 4.09E−05 | 8.05E−04 | 7.54E−06 | 1.38E−03 |
| "106.372" | 5.67E−06 | 6.62E−07 | 1.14E−07 | 1.33E−04 | 1.21E−07 | 2.55E−03 |
| "106.374" | 4.45E−04 | 2.02E−03 | 2.11E−02 | 2.00E−01 | 1.08E−01 | 3.93E−01 |
| "106.375" | 1.55E−02 | 2.31E−02 | 7.52E−02 | 1.47E−01 | 8.59E−01 | 3.07E−01 |
| "106.379" | 2.30E−01 | 3.79E−01 | 6.06E−01 | 3.97E−01 | 3.70E−02 | 4.36E−01 |
| "106.389" | 1.83E−01 | 3.49E−01 | 3.46E−01 | 8.92E−01 | 1.48E−01 | 3.77E−01 |
| "106.403" | 1.26E−04 | 1.18E−04 | 1.23E−04 | 1.35E−04 | 1.18E−04 | 6.61E−02 |
| "106.404" | 2.33E−04 | 1.54E−04 | 1.63E−04 | 1.27E−02 | 1.18E−04 | 1.44E−02 |
| "106.405" | 3.49E−03 | 2.27E−03 | 1.44E−03 | 6.31E−04 | 1.67E−04 | 2.60E−04 |
| "106.408" | 2.40E−02 | 2.28E−02 | 5.61E−02 | 1.06E−02 | 4.41E−06 | 9.82E−04 |
| "106.410" | 1.08E−03 | 1.13E−05 | 2.10E−06 | 1.54E−06 | 2.28E−06 | 5.77E−01 |
| "106.411" | 1.38E−02 | 3.83E−03 | 3.51E−04 | 1.61E−04 | 1.18E−04 | 2.10E−01 |
| "106.415" | 1.04E−01 | 5.43E−01 | 1.78E−01 | 9.60E−04 | 2.47E−03 | 7.02E−01 |
| "106.422" | 1.30E−01 | 3.17E−02 | 1.80E−01 | 4.88E−01 | 8.81E−02 | 4.75E−01 |
| "106.427" | 8.96E−03 | 2.22E−02 | 5.63E−02 | 5.36E−01 | 9.75E−01 | 1.71E−01 |
| "106.433" | 8.18E−02 | 3.86E−02 | 9.85E−02 | 1.74E−01 | 9.35E−01 | 8.19E−01 |
| "106.438" | 5.20E−02 | 7.37E−02 | 3.37E−01 | 8.40E−01 | 1.49E−02 | 3.87E−03 |
| "106.439" | 8.38E−04 | 1.04E−02 | 5.66E−01 | 1.09E−08 | 9.16E−05 | 3.25E−02 |
| "106.440" | 6.26E−01 | 6.06E−01 | 2.39E−02 | 1.71E−04 | 1.62E−01 | 1.90E−02 |
| "106.444" | 9.56E−02 | 6.33E−01 | 4.52E−01 | 4.61E−03 | 1.07E−03 | 4.19E−01 |
| "106.448" | 1.14E−01 | 4.48E−01 | 7.44E−01 | 8.27E−02 | 4.95E−03 | 2.01E−01 |
| "106.449" | 8.46E−04 | 5.63E−03 | 1.11E−01 | 5.59E−01 | 6.57E−01 | 1.41E−02 |
| "106.450" | 3.14E−01 | 3.25E−02 | 3.00E−03 | 1.14E−03 | 5.76E−04 | 4.94E−01 |

TABLE 7-continued

Comprehensive neuronal culture screening results for R-GECO1.0 variants

| | | | | | | |
|---|---|---|---|---|---|---|
| "106.453" | 4.63E−01 | 3.51E−02 | 5.00E−03 | 4.68E−04 | 2.56E−04 | 5.99E−03 |
| "106.457" | 1.64E−04 | 1.30E−03 | 2.48E−02 | 3.73E−01 | 4.30E−01 | 1.06E−02 |
| "106.459" | 1.34E−03 | 6.26E−04 | 5.90E−04 | 6.12E−04 | 5.69E−04 | 1.35E−01 |
| "106.460" | 5.30E−01 | 4.51E−01 | 9.59E−01 | 5.05E−01 | 1.65E−01 | 3.44E−02 |
| "106.461" | 4.67E−05 | 3.75E−05 | 3.41E−05 | 3.62E−05 | 2.52E−05 | 1.11E−01 |
| "106.462" | 4.25E−04 | 1.19E−04 | 3.88E−05 | 5.99E−05 | 6.94E−05 | 1.29E−01 |
| "106.463" | 1.97E−03 | 4.58E−04 | 2.18E−04 | 2.77E−04 | 2.87E−04 | 9.78E−01 |
| "106.475" | 5.96E−10 | 5.79E−08 | 1.31E−07 | 1.21E−10 | 2.83E−17 | 2.02E−02 |
| "106.479" | 3.85E−06 | 6.94E−04 | 1.24E−02 | 5.70E−07 | 1.67E−10 | 1.72E−01 |
| "106.483" | 7.57E−02 | 8.32E−02 | 1.03E−01 | 9.10E−01 | 4.51E−01 | 4.89E−01 |
| "106.487" | 8.92E−01 | 8.15E−01 | 8.87E−01 | 6.71E−01 | 5.69E−04 | 1.89E−02 |
| "106.494" | 7.92E−02 | 4.07E−02 | 1.62E−01 | 1.49E−01 | 1.17E−05 | 1.73E−01 |
| "106.496" | 1.91E−03 | 1.40E−03 | 3.12E−03 | 6.09E−05 | 4.80E−08 | 6.25E−01 |
| "106.501" | 5.89E−01 | 4.58E−01 | 2.32E−01 | 7.43E−02 | 7.30E−04 | 1.48E−01 |
| "106.511" | 7.32E−04 | 7.77E−04 | 9.06E−04 | 2.17E−03 | 5.69E−04 | 6.15E−02 |
| "106.520" | 5.08E−02 | 3.48E−02 | 1.25E−02 | 2.42E−02 | 2.46E−01 | 3.63E−02 |
| "106.521" | 2.58E−03 | 1.03E−03 | 6.90E−04 | 7.32E−04 | 5.69E−04 | 7.87E−01 |
| "106.524" | 2.91E−03 | 1.37E−03 | 9.83E−04 | 9.49E−04 | 5.69E−04 | 1.80E−01 |
| "106.525" | 2.03E−03 | 3.07E−04 | 2.01E−04 | 2.59E−04 | 1.18E−04 | 6.96E−03 |
| "106.526" | 2.97E−05 | 2.70E−05 | 2.61E−05 | 3.58E−05 | 2.52E−05 | 5.22E−01 |
| "106.527" | 3.88E−04 | 1.41E−04 | 1.61E−04 | 2.20E−04 | 3.25E−04 | 4.37E−01 |
| "106.528" | 2.39E−04 | 1.71E−04 | 2.08E−04 | 2.47E−04 | 1.18E−04 | 4.14E−02 |
| "106.531" | 5.35E−04 | 4.40E−05 | 3.97E−05 | 3.92E−05 | 2.52E−05 | 7.88E−01 |
| "106.532" | 2.72E−03 | 2.44E−03 | 6.70E−04 | 2.20E−04 | 2.52E−05 | 2.51E−01 |
| "106.533" | 1.39E−01 | 1.61E−02 | 1.92E−03 | 8.05E−04 | 5.69E−04 | 3.77E−01 |
| "106.537" | 3.36E−04 | 6.49E−05 | 3.54E−05 | 3.54E−05 | 2.52E−05 | 7.23E−01 |
| "106.545" | 2.52E−01 | 9.27E−02 | 8.00E−03 | 1.42E−02 | 5.90E−03 | 2.82E−02 |
| "106.555" | 1.10E−02 | 4.11E−03 | 7.77E−04 | 1.31E−03 | 5.69E−04 | 2.39E−01 |
| "106.560" | 8.35E−03 | 1.00E−04 | 3.62E−05 | 7.18E−05 | 3.58E−05 | 3.55E−03 |
| "106.561" | 1.52E−03 | 4.32E−05 | 8.37E−06 | 3.20E−05 | 2.65E−04 | 4.45E−01 |
| "106.562" | 1.61E−01 | 1.55E−03 | 2.67E−04 | 7.90E−04 | 4.31E−01 | 8.90E−02 |
| "106.563" | 2.68E−04 | 2.49E−03 | 1.50E−01 | 1.69E−02 | 8.03E−05 | 5.47E−01 |
| "106.569" | 8.88E−02 | 2.12E−02 | 1.80E−02 | 9.33E−01 | 1.33E−01 | 2.33E−01 |
| "106.570" | 9.52E−01 | 7.45E−01 | 6.78E−01 | 6.09E−01 | 4.68E−01 | 2.39E−01 |
| "106.600" | 1.06E−02 | 1.47E−02 | 1.10E−02 | 6.65E−02 | 3.10E−01 | 6.71E−01 |
| "106.601" | 5.05E−01 | 3.15E−02 | 1.64E−03 | 3.31E−01 | 3.13E−01 | 5.97E−08 |
| "106.602" | 8.35E−03 | 5.14E−04 | 8.46E−04 | 4.30E−02 | 1.14E−04 | 1.75E−03 |
| "106.603" | 2.53E−02 | 4.70E−03 | 3.82E−03 | 5.42E−03 | 6.19E−04 | 5.76E−04 |
| "106.604" | 1.24E−02 | 2.05E−01 | 7.91E−01 | 3.34E−01 | 6.81E−03 | 2.90E−01 |
| "106.605" | 1.62E−02 | 3.77E−02 | 2.10E−01 | 1.70E−01 | 6.68E−07 | 9.48E−02 |
| "106.606" | 7.22E−01 | 6.56E−01 | 4.47E−01 | 7.33E−02 | 8.39E−02 | 5.02E−01 |
| "106.607" | 2.97E−01 | 7.32E−01 | 8.95E−01 | 2.24E−01 | 2.28E−01 | 1.11E−03 |
| "106.608" | 8.22E−03 | 5.97E−03 | 3.97E−03 | 3.51E−01 | 5.73E−04 | 1.50E−04 |
| "106.609" | 2.54E−06 | 5.27E−07 | 1.59E−06 | 8.53E−05 | 7.30E−04 | 5.95E−01 |
| "106.610" | 6.40E−02 | 1.34E−02 | 2.22E−03 | 1.56E−03 | 1.92E−01 | 3.52E−01 |
| "106.611" | 3.14E−03 | 1.37E−03 | 1.58E−03 | 1.37E−02 | 3.14E−01 | 3.97E−01 |
| "106.612" | 8.32E−02 | 6.78E−02 | 1.56E−01 | 3.45E−02 | 3.95E−03 | 2.96E−01 |
| "106.613" | 4.17E−01 | 2.01E−01 | 4.91E−02 | 2.25E−01 | 1.22E−01 | 5.99E−05 |
| "106.614" | 9.86E−01 | 6.72E−01 | 5.85E−01 | 2.45E−01 | 2.25E−03 | 4.67E−04 |
| "106.615" | 1.74E−01 | 8.80E−02 | 6.50E−02 | 1.18E−01 | 1.32E−04 | 3.45E−01 |
| "106.616" | 5.43E−02 | 4.08E−02 | 5.06E−02 | 4.31E−02 | 1.81E−04 | 7.48E−01 |
| "106.617" | 5.68E−04 | 1.94E−04 | 3.33E−03 | 2.53E−02 | 4.75E−06 | 2.72E−01 |
| "106.618" | 9.83E−01 | 9.26E−01 | 4.46E−01 | 3.00E−01 | 1.56E−04 | 3.97E−01 |
| "106.619" | 6.21E−01 | 7.96E−01 | 8.83E−01 | 8.65E−01 | 6.15E−03 | 2.34E−01 |
| "106.620" | 9.32E−02 | 4.63E−02 | 4.77E−02 | 8.95E−01 | 1.25E−01 | 5.98E−04 |
| "106.622" | 9.69E−01 | 9.30E−01 | 6.28E−01 | 5.74E−01 | 1.06E−02 | 6.40E−01 |
| "106.623" | 5.09E−01 | 3.95E−01 | 3.72E−01 | 6.50E−01 | 3.02E−02 | 1.99E−01 |
| "106.624" | 2.36E−02 | 4.68E−03 | 4.28E−03 | 4.19E−01 | 6.44E−03 | 2.70E−01 |
| "106.625" | 8.47E−01 | 9.57E−01 | 8.24E−01 | 4.94E−01 | 4.05E−01 | 1.14E−01 |
| "106.626" | 7.86E−01 | 6.72E−01 | 5.08E−01 | 4.74E−01 | 7.38E−01 | 1.31E−01 |
| "106.627" | 8.85E−02 | 9.42E−02 | 1.80E−01 | 1.84E−01 | 9.94E−06 | 5.16E−04 |
| "106.628" | 2.94E−02 | 7.76E−04 | 2.91E−04 | 1.18E−02 | 2.52E−05 | 3.66E−05 |
| "106.629" | 9.30E−02 | 8.56E−02 | 1.08E−01 | 4.17E−02 | 9.30E−02 | 1.09E−02 |
| "106.630" | 5.96E−01 | 6.51E−01 | 2.55E−01 | 1.10E−02 | 1.43E−01 | 4.77E−05 |
| "106.631" | 8.40E−02 | 4.49E−02 | 1.59E−02 | 1.23E−01 | 8.49E−01 | 4.25E−04 |
| "106.632" | 8.27E−02 | 3.24E−02 | 1.28E−02 | 2.04E−02 | 3.99E−04 | 3.36E−05 |
| "106.633" | 1.14E−04 | 3.91E−05 | 2.14E−05 | 6.98E−05 | 1.20E−06 | 2.54E−03 |
| "106.634" | 5.01E−02 | 6.07E−02 | 1.91E−01 | 3.91E−01 | 3.48E−03 | 8.07E−05 |
| "106.635" | 7.28E−02 | 6.92E−05 | 4.06E−05 | 3.83E−05 | 2.20E−02 | 2.95E−03 |
| "106.636" | 6.79E−04 | 1.01E−04 | 4.14E−05 | 2.78E−05 | 5.44E−06 | 6.97E−04 |
| "106.637" | 4.84E−03 | 2.02E−03 | 9.74E−04 | 5.27E−04 | 1.63E−06 | 3.10E−05 |
| "106.638" | 2.93E−03 | 3.56E−04 | 5.41E−04 | 2.52E−03 | 1.21E−06 | 3.33E−05 |
| "106.639" | 9.09E−01 | 6.68E−01 | 4.98E−01 | 6.45E−01 | 9.38E−01 | 1.87E−06 |
| "106.640" | 7.00E−01 | 1.74E−01 | 1.55E−01 | 8.84E−01 | 5.69E−04 | 1.31E−03 |
| "106.641" | 2.53E−02 | 5.50E−02 | 1.25E−01 | 4.32E−01 | 5.90E−01 | 4.31E−02 |
| "106.642" | 8.92E−01 | 2.59E−01 | 1.84E−01 | 2.45E−02 | 2.50E−03 | 1.04E−03 |
| "106.643" | 5.49E−01 | 7.06E−01 | 1.19E−02 | 3.88E−05 | 6.59E−01 | 2.78E−02 |
| "106.644" | 1.43E−02 | 1.26E−03 | 2.06E−03 | 1.25E−02 | 1.71E−05 | 6.23E−02 |

TABLE 7-continued

Comprehensive neuronal culture screening results for R-GECO1.0 variants

| | | | | | | |
|---|---|---|---|---|---|---|
| "106.645" | 1.15E−01 | 5.09E−02 | 2.71E−02 | 6.15E−04 | 1.70E−04 | 3.21E−02 |
| "106.646" | 2.88E−04 | 3.07E−05 | 2.66E−05 | 7.22E−04 | 1.33E−06 | 7.58E−03 |
| "106.648" | 8.67E−03 | 8.72E−04 | 7.16E−04 | 5.30E−03 | 5.98E−04 | 1.18E−05 |
| "106.649" | 4.97E−01 | 3.44E−01 | 1.82E−01 | 1.39E−01 | 9.84E−03 | 1.38E−03 |
| "106.650" | 5.43E−03 | 1.25E−01 | 9.56E−01 | 1.96E−01 | 7.08E−05 | 1.28E−02 |
| "106.651" | 4.42E−02 | 9.69E−04 | 1.74E−04 | 2.41E−03 | 9.40E−01 | 3.16E−05 |
| "106.652" | 7.37E−11 | 2.41E−08 | 1.65E−02 | 8.39E−12 | 2.55E−17 | 4.41E−02 |
| "106.653" | 1.99E−01 | 5.41E−01 | 5.63E−01 | 8.63E−01 | 1.14E−01 | 2.08E−01 |
| "106.654" | 2.22E−03 | 2.83E−03 | 1.83E−02 | 9.30E−02 | 3.59E−04 | 8.43E−02 |
| "106.655" | 4.25E−04 | 3.08E−04 | 5.81E−03 | 4.00E−02 | 6.27E−06 | 1.99E−01 |
| "106.656" | 4.53E−05 | 3.53E−05 | 6.52E−05 | 3.79E−04 | 4.87E−06 | 9.86E−01 |
| "106.657" | 3.28E−02 | 1.81E−01 | 4.72E−01 | 7.27E−01 | 2.74E−01 | 3.98E−02 |
| "106.658" | 6.31E−01 | 7.05E−01 | 7.01E−01 | 1.11E−01 | 5.74E−05 | 1.53E−01 |
| "106.659" | 1.94E−04 | 4.14E−05 | 8.52E−05 | 7.36E−04 | 9.07E−06 | 1.22E−02 |
| "106.660" | 6.40E−01 | 5.85E−01 | 5.29E−01 | 9.16E−01 | 2.58E−01 | 2.95E−03 |
| "106.661" | 3.16E−05 | 2.04E−05 | 7.77E−05 | 3.78E−03 | 2.10E−03 | 1.01E−01 |
| "106.662" | 3.45E−01 | 2.21E−01 | 1.14E−01 | 7.75E−02 | 4.61E−02 | 8.54E−01 |
| "106.663" | 3.62E−03 | 2.33E−03 | 5.83E−03 | 1.14E−01 | 6.32E−03 | 1.34E−01 |
| "106.665" | 1.35E−02 | 1.80E−01 | 7.72E−01 | 1.70E−01 | 6.57E−04 | 1.45E−03 |
| "106.666" | 7.67E−01 | 3.61E−01 | 4.46E−01 | 1.37E−01 | 5.15E−01 | 5.69E−04 |
| "106.667" | 3.94E−03 | 1.02E−03 | 1.21E−03 | 2.05E−02 | 2.96E−01 | 1.54E−04 |
| "106.668" | 1.90E−04 | 1.16E−04 | 1.55E−04 | 8.28E−02 | 7.31E−01 | 3.04E−05 |
| "106.669" | 2.53E−03 | 1.07E−03 | 2.31E−04 | 2.28E−01 | 5.29E−01 | 1.73E−05 |
| "106.670" | 3.49E−01 | 1.05E−01 | 1.17E−02 | 1.88E−01 | 2.92E−02 | 5.79E−04 |
| "106.671" | 3.48E−01 | 3.90E−02 | 2.83E−03 | 9.27E−04 | 2.83E−03 | 6.10E−02 |
| "106.672" | 5.34E−05 | 1.13E−05 | 9.39E−06 | 5.06E−05 | 3.30E−04 | 2.50E−04 |
| "106.673" | 1.67E−01 | 2.18E−02 | 8.73E−03 | 2.12E−01 | 8.94E−01 | 3.47E−04 |
| "106.674" | 1.23E−01 | 1.34E−01 | 5.67E−02 | 3.32E−03 | 4.70E−03 | 4.56E−02 |
| "106.683" | 1.17E−04 | 9.83E−05 | 1.03E−04 | 6.03E−04 | 1.41E−05 | 5.23E−02 |
| "106.686" | 2.82E−02 | 2.36E−04 | 1.35E−04 | 2.56E−04 | 1.23E−02 | 8.48E−01 |
| "106.688" | 6.77E−02 | 1.02E−02 | 3.27E−03 | 3.27E−03 | 1.12E−02 | 5.69E−04 |
| "106.690" | 1.29E−04 | 1.18E−04 | 1.26E−04 | 1.94E−04 | 1.18E−04 | 4.79E−02 |
| "106.691" | 1.36E−03 | 2.77E−04 | 1.81E−04 | 4.38E−04 | 8.43E−02 | 3.35E−01 |
| "106.692" | 1.40E−04 | 1.18E−04 | 1.18E−04 | 1.71E−04 | 1.18E−04 | 2.97E−04 |
| "106.693" | 5.83E−04 | 5.69E−04 | 5.69E−04 | 6.04E−04 | 5.69E−04 | 2.39E−03 |
| "106.694" | 5.52E−04 | 1.40E−04 | 1.71E−04 | 2.97E−04 | 1.18E−04 | 1.63E−03 |
| "106.695" | 1.40E−04 | 1.18E−04 | 1.18E−04 | 1.20E−04 | 1.18E−04 | 1.42E−01 |
| "106.697" | 7.50E−04 | 5.69E−04 | 5.69E−04 | 6.26E−04 | 5.69E−04 | 5.69E−04 |
| "106.698" | 1.50E−04 | 4.02E−05 | 3.26E−05 | 1.18E−04 | 2.52E−05 | 4.65E−04 |
| "106.699" | 7.90E−06 | 5.98E−06 | 6.12E−06 | 8.76E−06 | 5.44E−06 | 4.41E−03 |
| "106.700" | 6.38E−04 | 6.20E−05 | 7.26E−05 | 1.23E−04 | 3.92E−05 | 2.86E−05 |
| "106.701" | 1.28E−06 | 1.36E−06 | 1.24E−06 | 1.69E−06 | 2.03E−06 | 2.83E−04 |
| "106.702" | 8.76E−06 | 5.64E−06 | 5.77E−06 | 1.06E−05 | 5.44E−06 | 1.28E−05 |
| "106.703" | 1.04E−05 | 5.44E−06 | 5.44E−06 | 5.98E−06 | 5.44E−06 | 8.09E−06 |
| "106.704" | 8.18E−06 | 5.91E−06 | 5.91E−06 | 9.72E−06 | 5.44E−06 | 1.08E−05 |
| "106.705" | 1.30E−06 | 1.21E−06 | 1.24E−06 | 2.38E−06 | 1.20E−06 | 6.84E−03 |
| "106.706" | 2.24E−04 | 3.00E−05 | 2.67E−05 | 3.49E−05 | 2.52E−05 | 8.46E−04 |
| "106.707" | 2.06E−05 | 1.93E−05 | 2.71E−05 | 8.07E−05 | 1.20E−06 | 1.36E−01 |
| "106.708" | 2.15E−06 | 1.67E−06 | 2.82E−06 | 8.77E−06 | 1.20E−06 | 4.90E−02 |
| "106.709" | 9.54E−03 | 4.18E−03 | 3.80E−03 | 6.63E−03 | 2.67E−05 | 4.98E−03 |
| "106.710" | 4.22E−01 | 1.14E−01 | 4.65E−02 | 7.29E−02 | 9.54E−01 | 9.67E−04 |
| "106.711" | 3.33E−04 | 1.01E−04 | 1.62E−04 | 4.66E−03 | 4.72E−05 | 8.14E−04 |
| "106.712" | 1.18E−07 | 2.51E−07 | 2.57E−06 | 2.62E−06 | 7.16E−10 | 7.45E−03 |
| "106.714" | 1.73E−04 | 1.41E−04 | 1.45E−04 | 3.80E−04 | 1.18E−04 | 3.51E−04 |
| "106.715" | 7.68E−05 | 3.97E−05 | 4.56E−05 | 4.74E−04 | 2.52E−05 | 5.50E−03 |
| "106.716" | 1.75E−03 | 3.99E−04 | 2.01E−04 | 1.57E−02 | 4.99E−01 | 1.24E−04 |
| "106.717" | 1.08E−02 | 3.77E−02 | 6.80E−02 | 2.06E−03 | 1.94E−10 | 3.23E−01 |
| "106.718" | 2.16E−04 | 4.19E−05 | 1.73E−04 | 8.52E−01 | 7.45E−05 | 1.53E−02 |
| "106.719" | 1.53E−06 | 3.83E−08 | 2.86E−08 | 4.52E−08 | 5.96E−08 | 2.06E−01 |
| "106.720" | 6.46E−03 | 3.74E−03 | 1.11E−03 | 5.51E−02 | 6.41E−06 | 2.85E−02 |
| "106.721" | 1.18E−05 | 7.14E−06 | 1.71E−05 | 8.49E−06 | 1.20E−06 | 3.18E−05 |
| "106.722" | 1.68E−04 | 3.20E−04 | 8.97E−05 | 3.15E−04 | 1.20E−06 | 1.15E−03 |
| "106.723" | 1.36E−05 | 9.25E−06 | 1.39E−05 | 1.40E−04 | 1.39E−06 | 7.58E−03 |
| "106.724" | 3.22E−04 | 8.81E−04 | 6.01E−03 | 5.96E−01 | 1.08E−02 | 6.51E−01 |
| "106.725" | 2.27E−08 | 4.67E−09 | 3.94E−09 | 7.07E−09 | 3.10E−09 | 9.41E−01 |
| "106.726" | 1.53E−02 | 1.95E−02 | 1.24E−02 | 7.08E−03 | 1.20E−06 | 1.68E−04 |
| "106.727" | 4.00E−06 | 1.36E−06 | 2.01E−06 | 2.16E−06 | 2.66E−07 | 3.22E−01 |
| "106.728" | 3.38E−01 | 5.62E−01 | 8.47E−01 | 2.65E−01 | 6.71E−04 | 2.69E−03 |
| "106.729" | 8.97E−06 | 7.29E−06 | 1.37E−05 | 6.93E−06 | 5.44E−06 | 2.48E−01 |
| "106.730" | 2.05E−03 | 7.07E−04 | 3.02E−03 | 1.48E−02 | 4.11E−02 | 1.62E−01 |
| "106.731" | 1.02E−06 | 6.32E−08 | 5.97E−08 | 7.01E−08 | 5.97E−08 | 6.24E−01 |
| "106.732" | 2.51E−01 | 1.47E−01 | 1.32E−01 | 3.07E−01 | 5.64E−03 | 1.73E−02 |
| "106.733" | 1.30E−04 | 2.72E−04 | 6.31E−03 | 7.32E−01 | 1.23E−04 | 9.03E−01 |
| "106.734" | 1.92E−04 | 7.08E−05 | 2.81E−05 | 2.04E−05 | 5.44E−06 | 9.83E−06 |
| "106.735" | 4.94E−01 | 3.64E−01 | 8.98E−01 | 5.79E−02 | 1.20E−06 | 6.34E−06 |
| "106.736" | 1.49E−02 | 2.86E−02 | 6.92E−02 | 3.65E−02 | 1.52E−08 | 6.34E−01 |
| "106.738" | 2.58E−08 | 7.56E−09 | 5.85E−09 | 8.55E−09 | 3.10E−09 | 5.34E−01 |
| "106.739" | 1.64E−03 | 5.69E−04 | 5.69E−04 | 5.69E−04 | 7.15E−04 | 3.15E−01 |

TABLE 7-continued

Comprehensive neuronal culture screening results for R-GECO1.0 variants

| | | | | | | |
|---|---|---|---|---|---|---|
| "106.740" | 2.06E−04 | 1.02E−04 | 1.40E−04 | 1.13E−04 | 2.52E−05 | 5.51E−04 |
| "106.741" | 1.63E−06 | 1.52E−06 | 3.92E−06 | 1.95E−05 | 2.89E−10 | 9.91E−01 |
| "106.742" | 3.48E−01 | 6.04E−01 | 8.62E−01 | 9.42E−01 | 1.05E−02 | 1.51E−02 |
| "106.744" | 6.65E−06 | 7.95E−08 | 6.77E−08 | 1.01E−07 | 2.66E−07 | 2.68E−02 |
| "106.745" | 1.10E−07 | 6.41E−09 | 3.59E−08 | 6.66E−07 | 7.16E−10 | 5.02E−02 |
| "106.747" | 2.55E−03 | 1.03E−03 | 1.13E−03 | 1.20E−03 | 5.69E−04 | 9.72E−05 |
| "106.748" | 8.31E−06 | 1.25E−06 | 1.20E−06 | 1.37E−06 | 1.20E−06 | 7.49E−01 |
| "106.749" | 4.24E−03 | 2.10E−04 | 1.29E−04 | 1.23E−04 | 8.96E−03 | 1.24E−04 |
| "106.750" | 5.55E−04 | 1.48E−03 | 4.41E−03 | 4.05E−03 | 9.83E−05 | 2.47E−04 |
| "106.751" | 2.57E−05 | 5.44E−06 | 5.44E−06 | 5.44E−06 | 1.14E−04 | 6.74E−01 |
| "106.752" | 4.52E−02 | 6.74E−01 | 5.26E−01 | 1.71E−03 | 1.12E−04 | 1.88E−04 |
| "106.753" | 8.57E−06 | 1.73E−05 | 2.33E−04 | 5.93E−05 | 5.44E−06 | 7.89E−01 |
| "106.754" | 7.29E−06 | 5.44E−06 | 5.44E−06 | 5.44E−06 | 2.52E−05 | 4.91E−02 |
| "106.755" | 3.23E−05 | 5.51E−06 | 5.44E−06 | 5.44E−06 | 1.47E−03 | 3.56E−04 |
| "106.756" | 2.03E−03 | 5.47E−05 | 8.12E−05 | 9.80E−05 | 2.52E−05 | 3.70E−05 |
| "106.757" | 4.30E−02 | 6.90E−04 | 5.69E−04 | 5.69E−04 | 5.69E−04 | 4.03E−03 |
| "106.758" | 8.12E−01 | 4.60E−01 | 3.51E−01 | 4.65E−02 | 5.69E−04 | 5.88E−03 |
| "106.759" | 1.53E−03 | 6.34E−05 | 4.30E−05 | 3.92E−05 | 2.52E−05 | 2.64E−05 |
| "106.760" | 2.01E−03 | 1.67E−04 | 1.20E−04 | 1.26E−04 | 2.33E−01 | 1.23E−04 |
| "106.761" | 3.99E−03 | 7.06E−04 | 5.69E−04 | 5.76E−04 | 5.69E−04 | 5.90E−04 |
| "106.762" | 3.14E−03 | 7.20E−06 | 5.44E−06 | 6.27E−06 | 5.48E−02 | 5.44E−06 |
| "106.763" | 3.19E−01 | 5.38E−02 | 3.00E−02 | 5.41E−02 | 2.60E−05 | 7.04E−06 |
| "106.764" | 2.32E−03 | 3.04E−05 | 2.58E−05 | 3.54E−05 | 2.52E−05 | 2.52E−05 |
| "106.765" | 1.25E−01 | 2.68E−01 | 8.91E−01 | 5.20E−03 | 2.52E−05 | 4.74E−04 |
| "106.767" | 9.15E−05 | 6.05E−06 | 5.44E−06 | 5.44E−06 | 2.52E−05 | 6.27E−06 |
| "106.768" | 7.47E−05 | 1.39E−06 | 1.20E−06 | 1.27E−06 | 1.60E−06 | 1.20E−06 |
| "106.769" | 3.23E−03 | 2.93E−05 | 2.52E−05 | 2.52E−05 | 9.11E−04 | 2.52E−05 |
| "106.770" | 1.96E−04 | 3.00E−05 | 2.67E−05 | 3.22E−05 | 2.52E−05 | 2.55E−05 |
| "106.771" | 3.64E−01 | 4.92E−01 | 9.42E−01 | 2.03E−01 | 1.37E−06 | 3.53E−06 |
| "106.772" | 7.17E−03 | 5.48E−03 | 2.97E−03 | 1.16E−03 | 5.69E−04 | 7.77E−04 |
| "106.773" | 3.46E−01 | 4.21E−01 | 2.37E−01 | 9.80E−03 | 5.44E−06 | 1.41E−04 |
| "106.774" | 1.72E−01 | 1.44E−01 | 2.22E−01 | 2.98E−01 | 1.20E−06 | 5.65E−04 |
| "106.775" | 9.59E−03 | 4.38E−02 | 2.34E−01 | 1.51E−02 | 1.79E−04 | 4.79E−04 |
| "106.776" | 2.41E−01 | 1.58E−01 | 8.61E−02 | 2.39E−01 | 2.17E−01 | 7.05E−02 |
| "106.777" | 2.75E−04 | 2.60E−05 | 7.63E−06 | 8.66E−06 | 5.44E−06 | 5.91E−06 |
| "106.778" | 8.18E−01 | 1.12E−01 | 9.19E−02 | 9.91E−04 | 1.18E−04 | 7.07E−04 |
| "106.779" | 3.08E−01 | 5.72E−01 | 4.81E−01 | 5.65E−04 | 1.20E−06 | 1.24E−06 |
| "106.780" | 2.06E−02 | 5.29E−04 | 1.21E−04 | 4.83E−05 | 2.52E−05 | 3.18E−05 |
| "106.781" | 6.56E−03 | 1.34E−02 | 1.49E−01 | 9.22E−01 | 2.03E−06 | 7.87E−06 |
| "106.782" | 1.33E−02 | 3.04E−02 | 5.29E−02 | 9.36E−02 | 5.44E−06 | 1.91E−05 |
| "106.783" | 1.81E−12 | 3.64E−13 | 6.42E−13 | 8.95E−02 | 4.34E−02 | 1.59E−01 |
| "106.784" | 1.21E−03 | 1.18E−04 | 1.18E−04 | 1.20E−04 | 1.21E−02 | 2.57E−03 |
| "106.785" | 4.30E−01 | 8.87E−01 | 5.79E−01 | 5.99E−05 | 5.44E−06 | 1.66E−01 |
| "106.786" | 2.14E−02 | 1.07E−03 | 3.90E−03 | 1.21E−02 | 2.52E−05 | 7.08E−02 |
| "106.787" | 8.21E−01 | 7.31E−01 | 6.90E−01 | 4.39E−02 | 3.30E−05 | 6.06E−02 |
| "106.792" | 6.11E−03 | 1.11E−02 | 7.74E−03 | 1.48E−03 | 1.12E−04 | 2.47E−06 |
| "106.793" | 2.47E−04 | 1.99E−04 | 2.39E−04 | 1.78E−02 | 5.52E−02 | 2.19E−04 |
| "106.794" | 4.34E−01 | 3.85E−01 | 1.36E−01 | 2.95E−01 | 3.54E−01 | 8.46E−06 |
| "106.795" | 3.07E−01 | 2.73E−01 | 1.29E−01 | 1.36E−01 | 2.54E−07 | 6.23E−03 |
| "106.796" | 1.68E−01 | 1.55E−01 | 2.29E−01 | 1.62E−01 | 1.03E−02 | 2.86E−04 |
| "106.798" | 4.18E−04 | 5.92E−03 | 2.47E−02 | 3.59E−01 | 1.52E−01 | 4.01E−05 |
| "106.799" | 5.47E−05 | 4.39E−04 | 1.72E−04 | 5.34E−03 | 1.43E−03 | 6.03E−06 |
| "106.800" | 3.56E−02 | 1.02E−01 | 6.11E−02 | 8.78E−01 | 6.11E−02 | 4.31E−05 |
| "106.801" | 9.56E−01 | 7.78E−01 | 7.05E−01 | 4.20E−01 | 9.84E−01 | 2.38E−02 |
| "106.802" | 9.82E−07 | 3.65E−07 | 8.55E−07 | 5.28E−03 | 1.38E−02 | 9.46E−07 |
| "106.803" | 1.93E−01 | 1.74E−01 | 2.00E−01 | 2.10E−02 | 4.39E−01 | 1.88E−02 |
| "106.804" | 2.22E−02 | 2.07E−02 | 4.75E−02 | 6.57E−01 | 1.89E−02 | 3.26E−04 |
| "106.805" | 5.93E−01 | 8.58E−01 | 7.38E−01 | 7.82E−01 | 7.99E−02 | 1.00E−01 |
| "106.806" | 1.04E−04 | 8.03E−05 | 1.45E−04 | 1.04E−01 | 2.66E−01 | 1.01E−08 |
| "106.807" | 6.54E−04 | 9.57E−04 | 3.39E−03 | 3.53E−01 | 9.37E−07 | 8.71E−06 |
| "106.808" | 7.96E−03 | 6.78E−03 | 3.44E−02 | 3.47E−02 | 7.82E−03 | 1.17E−03 |
| "106.810" | 3.72E−02 | 2.42E−01 | 4.68E−01 | 4.80E−03 | 1.20E−06 | 2.77E−01 |
| "106.811" | 1.22E−01 | 2.93E−01 | 1.06E−01 | 5.85E−03 | 5.44E−06 | 3.27E−02 |
| "106.812" | 9.58E−04 | 4.32E−03 | 2.31E−02 | 2.85E−04 | 2.52E−05 | 2.55E−03 |
| "106.813" | 8.74E−04 | 6.81E−04 | 1.12E−03 | 4.85E−05 | 5.69E−04 | 6.81E−04 |
| "106.814" | 7.37E−05 | 1.94E−04 | 4.13E−04 | 3.92E−05 | 1.14E−03 | 2.10E−04 |
| "106.815" | 1.64E−03 | 5.22E−03 | 9.80E−03 | 5.26E−04 | 1.14E−05 | 3.49E−04 |
| "106.816" | 7.15E−04 | 7.41E−04 | 6.04E−04 | 5.97E−04 | 5.69E−04 | 1.08E−03 |
| "106.817" | 3.85E−01 | 7.92E−01 | 4.52E−01 | 4.25E−01 | 2.52E−05 | 1.74E−03 |
| "106.818" | 9.04E−02 | 1.79E−01 | 6.10E−01 | 8.18E−03 | 1.89E−05 | 1.29E−04 |
| "106.819" | 5.99E−04 | 1.12E−03 | 7.30E−05 | 2.66E−13 | 4.58E−19 | 2.44E−05 |
| "106.822" | 3.79E−02 | 1.21E−02 | 6.69E−03 | 2.81E−03 | 9.83E−04 | 5.38E−02 |
| "106.823" | 5.17E−02 | 1.81E−01 | 4.39E−02 | 2.94E−03 | 5.44E−06 | 2.07E−02 |
| "106.824" | 6.80E−01 | 5.61E−01 | 9.67E−01 | 5.27E−03 | 2.52E−05 | 6.79E−03 |
| "106.825" | 1.96E−02 | 2.55E−02 | 6.51E−03 | 1.17E−04 | 1.20E−06 | 2.16E−03 |
| "106.826" | 8.91E−01 | 9.55E−01 | 2.58E−01 | 1.28E−03 | 8.05E−04 | 1.10E−02 |
| "108.830" | 1.48E−01 | 8.07E−02 | 3.83E−02 | 7.62E−02 | 9.61E−01 | 2.35E−01 |
| "108.831" | 6.52E−01 | 3.99E−01 | 1.96E−01 | 5.23E−02 | 1.04E−02 | 6.83E−01 |

TABLE 7-continued

Comprehensive neuronal culture screening results for R-GECO1.0 variants

| | | | | | | |
|---|---|---|---|---|---|---|
| "108.832" | 7.40E−03 | 3.57E−01 | 1.65E−01 | 3.32E−04 | 3.17E−04 | 1.54E−04 |
| "108.833" | 7.98E−02 | 2.62E−01 | 9.96E−01 | 1.26E−01 | 7.50E−04 | 7.32E−01 |
| "108.837" | 6.68E−01 | 8.86E−01 | 8.34E−01 | 9.39E−01 | 9.78E−01 | 4.14E−03 |
| "108.838" | 1.93E−08 | 1.64E−09 | 3.94E−09 | 5.26E−02 | 8.34E−03 | 1.17E−01 |
| "108.839" | 1.66E−02 | 1.21E−03 | 8.77E−04 | 8.28E−02 | 8.19E−08 | 2.87E−02 |
| "108.840" | 1.41E−03 | 3.52E−02 | 4.93E−01 | 9.07E−05 | 2.93E−05 | 2.80E−05 |
| "108.841" | 3.31E−01 | 5.47E−01 | 8.40E−01 | 2.41E−01 | 8.54E−01 | 2.97E−01 |
| "108.842" | 8.97E−05 | 9.27E−04 | 1.53E−01 | 2.43E−04 | 1.79E−06 | 6.80E−04 |
| "108.843" | 3.07E−03 | 3.48E−02 | 2.35E−01 | 1.18E−01 | 1.97E−05 | 6.17E−01 |
| "108.844" | 1.34E−02 | 5.87E−02 | 3.65E−01 | 8.16E−01 | 2.83E−04 | 9.66E−01 |
| "108.845" | 5.57E−01 | 9.75E−01 | 5.51E−01 | 6.11E−01 | 5.53E−02 | 7.86E−02 |
| "108.847" | 2.17E−01 | 3.49E−01 | 8.94E−01 | 1.54E−01 | 1.85E−01 | 1.46E−01 |
| "108.849" | 1.52E−05 | 3.44E−04 | 1.83E−01 | 1.04E−04 | 1.44E−06 | 4.14E−04 |
| "108.850" | 3.02E−30 | 3.13E−21 | 7.20E−05 | 3.12E−29 | 2.07E−54 | 2.22E−31 |
| "108.852" | 2.57E−02 | 9.08E−02 | 7.22E−01 | 3.30E−01 | 2.53E−04 | 6.76E−01 |
| "108.853" | 1.83E−02 | 6.40E−02 | 6.24E−01 | 2.21E−02 | 1.33E−04 | 2.05E−02 |
| "108.854" | 5.93E−03 | 5.79E−02 | 6.43E−01 | 1.56E−02 | 1.33E−04 | 8.18E−01 |
| "108.858" | 1.30E−03 | 4.80E−03 | 2.35E−01 | 9.04E−03 | 6.42E−04 | 4.72E−02 |
| "108.859" | 6.08E−04 | 2.45E−03 | 6.31E−02 | 1.05E−01 | 1.73E−04 | 2.46E−01 |
| "108.878" | 3.41E−01 | 1.35E−01 | 2.58E−01 | 3.38E−01 | 5.76E−04 | 2.14E−01 |
| "108.890" | 8.44E−02 | 8.21E−02 | 2.55E−02 | 9.58E−03 | 5.01E−01 | 8.76E−01 |
| "108.893" | 8.12E−01 | 5.26E−01 | 7.84E−01 | 5.56E−01 | 6.19E−04 | 2.55E−03 |
| "108.901" | 3.14E−01 | 2.77E−01 | 1.99E−01 | 7.44E−01 | 2.12E−01 | 2.09E−02 |
| "108.914" | 1.94E−02 | 1.65E−02 | 2.86E−02 | 1.64E−02 | 8.72E−01 | 4.74E−03 |
| "108.915" | 6.68E−01 | 8.94E−01 | 5.41E−01 | 6.37E−03 | 1.27E−01 | 7.46E−04 |
| "108.916" | 8.95E−01 | 7.64E−01 | 3.58E−01 | 1.06E−03 | 3.46E−01 | 8.14E−04 |
| "108.917" | 4.04E−01 | 8.15E−01 | 7.97E−01 | 1.26E−01 | 2.25E−01 | 1.84E−02 |
| "108.921" | 9.61E−01 | 8.18E−01 | 4.82E−02 | 2.36E−04 | 1.08E−02 | 8.29E−04 |
| "108.922" | 8.67E−01 | 4.83E−01 | 6.32E−02 | 1.21E−03 | 1.64E−01 | 1.18E−04 |
| "108.923" | 2.59E−01 | 5.13E−02 | 1.09E−02 | 8.83E−04 | 6.96E−01 | 9.71E−02 |
| "108.924" | 7.23E−01 | 8.17E−01 | 2.08E−01 | 2.52E−04 | 1.43E−02 | 5.94E−03 |
| "108.925" | 4.42E−01 | 6.34E−01 | 4.20E−01 | 7.10E−04 | 1.49E−02 | 5.99E−03 |
| "108.926" | 6.43E−01 | 4.78E−01 | 8.37E−02 | 2.74E−04 | 1.94E−01 | 5.59E−03 |
| "108.927" | 1.18E−01 | 2.07E−02 | 1.78E−03 | 3.34E−05 | 2.17E−01 | 9.34E−05 |
| "108.928" | 8.89E−01 | 2.53E−01 | 2.56E−02 | 9.63E−05 | 5.89E−02 | 1.77E−03 |
| "108.929" | 3.85E−02 | 7.70E−01 | 7.19E−01 | 9.52E−02 | 2.68E−01 | 2.31E−02 |
| "108.930" | 6.31E−01 | 8.91E−01 | 1.86E−01 | 1.27E−04 | 1.73E−02 | 2.36E−04 |
| "106.933" | 5.02E−02 | 1.76E−02 | 1.05E−03 | 1.07E−03 | 5.69E−04 | 2.23E−01 |
| "106.934" | 1.24E−01 | 6.47E−02 | 2.09E−02 | 1.23E−04 | 4.72E−05 | 2.76E−03 |
| "106.938" | 3.84E−01 | 5.22E−01 | 2.89E−01 | 2.06E−02 | 7.02E−02 | 7.17E−01 |
| "106.941" | 4.72E−01 | 1.09E−01 | 9.43E−03 | 8.08E−03 | 3.10E−04 | 7.29E−02 |
| "106.942" | 2.21E−02 | 1.85E−01 | 5.02E−01 | 3.87E−04 | 7.90E−06 | 2.26E−01 |
| "106.943" | 1.65E−01 | 1.66E−01 | 3.07E−02 | 1.34E−01 | 6.47E−01 | 2.17E−02 |
| "106.944" | 1.03E−03 | 4.53E−04 | 6.85E−04 | 5.68E−05 | 9.44E−04 | 8.10E−01 |
| "106.945" | 4.71E−04 | 3.73E−04 | 3.06E−04 | 3.59E−04 | 2.13E−05 | 7.69E−05 |
| "106.946" | 3.80E−04 | 7.42E−05 | 7.02E−05 | 8.55E−03 | 6.14E−04 | 2.34E−01 |
| "106.947" | 5.57E−03 | 3.86E−03 | 4.24E−03 | 1.39E−01 | 7.67E−03 | 3.17E−04 |
| "106.948" | 2.89E−01 | 1.62E−04 | 2.52E−04 | 1.15E−03 | 3.76E−02 | 6.66E−01 |
| "106.949" | 6.90E−03 | 2.52E−03 | 1.22E−03 | 8.65E−04 | 3.36E−03 | 1.45E−04 |
| "106.950" | 2.36E−03 | 4.50E−03 | 7.24E−03 | 1.21E−03 | 1.03E−03 | 8.96E−02 |
| "106.951" | 1.61E−04 | 2.04E−04 | 7.33E−05 | 3.07E−05 | 1.62E−04 | 6.37E−01 |
| "106.957" | 3.64E−02 | 1.51E−02 | 2.67E−02 | 4.02E−02 | 3.05E−03 | 1.45E−04 |
| "106.1000" | 3.33E−04 | 2.42E−03 | 9.27E−01 | 8.97E−05 | 7.34E−05 | 1.07E−04 |
| "106.1001" | 4.97E−04 | 1.34E−02 | 5.81E−01 | 6.86E−05 | 3.76E−05 | 1.81E−04 |
| "106.1003" | 1.41E−06 | 1.39E−05 | 2.93E−02 | 4.45E−06 | 1.08E−06 | 2.63E−03 |
| "106.1004" | 4.98E−06 | 7.95E−05 | 4.65E−02 | 1.74E−05 | 1.62E−05 | 2.31E−03 |
| "106.1005" | 2.68E−04 | 2.96E−03 | 4.95E−02 | 1.26E−01 | 5.81E−01 | 9.03E−01 |
| "106.1006" | 1.92E−06 | 1.66E−05 | 1.53E−02 | 5.36E−05 | 7.56E−07 | 3.12E−02 |
| "106.1007" | 5.72E−13 | 5.41E−13 | 7.18E−11 | 2.82E−01 | 2.45E−05 | 3.56E−04 |
| "106.1008" | 8.81E−03 | 1.15E−01 | 8.24E−01 | 1.80E−02 | 6.84E−04 | 9.21E−01 |
| "106.1009" | 3.82E−07 | 2.16E−06 | 1.11E−02 | 1.87E−05 | 9.77E−07 | 2.99E−01 |
| "106.1010" | 2.02E−04 | 2.41E−03 | 2.17E−01 | 2.10E−04 | 5.80E−05 | 3.15E−01 |
| "106.1011" | 4.08E−07 | 1.35E−06 | 4.89E−04 | 4.82E−04 | 3.06E−05 | 2.93E−02 |
| "106.1012" | 6.91E−06 | 5.56E−05 | 4.67E−03 | 8.03E−02 | 6.21E−06 | 6.30E−01 |
| "106.1013" | 5.84E−04 | 7.91E−04 | 5.23E−03 | 2.25E−01 | 3.36E−04 | 7.72E−01 |
| "106.1014" | 3.76E−04 | 2.09E−03 | 4.12E−02 | 3.90E−02 | 3.04E−02 | 8.21E−01 |
| "106.1015" | 2.73E−01 | 3.14E−01 | 4.47E−02 | 1.34E−03 | 5.69E−04 | 6.06E−03 |
| "106.1018" | 1.71E−01 | 5.96E−01 | 7.07E−01 | 4.70E−03 | 3.23E−04 | 8.76E−02 |
| "106.1020" | 1.17E−02 | 2.25E−02 | 2.59E−01 | 1.99E−02 | 2.31E−03 | 1.19E−02 |
| "106.1021" | 2.46E−02 | 1.37E−01 | 4.28E−01 | 1.94E−01 | 3.19E−03 | 6.38E−01 |
| "106.1022" | 4.24E−01 | 8.19E−01 | 6.72E−01 | 9.04E−02 | 4.31E−03 | 1.02E−01 |
| "106.1023" | 1.49E−03 | 1.62E−02 | 5.01E−01 | 2.12E−02 | 4.08E−03 | 2.22E−01 |
| "106.1024" | 6.58E−01 | 7.19E−01 | 8.41E−01 | 8.94E−02 | 2.66E−07 | 6.50E−03 |
| "106.1025" | 6.80E−01 | 5.97E−01 | 9.50E−01 | 1.43E−02 | 3.10E−09 | 3.32E−03 |
| "106.1027" | 2.57E−03 | 4.85E−03 | 1.22E−01 | 2.57E−03 | 3.89E−06 | 3.79E−02 |
| "106.1028" | 9.11E−01 | 5.87E−01 | 9.70E−01 | 4.86E−04 | 5.97E−08 | 2.28E−01 |
| "106.1029" | 5.43E−03 | 4.34E−03 | 4.84E−04 | 5.28E−05 | 5.44E−06 | 1.33E−01 |
| "106.1030" | 6.84E−02 | 6.84E−02 | 1.63E−01 | 2.12E−01 | 1.17E−05 | 3.14E−02 |

TABLE 7-continued

Comprehensive neuronal culture screening results for R-GECO1.0 variants

| | | | | | | |
|---|---|---|---|---|---|---|
| "106.1031" | 7.11E−01 | 7.35E−01 | 2.07E−01 | 2.13E−03 | 2.20E−08 | 2.14E−02 |
| "106.1032" | 8.40E−06 | 1.86E−04 | 1.67E−01 | 2.61E−05 | 1.54E−06 | 8.55E−05 |
| "106.1033" | 5.32E−06 | 1.55E−05 | 2.80E−04 | 4.09E−03 | 1.13E−05 | 1.81E−02 |
| "106.1034" | 3.53E−05 | 3.04E−05 | 9.58E−04 | 2.63E−01 | 2.32E−01 | 7.30E−01 |
| "106.1035" | 5.44E−06 | 1.91E−05 | 9.42E−04 | 5.58E−03 | 1.05E−05 | 4.30E−02 |
| "106.1036" | 3.12E−06 | 7.54E−06 | 1.24E−03 | 1.25E−04 | 9.98E−04 | 2.38E−04 |
| "106.1037" | 1.14E−08 | 7.96E−08 | 2.37E−05 | 4.24E−02 | 3.00E−03 | 6.90E−02 |
| "106.1038" | 1.11E−11 | 1.55E−11 | 1.58E−08 | 2.96E−05 | 6.71E−09 | 2.50E−07 |
| "106.1039" | 2.53E−03 | 1.20E−03 | 3.13E−03 | 2.10E−01 | 4.23E−02 | 8.79E−03 |
| "106.1040" | 1.05E−04 | 2.14E−04 | 3.78E−03 | 2.29E−01 | 8.89E−05 | 7.74E−03 |
| "106.1041" | 2.24E−01 | 1.08E−03 | 1.64E−02 | 5.60E−02 | 9.59E−02 | 9.96E−02 |
| "106.1042" | 1.11E−03 | 5.89E−04 | 1.33E−02 | 6.83E−02 | 1.31E−03 | 5.45E−02 |
| "106.1043" | 3.57E−03 | 1.40E−03 | 1.02E−04 | 1.40E−05 | 5.44E−06 | 1.09E−02 |
| "106.1044" | 7.01E−03 | 1.17E−03 | 3.84E−04 | 4.88E−05 | 2.52E−05 | 2.97E−01 |
| "106.1046" | 3.03E−01 | 3.79E−01 | 8.94E−01 | 1.22E−01 | 2.59E−01 | 4.79E−01 |
| "106.1048" | 1.62E−02 | 4.97E−03 | 1.44E−03 | 8.94E−01 | 6.90E−08 | 1.77E−02 |
| "106.1053" | 8.76E−06 | 1.65E−05 | 1.86E−03 | 2.16E−03 | 3.45E−05 | 3.57E−03 |
| "106.1054" | 2.23E−01 | 1.42E−01 | 8.05E−02 | 4.35E−04 | 7.16E−10 | 1.32E−02 |
| "108.1057" | 6.88E−01 | 7.03E−01 | 3.95E−01 | 6.88E−01 | 4.12E−01 | 7.64E−01 |
| "108.1058" | 9.46E−01 | 4.36E−01 | 2.03E−01 | 8.42E−01 | 1.39E−02 | 1.16E−01 |
| "108.1066" | 4.15E−01 | 1.82E−01 | 3.06E−01 | 8.85E−01 | 4.28E−03 | 5.47E−01 |
| "108.1069" | 1.00E+00 | 2.34E−01 | 3.35E−01 | 9.89E−02 | 4.47E−02 | 9.75E−01 |
| "108.1071" | 7.42E−01 | 2.15E−01 | 1.59E−01 | 8.69E−02 | 1.84E−03 | 2.60E−01 |
| "108.1072" | 5.77E−01 | 3.29E−01 | 1.66E−01 | 1.68E−01 | 6.37E−03 | 9.92E−01 |
| "108.1073" | 1.75E−01 | 1.14E−01 | 5.40E−02 | 1.80E−01 | 3.69E−04 | 1.83E−01 |
| "108.1074" | 1.83E−01 | 1.30E−01 | 5.76E−01 | 9.73E−01 | 2.20E−03 | 1.00E+00 |
| "108.1078" | 2.63E−02 | 2.23E−02 | 4.29E−02 | 3.19E−01 | 5.51E−01 | 9.83E−02 |
| "108.1079" | 6.06E−01 | 5.66E−01 | 8.81E−01 | 3.91E−01 | 1.47E−02 | 4.84E−01 |
| "108.1080" | 5.54E−01 | 6.50E−01 | 5.79E−01 | 5.39E−01 | 1.66E−03 | 3.86E−01 |
| "108.1082" | 1.62E−01 | 7.63E−02 | 3.33E−02 | 9.89E−01 | 1.08E−02 | 9.56E−02 |
| "108.1083" | 7.17E−01 | 2.65E−01 | 7.07E−01 | 5.58E−01 | 2.54E−04 | 7.58E−01 |
| "108.1084" | 3.17E−01 | 4.21E−01 | 2.33E−01 | 2.00E−01 | 1.76E−03 | 1.67E−01 |
| "108.1086" | 1.15E−01 | 5.22E−02 | 3.25E−01 | 7.10E−01 | 6.24E−03 | 8.43E−01 |
| "108.1103" | 2.32E−01 | 1.23E−01 | 5.36E−02 | 3.61E−02 | 1.45E−02 | 9.71E−01 |
| "106.1104" | 3.43E−03 | 3.46E−04 | 3.38E−03 | 3.61E−02 | 6.05E−06 | 2.91E−01 |
| "106.1105" | 6.02E−04 | 1.38E−04 | 1.35E−04 | 4.06E−04 | 1.18E−04 | 9.43E−01 |
| "106.1106" | 8.97E−06 | 1.25E−05 | 1.34E−05 | 1.07E−04 | 5.44E−06 | 6.72E−01 |
| "106.1107" | 7.32E−04 | 3.72E−04 | 5.40E−04 | 2.62E−03 | 4.21E−05 | 3.78E−02 |
| "106.1108" | 5.90E−04 | 5.69E−04 | 5.83E−04 | 6.26E−04 | 5.69E−04 | 1.85E−02 |
| "106.1109" | 6.81E−01 | 6.62E−01 | 4.60E−01 | 2.04E−01 | 3.63E−04 | 2.65E−02 |
| "106.1110" | 1.66E−01 | 2.43E−02 | 1.80E−02 | 7.83E−03 | 5.44E−06 | 3.89E−01 |
| "106.1113" | 2.26E−02 | 2.75E−03 | 2.17E−03 | 1.92E−03 | 5.69E−04 | 2.16E−01 |
| "106.1114" | 1.39E−04 | 1.97E−03 | 2.88E−01 | 8.58E−03 | 1.51E−06 | 2.18E−04 |
| "106.1115" | 5.76E−04 | 5.90E−04 | 6.12E−04 | 7.15E−04 | 5.69E−04 | 2.80E−02 |
| "106.1116" | 5.93E−01 | 2.22E−01 | 1.32E−01 | 1.61E−01 | 5.21E−05 | 8.69E−01 |
| "106.1117" | 8.32E−01 | 6.55E−01 | 3.59E−01 | 2.49E−02 | 9.58E−01 | 9.37E−02 |
| "106.1118" | 1.18E−01 | 1.99E−02 | 1.82E−02 | 1.82E−02 | 3.20E−01 | 1.45E−02 |
| "106.1119" | 1.37E−05 | 2.68E−05 | 1.26E−04 | 1.35E−04 | 1.80E−04 | 2.23E−01 |
| "106.1120" | 1.04E−03 | 1.52E−02 | 2.72E−01 | 4.39E−02 | 2.93E−05 | 7.30E−03 |
| "106.1121" | 1.27E−01 | 1.73E−01 | 7.62E−02 | 3.31E−02 | 5.14E−03 | 2.08E−01 |
| "106.1122" | 2.20E−03 | 7.47E−03 | 3.85E−02 | 6.26E−01 | 6.44E−02 | 3.54E−02 |
| "106.1123" | 1.35E−02 | 1.73E−02 | 2.10E−02 | 8.04E−01 | 3.47E−02 | 7.92E−01 |
| "106.1124" | 3.94E−02 | 2.46E−02 | 9.83E−02 | 5.69E−01 | 5.73E−03 | 1.28E−03 |
| "106.1125" | 2.06E−14 | 2.74E−13 | 8.42E−13 | 4.95E−14 | 7.13E−18 | 2.23E−04 |
| "106.1126" | 2.98E−06 | 8.58E−05 | 5.43E−03 | 4.94E−03 | 3.69E−05 | 4.08E−04 |
| "106.1128" | 7.25E−01 | 7.82E−01 | 9.36E−01 | 5.22E−01 | 4.56E−03 | 3.23E−03 |
| "106.1129" | 4.77E−01 | 9.05E−01 | 6.35E−01 | 5.31E−01 | 2.52E−05 | 6.70E−01 |
| "106.1130" | 2.25E−01 | 2.35E−01 | 1.20E−01 | 1.53E−01 | 4.38E−04 | 2.90E−02 |
| "106.1131" | 2.47E−01 | 9.18E−02 | 6.81E−02 | 8.00E−03 | 5.44E−06 | 1.48E−02 |
| "106.1135" | 1.02E−03 | 1.17E−03 | 1.39E−03 | 1.50E−03 | 6.62E−03 | 3.72E−01 |
| "106.1136" | 1.42E−01 | 1.38E−02 | 6.11E−02 | 1.25E−02 | 1.20E−03 | 9.57E−01 |
| "106.1139" | 2.83E−04 | 1.18E−04 | 1.27E−04 | 1.41E−04 | 1.18E−04 | 8.96E−01 |
| "106.1140" | 1.99E−01 | 1.31E−01 | 8.97E−02 | 8.01E−03 | 9.71E−02 | 1.72E−02 |
| "106.1144" | 6.81E−04 | 7.15E−04 | 1.20E−03 | 3.63E−03 | 5.69E−04 | 1.69E−01 |
| "106.1145" | 1.52E−03 | 1.40E−05 | 1.55E−05 | 2.78E−05 | 6.65E−05 | 1.14E−01 |
| "106.1163" | 8.83E−01 | 4.56E−01 | 1.11E−01 | 1.66E−01 | 6.70E−02 | 8.68E−01 |
| "106.1164" | 4.90E−01 | 3.30E−01 | 7.62E−02 | 2.80E−02 | 3.36E−03 | 4.81E−01 |
| "106.1165" | 6.57E−01 | 5.60E−02 | 9.27E−03 | 1.76E−02 | 1.41E−01 | 9.10E−01 |
| "106.1166" | 4.15E−03 | 9.58E−04 | 3.72E−04 | 1.58E−02 | 2.26E−03 | 4.57E−01 |
| "106.1167" | 4.44E−01 | 4.62E−01 | 8.14E−02 | 4.09E−02 | 1.14E−03 | 5.72E−01 |
| "106.1168" | 4.54E−03 | 4.79E−04 | 9.22E−04 | 2.30E−03 | 2.77E−05 | 8.51E−01 |
| "106.1169" | 8.56E−02 | 2.34E−02 | 2.02E−03 | 8.40E−03 | 6.34E−01 | 1.74E−01 |
| "106.1170" | 4.01E−02 | 5.47E−01 | 6.77E−01 | 2.84E−01 | 6.07E−07 | 2.60E−01 |
| "106.1175" | 9.05E−01 | 8.40E−01 | 3.48E−01 | 1.39E−02 | 8.38E−01 | 9.10E−01 |
| "106.1176" | 1.33E−01 | 5.79E−02 | 8.40E−02 | 9.39E−03 | 1.03E−02 | 6.54E−01 |
| "106.1177" | 4.24E−04 | 1.35E−04 | 1.27E−04 | 1.77E−04 | 1.54E−04 | 2.04E−01 |
| "106.1178" | 7.46E−04 | 2.06E−04 | 1.55E−04 | 2.23E−04 | 1.18E−04 | 2.59E−01 |
| "106.1179" | 6.82E−03 | 8.64E−04 | 7.96E−04 | 2.34E−03 | 5.69E−04 | 2.03E−01 |

TABLE 7-continued

Comprehensive neuronal culture screening results for R-GECO1.0 variants

| | | | | | | |
|---|---|---|---|---|---|---|
| "106.1180" | 9.64E−01 | 8.57E−01 | 2.30E−01 | 6.65E−02 | 3.33E−01 | 5.09E−03 |
| "106.1181" | 1.67E−03 | 4.53E−04 | 5.28E−04 | 4.29E−04 | 1.18E−04 | 4.16E−01 |
| "106.1183" | 2.90E−05 | 7.04E−06 | 5.77E−06 | 8.57E−06 | 1.00E−02 | 2.31E−02 |
| "106.1185" | 3.65E−06 | 1.20E−06 | 1.20E−06 | 1.51E−06 | 4.66E−06 | 8.86E−02 |
| "106.1186" | 8.74E−04 | 5.83E−04 | 5.69E−04 | 6.12E−04 | 5.31E−03 | 1.57E−03 |
| "106.1187" | 9.04E−03 | 8.95E−04 | 8.05E−04 | 9.27E−04 | 5.69E−04 | 8.10E−02 |
| "106.1189" | 6.75E−03 | 8.34E−04 | 5.69E−04 | 5.83E−04 | 5.90E−01 | 6.02E−02 |
| "106.1193" | 6.22E−01 | 6.86E−01 | 4.84E−01 | 1.28E−02 | 5.84E−06 | 1.52E−01 |
| "106.1195" | 8.08E−01 | 5.83E−02 | 8.34E−04 | 4.41E−04 | 1.96E−01 | 9.71E−02 |
| "106.1196" | 7.84E−02 | 2.76E−03 | 1.31E−04 | 9.94E−06 | 7.46E−06 | 8.42E−03 |
| "106.1197" | 4.93E−04 | 1.81E−04 | 4.46E−05 | 3.60E−05 | 1.87E−05 | 4.42E−02 |
| "106.1202" | 8.96E−03 | 5.82E−03 | 1.54E−03 | 8.74E−04 | 5.69E−04 | 8.94E−01 |
| "106.1203" | 3.13E−05 | 7.99E−06 | 6.34E−06 | 7.72E−06 | 5.44E−06 | 1.19E−01 |
| "106.1205" | 1.38E−03 | 5.46E−04 | 1.52E−04 | 1.54E−04 | 1.18E−04 | 4.61E−03 |
| "106.1209" | 1.45E−04 | 1.21E−04 | 1.26E−04 | 1.29E−04 | 1.18E−04 | 7.91E−02 |
| "106.1212" | 7.37E−01 | 8.36E−01 | 1.64E−01 | 3.94E−03 | 7.73E−02 | 1.41E−02 |
| "106.1215" | 6.59E−01 | 5.89E−01 | 3.49E−01 | 6.54E−01 | 1.54E−01 | 8.71E−01 |
| "106.1216" | 6.84E−06 | 4.40E−05 | 1.34E−03 | 2.65E−01 | 1.08E−05 | 6.87E−01 |
| "106.1217" | 9.61E−01 | 8.92E−01 | 5.95E−01 | 9.38E−01 | 3.93E−04 | 2.97E−04 |
| "106.1218" | 2.96E−02 | 5.62E−03 | 1.01E−02 | 7.40E−01 | 5.42E−05 | 1.67E−02 |
| "106.1219" | 1.44E−01 | 3.28E−02 | 2.93E−02 | 1.27E−02 | 1.48E−03 | 2.36E−01 |
| "106.1220" | 2.19E−02 | 5.70E−02 | 1.62E−01 | 6.17E−01 | 1.30E−02 | 4.69E−03 |
| "106.1221" | 4.42E−01 | 9.52E−01 | 4.38E−01 | 3.33E−01 | 7.90E−03 | 2.07E−01 |
| "106.1222" | 7.16E−01 | 9.68E−01 | 8.71E−01 | 1.71E−01 | 1.66E−02 | 5.66E−01 |
| "106.1223" | 6.72E−01 | 6.76E−01 | 9.35E−01 | 6.93E−01 | 4.33E−01 | 5.01E−03 |
| "106.1224" | 1.16E−01 | 7.86E−02 | 9.31E−02 | 8.10E−02 | 1.67E−02 | 7.51E−02 |
| "106.1225" | 1.21E−02 | 5.55E−02 | 3.67E−02 | 7.72E−01 | 3.88E−02 | 2.37E−02 |
| "106.1226" | 4.32E−01 | 9.25E−01 | 3.19E−01 | 2.92E−01 | 3.30E−02 | 4.35E−01 |
| "106.1228" | 4.79E−01 | 9.22E−01 | 3.42E−01 | 2.01E−01 | 1.27E−03 | 7.50E−01 |
| "106.1229" | 4.24E−02 | 7.03E−02 | 6.82E−02 | 6.21E−02 | 1.95E−02 | 2.38E−03 |
| "106.1230" | 1.80E−02 | 7.52E−02 | 1.83E−01 | 3.92E−01 | 3.51E−01 | 6.77E−06 |
| "106.1231" | 1.45E−02 | 1.17E−01 | 3.05E−01 | 7.75E−01 | 7.93E−04 | 9.19E−03 |
| "106.1232" | 5.46E−06 | 6.85E−08 | 3.76E−07 | 1.13E−05 | 5.15E−06 | 6.09E−03 |
| "106.1233" | 2.28E−04 | 4.52E−05 | 1.85E−04 | 8.24E−04 | 3.71E−06 | 9.95E−01 |
| "106.1235" | 5.10E−02 | 5.84E−02 | 8.44E−02 | 8.99E−02 | 3.93E−01 | 8.15E−01 |
| "106.1237" | 3.42E−01 | 3.01E−01 | 9.73E−01 | 2.99E−01 | 1.49E−01 | 3.72E−02 |
| "106.1238" | 2.68E−02 | 3.04E−02 | 1.37E−01 | 4.00E−01 | 2.50E−02 | 2.27E−01 |
| "106.1241" | 2.13E−02 | 1.72E−02 | 7.67E−02 | 2.55E−01 | 4.87E−01 | 2.39E−04 |
| "106.1244" | 9.48E−02 | 3.42E−02 | 3.21E−02 | 5.85E−01 | 5.35E−02 | 6.80E−02 |
| "106.1246" | 6.92E−02 | 7.75E−02 | 3.96E−01 | 1.30E−02 | 1.41E−02 | 1.98E−04 |
| "106.1247" | 2.10E−03 | 1.64E−02 | 3.09E−01 | 2.12E−02 | 3.02E−03 | 3.49E−03 |
| "106.1248" | 2.18E−02 | 9.59E−02 | 6.18E−01 | 3.71E−01 | 2.67E−02 | 2.18E−02 |
| "106.1249" | 8.01E−02 | 7.71E−02 | 2.58E−01 | 2.57E−01 | 9.46E−01 | 3.51E−03 |
| "106.1250" | 1.70E−03 | 1.37E−04 | 2.21E−03 | 2.66E−01 | 5.98E−05 | 4.26E−02 |
| "106.1251" | 1.11E−10 | 2.68E−08 | 3.19E−04 | 2.11E−01 | 3.64E−19 | 8.47E−02 |
| "106.1252" | 4.93E−04 | 1.36E−03 | 2.87E−02 | 3.80E−01 | 2.57E−05 | 7.08E−01 |
| "106.1253" | 9.11E−04 | 6.37E−03 | 2.06E−01 | 2.59E−02 | 1.50E−04 | 2.52E−03 |
| "106.1254" | 2.63E−03 | 4.50E−02 | 7.94E−01 | 1.32E−02 | 2.13E−05 | 9.50E−06 |
| "106.1255" | 1.58E−04 | 6.96E−03 | 7.96E−01 | 5.86E−05 | 6.34E−06 | 2.02E−02 |
| "106.1256" | 3.00E−02 | 7.11E−02 | 7.73E−01 | 8.18E−02 | 1.15E−05 | 6.70E−02 |
| "106.1257" | 2.01E−02 | 1.62E−01 | 8.78E−01 | 5.52E−03 | 1.81E−04 | 6.15E−03 |
| "106.1258" | 1.39E−02 | 4.50E−02 | 2.91E−01 | 5.51E−01 | 3.54E−05 | 2.40E−01 |
| "106.1259" | 5.64E−02 | 1.23E−01 | 4.64E−01 | 7.64E−02 | 2.91E−03 | 2.06E−02 |
| "106.1260" | 4.00E−03 | 2.49E−02 | 6.45E−01 | 4.07E−03 | 3.00E−05 | 1.85E−01 |
| "106.1261" | 7.35E−01 | 3.74E−01 | 2.35E−01 | 3.30E−01 | 9.73E−01 | 9.95E−04 |
| "106.1262" | 7.09E−02 | 6.85E−01 | 3.20E−01 | 3.17E−01 | 4.53E−01 | 5.67E−03 |
| "106.1264" | 9.99E−01 | 7.00E−01 | 7.54E−01 | 4.08E−01 | 1.81E−01 | 1.78E−03 |
| "106.1265" | 1.42E−01 | 1.50E−01 | 2.45E−01 | 6.61E−01 | 6.78E−03 | 2.81E−01 |
| "106.1267" | 1.98E−01 | 1.42E−01 | 5.35E−01 | 6.45E−01 | 5.85E−01 | 8.97E−04 |
| "106.1272" | 6.10E−01 | 4.26E−01 | 3.75E−01 | 4.38E−01 | 3.17E−01 | 6.32E−01 |
| "106.1274" | 1.25E−04 | 1.86E−05 | 5.59E−05 | 6.87E−05 | 6.69E−02 | 1.22E−01 |
| "106.1275" | 2.11E−01 | 2.55E−02 | 4.25E−02 | 2.22E−01 | 5.21E−01 | 7.80E−01 |
| "106.1277" | 8.07E−01 | 2.42E−01 | 1.48E−01 | 1.77E−01 | 7.64E−01 | 7.98E−01 |
| "106.1278" | 5.99E−01 | 9.21E−02 | 5.52E−02 | 3.45E−02 | 3.99E−01 | 1.07E−02 |
| "106.1282" | 8.20E−01 | 9.73E−01 | 5.42E−02 | 2.64E−04 | 1.73E−02 | 2.92E−05 |
| "106.1284" | 3.06E−02 | 4.71E−02 | 4.83E−02 | 8.96E−03 | 9.27E−01 | 2.41E−01 |
| "106.1285" | 4.98E−02 | 8.35E−03 | 9.48E−02 | 8.34E−01 | 6.00E−02 | 3.17E−01 |
| "106.1286" | 1.55E−02 | 1.02E−02 | 7.43E−02 | 7.42E−01 | 2.25E−01 | 4.58E−01 |
| "106.1287" | 3.31E−02 | 1.25E−01 | 9.37E−02 | 7.83E−03 | 2.00E−01 | 1.38E−02 |
| "106.1288" | 5.74E−02 | 8.04E−02 | 1.15E−01 | 2.28E−02 | 5.21E−01 | 5.04E−02 |
| "106.1289" | 6.10E−02 | 2.00E−01 | 1.35E−01 | 1.43E−01 | 8.62E−02 | 8.46E−01 |
| "106.1290" | 1.63E−01 | 5.86E−01 | 2.79E−01 | 3.97E−02 | 2.12E−01 | 6.30E−02 |
| "106.1292" | 4.59E−01 | 6.59E−01 | 4.30E−01 | 2.04E−01 | 1.88E−01 | 7.19E−01 |
| "106.1293" | 3.26E−01 | 8.29E−01 | 7.44E−01 | 1.68E−01 | 6.24E−01 | 6.19E−01 |
| "106.1294" | 7.34E−01 | 1.95E−01 | 4.45E−01 | 8.04E−01 | 1.38E−02 | 1.50E−02 |
| "106.1295" | 1.85E−02 | 6.82E−03 | 2.40E−02 | 1.11E−01 | 7.60E−02 | 1.28E−01 |
| "106.1296" | 3.39E−03 | 1.04E−02 | 3.61E−02 | 1.35E−01 | 2.56E−01 | 4.35E−01 |
| "106.1297" | 7.53E−02 | 6.59E−02 | 5.08E−01 | 3.94E−01 | 1.13E−02 | 4.83E−01 |

TABLE 7-continued

Comprehensive neuronal culture screening results for R-GECO1.0 variants

| | | | | | | |
|---|---|---|---|---|---|---|
| "106.1298" | 6.99E−01 | 8.42E−01 | 4.51E−01 | 1.12E−01 | 2.53E−01 | 3.49E−01 |
| "106.1300" | 1.41E−01 | 1.59E−02 | 4.74E−02 | 1.50E−01 | 2.80E−02 | 1.28E−02 |
| "106.1301" | 5.98E−01 | 2.22E−01 | 5.52E−01 | 4.98E−01 | 3.71E−03 | 1.02E−01 |
| "106.1302" | 3.77E−01 | 9.52E−01 | 6.11E−01 | 5.38E−01 | 6.96E−01 | 8.73E−01 |
| "106.1303" | 6.22E−01 | 8.13E−01 | 3.56E−01 | 4.80E−02 | 3.98E−01 | 2.52E−05 |
| "106.1304" | 1.73E−01 | 9.81E−02 | 1.98E−01 | 5.74E−01 | 4.74E−01 | 8.93E−01 |
| "106.1305" | 2.59E−01 | 1.53E−01 | 2.48E−01 | 3.79E−01 | 1.46E−01 | 1.57E−04 |
| "106.1307" | 6.59E−01 | 8.41E−01 | 7.00E−01 | 3.38E−01 | 1.86E−01 | 1.75E−04 |
| "106.1309" | 3.96E−02 | 1.34E−01 | 1.38E−02 | 1.43E−03 | 9.69E−01 | 2.73E−05 |
| "106.1310" | 9.78E−01 | 6.81E−01 | 3.38E−01 | 5.02E−02 | 8.66E−01 | 1.90E−03 |
| "106.1312" | 3.33E−01 | 4.00E−02 | 1.11E−02 | 2.20E−03 | 1.43E−01 | 6.34E−06 |
| "106.1315" | 2.79E−01 | 5.61E−01 | 4.95E−01 | 3.63E−02 | 6.97E−04 | 3.72E−02 |
| "106.1316" | 3.25E−02 | 1.17E−02 | 4.98E−03 | 2.86E−03 | 7.25E−01 | 2.52E−05 |
| "106.1318" | 8.93E−02 | 1.96E−01 | 5.84E−02 | 6.43E−03 | 3.34E−01 | 5.76E−04 |
| "106.1319" | 6.29E−02 | 1.23E−02 | 2.08E−03 | 7.77E−04 | 1.72E−01 | 5.76E−04 |
| "106.1320" | 5.30E−01 | 7.73E−01 | 7.23E−01 | 5.81E−01 | 1.78E−01 | 1.92E−03 |
| "106.1327" | 3.88E−04 | 2.89E−03 | 2.28E−02 | 4.10E−01 | 5.01E−02 | 7.97E−01 |
| "106.1333" | 1.63E−02 | 5.34E−02 | 5.34E−02 | 1.35E−01 | 2.05E−03 | 9.25E−02 |
| "106.1357" | 3.26E−01 | 2.64E−01 | 1.32E−01 | 1.84E−01 | 6.26E−04 | 6.08E−04 |
| "106.1358" | 2.42E−03 | 5.40E−04 | 1.18E−03 | 3.57E−04 | 4.32E−01 | 2.41E−02 |
| "106.1360" | 9.45E−01 | 5.95E−01 | 5.11E−01 | 4.09E−03 | 8.73E−01 | 1.46E−03 |
| "106.1368" | 1.37E−02 | 2.89E−02 | 1.36E−01 | 6.29E−01 | 9.60E−04 | 4.25E−01 |
| "106.1377" | 6.76E−01 | 9.89E−02 | 7.76E−02 | 1.44E−01 | 3.07E−03 | 1.49E−01 |
| "106.1386" | 2.64E−02 | 9.67E−03 | 9.37E−02 | 8.81E−01 | 2.66E−02 | 2.10E−02 |
| "106.1387" | 5.22E−02 | 1.31E−01 | 2.64E−01 | 3.70E−01 | 8.63E−01 | 4.37E−02 |
| "106.1388" | 1.34E−01 | 1.64E−01 | 4.47E−01 | 8.81E−01 | 7.47E−01 | 1.38E−02 |
| "106.1389" | 1.24E−01 | 5.07E−01 | 8.86E−01 | 7.68E−01 | 9.27E−01 | 3.16E−01 |
| "106.1390" | 1.55E−03 | 3.05E−03 | 4.92E−02 | 7.33E−01 | 2.33E−03 | 8.80E−02 |
| "106.1391" | 4.48E−04 | 3.29E−03 | 2.23E−02 | 2.19E−01 | 1.76E−01 | 3.03E−02 |
| "106.1392" | 9.20E−01 | 3.86E−01 | 1.87E−01 | 6.07E−01 | 1.11E−01 | 3.21E−02 |
| "106.1393" | 9.25E−03 | 5.48E−02 | 2.45E−01 | 6.26E−01 | 1.08E−01 | 6.85E−02 |
| "106.1396" | 6.78E−01 | 8.33E−02 | 3.73E−02 | 8.22E−04 | 2.05E−02 | 5.24E−01 |
| "106.1397" | 4.94E−05 | 3.13E−04 | 5.41E−03 | 5.59E−01 | 2.52E−05 | 1.06E−01 |
| "106.1399" | 4.84E−01 | 2.54E−01 | 4.10E−01 | 6.84E−01 | 2.51E−03 | 1.33E−02 |
| "106.1400" | 3.69E−03 | 9.92E−03 | 1.47E−01 | 6.07E−01 | 5.68E−02 | 1.22E−01 |
| "106.1401" | 4.05E−03 | 7.31E−02 | 5.89E−02 | 3.65E−01 | 3.70E−02 | 2.54E−02 |
| "106.1402" | 9.55E−06 | 9.32E−05 | 3.89E−03 | 2.02E−01 | 1.89E−01 | 2.14E−01 |
| "106.1403" | 1.98E−04 | 2.84E−03 | 7.08E−02 | 4.46E−01 | 1.09E−01 | 3.02E−01 |
| "106.1404" | 1.66E−03 | 3.71E−02 | 3.46E−01 | 1.62E−01 | 1.29E−02 | 3.74E−03 |
| "106.1405" | 2.97E−05 | 2.52E−05 | 2.83E−05 | 5.23E−05 | 2.52E−05 | 5.73E−03 |
| "106.1406" | 3.04E−05 | 2.52E−05 | 2.93E−05 | 1.36E−04 | 2.52E−05 | 1.68E−02 |
| "106.1407" | 7.12E−06 | 5.51E−06 | 6.27E−06 | 8.09E−06 | 5.44E−06 | 1.70E−02 |
| "106.1409" | 6.79E−01 | 2.78E−01 | 2.65E−01 | 9.07E−01 | 9.19E−04 | 2.31E−02 |
| "106.1423" | 6.81E−04 | 6.19E−04 | 7.41E−04 | 1.88E−01 | 5.69E−04 | 3.68E−01 |
| "106.1424" | 4.50E−02 | 1.13E−01 | 9.83E−02 | 8.38E−02 | 7.05E−01 | 2.02E−01 |
| "106.1425" | 2.06E−01 | 3.68E−01 | 5.11E−01 | 1.97E−01 | 8.07E−01 | 8.80E−02 |
| "106.1426" | 4.56E−02 | 1.24E−01 | 1.04E−01 | 5.40E−02 | 4.06E−02 | 4.09E−02 |
| "106.1427" | 6.06E−03 | 1.17E−03 | 5.45E−04 | 2.28E−02 | 9.73E−01 | 8.17E−01 |
| "106.1429" | 3.77E−03 | 1.51E−01 | 4.51E−01 | 4.04E−01 | 3.37E−01 | 6.26E−01 |
| "106.1430" | 8.01E−03 | 3.34E−02 | 1.31E−01 | 1.84E−01 | 2.75E−02 | 1.44E−01 |
| "106.1431" | 2.70E−04 | 5.14E−04 | 6.56E−03 | 6.73E−02 | 5.98E−01 | 2.96E−01 |
| "106.1432" | 7.45E−01 | 1.30E−01 | 3.27E−02 | 5.57E−02 | 2.43E−02 | 2.32E−01 |
| "106.1433" | 3.97E−01 | 8.99E−01 | 8.99E−01 | 3.73E−01 | 3.10E−01 | 9.75E−03 |
| "106.1434" | 7.90E−03 | 1.04E−02 | 1.60E−01 | 9.60E−01 | 6.40E−05 | 9.66E−06 |
| "106.1435" | 9.37E−01 | 3.46E−01 | 9.59E−02 | 4.68E−01 | 1.17E−01 | 7.30E−03 |
| "106.1438" | 1.86E−02 | 2.20E−01 | 7.33E−02 | 3.10E−01 | 2.09E−01 | 1.08E−01 |
| "106.1439" | 2.62E−01 | 6.62E−01 | 4.08E−01 | 9.26E−01 | 4.90E−03 | 2.62E−01 |
| "106.1440" | 5.91E−01 | 9.43E−01 | 9.73E−01 | 1.47E−01 | 6.57E−02 | 2.69E−01 |
| "106.1442" | 9.37E−02 | 3.04E−03 | 1.08E−04 | 4.06E−05 | 3.54E−05 | 1.87E−01 |
| "106.1443" | 3.44E−02 | 5.63E−02 | 9.76E−02 | 9.37E−02 | 2.74E−01 | 4.47E−02 |
| "106.1444" | 2.32E−02 | 1.44E−02 | 1.62E−01 | 4.02E−01 | 5.05E−01 | 1.18E−02 |
| "106.1445" | 7.01E−03 | 6.70E−03 | 2.63E−03 | 1.15E−02 | 7.06E−01 | 3.37E−02 |
| "106.1446" | 3.85E−02 | 5.75E−02 | 1.94E−02 | 6.48E−02 | 4.00E−01 | 7.19E−02 |
| "106.1447" | 5.19E−03 | 1.41E−02 | 6.46E−02 | 2.89E−02 | 1.92E−01 | 7.47E−01 |
| "106.1448" | 2.09E−02 | 2.31E−02 | 2.08E−02 | 4.96E−02 | 1.20E−01 | 4.96E−01 |
| "106.1449" | 2.56E−01 | 1.32E−01 | 3.85E−01 | 5.17E−01 | 9.75E−01 | 8.50E−01 |
| "106.1450" | 7.29E−01 | 4.51E−01 | 8.55E−01 | 9.13E−01 | 1.80E−02 | 2.69E−01 |
| "106.1451" | 1.41E−03 | 5.83E−04 | 6.99E−04 | 4.79E−02 | 3.10E−04 | 9.92E−03 |
| "106.1452" | 1.88E−04 | 5.62E−05 | 1.14E−04 | 8.12E−01 | 8.79E−03 | 3.65E−02 |
| "106.1453" | 9.48E−01 | 5.96E−01 | 8.58E−01 | 9.75E−01 | 9.88E−01 | 8.76E−01 |
| "106.1454" | 2.49E−01 | 1.13E−01 | 1.55E−01 | 8.62E−02 | 8.00E−01 | 2.55E−01 |
| "106.1456" | 1.01E−01 | 6.07E−02 | 7.19E−02 | 4.60E−01 | 5.75E−01 | 4.65E−01 |
| "106.1458" | 8.74E−04 | 1.26E−03 | 1.38E−03 | 2.57E−01 | 6.18E−01 | 1.47E−01 |
| "106.1459" | 3.20E−01 | 3.30E−01 | 2.94E−01 | 1.22E−01 | 7.67E−01 | 7.54E−01 |
| "106.1460" | 8.05E−01 | 9.10E−01 | 9.83E−01 | 6.06E−01 | 3.04E−01 | 6.01E−01 |
| "106.1461" | 9.04E−03 | 1.40E−02 | 9.40E−03 | 4.04E−02 | 1.09E−01 | 1.03E−01 |
| "106.1507" | 3.73E−01 | 2.31E−01 | 1.20E−01 | 9.56E−01 | 2.33E−01 | 4.36E−02 |
| "106.1510" | 6.53E−02 | 2.26E−01 | 7.69E−01 | 8.33E−01 | 1.16E−01 | 4.36E−01 |

TABLE 7-continued

Comprehensive neuronal culture screening results for R-GECO1.0 variants

| | | | | | | |
|---|---|---|---|---|---|---|
| "106.1513" | 9.54E−01 | 1.76E−01 | 1.15E−01 | 6.57E−01 | 7.99E−01 | 6.97E−04 |
| "106.1514" | 3.82E−02 | 4.80E−03 | 2.75E−03 | 1.68E−03 | 5.22E−02 | 5.69E−04 |
| "106.1515" | 2.18E−02 | 3.76E−01 | 9.18E−01 | 8.35E−01 | 8.60E−01 | 8.67E−02 |
| "106.1516" | 1.50E−01 | 1.75E−01 | 2.65E−01 | 7.89E−01 | 7.30E−01 | 1.71E−03 |
| "106.1517" | 8.27E−01 | 8.81E−01 | 6.74E−01 | 8.00E−01 | 7.77E−01 | 5.69E−04 |
| "106.1519" | 7.47E−01 | 2.02E−01 | 1.20E−01 | 5.97E−01 | 5.97E−01 | 2.76E−01 |
| "106.1520" | 6.77E−01 | 3.00E−01 | 4.20E−01 | 3.25E−01 | 4.56E−03 | 1.81E−02 |
| "106.1524" | 4.66E−03 | 1.33E−02 | 4.51E−02 | 8.56E−02 | 9.65E−01 | 5.20E−01 |
| "106.1527" | 8.54E−03 | 2.26E−02 | 4.17E−02 | 3.88E−02 | 1.52E−01 | 5.69E−04 |
| "106.1529" | 7.67E−01 | 7.77E−01 | 7.11E−01 | 7.53E−02 | 1.17E−01 | 8.69E−02 |
| "106.1533" | 6.31E−01 | 1.88E−01 | 1.98E−01 | 3.81E−01 | 2.58E−02 | 3.36E−04 |
| "106.1534" | 3.29E−01 | 7.40E−01 | 9.87E−01 | 1.15E−01 | 7.43E−03 | 8.92E−03 |
| "106.1536" | 1.27E−02 | 3.32E−02 | 1.40E−01 | 5.60E−02 | 5.70E−02 | 5.82E−03 |
| "106.1537" | 1.02E−01 | 1.35E−01 | 3.34E−01 | 1.58E−01 | 7.37E−01 | 5.59E−03 |
| "106.1538" | 8.54E−03 | 2.58E−02 | 1.48E−01 | 7.47E−02 | 7.16E−01 | 9.19E−04 |
| "106.1539" | 2.86E−02 | 2.38E−01 | 7.24E−01 | 2.81E−01 | 7.82E−01 | 1.13E−03 |
| "106.1540" | 5.83E−03 | 2.08E−02 | 1.09E−01 | 8.12E−02 | 5.77E−01 | 1.21E−02 |
| "106.1541" | 4.69E−03 | 1.61E−02 | 3.46E−02 | 4.50E−02 | 4.35E−02 | 5.38E−03 |
| "106.1542" | 1.90E−01 | 5.46E−02 | 1.80E−02 | 1.74E−01 | 1.08E−01 | 5.14E−01 |
| "106.1544" | 4.90E−03 | 1.49E−02 | 4.86E−02 | 9.99E−03 | 1.13E−01 | 1.43E−03 |
| "106.1545" | 7.28E−03 | 2.49E−02 | 8.78E−02 | 4.23E−02 | 9.62E−02 | 7.69E−03 |
| "106.1546" | 1.96E−02 | 6.21E−02 | 1.72E−01 | 4.66E−03 | 5.14E−01 | 1.01E−02 |
| "106.1547" | 6.92E−02 | 3.48E−01 | 9.06E−01 | 4.39E−01 | 7.62E−01 | 5.85E−01 |
| "106.1549" | 1.26E−01 | 3.61E−01 | 5.97E−01 | 5.26E−01 | 7.22E−01 | 8.62E−02 |
| "106.1551" | 1.02E−01 | 4.16E−01 | 8.03E−01 | 2.50E−01 | 8.99E−01 | 1.05E−02 |
| "106.1553" | 1.39E−01 | 3.69E−01 | 5.28E−01 | 7.82E−02 | 2.42E−01 | 5.11E−05 |
| "106.1561" | 2.05E−03 | 3.42E−03 | 2.54E−02 | 3.56E−02 | 2.23E−01 | 3.07E−01 |
| "106.1572" | 5.90E−04 | 5.69E−04 | 6.12E−04 | 9.72E−04 | 5.76E−04 | 2.38E−02 |
| "106.1576" | 2.00E−01 | 6.94E−01 | 3.26E−01 | 9.22E−01 | 5.15E−03 | 2.45E−01 |
| "106.1577" | 2.80E−05 | 2.58E−05 | 3.45E−05 | 5.36E−03 | 8.03E−03 | 4.59E−01 |
| "106.1578" | 1.26E−04 | 1.36E−04 | 2.15E−04 | 2.91E−03 | 1.75E−04 | 1.69E−02 |
| "106.1579" | 6.06E−03 | 1.17E−02 | 8.86E−02 | 3.33E−01 | 3.43E−01 | 5.52E−01 |
| "106.1580" | 9.83E−06 | 5.44E−06 | 8.57E−06 | 1.21E−03 | 8.70E−05 | 1.27E−02 |
| "106.1581" | 3.36E−04 | 3.36E−04 | 3.15E−03 | 8.76E−02 | 2.34E−01 | 8.05E−01 |
| "106.1582" | 4.40E−05 | 6.64E−05 | 9.48E−05 | 1.54E−03 | 1.18E−02 | 1.57E−02 |
| "106.1583" | 7.62E−06 | 2.43E−05 | 2.44E−03 | 1.16E−01 | 2.93E−01 | 3.38E−03 |
| "106.1584" | 7.81E−06 | 5.71E−06 | 8.37E−06 | 2.14E−03 | 4.74E−02 | 1.39E−02 |
| "106.1585" | 3.02E−06 | 1.20E−06 | 1.49E−06 | 3.50E−05 | 2.62E−03 | 1.99E−02 |
| "106.1586" | 8.47E−06 | 6.05E−05 | 1.99E−03 | 1.08E−01 | 8.73E−01 | 9.32E−01 |
| "106.1587" | 2.24E−03 | 6.26E−04 | 7.77E−04 | 2.37E−03 | 5.69E−04 | 4.85E−03 |
| "106.1588" | 1.55E−04 | 1.36E−04 | 1.87E−04 | 4.15E−04 | 1.18E−04 | 2.77E−01 |
| "106.1589" | 7.96E−04 | 5.69E−04 | 6.04E−04 | 8.05E−04 | 5.69E−04 | 9.59E−01 |
| "106.1590" | 2.62E−04 | 1.35E−04 | 1.45E−04 | 1.90E−04 | 1.18E−04 | 4.95E−03 |
| "106.1591" | 8.92E−04 | 1.65E−03 | 1.03E−01 | 9.65E−01 | 7.14E−04 | 4.56E−01 |
| "106.1592" | 3.30E−03 | 2.39E−03 | 3.36E−02 | 2.56E−01 | 8.29E−03 | 1.84E−01 |
| "106.1593" | 6.90E−04 | 5.69E−04 | 5.83E−04 | 6.49E−04 | 5.69E−04 | 2.73E−02 |
| "106.1595" | 2.77E−02 | 1.09E−01 | 3.27E−01 | 3.24E−01 | 8.36E−01 | 5.65E−01 |
| "106.1596" | 4.40E−05 | 2.90E−05 | 5.00E−05 | 8.03E−05 | 2.52E−05 | 1.05E−01 |
| "106.1598" | 5.97E−04 | 5.69E−04 | 5.69E−04 | 6.04E−04 | 5.69E−04 | 9.49E−01 |
| "106.1599" | 4.46E−06 | 1.30E−06 | 4.98E−06 | 7.38E−06 | 1.20E−06 | 4.34E−03 |
| "106.1600" | 5.09E−04 | 4.59E−02 | 3.13E−01 | 6.37E−01 | 4.16E−05 | 2.31E−02 |
| "106.1601" | 1.33E−06 | 1.24E−06 | 1.51E−06 | 3.12E−06 | 1.20E−06 | 1.94E−03 |
| "106.1602" | 1.69E−06 | 1.20E−06 | 1.25E−06 | 1.62E−06 | 1.20E−06 | 3.97E−03 |
| "106.1603" | 2.47E−06 | 8.40E−06 | 1.07E−04 | 1.90E−04 | 1.28E−06 | 1.90E−01 |
| "106.1604" | 2.97E−05 | 2.52E−05 | 3.37E−05 | 2.11E−04 | 2.52E−05 | 2.44E−02 |
| "106.1605" | 7.68E−05 | 4.08E−04 | 2.60E−03 | 9.47E−03 | 2.55E−05 | 2.06E−01 |
| "106.1606" | 1.63E−04 | 1.18E−04 | 1.18E−04 | 1.29E−04 | 1.18E−04 | 2.35E−02 |
| "106.1607" | 1.23E−04 | 1.81E−04 | 1.17E−03 | 1.22E−01 | 2.37E−02 | 8.01E−03 |
| "106.1608" | 2.02E−02 | 2.70E−01 | 5.34E−01 | 4.14E−01 | 1.68E−02 | 3.11E−04 |
| "106.1609" | 7.73E−03 | 4.53E−02 | 6.28E−01 | 9.61E−01 | 2.08E−02 | 5.83E−03 |
| "106.1610" | 2.90E−05 | 2.61E−05 | 2.77E−05 | 1.27E−04 | 1.01E−04 | 3.97E−03 |
| "106.1611" | 2.87E−05 | 2.50E−04 | 4.74E−02 | 4.23E−01 | 6.20E−02 | 1.48E−05 |
| "106.1624" | 3.16E−11 | 1.33E−12 | 6.53E−10 | 3.73E−06 | 7.16E−09 | 5.05E−13 |
| "106.1625" | 1.11E−05 | 4.64E−02 | 2.90E−04 | 4.88E−09 | 4.03E−09 | 3.17E−09 |
| "106.1626" | 5.84E−06 | 8.37E−06 | 6.19E−06 | 5.44E−06 | 4.22E−06 | 5.44E−06 |
| "106.1627" | 7.55E−02 | 2.82E−02 | 8.31E−02 | 2.08E−02 | 2.73E−02 | 2.37E−03 |
| "106.1628" | 7.37E−09 | 7.51E−07 | 5.02E−01 | 9.23E−09 | 9.08E−10 | 1.05E−09 |
| "106.1629" | 1.40E−05 | 1.79E−06 | 3.12E−06 | 1.51E−03 | 7.37E−01 | 5.18E−01 |
| "106.1630" | 9.26E−01 | 1.71E−01 | 1.67E−01 | 5.07E−01 | 1.35E−08 | 9.22E−07 |
| "106.1631" | 1.22E−15 | 2.88E−13 | 1.83E−06 | 1.96E−09 | 2.50E−20 | 1.21E−14 |
| "106.1632" | 1.23E−04 | 1.33E−04 | 6.45E−04 | 6.72E−01 | 3.92E−05 | 1.15E−01 |
| "106.1633" | 5.45E−02 | 1.97E−01 | 1.67E−01 | 6.13E−01 | 6.22E−04 | 8.55E−01 |
| "106.1634" | 2.00E−04 | 2.14E−02 | 7.71E−02 | 8.57E−01 | 6.27E−06 | 6.49E−06 |
| "106.1635" | 7.52E−02 | 3.10E−02 | 8.12E−02 | 1.13E−01 | 5.24E−02 | 5.00E−03 |
| "106.1636" | 8.60E−01 | 9.39E−01 | 7.21E−01 | 1.70E−02 | 2.05E−08 | 4.59E−11 |
| "106.1637" | 1.64E−04 | 2.72E−05 | 1.12E−04 | 6.60E−05 | 8.39E−10 | 3.53E−09 |
| "106.1638" | 1.04E−01 | 3.78E−01 | 8.94E−01 | 6.82E−01 | 4.96E−05 | 2.42E−02 |
| "106.1639" | 2.44E−01 | 4.45E−01 | 4.14E−01 | 4.55E−05 | 2.64E−02 | 9.61E−06 |

TABLE 7-continued

Comprehensive neuronal culture screening results for R-GECO1.0 variants

| | | | | | | |
|---|---|---|---|---|---|---|
| "106.1640" | 3.00E−01 | 9.66E−01 | 7.47E−01 | 5.32E−04 | 1.20E−06 | 2.21E−05 |
| "106.1641" | 1.76E−03 | 2.30E−02 | 5.87E−01 | 8.97E−05 | 1.20E−06 | 2.21E−01 |
| "106.1642" | 4.88E−01 | 2.25E−01 | 8.99E−02 | 4.09E−02 | 5.44E−06 | 2.62E−01 |
| "106.1643" | 1.34E−04 | 5.15E−03 | 3.61E−01 | 8.87E−06 | 1.38E−05 | 5.44E−06 |
| "106.1644" | 4.47E−04 | 1.22E−04 | 2.96E−04 | 1.70E−02 | 2.14E−01 | 1.47E−02 |
| "106.1645" | 1.27E−04 | 6.94E−05 | 8.30E−05 | 6.35E−01 | 7.48E−01 | 3.93E−02 |
| "106.1646" | 1.33E−03 | 2.25E−02 | 2.05E−01 | 1.31E−04 | 5.44E−06 | 5.50E−04 |
| "106.1647" | 1.87E−08 | 1.92E−08 | 9.71E−07 | 5.82E−10 | 5.26E−13 | 1.18E−09 |
| "106.1648" | 1.46E−08 | 1.11E−08 | 1.55E−08 | 7.29E−09 | 1.72E−13 | 4.28E−12 |
| "106.1649" | 3.95E−01 | 3.48E−01 | 8.87E−01 | 2.04E−01 | 1.41E−04 | 2.71E−02 |
| "106.1650" | 3.36E−05 | 3.50E−05 | 2.01E−04 | 1.44E−04 | 1.20E−06 | 1.93E−04 |
| "106.1651" | 1.79E−03 | 8.82E−03 | 3.87E−03 | 5.90E−04 | 2.52E−05 | 1.25E−04 |
| "106.1652" | 6.37E−04 | 1.65E−03 | 2.35E−03 | 4.09E−05 | 5.44E−06 | 9.93E−05 |
| "106.1653" | 8.42E−02 | 5.50E−02 | 3.21E−01 | 3.10E−04 | 3.66E−05 | 8.79E−04 |
| "106.1654" | 7.91E−04 | 1.57E−03 | 1.78E−02 | 9.31E−04 | 2.52E−05 | 1.11E−01 |
| "106.1655" | 3.07E−12 | 8.70E−12 | 8.38E−09 | 8.69E−09 | 2.85E−10 | 7.69E−06 |
| "106.1656" | 2.28E−03 | 2.24E−02 | 1.78E−02 | 2.50E−05 | 3.59E−07 | 6.98E−09 |
| "106.1657" | 2.49E−01 | 9.26E−01 | 2.30E−01 | 2.88E−01 | 5.44E−06 | 5.60E−02 |
| "106.1658" | 1.78E−01 | 1.12E−01 | 3.20E−01 | 4.47E−01 | 2.52E−05 | 3.80E−04 |
| "106.1659" | 7.70E−07 | 3.67E−04 | 1.32E−02 | 1.51E−08 | 4.58E−19 | 1.00E−11 |
| "106.1660" | 2.98E−02 | 1.82E−02 | 1.54E−01 | 2.49E−03 | 5.98E−06 | 1.35E−03 |
| "106.1661" | 7.53E−03 | 1.11E−01 | 1.17E−01 | 1.62E−03 | 7.96E−06 | 7.83E−02 |
| "106.1662" | 4.39E−14 | 5.12E−11 | 3.20E−03 | 2.90E−16 | 3.77E−16 | 6.84E−04 |
| "106.1663" | 2.67E−04 | 7.77E−03 | 5.52E−01 | 1.06E−05 | 1.32E−05 | 8.66E−01 |
| "106.1664" | 2.97E−04 | 2.18E−02 | 4.14E−02 | 6.96E−06 | 7.85E−05 | 8.88E−05 |
| "106.1665" | 5.17E−05 | 1.20E−04 | 3.19E−02 | 1.10E−04 | 8.97E−06 | 1.59E−01 |
| "106.1666" | 6.40E−02 | 7.25E−02 | 2.55E−01 | 3.72E−04 | 1.13E−04 | 2.02E−04 |
| "106.1667" | 1.79E−01 | 5.11E−01 | 4.15E−01 | 7.77E−04 | 5.69E−04 | 1.33E−02 |
| "106.1668" | 4.07E−09 | 2.40E−09 | 2.57E−09 | 1.27E−01 | 1.33E−03 | 6.95E−01 |
| "106.1669" | 9.86E−02 | 2.22E−02 | 6.60E−03 | 6.11E−03 | 7.98E−04 | 5.29E−02 |
| "106.1671" | 2.84E−02 | 1.79E−01 | 4.05E−01 | 4.69E−02 | 1.18E−02 | 9.80E−01 |
| "106.1672" | 1.34E−05 | 6.80E−06 | 1.32E−05 | 2.49E−06 | 5.44E−06 | 8.50E−01 |
| "106.1673" | 1.86E−02 | 3.70E−02 | 1.64E−01 | 3.55E−01 | 1.12E−03 | 9.54E−05 |
| "106.1674" | 2.80E−01 | 4.72E−01 | 5.20E−01 | 1.68E−01 | 3.02E−06 | 1.88E−02 |
| "106.1675" | 3.49E−01 | 1.02E−01 | 2.06E−01 | 2.79E−01 | 6.97E−02 | 2.71E−02 |
| "106.1676" | 4.84E−03 | 9.94E−03 | 6.48E−02 | 3.32E−03 | 5.44E−06 | 1.23E−03 |
| "106.1677" | 2.53E−03 | 2.54E−02 | 2.95E−01 | 6.20E−03 | 8.27E−06 | 6.90E−01 |
| "106.1678" | 3.85E−02 | 2.34E−01 | 1.95E−01 | 3.71E−04 | 1.57E−04 | 7.47E−03 |
| "106.1679" | 9.80E−01 | 4.98E−01 | 2.54E−01 | 3.65E−01 | 4.35E−05 | 5.87E−03 |
| "106.1680" | 1.16E−01 | 5.96E−02 | 1.20E−01 | 9.54E−01 | 1.03E−01 | 6.40E−01 |
| "106.1681" | 3.40E−03 | 1.96E−02 | 1.14E−01 | 7.43E−03 | 5.44E−06 | 1.10E−02 |
| "106.1682" | 4.30E−02 | 2.64E−02 | 9.15E−03 | 4.13E−01 | 1.71E−03 | 7.05E−01 |
| "106.1683" | 9.83E−06 | 1.69E−05 | 2.63E−03 | 3.60E−05 | 7.01E−03 | 3.21E−01 |
| "106.1684" | 2.72E−01 | 7.51E−01 | 2.92E−02 | 2.04E−05 | 5.44E−06 | 2.43E−04 |
| "106.1685" | 2.21E−01 | 1.11E−01 | 4.06E−01 | 2.07E−06 | 3.10E−09 | 2.01E−04 |
| "106.1686" | 2.16E−03 | 3.43E−03 | 1.70E−02 | 4.84E−04 | 5.44E−06 | 7.45E−05 |
| "106.1687" | 1.04E−01 | 6.37E−02 | 2.67E−01 | 3.23E−04 | 6.12E−06 | 6.97E−01 |
| "106.1688" | 7.37E−06 | 7.29E−06 | 6.27E−06 | 5.44E−06 | 5.44E−06 | 1.97E−03 |
| "106.1689" | 9.22E−01 | 2.64E−01 | 2.20E−01 | 2.29E−01 | 2.52E−05 | 3.88E−05 |
| "106.1690" | 1.03E−04 | 3.47E−04 | 2.04E−04 | 1.29E−05 | 1.20E−06 | 1.60E−06 |
| "106.1691" | 4.76E−01 | 4.41E−01 | 4.93E−02 | 6.34E−06 | 1.20E−06 | 1.87E−02 |
| "106.1692" | 4.11E−05 | 3.45E−05 | 3.45E−05 | 3.45E−05 | 2.52E−05 | 2.91E−04 |
| "106.1693" | 1.93E−01 | 2.91E−01 | 5.96E−01 | 1.08E−02 | 5.44E−06 | 5.31E−04 |
| "106.1694" | 7.85E−05 | 1.69E−04 | 7.88E−03 | 5.01E−05 | 5.44E−06 | 2.43E−05 |
| "106.1695" | 6.92E−01 | 5.88E−01 | 7.75E−01 | 4.93E−04 | 5.98E−06 | 2.72E−03 |
| "106.1696" | 1.88E−04 | 5.29E−05 | 3.20E−05 | 2.07E−02 | 2.85E−03 | 1.56E−02 |
| "106.1697" | 5.90E−01 | 3.35E−01 | 1.20E−02 | 1.10E−05 | 2.15E−06 | 6.63E−01 |
| "106.1698" | 1.60E−01 | 5.49E−02 | 2.14E−02 | 9.13E−01 | 1.09E−02 | 5.52E−03 |
| "106.1699" | 1.05E−03 | 5.79E−04 | 1.04E−03 | 3.29E−04 | 2.52E−05 | 1.37E−03 |
| "106.1700" | 1.75E−03 | 3.23E−04 | 6.20E−04 | 8.88E−04 | 2.52E−05 | 3.25E−01 |
| "106.1701" | 2.08E−04 | 7.36E−04 | 1.20E−02 | 2.90E−05 | 5.44E−06 | 7.12E−06 |
| "106.1702" | 2.21E−10 | 5.64E−09 | 8.77E−03 | 2.02E−09 | 8.01E−11 | 2.22E−09 |
| "106.1703" | 5.48E−02 | 4.55E−03 | 2.91E−02 | 1.42E−01 | 5.44E−06 | 7.85E−05 |
| "106.1704" | 9.06E−05 | 3.52E−05 | 7.22E−05 | 3.55E−01 | 8.21E−01 | 1.56E−01 |
| "106.1705" | 1.98E−04 | 1.18E−03 | 4.04E−02 | 2.47E−06 | 5.44E−06 | 6.17E−06 |
| "106.1706" | 1.37E−01 | 1.79E−02 | 6.31E−03 | 9.81E−02 | 6.49E−06 | 7.91E−01 |
| "106.1707" | 2.31E−01 | 6.96E−03 | 1.13E−03 | 5.99E−02 | 5.44E−06 | 3.46E−02 |
| "106.1708" | 2.26E−03 | 2.23E−02 | 7.02E−01 | 9.69E−03 | 2.52E−05 | 4.92E−02 |
| "106.1709" | 4.32E−02 | 8.49E−01 | 2.51E−01 | 8.18E−01 | 4.56E−03 | 4.24E−01 |
| "106.1710" | 1.21E−02 | 9.71E−02 | 5.01E−01 | 9.56E−01 | 4.02E−04 | 9.01E−01 |
| "106.1711" | 1.44E−01 | 9.78E−01 | 4.35E−01 | 1.33E−02 | 2.52E−05 | 2.43E−01 |
| "106.1712" | 3.19E−02 | 1.12E−03 | 2.52E−04 | 2.28E−01 | 2.99E−06 | 1.80E−01 |
| "106.1713" | 7.79E−01 | 8.89E−01 | 1.34E−01 | 1.49E−05 | 1.21E−01 | 8.60E−04 |
| "106.1714" | 4.08E−07 | 3.39E−05 | 2.02E−03 | 5.55E−04 | 7.46E−09 | 9.35E−03 |
| "106.1715" | 3.95E−07 | 5.98E−06 | 1.71E−04 | 4.54E−07 | 3.91E−11 | 6.55E−02 |
| "106.1716" | 5.01E−05 | 3.31E−06 | 1.24E−05 | 2.54E−03 | 2.00E−02 | 9.93E−03 |
| "106.1717" | 4.96E−03 | 5.36E−03 | 1.74E−02 | 3.07E−01 | 9.63E−01 | 8.40E−02 |
| "106.1718" | 4.32E−01 | 7.56E−01 | 4.81E−01 | 2.97E−03 | 3.91E−11 | 1.33E−05 |

TABLE 7-continued

Comprehensive neuronal culture screening results for R-GECO1.0 variants

| "106.1719" | 1.68E−01 | 3.69E−01 | 2.20E−07 | 2.68E−10 | 2.47E−10 | 3.74E−10 |
|---|---|---|---|---|---|---|
| "106.1720" | 2.82E−04 | 1.52E−03 | 1.57E−03 | 7.29E−08 | 7.16E−10 | 2.77E−09 |
| "106.1722" | 7.61E−04 | 1.65E−01 | 1.12E−03 | 7.91E−09 | 6.32E−09 | 5.39E−08 |
| "106.1723" | 2.91E−03 | 2.90E−05 | 3.70E−08 | 1.40E−08 | 1.06E−06 | 1.68E−08 |
| "106.1724" | 2.77E−09 | 3.42E−07 | 4.02E−01 | 8.92E−11 | 3.96E−10 | 3.72E−09 |
| "106.1725" | 4.61E−10 | 1.51E−06 | 3.39E−01 | 1.96E−12 | 2.39E−12 | 7.19E−13 |
| "106.1726" | 3.42E−03 | 2.18E−02 | 4.34E−02 | 1.46E−02 | 3.10E−09 | 6.29E−02 |
| "106.1727" | 1.06E−03 | 1.76E−04 | 4.86E−05 | 2.23E−01 | 1.23E−03 | 7.69E−03 |
| "106.1728" | 4.30E−01 | 8.50E−02 | 2.62E−01 | 7.86E−06 | 5.26E−13 | 6.89E−11 |
| "106.1729" | 2.75E−04 | 2.86E−03 | 7.43E−01 | 1.32E−09 | 4.57E−11 | 1.90E−09 |
| "106.1730" | 1.66E−07 | 1.17E−07 | 1.92E−05 | 3.73E−05 | 8.19E−02 | 1.43E−03 |
| "106.1731" | 6.73E−08 | 1.33E−07 | 6.43E−07 | 1.32E−08 | 3.91E−11 | 1.14E−01 |
| "106.1732" | 1.26E−05 | 2.02E−05 | 1.49E−05 | 3.34E−05 | 5.44E−06 | 2.51E−03 |
| "106.1733" | 3.45E−16 | 6.71E−16 | 2.66E−11 | 2.02E−04 | 3.47E−10 | 4.98E−01 |
| "106.1734" | 9.77E−02 | 6.37E−03 | 7.74E−03 | 2.43E−01 | 1.35E−08 | 3.45E−03 |
| "106.1735" | 4.16E−02 | 2.89E−02 | 3.17E−03 | 1.75E−09 | 3.91E−11 | 8.45E−06 |
| "106.1736" | 3.84E−01 | 9.24E−01 | 5.98E−01 | 6.16E−04 | 3.10E−09 | 1.45E−05 |
| "106.1737" | 2.76E−03 | 6.18E−03 | 2.59E−03 | 9.23E−06 | 5.97E−08 | 1.94E−05 |
| "106.1738" | 5.32E−01 | 6.54E−01 | 1.65E−01 | 2.68E−09 | 1.38E−03 | 4.86E−02 |
| "106.1739" | 1.97E−04 | 1.79E−02 | 1.82E−01 | 3.01E−11 | 1.10E−08 | 2.50E−06 |
| "106.1740" | 1.23E−04 | 1.21E−05 | 2.69E−04 | 7.43E−03 | 1.19E−09 | 2.72E−04 |
| "106.1741" | 1.53E−07 | 5.34E−06 | 4.31E−02 | 1.36E−11 | 2.22E−02 | 4.11E−06 |
| "106.1742" | 7.05E−02 | 3.14E−03 | 2.55E−05 | 6.16E−13 | 8.97E−15 | 3.52E−01 |
| "106.1744" | 9.33E−02 | 3.42E−02 | 2.42E−06 | 4.62E−21 | 1.69E−19 | 9.88E−01 |

Figures 7A, 7B, 7C, 7D:
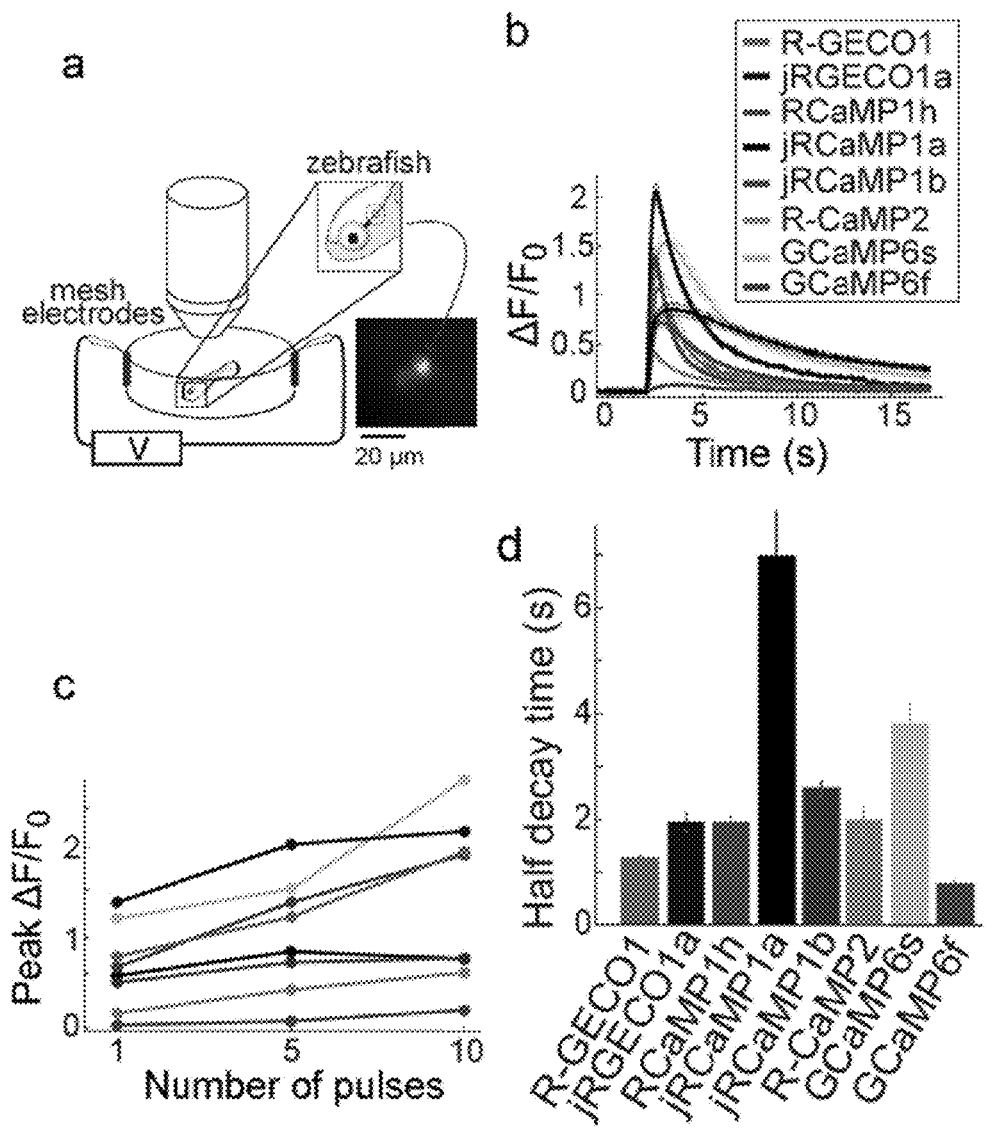
FIGS. 7A-D include data of red GECIs performance in the zebrafish trigeminal neurons (a) Schematic representation of zebrafish trigeminal neurons assay. Zebrafish larvae (3-4 days post fertilization) were paralyzed, embedded in agarose, and stimulated with electrodes (20 ms pulses; 1, 5, and 10 pulses at 20 Hz; Methods); (b) Response transients to five pulses stimulus (mean±s.e.m; n=5 fish for R-GECO1; 7, jRGECO1a; 6, R-CaMP2; 6, RCaMP1h; 7, jRCaMP1a; 6, jRCaMP1b; 6, GCaMP6s; 6, GCaMP6f); (c) Averaged peak $\Delta F/F_0$ (same fish as in b) in response to one, five, and ten pulses stimuli; and (d) Half decay time for different red and green GECIs (10 pulses stimulus, mean±s.e.m., same fish as in b).

Red GECIs were also expressed pan-neuronally in transgenic zebrafish under the elavl3/HuC promoter (elavl3: GECI). Fish showing strong expression in the trigeminal (Tg) neurons 3-4 days post fertilization (dpf) were selected for imaging. Tg neurons are usually silent and fire one or few spikes in response to touch (Douglass, Kraves et al. 2008). Brief trains of electrical stimulation pulses (20 ms each; 1, 5, and 10 pulses at 20 Hz), which are known to stimulate Tg neurons (Akerboom, Carreras Calderon et al. 2013), were used to elicit responses in these cells and image calcium transients (FIG. 7a; widefield one-photon imaging, Methods). Similar to results from cultured rat hippocampal neurons, mice, and *Drosophila*, jRGECO1a was the most sensitive red GECI tested in this assay: its response to one and five pulses outperformed all other GECIs, including GCaMP6f and GCaMP6s (FIG. 14b, c). For longer stimuli the jRGECO1a response showed saturation. jRCaMP1a and jRCaMP1b exhibited large improvements in sensitivity over their parent indicator, RCaMP1h, and also higher sensitivity than R-CaMP2, with jRCaMP1b showing faster kinetics than jRCaMP1a (FIG. 7d).

Figures 8A, 8B, 8C:
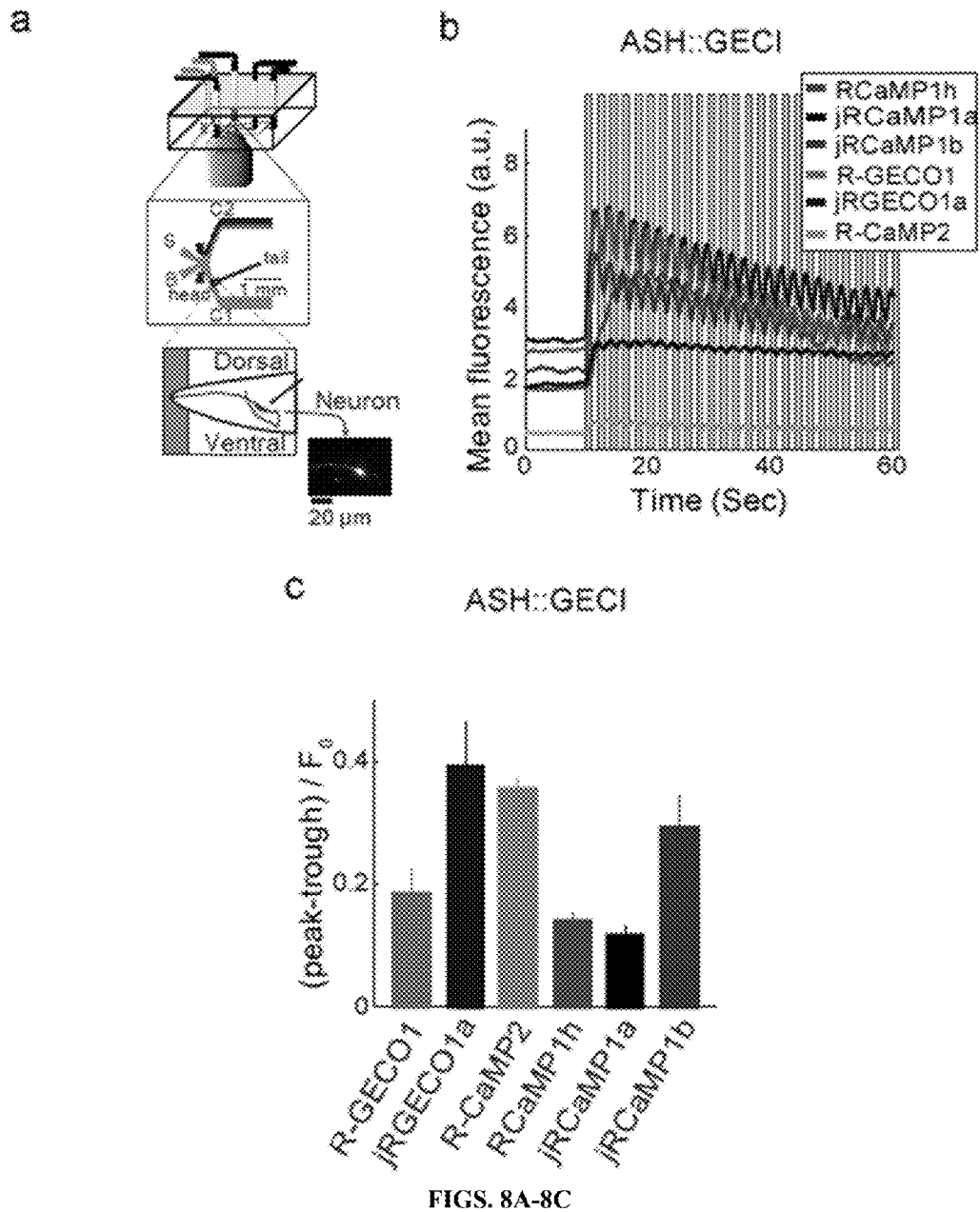
FIGS. 8A-C include data of red GECIs performance in the *C. elegans* ASH neurons (a) Schematic representation of the *Caenorhabditis elegans* ASH neurons assay. Worm was inserted to a microfluidic device, oriented with its head exposed to fluid flow, and paralyzed. After 10 s of buffer (B) flow, worms were exposed to 1 s glycerol (G) and 1 s buffer flow alternatively for 4 min. (Methods). Liquid flow was directed through side control channels (C1 and C2); (b) Fluorescence transients following exposure to glycerol reflect changes in intracellular calcium concentration (mean across worms, n=10 worms for jRGECO1a; 8, jRCaMP1a; 9, jRCaMP1b; 8, R-GECO1; 12, R-CaMP2; 9, RCaMP1h); and (c) Quantification of signal modulation for the different GECIs tested (difference between fluorescence peak and trough in each 2 s cycle, divided by the signal average fluorescence during the first 10 s (mean±s.e.m., same data as in (b)).

Red GECIs were also tested in ASH neurons of *Caenorhabditis elegans*. Worms were restrained in a custom-built microfluidic chamber (Chronis, Zimmer et al. 2007) within S basal buffer (Brenner 1974) (FIG. 8a; Methods). After ten seconds of imaging, worms were exposed to repeated stimulation consisting of one second flow of 1 M glycerol, followed by another one second of buffer flow, for a total time of 240 seconds. All tested GECIs exhibited an initial increase in the fluorescence signal, followed by modulation of the fluorescence signal and a slow decay. jRGECO1a and jRCaMP1b showed the best performance in tracking the stimuli, with a large initial increase in fluorescence and subsequent large modulations (FIG. 8b,c). RCaMP1h, jRCaMP1a, R-GECO1, and R-CaMP2 showed smaller signal modulations. R-CaMP2 had also low baseline fluorescence (FIG. 8c).

Materials and Methods

All surgical and experimental procedures were in accordance with protocols approved by the HHMI Janelia Research Campus Institutional Animal Care and Use Committee and Institutional Biosafety Committee.

Red GECI variants. NES-red GECI variants were used throughout this study. Amino acid positions are numbered in jRGECO1 and jRCaMP1 variants (Supp. Tables 1-2) starting from GGSHHHHHHGMASM... (1-14...) (SEQ ID NO: 9). NES positions are excluded from the numbering.

Protein Expression and Purification. Protein sensor purifications, calcium titrations, and pKa measurements were performed as described (Chen, Wardill et al. 2013). Red fluorescence was measured with excitation at 570 nm (5 nm bandpass) and emission at 600 nm (5 nm bandpass). Chromophore extinction coefficients ($\epsilon_{apo}$ and $\epsilon_{sat}$) and quantum yields ($\Phi_{apo}$ and $\Phi_{sat}$) were measured as described (Akerboom, Chen et al. 2012). Data are presented as mean±standard deviation across independently purified protein samples.

Spectroscopy of Purified Proteins. Purified proteins were measured in 30 mM MOPS, 100 mM KCl, pH 7.2 (calcium calibration buffer C3008MP, ThermoFisher) containing either 10 mM CaEGTA (calcium buffer) or 10 mM EGTA (EGTA buffer). Absorption spectra were taken on a UV/VIS spectrometer (Lambda 35, PerkinElmer). Fluorescence emission and excitation spectra were measured on a LS-55 fluorimeter (Perkin-Elmer) with 5 nm slits, and ex/em wavelengths of 555 nm/600 nm. Absolute quantum yields were measured using a Quantaurus-QY integrating-sphere spectrometer (model C11374, Hamamatsu). Very low concentration solutions were not measurable on the Quantaurus, e.g. jRGECO1a in EGTA buffer, so relative quantum yields were determined from measured absorption in the UV/VIS and integrated fluorescence measured in the fluorimeter, in comparison to the reference fluorophore mCherry (measured absolute QY of 0.22) under identical excitation conditions. Extinction coefficients for RGECO variants were determined using the alkali denaturation method, assuming the denatured extinction coefficient for RGECO variants is the same as denatured mCherry, 37,000 $M^{-1}cm^{-1}$ at 455 nm at pH 13. For RCaMP variants, the denatured absorption spectra is complicated by an absorbance peak at 383 nm that first appears with increasing pH at pH 11.5, and is irreversibly formed. So for RCaMP variants Fluorescence Correlation Spectroscopy (FCS) was used, described below, to quantify concentration by counting fluorophores, using mCherry as a concentration reference. FCS was performed on 10-100 nMolar protein solutions using 1060 nm excitation at low laser power (1-3 mW) to determine the autocorrelation $G(\tau)$ of the fluorescence signal. The number of fluorophores inside the beam volume is found from $1/G(0)$. The beam volume was found from identical FCS measurements on the reference protein mCherry at known concentration. jRGECO variant extinction coefficients were measured using both methods with similar and results Widefield Measurement of Photoswitching and Photobleaching. Fluorescence time course measurements were carried out on aqueous droplets of purified protein isolated in octanol (Kremers, Hazelwood et al. 2009), and sandwiched between two coverslips. An epi-illumination microscope (AxioImager, Zeiss) with a 20×0.8 NA air objective was used. Co-linear laser excitation was provided to the microscope at 488 nm (Sapphire 488, Coherent) and 561 nm (Sapphire 561, Coherent) using a beam-combining dichroic, and computer-controlled shutters determined exposure sequence. Fluorescence collected by the objective passed through dichroic and bandpass filters (Di02-R561 and 625/90, Semrock), and was detected by a fiber-coupled avalanche photodiode (SPCM-AQRH14, Pacer). Laser power was measured at the output of the objective, and laser beam area in the focal plane was imaged and measured using a CCD camera, in order to determine the laser intensity.

Two-Photon Spectroscopy. Two-photon spectra and FCS were performed as previously described by (Akerboom, Carreras Calderon et al. 2013). Briefly, protein solutions in coverslip-bottomed dishes were measured on an inverted microscope using a 60×1.2 NA water-immersion objective. Near-infrared laser excitation over the range of 700 nm-1500 nm was provided by either a Ti:sapphire laser (Chameleon Ultra II, Coherent) or an OPO (Chameleon Compact OPO, Coherent). An overlap range 1000-1080 nm was used to connect the fluorescence spectra generated from the two different excitation sources. The Ti:sapphire beam was long-pass filtered (715/LP, Semrock) to remove contaminating visible red spontaneous emission emanating from the Ti:sapphire laser cavity. A single dichroic mirror (675DCSPXR, Omega) was used to bring the Ti: Sapphire or OPO beams to the objective. Fluorescence collected from protein samples, filtered by the dichroic mirror and a 720/SP short-pass and a 625/90 bandpass filter (Semrock), was detected by an avalanche photodiode detector (SPC-M_AQRH-14, Pacer). Output pulses from the detector were fed to an autocorrelator (Flex03LQ, Correlator.com), and the system operated under computer control with automated data acquisition.

Two-photon action spectra were determined from excitation spectra of 1 µM protein solutions obtained at low laser power (0.5 mW), and comparing these to spectra measured under identical conditions for the reference dyes fluorescein and rhodamine B, for which published 2-photon cross section data (Xu and Webb 1996, Makarov, Drobizhev et al. 2008) was used to determine action spectra of the red GECIs. This setup was also used to perform FCS in order to measure chromophore concentration at low laser power, and two-photon peak brightness (Mutze, Iyer et al. 2012) at high laser power. Peak brightness is the experimentally determined maximum rate of fluorescence per molecule for a given focusing geometry, and is a measure of the brightness and photostability of a fluorophore under 2-photon excitation. To determine peak brightness, 20-100 nM solutions of protein in calcium buffer were illuminated at either 1070 nm or 1130 nm at increasing laser power, where at each power setting the mean fluorescence rate F and the mean number of fluorophores N in the laser beam volume were determined by FCS. The 2-photon peak brightness was then found from the maximum value of the quantity F/N as the laser power was increased.

Two-Photon Bleaching. Two-photon bleaching of red GECIs was performed on isolated aqueous droplets of protein in a resonant-galvo scanning 2-photon microscope (WM-200, Thorlabs). The microscope used a 40×1.15 NA water immersion objective, a primary dichroic (680-1600 nm longpass filter, Thorlabs), and a secondary dichroic (FF562-Di03, Semrock) with green (530/43, Semrock) and red (605/70, Chroma) filters each followed by GaAsP PMTs (H7422PA-40, Hamamatsu). Laser excitation was provided at 1000 nm or 1070 nm from a Ti: Sapphire laser. In order to completely bleach the protein droplets of ~5 um thickness, repetitive z-stacks through the protein droplets were taken. Beam scan area was 160 um×160 um, and the scan rate was 8 frames/sec.

Neuronal culture screen. R-GECO1and RCaMP1h were both expressed throughout the cytoplasm and nucleus (data not shown). Partitioning of red GECIs across nucleus and cytoplasm affects the fluorescence responses to single action potentials. A nuclear export sequence (NES: MLQNELA-LKLAGLDINKTG) (SEQ ID NO: 8), derived from the cAMP-dependent protein kinase inhibitor alpha subunit, was added to the N-termini of R-GECO1, RCaMP1h, and all their variants. This restricted expression to the cytoplasm (FIG. 1b). R-CaMP2 was excluded from the nucleus without the NES and was therefore not tagged with the NES.

Mutants red GECIs were made using mismatched oligonucleotides and cloned into the vector using gene assembly. Red GECI variants were expressed after transfection by electroporation into rat primary hippocampal neurons (P0) using the Lonza Nucleofector system (P3 Primary Cell 96-well Kit). Transfected neurons were plated in glass-bottom 96-well plates (MatTek) and cultured as described in (Wardill, Chen et al. 2013). The imaging buffer was 145 mM NaCl, 2.5 mM KCl, 10 mM glucose, 10 mM HEPES, pH 7.4, 2 mM $CaCl_2$, 1 mM $MgCl_2$, and it included glutamate and GABA receptor antagonists (10 µM CNQX, 10 µM (R)-CPP, 10 µM gabazine, 1 mM (S)-MCPG, Tocris Bioscience). Synaptic transmission was inhibited to make calcium increases solely dependent on opening of voltage sensitive calcium channels.

APs (83 Hz) were evoked by field stimulation as described (Wardill, Chen et al. 2013), except that stimulation and imaging was in 96-well plates with modified electrodes. Illumination was provided by an LED and TxRed (Excitation: 540-580 nm; Dichroic: 585 nm long-pass; Emission: 593-668 nm) and GFP (Excitation: 450-490 nm; Dichroic: 495 nm long-pass; Emission: 500-550 nm) filter sets. Imaging conditions and analysis were similar to prior experiments (Chen, Wardill et al. 2013). For measuring the photoswitching in jRGECO1a expressing neurons (FIG. 12), blue light stimulation was added by using a blue LED and replacing the green excitation filter with a 561 shortpass filter (Semrock).

Labeling V1 Neurons. Constructs used to produce AAV included pGP-AAV-syn-red GECI-WPRE and the cre-recombinase-activated construct pGP-AAV-syn-flex-red GECI-WPRE. Virus was slowly injected through a thinned skull (25-30 nl in 5 min) into the primary visual cortex (1-2 injection sites, variables depths; 2.7 mm lateral and 0.2 mm anterior to lambda suture; 250 µm deep for L2/3 imaging, 250 µm and 450 µm for L4 imaging, 500 µm for L5 imaging, and 650 µm and 900 µm for L6 imaging).

Cranial Window Implantation. Three to four weeks after virus injection, mice were anesthetized using isoflurane (3% for induction, 1.5-2% during surgery) and a 2-3 mm circular craniotomy was made above V1 (centered around the injection site). The craniotomy was covered by 1% agarose (UltraPure Agarose, Invitrogen). A round 3 mm glass coverslip (Warner Instruments, #1 thickness) was cemented to the skull to reduce motion of the exposed brain. A custom titanium head post was fixed to the skull using black dental cement (Contemporary Ortho-Jet). For simultaneous imaging and cell-attached recording, the exposed brain was covered with a thick 1% agarose layer, and partially covered with a D-shape coverslip. The animal was then placed under a microscope on a warm blanket (37° C.) and kept anesthetized using 0.5% isoflurane and sedated with chlorprothixene (20-40 µl at 0.33 mg/ml, i.m.).

Imaging in the Visual Cortex. Imaging was performed with a custom-built two-photon microscope equipped with a resonant scanner. The light source was an Insight DS Dual 120 femtosecond-pulse laser (Spectra-Physics) running at 1040 nm and 1100 nm for jRGECO1a and jRCaMP1 indicators, respectively. The objective was a 16×water immersion lens with 0.8 NA (Nikon). Images were acquired using ScanImage 5 (vidriotechnologies.com) (Pologruto, Sabatini et al. 2003). For L2/3, L4, and L5 imaging, functional images (512×512 pixels, 250×250 µm$^2$) were collected at 15 Hz. Typical laser power was 15-60, 30-75, and 50-100 mW at the front aperture of the objective for L2/3, L4, and L5 imaging, respectively. For L6 imaging, functional images (512×512 pixels, 165×165 and 125×125 µm$^2$) were collected at 5 Hz. Laser power was 100-150 mW at the front aperture of the objective lens.

Visual Stimuli. Moving grating stimuli were generated using the Psychophysics Toolbox in MATLAB (Mathworks). Each stimulus trial consisted of a 4s blank period (uniform grey at mean luminance) followed by a 4 s drifting sinusoidal grating (0.05 cycles per degree, 1 Hz temporal frequency). Eight drifting directions were used, separated by 45 degrees, and 5 trials were recorded for each direction, giving a total of 40 stimulus trials per recording session (320 s recording time). The gratings were presented with an LCD monitor (30×40 cm), placed 25 cm in front of the center of the right eye of the mouse. The monitor subtended an angle of ±38° horizontally and ±31 vertically around the eye of the mouse. For experiments with cell-attached recording (FIG. 5), pipette access required the use of a smaller LCD monitor (12×16 cm) placed, 10 cm in front of the right eye. During simultaneous imaging and electrophysiology, the optimal grating stimulus was repeatedly played, but the contrast of the stimulus grating was adjusted online to record variable spike rates. To minimize stimulus contamination in the red detection channel, a green colored plexiglass filter (500-555 nm FWHM) was placed in front of the mouse eye.

Analysis of V1 Functional Imaging. Mechanical drift in the imaging plane was corrected using the TurboReg plug-in in ImageJ. All remaining analyses were performed in MATLAB. Regions of interest (ROIs) corresponding identifiable cell bodies were selected using a semi-automated algorithm (Akerboom, Chen et al. 2012, Chen, Wardill et al. 2013). Depending on the neuron's appearance, annular or circular ROIs were placed over the cytosolic regions of each cell. The fluorescence time course was measured by averaging all pixels within the ROI, after correction for neuropil contamination. The neuropil signal $F_{neuropil}(t)$ surrounding each cell was measured by averaging the signal of all pixels within a 20 µm circular region from the cell center (excluding all somata). The fluorescence signal of a cell body was estimated as:

$$F_{cell\_true}(t)=F_{cell\_measured}(t)-r \cdot F_{neuropil}(t),$$

with r=0.7. Neuropil correction was applied only to cells with baseline fluorescence ($F_0$) signal stronger than the surrounding neuropil signal by more than 3%; other cells (approximately 15-20%) were excluded from the analysis because $F_0$ could not be reliably estimated. After neuropil correction, the $\Delta F/F_0$ of each trial was calculated as $(F-F_0)/F_0$, where $F_0$ was averaged over a 1 s period immediately before the start of grating stimulation. Visually responsive neurons were defined as cells with $\Delta F/F_0 > 0.05$ during at least one stimulus period, and using ANOVA across blank and eight direction periods (p<0.01).

The decay time of fluorescence was calculated after the end of the preferred stimulus. For each cell responses were averaged from five trials; baseline fluorescence and standard deviation were calculated from 1 s before the start of the stimulus. Only responsive cells with fluorescence response 4 times the standard deviation of the baseline during the last 1 s of the stimulus were analyzed. The time required for each trace to reach half of its peak value (baseline fluorescence subtracted) was calculated by linear interpolation. The same cells were used for plotting the average response showed in FIG. 3c. Since each cell responded at slightly different times, depending on its receptive field structure, each trace was shifted so that their maxima align. For visual display, traces were smoothed with a 3 sample moving average kernel.

The orientation selectivity index (OSI, FIG. 14) was calculated for visually responsive cells. First, the preferred orientation ($\theta_{pref}$) of the cell was determined as the stimulus that produced the strongest response. The orientation-tuning curve was constructed by measuring the mean $\Delta F/F_0$, averaged over the stimulus period, for each orientation. The tuning curve was fitted with the sum of two Gaussians centred on $\theta_{pref}$ and $\theta_{pref}+\pi/2$, both with width $\sigma$, amplitudes A1 and A2, and a constant baseline B. The OSI was defined as $OSI=(R_{pref}-R_{ortho})/(R_{pref}+R_{ortho})$, where $R_{pref}$ and $R_{ortho}$ are the response amplitudes at the preferred ($\theta_{pref}$) and the orthogonal orientation ($\theta_{pref}+\pi/2$) respectively.

Simultaneous Electrophysiology and Functional Imaging in V1. In vivo cell-attached recordings were performed using glass pipettes (~7-12 MΩ) filled with solution containing the following (in mM): 125 NaCl, 5 KCl, 10 glucose, 10 HEPES, 2 CaCl$_2$, 2 MgSO$_4$, and 0.1 Alexa Fluor 488; pH 7.4). Signals were amplified using an AxoPatch 200B amplifier (Molecular Devices), filtered at 5 kHz, and digitized at 10 kHz. Spikes were recorded using current clamp mode. The frame trigger pulses of ScanImage 5 were also recorded and used offline to synchronize individual frames to electrophysiological recordings. After establishment of a low-resistance seal (15-50 MΩ), the orientation of the stimulus was quickly optimized for individual neurons using recorded spikes. The optimal grating stimulus was repeated at variable contrast levels to acquire a large range of spiking rates.

Images (512×512 pixels, typically 40×40 µm$^2$) were acquired at 30 Hz and 15 Hz for jRGECO1a and jRCaMP1a respectively. Ring-shaped ROIs were placed over the cytosolic regions of the cells, and neuropil contamination was subtracted. To quantify the efficiency for detecting single APs (FIG. 5e), single AP events were identified with nearby APs at least 1 s away, and 2 APs within a time window of 100 and 150 ms for jRGECO1a and jRCaMP1a respectively, with nearby APs at least 1 s away. Noise traces were taken from periods without APs. $F_0$ values were calculated as the average of 10 frames before the first AP, and peak $\Delta F/F_0$ was calculated as the maximum of $\Delta F/F_0$ trace after the first spike firing, or the maximal of $\Delta F/F_0$ noise value for the noise traces. Then a receiver operating characteristic analysis was used to obtain the false positive and true positive rates for any given threshold. Similarly, d' was calculated for peak $\Delta F/F_0$ distribution for 1-8 APs vs. the noise traces peaks. Time window in which the APs were fired varied with the number of spikes and the GECI (jRGECO1a: 100 ms for 2APs; 125, 3APs; 150, 4APs; 175, SAPS; 200, 6-BAPS; jRCaMP1a: 150, 2APs; 200, 3APs; 250, 4APs; 300, SAPS; 350, 6-BAPS)

*Drosophila* NMJ Imaging. $w^{1118}$; ;PBac{20XUAS-IVS-NES-GECI-p10}VK00005 transgenic flies were crossed with a $w^{1118}$; ;R57C10-Gal4 in VK00020, R57C10-Gal4 in VK00040 pan-neuronal driver line. The NMJ assay has been described (Chen, Wardill et al. 2013). Briefly, actively crawling female $3^{rd}$ instar larvae were dissected under minimum illumination intensity. Type Ib boutons on muscle 13 from segment A3-A5 were wide-field imaged in HL-6 saline while corresponding axons were electrically stimulated with a suction electrode driven by a customized stimulator. Temperature and pH were monitored during imaging. A mercury lamp (X-CITE exacte) light source was used for excitation and power of less than 5 mW at the objective front aperture was used. The illumination intensity kept low so that photobleaching was negligible within each trial. The filters for RGECO and RCaMP imaging were: exciter: 543/22; dichroic: 562; emitter: 593/40. EMCCD cooled to $-70°$ C. was acquiring at 30 fps. Data were analyzed in MATLAB (Mathworks).

Zebrafish Trigeminal Neurons Imaging. Mitfa$^{-/-}$ (nacre) zebrafish were maintained under standard conditions at 28° C. and a 14:10 hours light:dark cycle. Embryos (1-2 cell stage) were injected with 20 ng/µl DNA plasmids encoding the red GECI variants under the control the (near) pan-neuronal e1avl3/HuC promoter (e1avl3:GECI), and 40 ng/µL Tol2 transposase mRNA diluted in E3 medium with 0.025% Phenol Red. Three and four day post-fertilization embryos showing expression in isolated trigeminal neurons were treated with 1 mg/mL bath-applied α-bungarotoxin for 30 minutes to block tail movements. Larvae were mounted sideways in 1.5% low melting temperature agarose, and imaged using a microscope with a 20×, NA=1 objective lens (Olympus) and an sCMOS camera (Hamamatsu Orca Flash 4). Trains of 1, 5 and 10 field stimuli (20 ms each; 20 Hz) were applied using two mesh electrodes located inside the bath and a stimulator (Grass SD9). Stimulation voltage was calibrated to elicit an identifiable response to a single pulse in GCaMP6f expressing neurons. One spike in a trigeminal neuron has previously been shown to be sufficient to elicit tail movement (Douglass, Kraves et al. 2008). Image acquisition and stimulus control were handled using Hamamatsu HCImage (4.2.5.0) software. ROI were selected manually, and data was analyzed using MATLAB (MathWorks).

*Caenorhabditis elegans* ASH Neurons Imaging. Red GECIs were expressed in the *C. elegans* ASH sensory neurons under the sra-6 promoter. Animals were restrained in custom-built microfluidic chambers in S basal buffer (Brenner 1974), and paralyzed with 10 mM tetramisole hydrochloride (Sigma-Aldrich) during data acquisition to reduce movement. 1M glycerol was delivered to the nose of the animal in alternating one second intervals for 4 minutes as in (Kato, Xu et al. 2014). Worms were illuminated with a solid-state lamp (Lumencor SOLA-LE, $\lambda$=560 nm), and fluorescence images ($\lambda$=630 nm) were collected at 10 fps using a 40× objective and an EMCCD camera (Andor iXon3, Metamorph Software).

Reagent distribution. DNA constructs, AAV particles and Drosophila with red GECIs variants were deposited for distribution at Addgene (www.addgene. org), the University of Pennsylvania Vector Core (www.med.upenn.edu/gtp/vectorcore) and the Bloomington Drosophila Stock Center (flystocks.bio. indiana.edu), respectively.

Discussion. GFP-based GECIs are well-established tools for studying neuronal activity across many model organisms. Current state-of-the-art green GECIs, such as GCaMP6, have sufficient sensitivity to detect single action potentials in diverse cell types and even detect activity of single synapses. They can be targeted to specific cell types and subcellular compartments. Red GECIs can potentially be used in a similar manner with additional advantages. For example, they suffer less from tissue scattering and absorption. In addition, rhodopsin-based optogenetic tools have substantial absorption in the blue region of the wavelength spectrum, which overlaps with the excitation spectrum of GFP. Red GECIs can be imaged without exciting ChR2. The red GECIs developed herein rival best-of-class green GECIs in terms of sensitivity for detecting neural activity, thereby closing a significant performance gap between red and green GECIs.

The new mApple-based jRGECO1a and the mRuby-based jRCaMP1a and jRCaMP1b are all improved several-fold compared to their parent indicators. jRGECO1a exhibits similar performance to the GCaMP6 indicators. jRCaMP1a and jRCaMP1b are less sensitive, but do not show photoswitching after illumination with blue light, making them suitable for experiments that combine calcium imaging and optogenetics. This improved performance will enable a wide range of applications for red GECIs, for example, dual color imaging, where green and red GECIs are used in parallel to study the relation between two components of a neural circuit.

Red GECIs will be useful for all-optical electrophysiology experiments, especially when there is spatial overlap between the stimulated and imaged parts of the neural circuit. The large spectral separation between the ChR2 activation spectrum and the red GECI excitation spectrum (Akerboom, Carreras Calderon et al. 2013) is preferable in situations when using a red-shifted light sensitive ion channel and a green GECI produce cross-talk (Rickgauer, Deisseroth et al. 2014, Packer, Russell et al. 2015). The two-photon absorption spectra of red GECIs peak around 1040 nm, which overlaps with the output of cost-effective and powerful fiber lasers.

Red GECIs still face challenges. First, all tested red GECIs show a smaller maximal fluorescence change upon calcium binding (3- to 4-fold less than the GCaMP6 indicators). This limits the overall dynamic range of red GECIs. Second, the relatively low absorption cross-section of the red GECIs (FIG. 9) further reduces the achievable signal-to-noise ratio for in vivo imaging. Third, red GECIs show complex behavior with long-term expression in the mouse brain. The presence of green fluorescence and RFP aggregates suggest the existence of multiple protein species, some of which do not produce functional signals (FIGS. 22, 23). Engineering red GECIs to produce less non-productive fluorescence might require re-engineering the RFP itself, a direction that will be pursued in the future.

All publications, patents, and patent applications mentioned in this specification are herein incorporated by reference to the same extent as if each individual publication, patent, or patent application was specifically and individually indicated to be incorporated by reference.

REFERENCES

Ahrens, M. B., M. B. Orger, D. N. Robson, J. M. Li and P. J. Keller (2013). "Whole-brain functional imaging at cellular resolution using light-sheet microscopy." *Nature Methods* 10(5): 413-420.

Akerboom, J., N. Carreras Calderon, L. Tian, S. Wabnig, M. Prigge, J. Tolo, A. Gordus, M. B. Orger, K. E. Severi, J. J. Macklin, R. Patel, S. R. Pulver, T. J. Wardill, E. Fischer, C. Schuler, T. W. Chen, K. S. Sarkisyan, J. S. Marvin, C. I. Bargmann, D. S. Kim, S. Kugler, L. Lagnado, P. Hegemann, A. Gottschalk, E. R. Schreiter and L. L. Looger (2013). "Genetically encoded calcium indicators for multi-color neural activity imaging and combination with optogenetics." *Frontiers in molecular neuroscience* 6: 2.

Akerboom, J., T. W. Chen, T. J. Wardill, L. Tian, J. S. Marvin, S. Mutlu, N. C. Calderon, F. Esposti, B. G. Borghuis, X. R. Sun, A. Gordus, M. B. Orger, R. Portugues, F. Engert, J. J. Macklin, A. Filosa, A. Aggarwal, R. A. Kerr, R. Takagi, S. Kracun, E. Shigetomi, B. S. Khakh, H. Baier, L. Lagnado, S. S. Wang, C. I. Bargmann, B. E. Kimmel, V. Jayaraman, K. Svoboda, D. S. Kim, E. R. Schreiter and L. L. Looger (2012). "Optimization of a GCaMP Calcium Indicator for Neural Activity Imaging." *Journal of neuroscience* 32(40): 13819-13840.

Akerboom, J., J. D. Rivera, M. M. Guilbe, E. C. Malave, H. H. Hernandez, L. Tian, S. A. Hires, J. S. Marvin, L. L. Looger and E. R. Schreiter (2009). "Crystal structures of the GCaMP calcium sensor reveal the mechanism of fluorescence signal change and aid rational design." *J Biol Chem* 284(10): 6455-6464.

Brainard, D. H. (1997). "The Psychophysics Toolbox." *Spatial vision* 10(4): 433-436.

Brenner, S. (1974). "The genetics of *Caenorhabditis elegans*." *Genetics* 77(1): 71-94.

Chen, J. L., S. Carta, J. Soldado-Magraner, B. L. Schneider and F. Helmchen (2013). "Behaviour-dependent recruitment of long-range projection neurons in somatosensory cortex." *Nature* 499(7458): 336-340.

Chen, T. W., T. J. Wardill, Y. Sun, S. R. Pulver, S. L. Renninger, A. Baohan, E. R. Schreiter, R. A. Kerr, M. B. Orger, V. Jayaraman, L. L. Looger, K. Svoboda and D. S. Kim (2013). "Ultrasensitive fluorescent proteins for imaging neuronal activity." *Nature* 499(7458): 295-300.

Chronis, N., M. Zimmer and C. I. Bargmann (2007). "Microfluidics for in vivo imaging of neuronal and behavioral activity in *Caenorhabditis elegans*." *Nat Methods* 4(9): 727-731.

Crivici, A. and M. Ikura (1995). "Molecular and structural basis of target recognition by calmodulin." *Annual review of biophysics and biomolecular structure* 24: 85-116.

Douglass, A. D., S. Kraves, K. Deisseroth, A. F. Schier and F. Engert (2008). "Escape Behavior Elicited by Single, Channelrhodopsin-2-Evoked Spikes in Zebrafish Somatosensory Neurons." *Current Biology* 18(15): 1133-1137.

Gong, S., M. Doughty, C. R. Harbaugh, A. Cummins, M. E. Hatten, N. Heintz and C. R. Gerfen (2007). "Targeting Cre recombinase to specific neuron populations with bacterial artificial chromosome constructs." *J Neurosci* 27(37): 9817-9823.

Horton, N. G., K. Wang, D. Kobat, C. G. Clark, F. W. Wise, C. B. Schaffer and C. Xu (2013). "three-photon microscopy of subcortical structures within an intact mouse brain." *Nature Photonics* 7(3).

Huber, D., D. A. Gutnisky, S. Peron, D. H. O'Connor, J. S. Wiegert, L. Tian, T. G. Oertner, L. L. Looger and K. Svoboda (2012). "Multiple dynamic representations in the motor cortex during sensorimotor learning." *Nature* 484 (7395): 473-478.

Inoue, M., A. Takeuchi, S. Horigane, M. Ohkura, K. Gengyo-Ando, H. Fujii, S. Kamijo, S. Takemoto-Kimura, M. Kano, J. Nakai, K. Kitamura and H. Bito (2015). "Rational design of a high-affinity, fast, red calcium indicator R-CaMP2." *Nature Methods* 12(1): 64-70.

Kato, S., Y. Xu, Christine E. Cho, L. F. Abbott and Cornelia I. Bargmann (2014). "Temporal Responses of *C. elegans* Chemosensory Neurons Are Preserved in Behavioral Dynamics." *Neuron* 81(3): 616-628.

Kerlin, A. M., M. L. Andermann, V. K. Berezovskii and R. C. Reid (2010). "Broadly tuned response properties of diverse inhibitory neuron subtypes in mouse visual cortex." *Neuron* 67(5): 858-871.

Kredel, S., F. Oswald, K. Nienhaus, K. Deuschle, C. Rocker, M. Wolff, R. Heilker, G. U. Nienhaus and J. Wiedenmann (2009). "mRuby, a bright monomeric red fluorescent protein for labeling of subcellular structures." *PLoS ONE* 4(2): e4391.

Kremers, G.-J., K. L. Hazelwood, C. S. Murphy, M. W. Davidson and D. W. Piston (2009). "Photoconversion in orange and red fluorescent proteins." *Nat Meth* 6(5): 355-358.

Li, N., T. W. Chen, Z. V. Guo, C. R. Gerfen and K. Svoboda (2015). "A motor cortex circuit for motor planning and movement." *Nature* 519(7541): 51-56.

Makarov, N. S., M. Drobizhev and A. Rebane (2008). "Two-photon absorption standards in the 550-1600 nm excitation wavelength range." *Optics Express* 16(6): 4029-4047.

Margolis, D. J., H. Lütcke, K. Schulz, F. Haiss, B. Weber, S. Kügler, M. T. Hasan and F. Helmchen (2012). "Reorganization of cortical population activity imaged throughout long-term sensory deprivation." *Nature Neuroscience* 15(11): 1539-1546.

Moore, M. M., S. K. Oteng-Pabi, A. T. Pandelieva, S. L. Mayo and R. A. Chica (2012). "Recovery of Red Fluorescent Protein Chromophore Maturation Deficiency through Rational Design." *PLoS ONE* 7(12): e52463.

Mrsic-Flogel, T. D., S. B. Hofer, K. Ohki, R. C. Reid, T. Bonhoeffer and M. Hubener (2007). "Homeostatic regulation of eye-specific responses in visual cortex during ocular dominance plasticity." *Neuron* 54(6): 961-972.

Mutze, J., V. Iyer, J. J. Macklin, J. Colonell, B. Karsh, Z. Petrasek, P. Schwille, L. L. Looger, L. D. Lavis and T. D. Harris (2012). "Excitation spectra and brightness optimization of two-photon excited probes." *Biophysical journal* 102(4): 934-944.

Nagel, G., T. Szellas, W. Huhn, S. Kateriya, N. Adeishvili, P. Berthold, D. Ollig, P. Hegemann and E. Bamberg (2003). "Channelrhodopsin-2, a directly light-gated cation-selective membrane channel." *Proc Natl Acad Sci USA* 100(24): 13940-13945.

Niell, C. M. and M. P. Stryker (2008). "Highly selective receptive fields in mouse visual cortex." *J Neurosci* 28(30): 7520-7536.

O'Connor, D. H., S. A. Hires, Z. V. Guo, N. Li, J. Yu, Q. Q. Sun, D. Huber and K. Svoboda (2013). "Neural coding during active somatosensation revealed using illusory touch." *Nature Neuroscience* 16(7): 958-965.

Ohkura, M., T. Sasaki, J. Sadakari, K. Gengyo-Ando, Y. Kagawa-Nagamura, C. Kobayashi, Y. Ikegaya and J. Nakai (2012). "Genetically Encoded Green Fluorescent Ca2+ Indicators with Improved Detectability for Neuronal Ca2+ Signals." *PLoS ONE* 7(12): e51286.

Packer, A. M., L. E. Russell, H. W. P. Dalgleish and M. Hausser (2015). "Simultaneous all-optical manipulation and recording of neural circuit activity with cellular resolution in vivo." *Nature Methods* 12(2): 140-146.

Pelli, D. G. (1997). "The VideoToolbox software for visual psychophysics: transforming numbers into movies." *Spatial vision* 10(4): 437-442.

Peron, S., T. W. Chen and K. Svoboda (2015). "Comprehensive imaging of cortical networks." *Curr Opin Neurobiol* 32: 115-123.

Peron, S. P., J. Freeman, V. Iyer, C. Guo and K. Svoboda (2015). "A Cellular Resolution Map of Barrel Cortex Activity during Tactile Behavior." *Neuron* 86(3): 783-799.

Pologruto, T. A., B. L. Sabatini and K. Svoboda (2003). "ScanImage: flexible software for operating laser scanning microscopes." *Biomed Eng Online* 2(1): 13.

Rickgauer, J. P., K. Deisseroth and D. W. Tank (2014). "Simultaneous cellular-resolution optical perturbation and imaging of place cell firing fields." *Nature Neuroscience* 17(12): 1816-1824.

Shaner, N. C., M. Z. Lin, M. R. McKeown, P. A. Steinbach, K. L. Hazelwood, M. W. Davidson and R. Y. Tsien (2008). "Improving the photostability of bright monomeric orange and red fluorescent proteins." *Nature Methods* 5(6): 545-551.

Svoboda, K. and S. M. Block (1994). "Biological applications of optical forces." *Ann. Rev. of Biophys. and Biomol. Struct.* 23: 247-285.

Thevenaz, P., U. E. Ruttimann and M. Unser (1998). "A pyramid approach to subpixel registration based on intensity." *IEEE Trans Image Process* 7(1): 27-41.

Tian, L., S. A. Hires, T. Mao, D. Huber, M. E. Chiappe, S. H. Chalasani, L. Petreanu, J. Akerboom, S. A. McKinney, E. R. Schreiter, C. I. Bargmann, V. Jayaraman, K. Svoboda and L. L. Looger (2009). "Imaging neural activity in worms, flies and mice with improved GCaMP calcium indicators." *Nature Methods* 6(12): 875-881.

Wardill, T. J., T.-W. Chen, E. R. Schreiter, J. P. Hasseman, G. Tsegaye, B. F. Fosque, R. Behnam, B. C. Shields, M. Ramirez, B. E. Kimmel, R. A. Kerr, V. Jayaraman, L. L. Looger, K. Svoboda and D. S. Kim (2013). "A Neuron-Based Screening Platform for Optimizing Genetically-Encoded Calcium Indicators." *PLoS ONE* 8(10): e77728.

Wu, J., A. S. Abdelfattah, L. S. Miraucourt, E. Kutsarova, A. Ruangkittisakul, H. Zhou, K. Ballanyi, G. Wicks, M. Drobizhev, A. Rebane, E. S. Ruthazer and R. E. Campbell (2014). "A long Stokes shift red fluorescent Ca2+ indicator protein for two-photon and ratiometric imaging." *Nat Commun* 5: 5262.

Wu, J., L. Liu, T. Matsuda, Y. Zhao, A. Rebane, M. Drobizhev, Y.-F. Chang, S. Araki, Y. Arai, K. March, T. E. Hughes, K. Sagou, T. Miyata, T. Nagai, W.-h. Li and R. E. Campbell (2013). "Improved Orange and Red Ca2+ Indicators and Photophysical Considerations for Optogenetic Applications." *ACS Chemical Neuroscience* 4(6): 963-972.

Xu, C. and W. W. Webb (1996). "Measurement of two-photon excitation cross sections of molecular fluorophores with data from 690 to 1050 nm." *Journal of the Optical Society of America B* 13(3): 481-491.

Zhao, Y., S. Araki, J. Wu, T. Teramoto, Y. F. Chang, M. Nakano, A. S. Abdelfattah, M. Fujiwara, T. Ishihara, T. Nagai and R. E. Campbell (2011). "An expanded palette of genetically encoded Ca(2) indicators." *Science* 333 (6051): 1888-1891.

It will be understood that various details of the presently disclosed subject matter can be changed without departing from the scope of the subject matter disclosed herein. Furthermore, the foregoing description is for the purpose of illustration only, and not for the purpose of limitation.

---

We claim:

1. A purified or isolated nucleic acid molecule comprising a sequence that encodes a genetically encoded calcium indicator (GECI) polypeptide having at least 96% sequence identity to the amino acid sequence of SEQ ID NO: 2 or SEQ ID NO: 4, or at least 95% sequence identity to the amino acid sequence of SEQ ID NO: 6.

2. The nucleic acid molecule of claim 1, comprising a sequence that encodes a GECI polypeptide having at least 99% sequence identity to the amino acid sequence of SEQ ID NO: 2, SEQ ID NO: 4, or SEQ ID NO: 6.

3. The nucleic acid molecule of claim 1, comprising a sequence that encodes a GECI polypeptide consisting of the amino acid sequence of SEQ ID NO: 2, SEQ ID NO: 4, or SEQ ID NO: 6.

4. A vector comprising the purified or isolated nucleic acid molecule of claim 1.

5. A cell comprising the vector of claim 4, wherein the cell is not integrated into a human organism.

6. A cell comprising the purified or isolated nucleic acid molecule of claim 1, wherein the cell is not integrated into a human organism.

7. A purified or isolated nucleic acid molecule comprising the sequence of SEQ ID NO: 1, SEQ ID NO: 3, or SEQ ID NO: 5.

8. A vector comprising the purified or isolated nucleic acid molecule of claim 7.

9. A method of monitoring activity of a cell as a function of calcium levels in the cell, comprising:
   (i) transfecting the cell such that it comprises a polypeptide encoded by the purified or isolated nucleic acid molecule of claim 1;
   (ii) electrically stimulating the cell;
   (iii) detecting changes in fluorescence levels emitted from the cell over time; and
   (iv) correlating the fluorescence levels to calcium levels, wherein higher fluorescence levels correlate to higher calcium levels and lower fluorescence levels correlate to lower calcium levels, wherein steps are performed in vitro with a human or non-human cell.

10. The method of claim 9, wherein the cell is in a biological sample from a subject.

11. A method of monitoring activity of a cell as a function of calcium levels in the cell, comprising:
   (i) introducing into the cell the nucleic acid molecule of claim 1 such that it comprises a polypeptide encoded by the nucleic acid molecule;
   (ii) electrically stimulating the cell;
   (iii) detecting changes in fluorescence levels emitted from the cell over time, and
   (iv) correlating the fluorescence levels to calcium levels, wherein higher fluorescence levels correlate to higher calcium levels and lower fluorescence levels correlate to lower calcium levels, wherein the steps are performed in vivo in a non-human subject.

12. The method of claims 11, wherein the subject is a mouse, a fish, a worm or a fly.

13. The method of claim 12, wherein the subject is a mouse and the cell is in the primary visual cortex.

14. The method of claim 11, wherein the cell is a motor neuron with terminals in the neuro-muscular junction (NMJ), a trigeminal neuron, or an ASH neuron.

15. The method of claim 11, wherein the detecting step comprises imaging.

16. The method of claim 11, wherein the cell is a neuronal cell, a muscle cell or a cardiomyocyte.

17. The method of claim 11, wherein the nucleic acid molecule is introduced into the cell using viral-based delivery.

18. The method of claim 11, wherein the subject is a transgenic animal.

* * * * *